US011926839B2

(12) United States Patent
Chen et al.

(10) Patent No.: US 11,926,839 B2
(45) Date of Patent: Mar. 12, 2024

(54) PLATFORM FOR T LYMPHOCYTE GENOME ENGINEERING AND IN VIVO HIGH-THROUGHPUT SCREENING THEREOF

(71) Applicant: YALE UNIVERSITY, New Haven, CT (US)

(72) Inventors: Sidi Chen, Milford, CT (US); Matthew Dong, San Francisco, CA (US)

(73) Assignee: YALE UNIVERSITY, New Haven, CT (US)

( * ) Notice: Subject to any disclaimer, the term of this patent is extended or adjusted under 35 U.S.C. 154(b) by 1096 days.

(21) Appl. No.: 16/605,715

(22) PCT Filed: Apr. 17, 2018

(86) PCT No.: PCT/US2018/027967

§ 371 (c)(1),
(2) Date: Oct. 16, 2019

(87) PCT Pub. No.: WO2018/195073

PCT Pub. Date: Oct. 25, 2018

(65) Prior Publication Data

US 2022/0259616 A1 Aug. 18, 2022

Related U.S. Application Data

(60) Provisional application No. 62/602,290, filed on Apr. 18, 2017.

(51) Int. Cl.
*C12N 15/00* (2006.01)
*C12N 5/0783* (2010.01)
(Continued)

(52) U.S. Cl.
CPC .......... *C12N 15/85* (2013.01); *C12N 5/0638* (2013.01); *C12N 15/111* (2013.01); *G01N 15/14* (2013.01);
(Continued)

(58) Field of Classification Search
None
See application file for complete search history.

(56) References Cited

U.S. PATENT DOCUMENTS

2005/0214823 A1 9/2005 Blume et al.
2009/0187997 A1 7/2009 Stern et al.
(Continued)

FOREIGN PATENT DOCUMENTS

CN 106591366 A * 4/2017
CN 110114461 A * 8/2019 .......... A61K 9/1271
(Continued)

OTHER PUBLICATIONS

WIPO English translation of CN110114461 (Year: 2019).*
(Continued)

*Primary Examiner* — M Franco G Salvoza
(74) *Attorney, Agent, or Firm* — Saul Ewing LLP; Kathryn Doyle; Domingos J. Silva

(57) ABSTRACT

The present invention includes compositions and methods for T cell genome editing and screening in vivo. In certain aspects, the invention includes an sgRNA library for genome-scale mutagenesis.

3 Claims, 112 Drawing Sheets

Specification includes a Sequence Listing.

(51) Int. Cl.
*C12N 15/11* (2006.01)
*C12N 15/85* (2006.01)
*G01N 15/14* (2006.01)

(52) U.S. Cl.
CPC .... *A01K 2217/15* (2013.01); *A01K 2227/101* (2013.01); *A01K 2227/105* (2013.01); *A01K 2267/03* (2013.01); *C12N 2310/20* (2017.05); *C12N 2510/00* (2013.01); *C12N 2740/16043* (2013.01)

(56) References Cited

U.S. PATENT DOCUMENTS

| | | | | |
|---|---|---|---|---|
| 2016/0168594 | A1* | 6/2016 | Zhang ................ | A01K 67/0275 435/320.1 |
| 2016/0311908 | A1 | 10/2016 | Arena et al. | |

FOREIGN PATENT DOCUMENTS

| | | | |
|---|---|---|---|
| WO | 2016011080 | A2 | 1/2016 |
| WO | 2017004153 | A1 | 1/2017 |
| WO | 2017075451 | A1 | 5/2017 |
| WO | 2017081097 | A1 | 5/2017 |
| WO | 2017083722 | A1 | 5/2017 |
| WO | 2017152015 | A1 | 9/2017 |
| WO | 2017192924 | A1 | 11/2017 |
| WO | 2018161009 | A1 | 9/2018 |

OTHER PUBLICATIONS

WIPO English translation of CN106591366 (Year: 2017).*
Extended European Search Report dated May 3, 2022 for European patent application No. 19788924.9.
International Search Report and Written Opinion dated Aug. 29, 2019 for Intl. Appl. No. PCT/US2019/027956.
International Search Report dated Oct. 24, 2018 in International Patent Application No. PCT/US18/27967.
Braun, Christian et al., "Versatile in vivo regulation of tumor phenotypes by dCas9-mediated transcriptional perturbation", PNAS, 113(27) E3892-E3900 (Jun. 2016).
Supporting information, 68 pages (2010), for Braun, Christian et al., "Versatile in vivo regulation of tumor phenotypes by dCas9-mediated transcriptional perturbation", PNAS, 113(27) E3892-E3900 (Jun. 2016).
Chavez, Alejandro et al., "Comparison of Cas9 activators in multiple species", Nature Methods, 13(7):563-567 (May 2016).
Supplementary information, 14 pages (2016), for Chavez, Alejandro et al., "Comparison of Cas9 activators in multiple species", Nature Methods, 13(7):563-567 (May 2016).
Chavez, Alejandro et al., "Highly efficient Cas9-mediated transcriptional programming", Nature Methods, 12(4):326-328 (Apr. 2015).
Chen, Runqiang et al., "In vivo RNA interference screens identify regulators of antiviral CD4+ and CD8+ T cell differentiation", Immunity, 41(2):325-338 (Aug. 2014).
Chow, Ryan et al., "AAV-mediated direct in vivo CRISPR screen identifies functional suppressors in glioblastoma", Nature Neuroscience, 20:1329-1341 (Oct. 2017).
De Charette, Marie et al., "Turning tumour cells into antigen presenting cells: The next step to improve cancer immunotherapy?", European Journal of Cancer, Elsevier, Amsterdam NL, 68:134-147 (Oct. 2016).
Gaujoux, Renaud et al., "A flexible R package for nonnegative matrix factorization", BMC Bioinformatics, 11(367,):1-9 (2010).
Germano, Giovanni et al., "Inactivation of DNA repair triggers neoantigen generation and impairs tumour growth", Nature, 552(7683):116-120 (Nov. 2017).
Gilbert, Luke A. et al., "CRISPR-mediated modular RNA-guided regulation of transcription in eukaryotes", Cell, 154(2):442-451 (Jul. 2013).
Gilbert, Luke A. et al., "Genome-Scale CRISPR-Mediated Control of Gene Repression and Activation", Cell, 159(3):647-661 (Oct. 2014).
Hu, Zhuting et al., "Towards personalized, tumour-specific, therapeutic vaccines for cancer", Nature Reviews Immunology, 18(3):168-182 (Dec. 2017).
Huang, Dai Wei et al., "Bioinformatics enrichment tools: paths toward the comprehensive functional analysis of large gene lists", Nucleic Acids Research, 37(1):1-13 (Nov. 2008).
Kampmann, Martin, "CRISPRi and CRISPRa Screens in Mammalian Cells for Precision Biology and Medicine", Biology and Medicine, ACS Chem. Bio., 13(2):406-416 (2017).
Konermann, Silvana et al., "Genome-scale transcriptional activation by an engineered CRISPR-Cas9 complex", Nature, 517(7536):583-588 (Jan. 2015).
Langmead, Ben et al., "Ultrafast and memory-efficient alignment of short DNA sequences to the human genome", Genome Biology, 10(R25):1-10 (Mar. 2009).
Liao, Hsin-Kai et al., "In Vivo Target Gene Activation via CRISPR/Cas9-Mediated Trans-epigenetic Modulation", Cell, 171(7):1495-1507 (Dec. 2017).
Lun, Aaron et al., "A step-by-step workflow for low-level analysis of single-cell RNA-seq data with Bioconductor", F1000 Research 5(2122):1-64 (Aug. 2016).
Mi, Huaiyu et al., "Large-scale function analysis with the PANTHER classification system", Nature Protocols 8:1551-1566 (2013).
Qi, Lei et al., "Repurposing CRISPR as an RNA-Guided Platform for SequenceSpecific Control of Gene Expression", Cell, 152(5):1173-1183 (2013).
Robinson, Mark et al., "edgeR: a Bioconductor package for differential expression analysis of digital gene expression data", Bioinformatics, Gene Expression 26(1):139-140 (2009).
Sanjana, Neville et al., "Improved vectors and genome-wide libraries for CRISPR screening", National Methods, 11(8):783-784 (2014).
Sau, Samaresh et al., "Multifunctional Nanoparticles for Cancer Immunotherapy: A Groundbreaking Approach for Reprogramming Malfunctioned Tumor Environment", Journal of Controlled Release, 274:24-34 (Jan. 2018).
Siebenkas, Cornelia et al., "Inhibiting DNA methylation activates cancer testis antigens and expression of the antigen processing and presentation machinery in colon and ovarian cancer cells", PLOS ONE, 12(6):e0179501, pp. 1-15 (Jun. 2017).
Tanenbaum, Marvin E., et al., "A protein-tagging system for signal amplification in gene expression and fluorescence imaging", Cell, 159(3):635-646 (Oct. 2014).
Wang, Guangchuan et al., "Multiplexed activation of endogenous genes by CRISPRa elicits potent antitumor immunity", Nature Immunology, 20(11):1494-1505 (Oct. 2019).
Zheng, Chunhong et al., "Landscape of Infiltrating T Cells in Liver Cancer Revealed by Single-Cell Sequencing", Cell, 169:1342-1356 (Jun. 2017).
Zhou, Penghui , et al., "In vivo Discovery of Immunotherapy Targets in the Tumor Microenvironment", Nature, 506(7486):52-57 (2014).

* cited by examiner

FIG. 5C

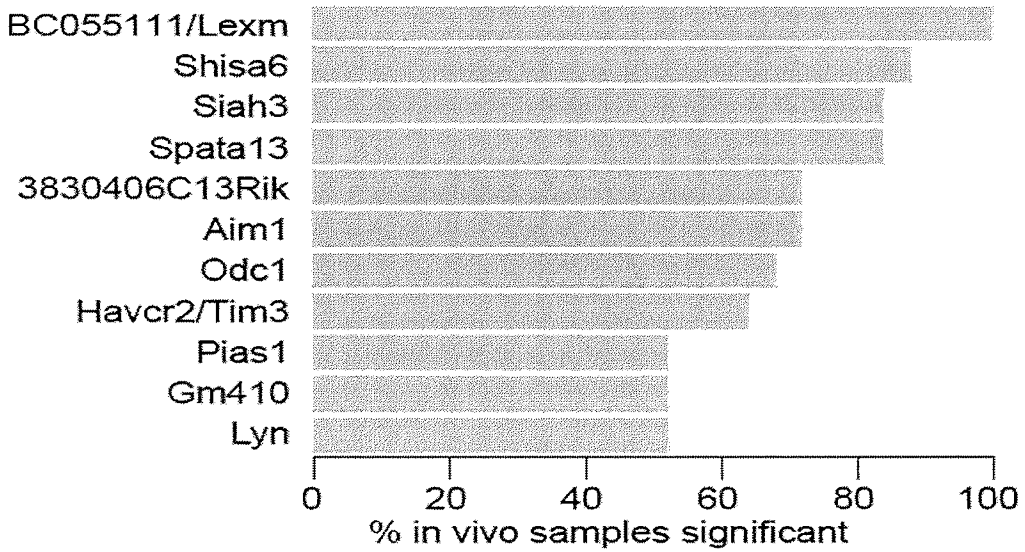

FIG. 5D

| Enriched GO term | n | p value |
|---|---|---|
| Antibacterial humoral response | 8 | 7.83E-05 |
| Defense response to Gram-positive bacterium | 12 | 2.23E-04 |
| Positive regulation of ERK1 and ERK2 cascade | 17 | 4.66E-04 |
| Innate immune response in mucosa | 6 | 4.83E-04 |
| Regulation of synaptic transmission, GABAergic | 5 | 6.38E-04 |
| NF-kappa B signaling pathway | 12 | 1.00E-03 |
| CCR chemokine receptor binding | 6 | 1.97E-03 |
| Chemokine receptor binding | 5 | 2.44E-03 |
| Ras guanine nucleotide exchange factor, domain | 7 | 2.84E-03 |
| Extrinsic component of cytoplasmic side of plasma membrane | 10 | 3.25E-04 |
| Nuclear nucleosome | 7 | 2.75E-03 |
| Perikaryon | 13 | 3.49E-03 |
| Plasma membrane | 184 | 1.05E-02 |
| Immunological synapse | 5 | 2.32E-02 |

FIG. 6C
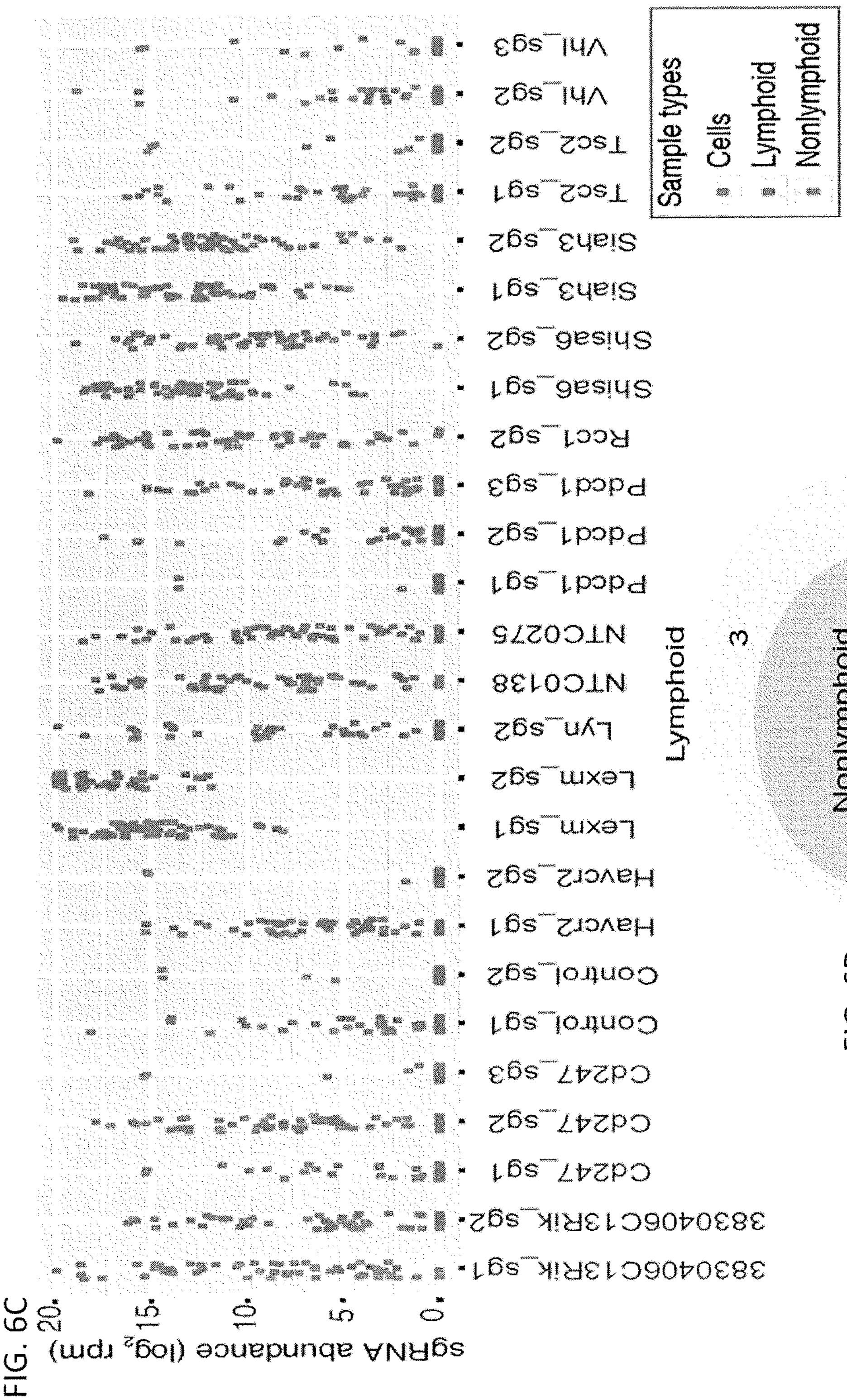
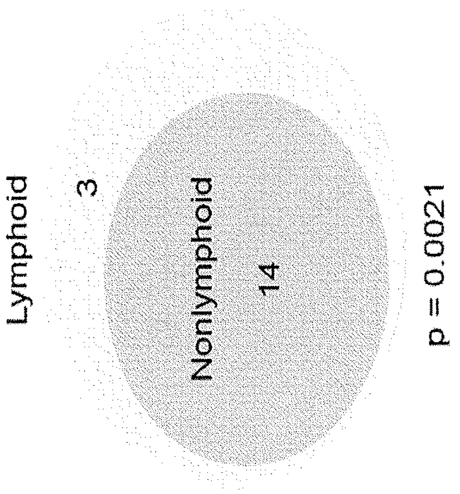
FIG. 6D

FIG. 8E
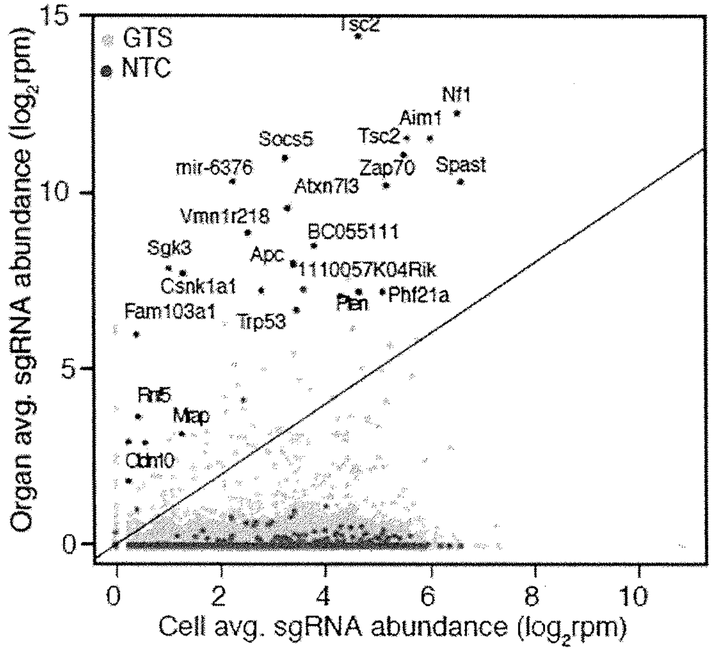
FIG. 8F
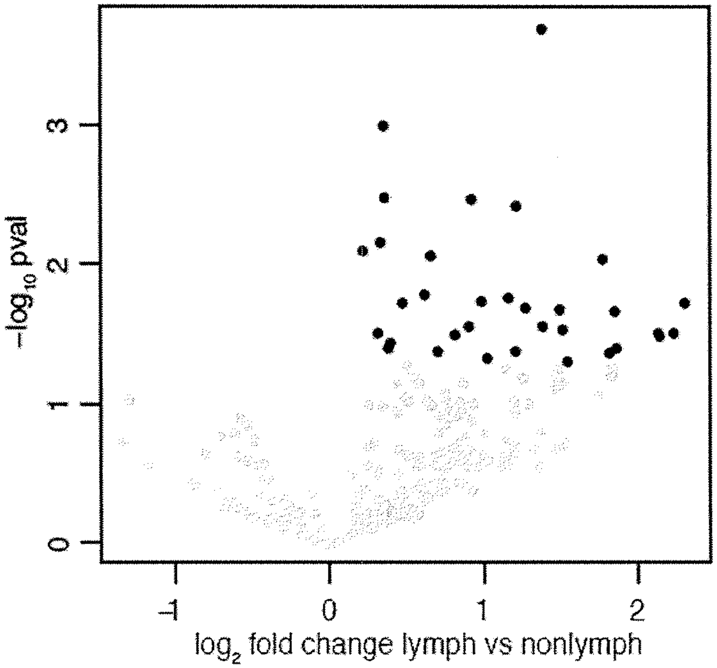
FIG. 8G
| GO term | n | Enrichment p value |
|---|---|---|
| Differentiation | 82 | 7.73E-05 |
| Alternative splicing | 469 | 4.46E-06 |
| Cell membrane | 359 | 6.99E-04 |
| Cell adhesion | 63 | 1.18E-03 |
| Receptor | 256 | 1.26E-03 |

| sgRNA | foldChng_vs_NTCavg | t-test_vs_NTCavg |
|---|---|---|
| Lexm_sg2 | 4.039740667 | 1.68E-57 |
| Lexm_sg1 | 3.297240882 | 1.68E-40 |
| Shisa6_sg1 | 2.906492389 | 6.41E-29 |
| Siah3_sg1 | 2.942100616 | 9.73E-28 |
| Siah3_sg2 | 2.613933621 | 1.37E-21 |
| Havcr2_sg2 | 0.006495433 | 6.32E-20 |
| Pdcd1_sg1 | 0.007311084 | 6.34E-20 |
| Cd247_sg3 | 0.0318748 | 7.89E-20 |
| Tsc2_sg2 | 0.118302181 | 3.04E-15 |
| Vhl_sg3_duplex | 0.14566173 | 4.02E-15 |
| Shisa6_sg2 | 2.181069602 | 3.07E-13 |
| Rcc1_sg2 | 2.211589617 | 1.92E-10 |
| Cd247_sg1 | 0.324099608 | 1.31E-08 |
| Vhl_sg2_duplex | 0.357798703 | 4.81E-07 |
| Pdcd1_sg2 | 0.366709515 | 1.07E-06 |
| 3830406C13Rik_sg1 | 1.876787973 | 2.74E-06 |
| Cd247_sg2 | 1.693861488 | 3.32E-05 |
| Tsc2_sg1 | 0.770257006 | 0.132053653 |
| 3830406C13Rik_sg2 | 1.139354263 | 0.387359469 |
| Havcr2_sg1 | 1.104986069 | 0.440164842 |
| Pdcd1_sg3 | 1.069296326 | 0.658715105 |
| Lyn_sg2 | 1.033384757 | 0.854463638 |

FIG. 13

```
LOCUS           pSC017             9335 bp    DNA      circular
COMMENT     SIDI CHEN| MATTHEW DONG|
COMMENT     VNTREPLTYPE|Plasmid
FEATURES             Location/Qualifiers
     misc_feature    4792..5598
                     /dnas_title="AmpR"
                     /vntifkey="21"
                     /label=AmpR
     rep_origin      complement(5724..6339)
                     /dnas_title="pUC ori"
                     /vntifkey="33"
                     /label=pUC ori
     rep_origin      3991..4421
                     /dnas_title="f1 ori"
                     /vntifkey="33"
                     /label=f1 ori
     LTR             3202..3437
                     /dnas_title="3' LTR SIN"
                     /vntifkey="19"
                     /label=3' LTR SIN
     polyA_signal    3514..3644
                     /dnas_title="SV40 polyA"
                     /vntifkey="25"
                     /label=SV40 polyA
     source          1..6686
                     /dnas_title="pSC017_pLKO-U6-sgBsmBI-EFS-Thy11CO-spA"
     promoter        2301..2556
                     /note="EFS-NS"
     misc_feature    2301..2327
                     /note="pCM111_R2, readout PCR2 priming site"
     misc_feature    2289..2310
                     /note="pCM111_R1"
     LTR             1..413
                     /dnas_title="RSV/5'LTR"
                     /vntifkey="19"
                     /label="RSV/5'LTR"
     misc_feature    568..932
                     /dnas_title="gag"
                     /vntifkey="21"
                     /label=gag
     misc_feature    464..601
                     /dnas_title="psi"
                     /vntifkey="21"
                     /label=psi
     misc_feature    1078..1319
                     /dnas_title="RRE"
                     /vntifkey="21"
                     /label=RRE
     promoter        1717..1966
                     /dnas_title="hU6 (-250)"
                     /vntifkey="29"
                     /label=hU6 (-250)
     promoter        1896..1961
                     /dnas_title="Human U6 Promoter"
                     /vntifkey="29"
                     /label=Human U6 Promoter
     primer_bind     1717..1736
                     /note="HK0035"
     misc_feature    2113..2230
                     /dnas_title="cPPT"
                     /vntifkey="21"
                     /label=cPPT
     misc_feature    1966..2063
                     /note="chimeric RNA backbone 1 (BsmBI)"
     primer_bind     2029..2048
                     /note="HK0036 (Rv)"
     primer_bind     1971..1991
                     /note="HK0037"
     source          1..2282
                     /dnas_title="pLKO_TRC005"
     misc_feature    2581..3069
                     /note="Thy1.1 mouse"
     misc_feature    3076..3123
                     /note="Short polyA"
     misc_feature    2463..3201
                     /note="gB_pSC017"
     misc_feature    2307..2326
                     /note="EFS-F1"
     misc_feature    3124..3143
                     /note="pSC008_R1"
     misc_feature    1884..1924
                     /note="array_F1"
     misc_feature    2152..2195
                     /note="array_R1"
     misc_feature    1884..1924
                     /note="HK0157"
     misc_feature    2151..2195
                     /note="HK0158"
     misc_feature    1701..1719
                     /note="pHK025-F3"
     misc_feature    1943..1966
                     /note="PCR2 BC priming site F"
     misc_feature    2142..2166
                     /note="PCR2 BC priming site R"
     misc_feature    1717..1736
                     /note="pSC008PCR1_F1"
     misc_feature    2497..2516
                     /note="pSC008PCR1_R2"
     misc_feature    1390..1411
                     /note="pSC008PCR1_F2"
     misc_feature    2304..2325
                     /note="pSC008PCR1_R1"
     misc_feature    2823..2844
                     /note="pSC008PCR1_R3"
     misc_feature    1653..1674
                     /note="pSC008PCR1_F3"
     misc_feature    1932..1966
                     /note="pCM111PCR2primingSite"
     misc_feature    1907..1966
                     /note="array_F"
     misc_feature    2904..2910
                     /note="Codon optimized remove BsmbI"
```

FIG. 14A

```
LOCUS       pSC008            9335 bp    DNA     circular

COMMENT     SIDI CHEN| MATTHEW DONG|
COMMENT     VNTREPLTYPE|Plasmid
FEATURES             Location/Qualifiers
     misc_feature    4802..5608
                     /dnas_title="AmpR"
                     /vntifkey="21"
                     /label=AmpR
     rep_origin      complement(5734..6349)
                     /dnas_title="pUC ori"
                     /vntifkey="33"
                     /label=pUC ori
     rep_origin      4001..4431
                     /dnas_title="f1 ori"
                     /vntifkey="33"
                     /label=f1 ori
     LTR             3212..3447
                     /dnas_title="3' LTR SIN"
                     /vntifkey="19"
                     /label=3' LTR SIN
     polyA_signal    3524..3654
                     /dnas_title="SV40 polyA"
                     /vntifkey="25"
                     /label=SV40 polyA
     source          1..6696
                     /dnas_title="pSC008_pLKO-U6-BsmBI-chRNA(+85)-EFS-Thy11"
     promoter        2301..2556
                     /note="EFS-NS"
     misc_feature    2301..2327
                     /note="pCM111_R2, readout PCR2 priming site"
     misc_feature    2289..2310
                     /note="pCM111_R1"
     LTR             1..413
                     /dnas_title="RSV/5'LTR"
                     /vntifkey="19"
                     /label="RSV/5'LTR"
     misc_feature    568..932
                     /dnas_title="gag"
                     /vntifkey="21"
                     /label=gag
     misc_feature    464..601
                     /dnas_title="psi"
                     /vntifkey="21"
                     /label=psi
     misc_feature    1078..1319
                     /dnas_title="RRE"
                     /vntifkey="21"
                     /label=RRE
     promoter        1717..1876
                     /dnas_title="hU6 (-250)"
                     /vntifkey="29"
                     /label=hU6 (-250)
     promoter        1896..1961
                     /dnas_title="Human U6 Promoter"
                     /vntifkey="29"
                     /label=Human U6 Promoter
     misc_feature    1877..2076
                     /note="PCR from pU6"|
     promoter        1877..1895
                     /dnas_title="hU6 (-250)"
                     /vntifkey="29"
                     /label=hU6 (-250)
     primer_bind     1717..1736
                     /note="HK0035"
     misc_feature    2113..2230
                     /dnas_title="cPPT"
                     /vntifkey="21"
                     /label=cPPT
     misc_feature    1966..2063
                     /note="chimeric RNA backbone 1 (BsmBI)"
     primer_bind     2029..2048
                     /note="HK0036 (Rv)"
     primer_bind     1971..1991
                     /note="HK0037"
     source          1..2282
                     /dnas_title="pLKO_TRC005"
     misc_feature    2581..3069
                     /note="Thy1.1 mouse"
     misc_feature    3076..3123
                     /note="Short polyA"
     misc_feature    2463..3211
                     /note="gB_Thy1.1_shortpolyA"
     misc_feature    2307..2326
                     /note="EFS-F1"
     misc_feature    3134..3153
                     /note="pSC008_R1"
```

FIG. 14B

```
LOCUS           pSC021              9335 bp     DNA      circular

COMMENT      SIDI CHEN| MATTHEW DONG|
COMMENT      VNTREPLTYPE|Plasmid
FEATURES             Location/Qualifiers
     misc_feature    5127..5933
                     /dnas_title="AmpR"
                     /vntifkey="21"
                     /label=AmpR
     rep_origin      complement(6059..6674)
                     /dnas_title="pUC ori"
                     /vntifkey="33"
                     /label=pUC ori
     rep_origin      4326..4756
                     /dnas_title="f1 ori"
                     /vntifkey="33"
                     /label=f1 ori
     LTR             3537..3772
                     /dnas_title="3' LTR SIN"
                     /vntifkey="19"
                     /label=3' LTR SIN
     polyA_signal    3849..3979
                     /dnas_title="SV40 polyA"
                     /vntifkey="25"
                     /label=SV40 polyA
     source          1..7021
                     /dnas_title="pLKO_TRC005"
     misc_feature    2289..2300
                     /note="pCM111_R1"
     LTR             1..413
                     /dnas_title="RSV/5'LTR"
                     /vntifkey="19"
                     /label="RSV/5'LTR"
     misc_feature    568..932
                     /dnas_title="gag"
                     /vntifkey="21"
                     /label=gag
     misc_feature    464..601
                     /dnas_title="psi"
                     /vntifkey="21"
                     /label=psi
     misc_feature    1078..1319
                     /dnas_title="RRE"
                     /vntifkey="21"
                     /label=RRE
     promoter        1717..1966
                     /dnas_title="hU6 (-250)"
                     /vntifkey="29"
                     /label=hU6 (-250)
     promoter        1896..1961
                     /dnas_title="Human U6 Promoter"
                     /vntifkey="29"
                     /label=Human U6 Promoter
     misc_feature    2113..2230
                     /dnas_title="cPPT"
                     /vntifkey="21"
                     /label=cPPT
     misc_feature    1966..2063
                     /note="chimeric RNA backbone 1 (BsmBI)"
     misc_feature    2916..3404
                     /note="Thy1.1 mouse"
```

FIG. 14C

```
LOCUS       pMD002              9335 bp     DNA     circular
COMMENT     SIDI CHEN| MATTHEW DONG|
COMMENT     VNTOAUTHORNAME|UNKNOWN|
COMMENT     VNTREPLTYPE|Plasmid
FEATURES            Location/Qualifiers
     misc_feature    7377..8183
                     /dnas_title="AmpR"
                     /vntifkey="21"
                     /label=AmpR
     rep_origin      complement(8309..8924)
                     /dnas_title="pUC ori"
                     /vntifkey="33"
                     /label=pUC ori
     rep_origin      6576..7006
                     /dnas_title="f1 ori"
                     /vntifkey="33"
                     /label=f1 ori
     LTR             5787..6022
                     /dnas_title="3' LTR SIN"
                     /vntifkey="19"
                     /label=3' LTR SIN
     misc_RNA        5128..5716
                     /dnas_title="WPRE"
                     /vntifkey="53"
                     /label=WPRE
     polyA_signal    6099..6229
                     /dnas_title="SV40 polyA"
                     /vntifkey="25"
                     /label=SV40 polyA
     source          2283..9271
                     /dnas_title="pMD002-pHKO_09-pLKO-U6-BsmBI-chRNA(+85)
                     -EF1a-mCherry-2A-cOVA"
     promoter        2289..3546
                     /dnas_title="EF-1a"
                     /vntifkey="29"
                     /label=EF-1a
     PCR_primer      complement(2429..2446)
                     /dnas_title="TCAATTGCCGACCCCTCC"
                     /pair=""
                     /primer="TCAATTGCCGACCCCTCC"
                     /current=0
     PCR_primer      complement(2436..2453)
                     /note="XRP008 partial binding site"
                     /current=0
     variation       2677..2677
                     /note="C in all sequences"
     PCR_primer      3388..3411
                     /note="EF1A-F seq primer"
                     /current=0
     PCR_primer      2289..2319
                     /dnas_title="TGCAAAGATGGATAAAGTTTTAAACAGAGAG"
                     /pair=""
                     /primer="TGCAAAGATGGATAAAGTTTTAAACAGAGAG"
                     /current=0
     primer_bind     5485..5504
                     /note="HKO034 (Rv)"
     primer_bind     2488..2507
                     /note="HKO038 (Rv)"
     gene            3562..4266
                     /dnas_title="mcherry"
                     /gene="mCherry"
     PCR_primer      3562..3585
                     /dnas_title="GTGAGCAAGGGCGAGGAGGATAAC"
                     /pair=""
                     /primer="GTGAGCAAGGGCGAGGAGGATAAC"
                     /current=0
     PCR_primer      3562..3585
                     /dnas_title="GTGAGCAAGGGCGAGGAGGATAAC"
                     /pair=""
                     /primer="GTGAGCAAGGGCGAGGAGGATAAC"
                     /current=0
     PCR_primer      complement(4245..4266)
                     /dnas_title="CTTGTACAGCTCGTCCATGCCG"
                     /pair=""
                     /primer="CTTGTACAGCTCGTCCATGCCG"
                     /current=0
```

FIG. 14D

```
PCR_primer      3553..3572
                /dnas_title="GCCACCATGGTGAGCAAGGG"
                /pair=""
                /primer="GCCACCATGGTGAGCAAGGG"
                /current=0
LTR             1..413
                /dnas_title="RSV/5'LTR"
                /vntifkey="19"
                /label="RSV/5'LTR"
misc_feature    568..932
                /dnas_title="gag"
                /vntifkey="21"
                /label=gag
misc_feature    464..601
                /dnas_title="psi"
                /vntifkey="21"
                /label=psi
misc_feature    1078..1319
                /dnas_title="RRE"
                /vntifkey="21"
                /label=RRE
promoter        1717..1876
                /dnas_title="hU6 (-250)"
                /vntifkey="29"
                /label=hU6 (-250)
primer_bind     1717..1736
                /note="HKO035"
misc_feature    2113..2230
                /dnas_title="cPPT"
                /vntifkey="21"
                /label=cPPT
promoter        1896..1961
                /dnas_title="Human U6 Promoter"
                /vntifkey="29"
                /label=Human U6 Promoter
misc_feature    1877..2076
                /note="PCR from pU6"
misc_feature    1966..2063
                /note="chimeric RNA backbone 1 (BsmBI)"
promoter        1877..1895
                /dnas_title="hU6 (-250)"
                /vntifkey="29"
                /label=hU6 (-250)
primer_bind     2029..2048
                /note="HKO036 (Rv)"
primer_bind     1971..1991
                /note="HKO037"
source          1..2282
                /dnas_title="pLKO_TRC005"
misc_feature    4267..4329
                /note="2A"
CDS             4330..5112
                /label=ORF frame 1
                /translation="MGSIGAASMEFCFDVFKELINSWVESQTNGIIRNVLQPSSVDSQ
                TAMVLVNAIVFKGLWEKTFKDEDTQAMPFRVTEQESKPVQMMYQIGLFRVASMASEKM
                KILELPFASGTMSMLVLLPDEVSGLEQLESIINFEKLTEWTSSNVMEERKIKVYLPRM
                KMEEKYNLTSVLMAMGITDVFSSSANLSGISSAESLKISQAVHAAHAEINEAGREVVG
                SAEAGVDAASVSEEFRADHPFLFCIKHIATNAVLFFGRCVSP*"
misc_feature    4453..4453
                /note=""
misc_feature    4330..5109
                /note="cOVA"
misc_feature    4267..4285
                /note="Fw anneal"
misc_feature    4232..4285
                /note="pMD002-F1"
misc_feature    5084..5112
                /note="Rv anneal"
misc_feature    5084..5152
                /note="pMD002/3-R1"
PCR_primer      4139..4154
                /dnas_title="TGCCCGGCGCCTACAA"
                /pair="mCherry-int-F1"
                /primer="TGCCCGGCGCCTACAA"
                /current=0
PCR_primer      complement(5153..5190)
                /dnas_title="AGGAGCAACATAGTTAAGAATACCAGTCAATCTTTCAC"
                /pair="pMD2/3-con-R1"
                /primer="AGGAGCAACATAGTTAAGAATACCAGTCAATCTTTCAC"
                /current=1
```

FIG. 14E

DHX37

Domains: DEXDc — P-loop_NTPase — HrpA — HELICc — HA2

Positions: 1 ... 1157

| Species | DEXDc region | HELICc region |
|---|---|---|
| Macropus | EIQEARLRLPILSEEQVIMEAVAEHPTVIICGETGSGKTTQVPQFLNEAGYSSEHGLIGI | VTRPPFEGRLCVAINVAERSLIIPGKVVDCGKVKKFYIDKVTGVSSFRVTWVSQAS |
| Sus | EMQERLKLPILAEEQVIMEAVAEHPTVIVCGETGSGKTTQVPQFLNEAGYSREGGWGP | LWRRPPG--ICCAGCSGGALPGLSLAGLQESV-CTFPGSRTRGVWKEISIAKPGAS |
| Tursiops | EMQAERLRLPILSEEQVIMEAVAEHPTVIVCGETGSGKTTQVPQFLNEAGTAGRDSLGI | VFQPPPEGTRLCVAINVAERSLIIPGIKVVDCGKVKKFYIDKVTGVSSFRITWVSQAS |
| Ornithorhynchus | EIQEARLRLPILSEEQVIMEAVAEHPTVIXCGETGSGKTTQVPQFINEAGTAGRDSLGI | VFKPPPEGRLCVAINVAEHSLHTPNIKVVDCGKVKKFFIDKVTGVSSFKVSWVSQAS |
| Monodelphis | EVQEARLRLPILSEEQVIMEAVSENPTVIXCGETGSGKTTQVPQFINEAGYSSD-GLIGI | VFRPPPEGTRLCVAINVAETSLIIPGIKVVDCGKVKKFFIDKVTGVSSFRVTWVSQAS |
| Microcebus | EMQXXXXXXXXXXXXXXXXXXXXXXXXXXXXXXXXXXXXXXXXXXXXXXXXXXXXXXX | VFRP-GSEGARLCVAINVAETSLIIPGIKVVDCGKVKKFFIDKVTGVSSFRITWVSQAS |
| Ochotona | EMQAERLRLPILSEEQVIMEAVAEHPTVIVCGETGSGKTTQVPQFLNEAGYSSNNSLIGV | VFRPPPEGTRLCVAINVAETSLIIPGIKVVDCGKVKKFYIDKVTGVSSFRVTWVSQAS |
| Cavia | EMQAERQLPILSEEQVIMEAVAEHPWG--SCAETGSEKTTQVPQFLNEAGYGGENSGIGV | VFRPPPEGTRLCVAINVAETSLIIPGIKVVDCGKVKKFYIDNSHTIQLSHN------- |
| Dasypus | EMQEERLKLPILSEEQVIMEAVAEHPTVIVCGETGSGKTTQVPQFLNEAGYSSDQSLIGV | VFRPPEGARLCVAINVAETSLIIPGIKVVDCGKVKKFYIDKVTGVSSFRVTWVSQAS |
| Dipodomys | EMQEERLKLPILAEEQVIMEAVAEHPTVIVCGETGSGKTTQVPQFLNEAGYSSEDSLIGV | VFQPPPEGTRLCVAINVAETSLIIPGIKVVDCGKVKKFYIDKVTGVSSFRVTWVSQAS |
| Rattus | EMQEERLKLPILSEEQVIMEAVAEHPTVIVCGETGSGKTTQVPQFLNEAGYSSEDSIIGV | VFQPPPEGTRLCVAINVAETSLIIPGIKVVDCGKVKKFYIDKVTGVSSFRVTWVSQAS |
| Mus | EMQEERLKLPILSEEQAIMEAVAEHPTVIVCGETGSGKTTQVPQFLNEAGYSSEDSIIGV | VFQPPPEGTRLCVAINVAETSLIIPGIKVVDCGKVKKFYIDKVTGVSSFRVTWVSQAS |
| Procavia | EMQEERLKLPILAEEQVIMEAVAEHPTVIVCGETGSGKTTQVPQFLNEAGYSSEDSIIGV | VFAPPPEGTRLCVAINVAETSLIIPGIKVVDCGKVKKFYIDKVTGVSSFRVTWVSQAS |
| Bos | EQMEERLKLPILAEEQIMEAVAEHPTVIVCGETGSGKTTQVPQFLNEAGYSSEDSIIGV | VFQPPPEGTRLCVAINVAETSLIIPGIKVVDCGKVKKFYIDKVTGVSSFRVTWVSQAS |
| Pteropus | EMQEERLRLPILSEEQVIMEAVAEHPTVIVCGETGSGKTTQVPQFLNEAGYSSEDSIIGV | VFQPPPEGTRLCVAINVAETSLIIPGIKVVDCGKVKKFYIDKVTGVSSFRVTWVSQAS |
| Felis | EMQEERLRLPILAEEQVIMEAVAEHPTVIVCGETGSGKTTQVPQFLNEAGYSSEDSIIGV | VFQPPPEGTRLCVAINVAETSLIIPGIKVVDCGKVKKFYIDKVTGVSSFRVTWVSQAS |
| Mustela | EMQEERLKLPILAEEQAIMEAVAEHPTVIVCGETGSGKTTQVPQFLNEAGYSSEDSNIGV | VEKPPPEGTRLCVAINVAETSLIIPGIKVVDCGKVKKFYIDKVTGVSSFRVTWVSQAS |
| Canis | EMQEERLKLPILAEEQVIMEAVAEHPTVIVCGETGSGKTTQVPQFLNEAGYSSEDSNIGI | VFKPPPEGTRLCVAINVAETSLIIPGIKVVDCGKVKKFYIDKVTGVSSFRVTWVSQAS |
| Ailuropoda | EMQEERLKLPILAEEQVIMEAVAEHPTVIVCGETGSGKTTQVPQFLNEAGYSSDNSLIGI | VFKPPPEGTRLCVAINVAETSLIIPGIKVVDCGKVKKFYIDKVTGVSSFRVTWVSQAS |
| Equus | EMQEERLKLPILAEEQVIMEAVAEHPTVIVCGETGSGKTTQVPQFLNEAGYSSDNSLIGV | VFKPPPEGTRLCVAINVAETSLIIPGIKVVDCGKVKKFYIDKVTGVSSFRVTWVSQAS |
| Ictidomys | EMQEERLKLPILAEEQVIMEAVADNPTVIVCGETGSGKTTQVPQFLNEAGYSSEDDSLIGV | VFKPPPEGTRLCVAINVAETSLIIPGIKVVDCGKVKKFYIDKVTGVSSFRVTWVSQAS |
| Oryctolagus | EMQEERLKLPILAEEQVIMEAVAEHPTVIICGETGSGKTTQVPQFLNEAGYSSDDGIGV | VTPPPEGTRLCVAINVAETSLIIPGIKVVDCGKVKKFYIDKVTGVSSFRVTWIQAS |
| Loxodonta | EMQEERLKLPILAEEQVIMEAVAENPTIIVCGETGSGKTTQVPQFLNEAGYSSEDSIIGV | VEKPPPEGTRLCVAINVAETSLIIPGIKVVDCGKVKKFYIDKVTGVSSFRVTWVSQAS |
| Otolemur | EIQEERLKLPILSEEQVIMEAVAEHPTVIVCGETGSGKTTQVPQFLNEAGYSSDNSIGH | VEKPPPEGTRLCVAINVAETSLIIPGIKVVDCGKVKKFYIDKVTGVSSFRVTWVSQAS |
| Nomascus | EMQEERLKLPILSEEQVIMEAVAEHPTVIVCGETGSGKTTQVPQFLNEAGYSSEDSIIGV | VEKPPPEGTRLCVAINVAETSLIIPGIKVVDCGKVKKFYIDKVTGVSSFRVTWVSQAS |
| Callithrix | EMQEERLKLPILSEEQVIMEAVAEHPTVIVCGETGSGKTTQVPQFLNEAGYSSEGSIGV | VEKPPPEGTRLCVAINVAETSLIIPGIKVVDCGKVKKFYIDKVTGVSSFRVTWVSQAS |
| Macaca | EMQEERLKLPILSEEQVIMEATVEERPIVIVCGETGSGKTTQVPQFLNEAGYSSESGSIGV | VEKPPPEGTRLCVAINVAETSLIIPGIKVVDCGKVKKFYIDKVTGVSSFRVTWVSQAS |
| Papio | EMQEERLKLPILSEEQVIMEAVAEHPTVIVCGETGSGKTTQVPQFLNEAGYSSEGSIGV | VEKPPPEGTRLCVAINVAETSLIIPGIKVVDCGKVKKFYIDKVTGVSSFRVTWVSQAS |
| Chlorocebus | EMQEERLKLPILSEEQVIMEAVAEHPTVIVCGETGSGKTTQVPQFLNEAGYSSEGSIGV | VEKPPPEGTRLCVAINVAETSLIIPGIKVVDCGKVKKRDIDKVTGVSSFCVTWVSQAS |
| Pongo | EMQEERLKLPILSEEQVIMEAVAEHPTVIVCGETGSGKTTQVPQFLNEAGYS------- | VEKPPPSGTRLCVAINVAETSLIIPGIKVVDCGKVKKFYIDKVTGVSSFRVTWVSQAS |
| Gorilla | EMQEERLKLPILSEEQVIMEAVAEHPTVIVCGETGSGKTTQVPQFLNEAGFSSEDSIIGV | VEKPPPEGTRLCVAINVAETSLIIPGIKVVDCGKVKKFYIDKVTGVSSFRVTWVSQAS |
| Homo | EMQEERLKLPILSEEQVIMEAVAEHPTVIVCGETGSGKTTQVPQFLNEAGFSSEDSIIGV | VEKPPPEGTRLCVAINVAETSLIIPGIKVVDCGKVKKFYIDKVTGVSSFRVTWVSQAS |

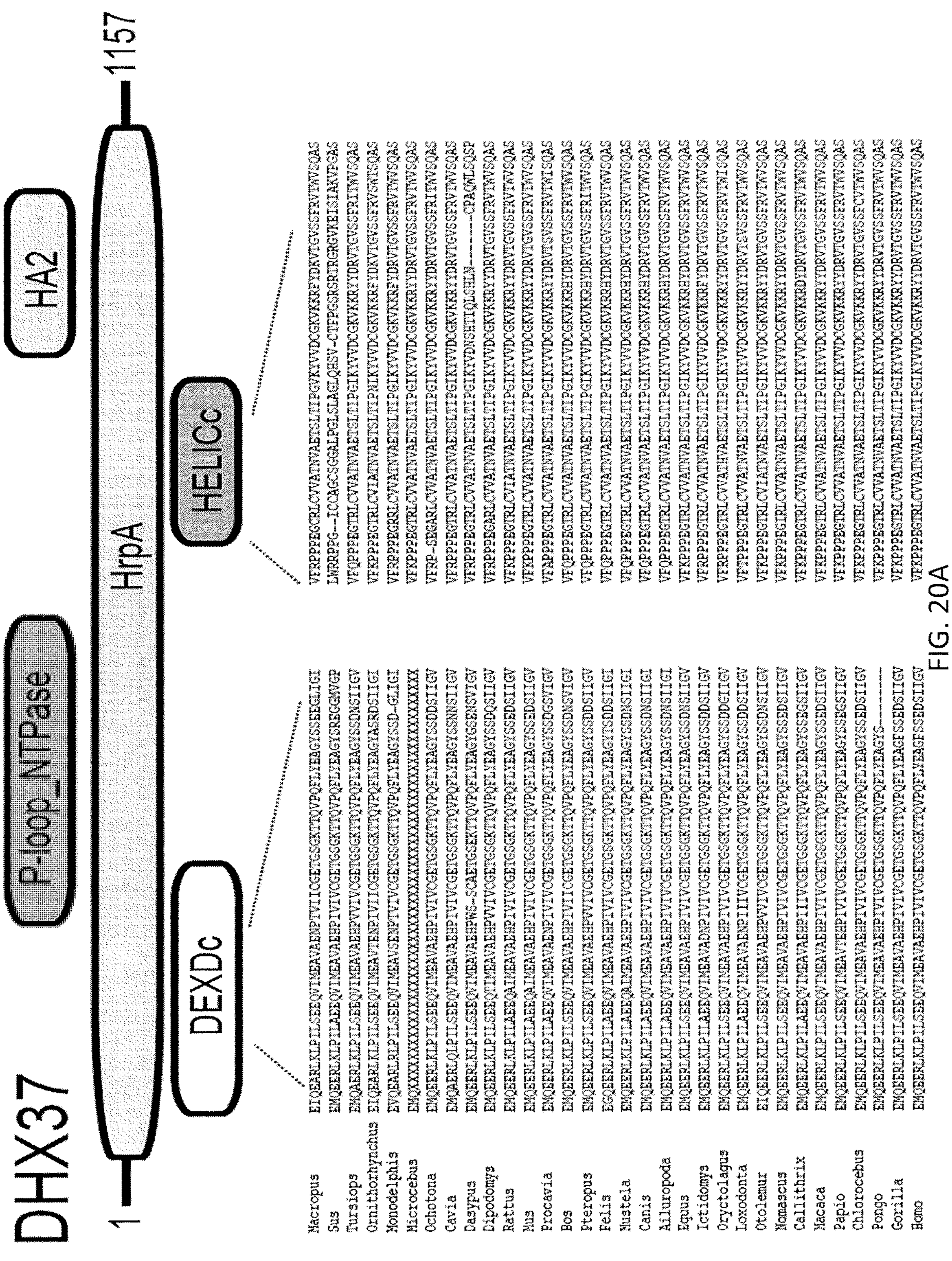

FIG. 20A

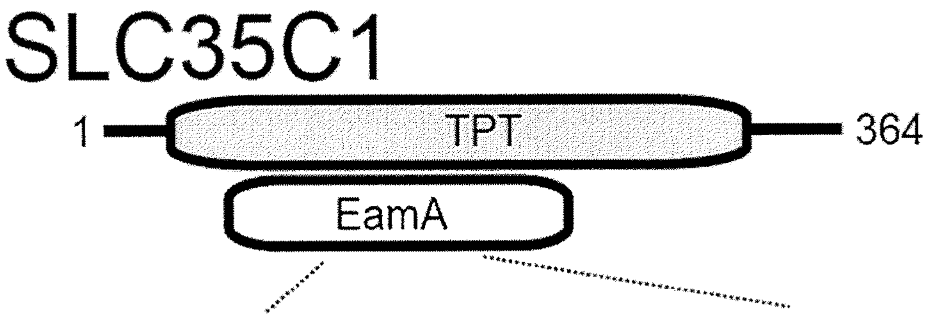

| | |
|---|---|
| Erinaceus | TAKACAQTVLAVLHYEEAKSFLWWASNLMVLGGSFAYTWVRGWEMKRVQEEPGPREDQKS |
| Monodelphis | TAKACAQTVLAVLYFNETKSFLWWTSNLMVLGGSSAYTWVKGLEMKKAQGEPSPKEGEKD |
| Sarcophilus | TAKACAQTVLAVLYFEETKSFLWWTSNLMVLGGSSAYTWVKGLEMKKAQEELAPREGEKG |
| Tursiops | TAKACAQTVLAVLYYEETKSFLWWMSNMMVLGGSSAYTWVRGWEMKKIQEEPRPKEDEKS |
| Echinops | TAKACAQTVLAVXXXXXXXXXXXXXXXMMVLGGSWAYTCVRGWEMKKVQEEPSPKEDEKS |
| Ornithorhynchus | TAKACAQTVLAVLGYEETKSFLWWTSNMMVLGGSSAYTWVKGLEMKKAQEEPGPKAGEKG |
| Rattus | TAKACAQTVLAVLYYEEIKSFLWWTSNLMVLGGSSAYTWVRGWEMQKTQEDPSSKEGEKS |
| Mus | TAKACAQTVLAVLYYEEIKSFLWWTSNLMVLGGSSAYTWVRGWEMQKTQEDPSSKDGEKS |
| Dasypus | TAKACAQTVLAVLYFEETKSLLWWTSNMMVLGGSSTYTWVRGWEMKKVQEEPSPREDEKN |
| Ovis | TAKACAQTVLAVLYYEEAKSFLWWTSNMMVLGGSSAYTWVRGREMKKTQEEPHPRENEKS |
| Bos | TAKACAQTVLAVLYYEEAKSFLWWTSNMMVLGGSSAYTWVRGREMKKTQEEPHPRENEKS |
| Otolemur | TAKACAQTVLAVLYYEETKSFLWWTSNMMVLGGSSAYTWVRGWEMKKTQEEPSPKEDEKS |
| Microcebus | TAKACAQTVLAVLYYEETKSFLWWTSNMMVLGGSSAYTWVRGWEMKKTQEEPSPKEGEKS |
| Loxodonta | TAKACAQTVLAVLYYEETKSFLWWTSNMMVLGGSSAYTWVRGWEMKKVQEEPSPKEGEKS |
| Procavia | TAKACAQTVLAVLYYEETKSFLWWTSNMMVLGGSSAYTWVRGWEMKKLQEEPSPRESEKI |
| Dipodomys | TAKACAQTVLAVLYYEETKSFLWWTSNLMVLGGSSAYTWVRGWEMKKTPEDPSPKEGEKS |
| Ictidomys | TAKACAQTVLAVLYFEETKSFLWWTSNAMVLGGSSAYTWVRGWEMK-SQEDPGPREGEKS |
| Ochotona | TAKACAQTVLAVLYYEETKSFLWWTSNLMVLGGSSAYTWVRGWEMQKVQHDPSPKENEKS |
| Oryctolagus | TAKACAQTVLAVLYYEEAKSFLWWTSNLMVLGGSSAYTWVRGWEMKKEQEDPSPKEGDKS |
| Cavia | TAKACFQTVLAVLYYEETKSFLWWTSNLMVLGGSSAYTWVRGWEMKKVQEDPSPREDEKS |
| Pteropus | TAKACAQTVLAVLYYEETKSFLWWTSNMMVLGGSSAYTWVRGWEMKKIQEDPSPKEDEKS |
| Canis | TAKACAQTVLAVLYYEETKSFLWWTSNMMVLGGSSAYTWVRGWEMKKIQEDPSPKEDEKS |
| Felis | TTKACAQTVLAVLYYEETKSFLWWTSNMMVLGGSSAYTWVRGWEMKKIQEEPSPKEDEKS |
| Mustela | TAKACAQTVLAVLYYEETKSFLWWTSNMMVLGGSSAYTWVRGWEMKKIQEEPSPKEEEKS |
| Ailuropoda | TAKACAQTVLAVLYYEETKSFLWWTSNMMVLGGSSAYTWVRGWEMKKIQEEPSPKEEEKS |
| Myotis | TAKACAQTVLAVLYYEETKSFLWWTSNMMVLGGSSAYTWVRGWEMKKVQEEPSPKDNEKS |
| Equus | TAKACAQTVLAVLYYEDTKSFLWWTSNMMVLGGSSAYTWVRGWEMKKVQEEPSPKEEEKS |
| Tarsius | TAKACAQTVLAVLYYEETKSFFWWMSNMMVLGGSSAYTWVRGWEMKKTQEEPSPKEDEKS |
| Chlorocebus | TAKACAQTVLAVLYYEEAKSFLWWTSNMMVLGGSSAYTWVRGWEMKKIPEEPSPKEGEKS |
| Macaca | TAKACAQTVLAVLYYEEAKSFLWWTSNMMVLGGSSAYTWVRGWEMKKIPEEPSPKEGEKS |
| Papio | TAKACAQTVLAVLYYEEAKSFLWWTSNMMVLGGSSAYTWVRGWEMKKIPEEPSPKEGEKS |
| Callithrix | TAKACAQTVLAVLYYEETKSFLWWTSNMMVLGGSSAYTWVRGREMKKTPEELSPKEGEKS |
| Gorilla | TAKACAQTVLAVLYYEETKSFLWWTSNMMVLGGSSAYTWVRGWEMKKTPEEPSPKDSEKS |
| Pan | TAKACAQTVLAVLYYEETKSFLWWTSNMMVLGGSSAYTWVRGWEMKKSPEEPSPKDSEKS |
| Homo | TAKACAQTVLAVLYYEETKSFLWWTSNMMVLGGSSAYTWVRGWEMKKTPEEPSPKDSEKS |
| Pongo | TAKACAQTVLAVLYYEETKSFLWWTSNMMVLGGSSAYTWVRGWEMKKTPEEPSPKEGEKS |
| Nomascus | TAKACAQTVLAVLYYEETKSFLWWTSNMMVLGGSSAYTWVRGWEMKKTQEEPSPKEGEKS |

FIG. 20C

FIG. 27A
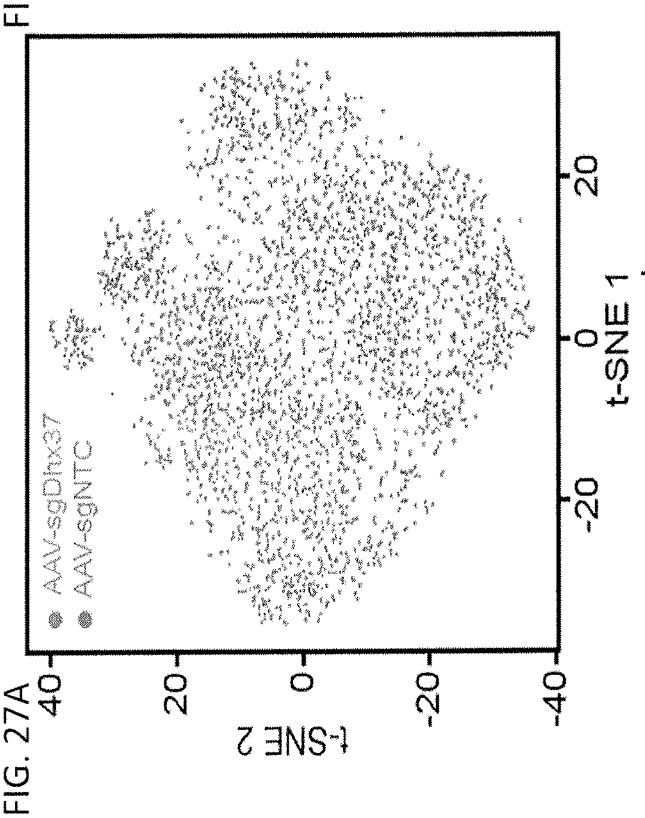
FIG. 27B
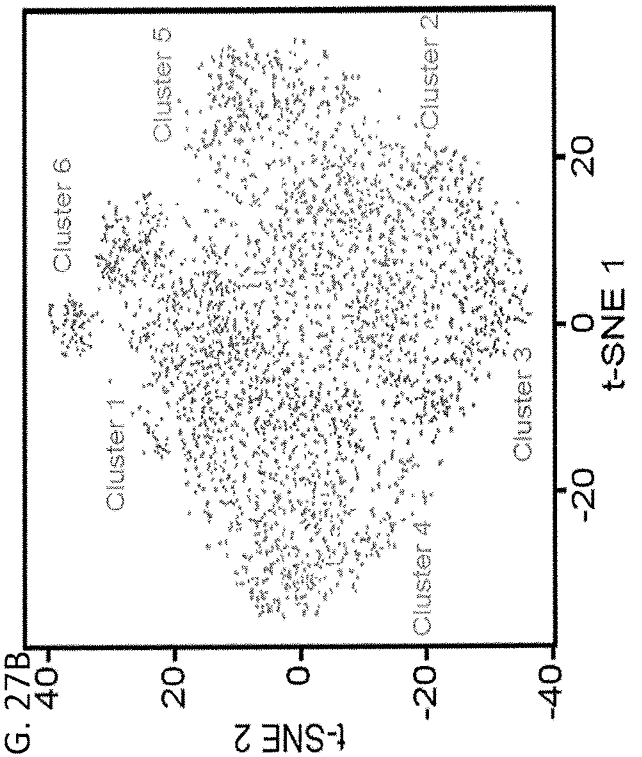
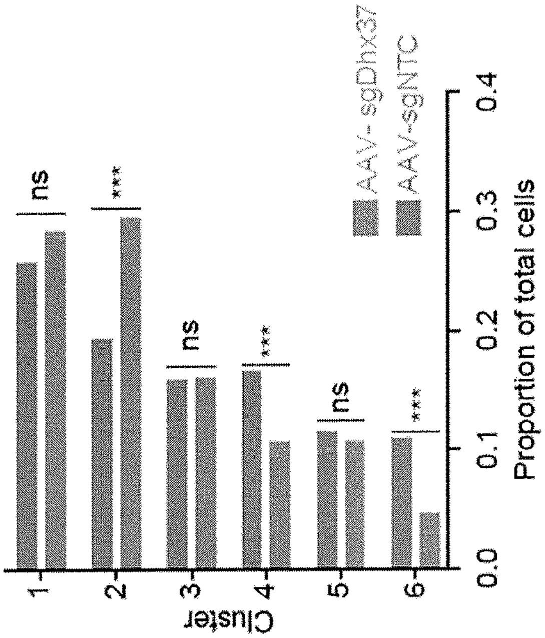
FIG. 27C

| Term | P Value |
|---|---|
| GO:0006954~inflammatory response | 3.53E-04 |
| GO:0006955~immune response | 4.52E-04 |
| GO:0043066~negative regulation of apoptotic process | 1.02E-03 |
| GO:0010951~negative regulation of endopeptidase activity | 2.20E-03 |
| GO:0048305~immunoglobulin secretion | 2.80E-03 |
| GO:0071333~cellular response to glucose stimulus | 3.11E-03 |
| GO:0031295~T cell costimulation | 4.90E-03 |

PLATFORM FOR T LYMPHOCYTE GENOME ENGINEERING AND IN VIVO HIGH-THROUGHPUT SCREENING THEREOF

CROSS-REFERENCE TO RELATED APPLICATION

The present application is a 35 U.S.C. § 371 national phase application from, and claims priority to, International Application No. PCT/US2018/027967, filed Apr. 17, 2018, and published under PCT Article 21(2) in English, which is entitled to priority under 35 U.S.C. § 119(e) to U.S. Provisional Patent Application No. 62/602,290 filed Apr. 18, 2017, each of which is incorporated herein by reference in its entirety.

STATEMENT REGARDING FEDERALLY SPONSORED RESEARCH OR DEVELOPMENT

This invention was made with government support under CA209992, CA121974, CA196530, and GM007205 awarded by the National Institutes of Health. The government has certain rights in the invention.

REFERENCE TO AN ELECTRONIC SEQUENCE LISTING

The Sequence Listing submitted herewith as an ASCII txt file named "047162-7121US1," created on Apr. 22, 2023 and having a size of 30,645 bytes, is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Mar. 20, 2020, is named 047162-7121US1_SequenceListing_ST25.txt and is 29,900 kilobytes in size.

BACKGROUND OF THE INVENTION $CD8^+$ T cells play a central role in maintaining the cellular integrity of the body by mounting cell-mediated adaptive immune responses against intracellular pathogens and tumors. Selective activation of pathogen-specific $CD8^+$ T cells is mediated by the recognition of cognate antigen on surface major histocompatibility complex (MHC) class I (MHC-I), which results in T cell proliferation, cytokine secretion, and the selective killing of target cells. Defects in this cell population can lead to recurrent infections or cancer, while dysregulated activation of $CD8^+$ T cells can cause autoimmunity and severe immunopathology.

$CD8^+$ T cells have become the focus of many new cancer therapeutics due to their specificity for intracellular antigens and their role in cell-mediated immune responses. The most potent drugs recently developed are immune checkpoint inhibitors. This new class of drugs enhances the anti-tumor response of $CD8^+$ T cells by neutralizing the activity of CTLA-4 or PD-1. Blocking the activity of CTLA-4 permits the activation of naive $CD8^+$ T cells in the absence of sufficient antigen. Inhibiting PD-1 activity reinvigorates exhausted $CD8^+$ T cells to proliferate and kill malignant cells. These drugs have been shown to be effective in treating multiple cancer types including melanoma and lung cancer. Ongoing studies are being conducted looking at the efficacy of these drugs used either as monotherapy or in combinations. Further studies have identified 4-1BB, CD27, CD28, ICOS, LAG3, OX-40, TIM3, and VISTA for potential checkpoint modulation. Newer therapeutics have adapted $CD8^+$ T cell machinery to activate under the control of a transgenically expressed chimeric antigen receptor (CAR-T). This method has proven to be effective at treating hematopoietic malignancies. Although checkpoint blockade and CAR-T immunotherapies have been shown to be effective when conventional therapies have failed, these modes of therapy are still in early stage of development, as a large fraction of patients do not respond or have undesired side effects. More systematic approaches shall be used to identify new regulators of T cell functions to better enhance the body's anti-tumor response.

Studies using gene-set specific RNAi/shRNA libraries have been used to identify novel T cell genes that enhance $CD8^+$ T cell function and cytokine production. These molecular tools operate by suppressing the translation of targeted mRNA through complementary binding, but the effects of RNAi are limited by the expression levels of the targeted mRNA as well as the introduced small interfering RNA.

The development and application of CRISPR technologies have dramatically enhanced the ability to perform genome editing. High-throughput genetic screens have been developed and utilized for discovery of novel genes in multiple applications. Application of CRISPR targeting in T cell is a first step to manipulate its genome, which, together with the screening technology, leads to the hypothesis that high-throughput genetic screening will open the door for unbiased discovery of key factors in T cell biology in a massively parallel manner. However large-scale genome editing of T cells have not been reported, possibly due to multiple technological obstacles, the complexity of lymphocyte repertoires, the tissue architecture of lymphoid or non-lymphoid organs, or the tumor microenvironment.

There is a need in the art for compositions and methods that can be used for large-scale genome editing in T cells. The present invention satisfies this need.

SUMMARY OF THE INVENTION

As described herein, the present invention relates to compositions and methods for T cell genome editing and screening in vitro and in vivo.

One aspect of the invention includes a vector comprising a 5' long terminal repeat (LTR) sequence, a U6 promoter sequence, a BsmB1 restriction site, an EFS sequence, an sgRNA expression cassette, a Thy1.1 cassette, a 3' LTR sequence and an ampicillin resistance gene sequence (AmpR).

Another aspect of the invention includes an sgRNA library comprising a plurality of vectors, wherein each vector comprises an expression cassette for an sgRNA comprising a nucleotide sequence selected from the group consisting of SEQ ID NOs: 1-129,209.

Yet another aspect of the invention includes an sgRNA library comprising a plurality of vectors, wherein each vector comprises an expression cassette for an sgRNA comprising a nucleotide sequence selected from the group consisting of SEQ ID NOs: 129,222-140,680.

Another aspect of the invention includes a method of performing genome editing and screening of a T cell in vitro. The method comprises contacting the T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 1-129,209. The T cell undergoes genome editing and the T cell is screened in vitro.

Still another aspect of the invention includes a method of performing genome editing and screening of a T cell in vitro. The method comprises contacting the T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 129,222-140,680. The T cell undergoes genome editing and the T cell is screened in vitro.

Yet another aspect of the invention includes a method of performing genome editing and screening of a T cell in vivo. The method comprises contacting an isolated T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 1-129,209. The T cell undergoes genome editing to generate a modified T cell. The modified T cell is administered to an animal and the T cell is screened in vivo.

Another aspect of the invention includes a method of performing genome editing and screening of a T cell in vivo. The method comprises contacting an isolated T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 129,222-140,680. The T cell undergoes genome editing to generate a modified T cell. The modified T cell is administered to an animal and the T cell is screened in vivo.

In some embodiments, Cas9 is encoded in a vector. In some embodiments, Cas9 is a protein.

Still another aspect of the invention includes a kit comprising an sgRNA library comprising a plurality of vectors, wherein each vector comprises an expression cassette for an sgRNA comprising a nucleotide sequence selected from the group consisting of SEQ ID NOs: 1-129,209, and instructional material for use thereof.

Yet another aspect of the invention includes a kit comprising an sgRNA library comprising a plurality of vectors, wherein each vector comprises an expression cassette for an sgRNA comprising a nucleotide sequence selected from the group consisting of SEQ ID NOs: 129,222-140,680, and instructional material for use thereof.

Another aspect of the invention includes a vector comprising a 5' long terminal repeat (LTR) sequence, a U6 promoter sequence, a BsmB1 restriction site, an EFS sequence, an sgRNA expression cassette, an mCherry sequence, a 2A peptide, a cOVA sequence, a 3' LTR sequence and an ampicillin resistance gene sequence (AmpR).

Still another aspect of the invention includes a vector comprising a 5' inverted terminal repeat (ITR) sequence, a U6 promoter sequence, a BbsI restriction site, an sgRNA expression cassette, an EFS sequence, a SB100x cassette, a 3' ITR sequence and an ampicillin resistance gene sequence (AmpR).

Yet another aspect of the invention includes a vector comprising a 5' inverted terminal repeat (ITR) sequence, a U6 promoter sequence, a BbsI restriction site, an sgRNA expression cassette, an EFS sequence, a SB100x cassette, a Thy1.1 cassette, a 3' ITR sequence and an ampicillin resistance gene sequence (AmpR).

Another aspect of the invention includes a vector comprising a 5' inverted terminal repeat (ITR) sequence, a U6 promoter sequence, a BbsI restriction site, an sgRNA expression cassette, a 3' ITR sequence and an ampicillin resistance gene sequence (AmpR).

Still another aspect of the invention includes a vector comprising a 5' inverted terminal repeat (ITR) sequence, a U6 promoter sequence, a BbsI restriction site, an sgRNA expression cassette, an EFS sequence, a Thy1.1 cassette, a 3' ITR sequence and an ampicillin resistance gene sequence (AmpR).

Yet another aspect of the invention includes a vector comprising a 5' inverted terminal repeat (ITR) sequence, a U6 promoter sequence, a BbsI restriction site, an sgRNA expression cassette, an EFS sequence, a SB100x cassette, a GFP-NLS fusion cassette, a 3' ITR sequence and an ampicillin resistance gene sequence (AmpR).

In various embodiments of the above aspects or any other aspect of the invention delineated herein, the vector comprises the nucleic acid sequence selected from the group consisting of SEQ ID NO: 129,213, SEQ ID NO: 129,214, and SEQ ID NO: 129,215.

In one embodiment, the sgRNA expression cassette expresses an sgRNA comprising a nucleotide sequence selected from the group consisting of SEQ ID NOs: 1-129,209. In another embodiment, the sgRNA expression cassette expresses an sgRNA comprising a nucleotide sequence selected from the group consisting of SEQ ID NOs: 129,222-140,680. In yet another embodiment, the sgRNA expression cassette expresses an sgRNA consisting of a nucleotide sequence selected from the group consisting of SEQ ID NOs: 1-129,209. In still another embodiment, the sgRNA expression cassette expresses an sgRNA consisting of a nucleotide sequence selected from the group consisting of SEQ ID NOs: 129,222-140,680.

In one embodiment, each vector comprises an expression cassette for an sgRNA consisting of a nucleotide sequence selected from the group consisting of SEQ ID NOs: 1-129,209. In another embodiment, each vector comprises an expression cassette for an sgRNA consisting of a nucleotide sequence selected from the group consisting of SEQ ID NOs: 129,222-140,680.

In one embodiment, the plurality of vectors comprise a 5' long terminal repeat (LTR) sequence, a U6 promoter sequence, a BsmB1 restriction site, an EFS sequence, an sgRNA expression cassette, a Thy1.1 cassette, a 3' LTR sequence and an ampicillin resistance gene sequence (AmpR).

In one embodiment, the T cell is selected from the group consisting of: a CD8+ cell, a CD4+ cell, or a T regulatory (Treg) cell, a Th1 cell, a Th2 cell, a Th17 cell, a follicular helper T cell (Tfh), a T memory cell, a T effector cell, a T effector memory cell, an engineered T cell, and a CART cell.

In one embodiment, the method further comprises isolating and/or enriching a modified T cell.

In one embodiment, the animal is a human. In one embodiment, the condition is cancer.

In one embodiment, the screening provides information about a gene involved in a condition afflicting the animal. In another embodiment, screening comprises at least one method selected from the group consisting of nucleotide sequencing, sgRNA PCR, and flow cytometry.

In one embodiment, the kit further comprises Cas9. In some embodiments, Cas9 is encoded in a vector. In some embodiments, Cas9 is a protein.

In one embodiment, the vector comprises the nucleic acid sequence of SEQ ID NO: 129,216. In another embodiment, the vector comprises the nucleic acid sequence of SEQ ID NO: 129,217. In yet another embodiment, the vector comprises the nucleic acid sequence of SEQ ID NO: 129,218. In still another embodiment, the vector comprises the nucleic acid sequence of SEQ ID NO: 129,219. In one embodiment, the vector comprises the nucleic acid sequence of SEQ ID NO: 129,220. In another embodiment, the vector comprises the nucleic acid sequence of SEQ ID NO: 129,221.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A is a schematic of the design of a T cell CRISPR knockout vector, which contains an sgRNA expression cassette and a Thy1.1 expression cassette. FIG. 1B shows the schematics of an experiment described herein involving: library cloning, virus production, naive $CD8^+$ T cell isolation and infection, adoptive transfer, and CRISPR-targeted $CD8^+$ $T_{eff}$ cell survival analysis in organs by high-throughput sgRNA sequencing. Organs collected include the liver, pancreas, lung, muscle and brain as representative non-lymphoid organs, and the spleen and several types of lymph nodes (LNs) as lymphoid organs. The LNs collected include three groups: LN1—skin draining lymph nodes (sLNs) that are comprised of inguinal, axillary, and brachial lymph nodes; LN2—cervical lymph nodes (cLNs) that entail the 6 superficial lymph nodes; and LN3—abdominal lymph nodes (aLNs) include the mesenteric and the pancreatic lymph nodes. FIG. 1C is a set of FACS plots showing naive Cas9 $CD8^+$ T cell infectivity with lentivirus encoding the genome-scale CRISPR library (MKO). Thy1.1 surface staining shows a population of transduced T cells with a significantly elevated Thy1.1 expression compared to untransduced. FIG. 1D is a dot plot of the number of detected sgRNAs for all organ samples, grouped by organ type. Number of samples for each type are: LN (n=20 total, 3 per mouse, 7 mice total. LN3 is not available for m4), spleen, brain, liver, lung, muscle and pancreas (n=7 each, one per mouse, 7 mice total). Data are shown as mean±s.e.m. FIGS. 1E-1F are pie charts of sgRNA compositions in representative organs. SgRNAs that comprised ≥2% of total reads for each sample are shown, with the remaining reads classified as “Other.” For clarity, only the gene names associated with each sgRNA are shown. Monoclonal (one major clones with >=90% of total reads), oligoclonal (3 to 10 major clones each with >=2% of total reads) and polyclonal (more than 10 clones with 2% or more reads) compositions of T cell variants exist in various organs such as LN, spleen, liver, pancreas, lung, brain and muscle. FIG. 1G is a box-dot plot of overall sgRNA library representation in all samples, including plasmid library (blue, n=1), cellular libraries of pre-injection library-infected naive $CD8^+$ T cells (green, n=3), and various organs containing $CD8^+$ $T_{eff}$ cells from multiple mice 7 days post-injection (orange, n=7 mice, 62 total samples). SgRNA representation is depicted in terms of $\log_2$ reads per million (rpm). Analyzed tissues include the lymph node (LN), spleen, brain, liver, lung, muscle, and pancreas. FIG. 1H shows correlation analysis of sgRNA library representation in all samples from the genome-scale screen for trafficking and survival in $CD8^+$ T cells with diverse TCR. Heatmap of pairwise Pearson correlations of sgRNA library representation across all samples in the first WT screen using Cas9 $CD8^+$ T cells that have a diverse TCR repertoire. Samples included plasmid library (n=1), cellular libraries of pre-injection library-infected naive $CD8^+$ T cells (n=3), and various organs containing CD8+ $T_{eff}$ cells from multiple mice 7 days post-injection (n=7 mice, 62 total samples). Correlations were calculated based on $\log_2$ rpm values. Cell and plasmid samples were highly correlated with each other, while organ samples were mostly correlated with other organ samples. FIG. 1I is a waterfall plot of the top sgRNAs across all organs ranked by number of organs being enriched in (FDR<0.5%). Inset shows all sgRNAs significantly enriched in ≥20% of organ samples. FIG. 1J is a barplot of the number of genes with 0, 1, 2 or 3 independent sgRNAs that were significantly enriched in at least one organ sample (FDR<0.5%). A total of 115 genes were found to have at least 2 independent sgRNAs enriched. Cd247, Bpifb3, and Tsc2 were found to have 3 independent enriched sgRNAs. FIG. 1K is a Venn diagram of the three enrichment criteria to identify the top gene hits (≥2% read abundance in one sample (n=227), significant in ≥20% of samples (considering all associated sgRNAs) (n=118), and ≥2 independent enriched sgRNAs (n=115)). A total of 11 genes satisfied all three criteria (Apc, Cd247, Csnk1a1, Fam103a1, Fam134b, Nf1, Pdcd1, Phf21a, Prkar1a, Rab11b, and Tsc2).

FIG. 2A is a dot plot of the number of significantly enriched sgRNAs for all organ samples, grouped by organ type. Statistical significance of sgRNA enrichment was determined by comparison to NTCs, with a threshold of FDR<0.2%. The number of significantly enriched sgRNAs varied between samples, ranging from 10 to 392. Data are shown as mean±s.e.m. FIG. 2B is a heatmap of the most highly enriched sgRNAs across all lymph node samples (average log2 rpm>=1); rows correspond to sgRNAs and columns correspond to different organ samples. SgRNA abundances are depicted in terms of log2 rpm. FIG. 2C is a waterfall plot of the top-ranked sgRNAs across all organs (FDR<0.2%). Inset shows 36 sgRNAs significantly enriched in ≥50% of organ samples. FIG. 2D is a bar plot of the number of genes with 0, 1, 2 or 3 independent sgRNAs that were significantly enriched in at least one organ sample (FDR<0.2%). A total of 80 genes were found to have 2 independent sgRNAs enriched. Pdcd1, Slc35c1, and Tsc2 were found to have 3 independent enriched sgRNAs. FIG. 2E is a set of Venn diagrams of the three enrichment criteria to identify the top gene hits (≥2% read abundance in one sample (n=253), significant in ≥25% of samples (n=79), and ≥2 independent enriched sgRNAs (n=83)). A total of 9 genes satisfied all three criteria. These genes included Aim1, Apc, Csnk1a1, Fam103a1, Nf1, Pdcd1, Prkar1a, Spast, and Tsc2. FIG. 2F: Top panel: Venn diagram comparing the significantly enriched sgRNAs (FDR<0.2%) in lymphoid vs. non-lymphoid organs. A total of 1,566 sgRNAs were enriched in at least one lymphoid sample, while 1,332 sgRNAs were enriched in at least one non-lymphoid sample. Of these, 761 sgRNAs were enriched in both lymphoid and non-lymphoid samples (significance of overlap, p≈0 by hypergeometric test); bottom panel: Venn diagram comparing the significantly enriched sgRNAs in lymph node vs. spleen. A total of 1,426 sgRNAs were found to be enriched in at least one lymph node, while 360 sgRNAs were enriched in at least one spleen sample. Of these, 220 sgRNAs were enriched in both lymph node and spleen samples (significance of overlap, p≈0 by hypergeometric test). FIG. 2G is a 5-way Venn diagram of enriched sgRNAs in non-lymphoid tissues (brain, liver, lung, muscle, pancreas). A total of 83 sgRNAs were enriched in all 5 non-lymphoid organs.

FIG. 3A is a schematic of an experiment described herein involving: crossing an OT-I mouse to a Cas9 mouse, naïve $CD8^+$ T cell isolation from OT-I; Cas9 mice, $CD8^+$ T cell transduction, adoptive transfer into E0771-mCh-cOVA tumor-bearing $Rag1^{-/-}$ mice, $CD8^+$ $T_{eff}$ cell survival and infiltration analysis in draining lymph nodes, non-draining lymph node, spleen, and tumor of E0771-mCh-cOVA tumor-bearing $Rag1^{-/-}$ mice by FACS. FIG. 3B shows titration of SIINFEKL (SEQ ID NO: 129,210) peptide for MHC-I presentation in E0771 cells. E0771 cells were pulsed with different concentrations of SIINFEKL peptide, and the MHC-I—peptide complex (SIINFEKL:H-K2b) was measured by mean fluorescent intensity (MFI) of surface staining using FACS. FIG. 3C shows measurement of antigen presentation in E0771-mCh-cOVA cell lines. E0771 cells were transduced with a lentiviral vector encoding mCherry-2A-cOVA transgene, and multiple clonal lines were generated by single cell cloning. MHC-I—peptide complex (SIINFEKL: H-K2b) was measured by mean fluorescent intensity (MFI) of surface staining using FACS. FIG. 3D is a growth curve of mammary fatpad transplanted E0771-mCh-cOVA tumors in $Rag1^{-/-}$ mice following different treatments. PBS control (n=3), adoptive transfer of OT-I; Cas9 $CD8^+$ $T_{eff}$ cells infected with vector (n=3), and adoptive transfer of OT-I; Cas9 $CD8^+$ $T_{eff}$ cells infected with MKO (n=8). Arrow indicates the time of adoptive transfer of MKO or vector transduced OT-I; Cas9 $CD8^+$ $T_{eff}$ cells. Data are shown as mean±s.e.m. FIG. 3E shows representative FACS plots of adoptively transferred $T_{eff}$ cells in draining and non-draining LNs (dLN and ndLN, respectively), spleen, lung, and tumor (TILs) from E0771-mCh-cOVA tumor-bearing $Rag1^{-/-}$ mice. FIG. 3F shows quantitative analysis of FACS data of adoptively transferred OT-I; Cas9 $CD8^+$ $T_{eff}$ cells in dLN, ndLN, spleen, lung, and tumor from E0771-mCh-cOVA tumor-bearing $Rag1^{-/-}$ mice. Data are shown as mean±standard deviation.

FIG. 4A is a schematic of an experiment described herein involving: crossing an OT-I mouse to a Cas9 mouse to generate OT-I; Cas9 mice, T cell isolation from spleen and LNs of OT-I; Cas9 mice, T cell transduction with MKO library, adoptive transfer into E0771-mCh-cOVA tumor-bearing $Rag1^{-/-}$ mice, and T cell library representation analysis in organs by sgRNA library sequencing. FIG. 4B is a box-dot plot of overall sgRNA library representation in all samples, including cellular libraries of infected OT-I; Cas9 $CD8^+$ $T_{eff}$ cells before infection (n=3), and various tissues from multiple mice (n=5 mice, 25 total samples). SgRNA representation is depicted in terms of $\log_2$ rpm. Analyzed tissues include draining lymph nodes (dLN), non-draining lymph nodes (ndLN), spleen, lung, and tumor. FIG. 4C is a bar plot of number of detected sgRNAs for all in vivo samples, grouped by sample type. Number of samples for each type are: dLN, ndLN, spleen, lung, and tumor (n=5 each, one per mouse, 5 mice total). FIG. 4D shows pie charts of sgRNA compositions in representative organs. SgRNAs that comprised ≥2% of total reads for each sample are shown, with the remaining reads classified as "Other. " FIG. 4E is a heatmap of the most highly enriched sgRNAs across all tissues (average $\log_2$ rpm≥1), where rows correspond to sgRNAs and columns correspond to different organ or tumor samples. The tissue type of each sample is annotated at the top of the heatmap. Each sample was further classified as lymphoid, nonlymphoid, or tumor to facilitate downstream analyses. SgRNA abundances are depicted in terms of $\log_2$ rpm. FIG. 4F is a bar plot of the number of significantly enriched sgRNAs for all in vivo samples, grouped by sample type as in FIG. 4C. Statistical significance of sgRNA enrichment was determined by comparison to NTCs, with a threshold of FDR<0.2%. The number of significantly enriched sgRNAs varied between samples, ranging from 7 to 179. FIG. 4G is a box-dot plot of overall sgRNA library representation in all samples, including cellular libraries of infected OT-I; Cas9 $CD8^+$ $T_{eff}$ cells before injection (n=3), and tumors from multiple mice (n=10 mice, 10 total tumors). sgRNA representation is depicted in terms of $\log_2$ rpm. FIG. 4H is a waterfall plot of the top-ranked sgRNAs across all tumors (21 sgRNAs significantly enriched in ≥50% of tumors, FDR<0.5%). Inset, waterfall plot of all sgRNAs that were significantly enriched in ≥20% of tumors. FIG. 4I is a barplot of the number of genes with 0-4 independent sgRNAs that were significantly enriched in at least one organ sample (FDR<0.5%). A total of 26 genes were found to have at least 2 independent sgRNAs enriched. Pdcd1 and Stradb were each found to have 4 independent enriched sgRNAs. FIG. 4J is a Venn diagram of the three enrichment criteria to identify the top gene hits (≥2% read abundance in one sample (n=36), significant in ≥20% of samples (n=220), and ≥2 independent enriched sgRNAs (n=26)). A total of 6 genes satisfied all three criteria (Cd247, Fam103a1, Hacvr2, Pdcd1, Prkar1a, and Stradb).

FIGS. 5A-5G are a series of plots and images illustrating significantly enriched sgRNAs and genes of MKO mutagenized OT-I; Cas9 $CD8^+$ $T_{eff}$ cells in $Rag1^{-/-}$ mice with transplanted tumors expressing cOVA antigen. FIG. 5A is a scatter plot of sgRNA abundance average across all organ samples (n=20) compared to cell samples (n=3). SgRNA abundance is depicted in terms of $\log_2$ rpm. SgRNAs that were found to be statistically significantly (Sig., compared to distribution of NTC, FDR<0.1%) have their target gene names labeled. FIG. 5B is a scatter plot of sgRNA abundance in tumor (average across all tumor samples, n=5) compared to in vitro (average across all cell samples, n=5). SgRNA abundance is depicted in terms of $\log_2$ rpm. SgRNAs that were found to be statistically significantly higher in organ samples compared to cell samples (Benjamini-Hochberg adjusted p-value<0.05, t-test) are colored in pink, with gene names labeled. FIG. 5C is a waterfall plot of the top-ranked sgRNAs across all organs (11 sgRNAs. significantly enriched in ≥50% of samples, FDR<0.2%). FIG. 5D shows DAVID gene ontology analysis of all genes found to be enriched in organ or tumor samples (showing enriched GO terms, the number of enriched genes corresponding to each GO term, and the associated p-value of enrichment). FIG. 5E is a 3-way Venn diagram comparing the significantly enriched sgRNAs (FDR<0.2%) in lymphoid, non-lymphoid, and tumor samples. A total of 392 sgRNAs were found to be enriched in at least one lymphoid sample, 320 sgRNAs were enriched in at least one non-lymphoid sample, and 395 sgRNAs were enriched in at least one tumor sample. The sgRNAs associated with each of the three groups were found to significantly overlap (lymphoid vs. non-lymphoid, $p=2.11\times10^{-159}$; lymphoid vs. tumor, $p=3.02\times10^{-88}$; non-lymphoid vs. tumor, $p=1.97\times10^{-137}$, hypergeometric test). FIG. 5F is a 3-way Venn diagram comparing the significantly enriched sgRNAs in draining lymph node (dLN), non-draining lymph node (ndLN), and spleen samples. A total of 90 sgRNAs were found to be enriched in at least one dLN sample, 148 sgRNAs were enriched in at least one ndLN sample, and 278 sgRNAs were enriched in at least one spleen sample. The sgRNAs associated with each of the three groups were found to significantly overlap (dLN vs. ndLN, $p=6.07\times10^{-317}$; dLN vs. spleen, $p=2.58\times10\times10$; ndLN vs. spleen, $p=2.01\times10^{-263}$, hypergeometric test). FIG. 5G is a 2-way Venn diagram comparing the hits from the second screen (OT-I; Cas9 $CD8^+$ $T_{eff}$ cells in $Rag1^{-/-}$ host bearing tumors with cOVA antigen) to the first screen (Cas9 $CD8^+$ T cells in WT host), showing a highly significant overlap (hypergeometric test, $p=1\times10^{-23}$). Shared genes including multiple immune genes (such as Tim3/Havcr2, Lexm/BC055111, Zap70, Cd247 and PD-1/Pdcd1), a couple tumor suppressor genes (Aim1 and Nf1), as well as many genes with undocumented function in $CD8^+$ T cells or completely unknown genes (such as Shisa6, Siah3, Ccdc105, Ccdc81 and 3830406C13Rik).

FIGS. 6A-6D are a series of plots and images illustrating the validation of a selected set of significantly enriched genes using minipools mutagenized OT-I; Cas9 $CD8^+$ T cells intravenously injected into WT mice. FIG. 6A is a schematic of an experiment described herein involving: minipool library cloning, virus production, T cell infection, adoptive transfer, $CD8^+$ $T_{eff}$ cell survival analysis in organs by sgRNA library sequencing. FIG. 6B is an overall heatmap of the abundances of each sgRNA represented in the minipool library; rows correspond to sgRNAs and columns correspond to different cell or organ samples. The tissue type of each sample and host mouse genotype is annotated at the top of the heatmap. Each sample was further classified as cells, lymphoid, or non-lymphoid to facilitate downstream analyses. SgRNA abundances are depicted in terms of $\log_2$ rpm. FIG. 6C is a dot plot of all minipool sgRNAs across all cell and organ samples. Cells are denoted in pink, lymphoid samples in green, and non-lymphoid samples in blue. SgRNA abundances are depicted in terms of $\log_2$ rpm. FIG. 6D is a Venn diagram comparing the significantly enriched sgRNAs (compared to NTC, Welch t-test, $p<0.05$) in lymphoid vs. non-lymphoid organs. A total of 14 sgRNAs were enriched in non-lymphoid samples, all contained within the 17 sgRNAs enriched in lymphoid sample (significance of overlap, $p=0.0021$ by hypergeometric test).

FIG. 7A shows schematics of an experiment described herein involving: virus production, $CD8^+$ T cell isolation and infection with a genome-scale CRISPR library (MKO), Thy1.1 surface staining, and FACS analysis. FIG. 7B shows FACS plots of naive OT-I; Cas9 $CD8^+$ T cells infection with multiple dilution of MKO lentivirus (Thy1.1 gating) using two batches of viruses collected at different time points. FIG. 7C shows overlaid histograms of Thy1.1 expression of Cas9 $CD8^+$ T cells infected T cells with comparable viral titers from two batches of viruses. Shaded histogram represents uninfected control. Black histogram represents MKO library virus isolated 48 hours post-transfection. Red histogram represents MKO library virus isolated 72 hours post-transfection. FIG. 7D shows quantification of MKO lentivirus from two batches of virus by surface staining of Thy1.1-infected $CD8^+$ T cells. Data were shown as geometric mean of MFI. FIG. 7E shows quantification of MKO lentivirus from two batches of virus by surface staining of Thy1.1-infected $CD8^+$ T cells. Data were shown as % $Thy1.1^+$ $CD8^+$ T cells.

FIGS. 8A-8G are a series of plots and images illustrating overall sgRNA quantification for the analysis of genome-scale CRISPR perturbation of Cas9 $CD8^+$ T cell survival in WT mice. FIG. 8A is a heatmap of pairwise Pearson correlations of sgRNA library representation across all samples in the first screen. Correlations were calculated based on $\log_2$ rpm values. Cell and plasmid samples were highly correlated with each other, while organ samples were most correlated with other organ samples. FIG. 8B is a bar plot of the number of detected sgRNAs for all plasmid (red, n=1), cell (orange, n=3), and organ (blue, n=62) samples. The number of detected sgRNAs is depicted on a $\log_{10}$ scale. While the plasmid library and the cell pool had comparable numbers of detected sgRNAs (average $\log_{10}$ sgRNA count=5.04 and 4.93, respectively), organ samples had fewer detected sgRNAs by several orders of magnitude (average $\log_{10}$ sgRNA count=2.44). FIG. 8C is a bar plot of the number of significantly enriched sgRNAs for all organ samples, grouped by organ type. Statistical significance of sgRNA enrichment was determined by comparison to NTCs, with a threshold of FDR<0.2%. The number of significantly enriched sgRNAs varied between samples, ranging from 10 to 392. FIG. 8D is a heatmap of the most highly enriched sgRNAs across all organs (average $\log_2$ rpm≥1), where rows correspond to sgRNAs and columns correspond to different organ samples. The tissue type of each sample is annotated at the top of the heatmap. Each sample was further classified as lymphoid or nonlymphoid to facilitate downstream analyses. SgRNA abundances are depicted in terms of $\log_2$ rpm. FIG. 8E is a scatter plot of sgRNA abundance in vivo (average across all organ samples, n=62) compared to in vitro (average across all cell samples, n=3). SgRNA abundance is depicted in terms of $\log_2$ rpm. SgRNAs that were found to be statistically significantly higher in organ samples compared to cell samples are colored red (Benjamini-Hochberg adjusted p-value<0.05, t-test), with representative genes labeled. NTCs are colored dark gray, while all other gene-targeting sgRNAs (GTSs) are light gray. FIG. 8F is a volcano plot of sgRNA abundance, comparing lymphoid vs non-lymphoid organs. Only sgRNAs with an average $\log_2$ pm abundance≥1 are shown. The x-axis denotes the average $\log_2$ fold change of lymphoid vs non-lymphoid samples, while the y-axis denotes the $-\log_{10}$ p-value of the comparison (t-test). SgRNAs that were significantly enriched in lymphoid samples relative to non-lymphoid samples are colored red ($p<0.05$). FIG. 8G shows results from gene ontology analysis of all genes found to be enriched in organs (showing enriched GO terms, the number of enriched genes corresponding to each GO term, and the associated p-value of enrichment). A representative set of terms were shown.

" FIG. 9A shows LN1 pie charts. FIG. 9B shows LN2 pie charts. FIG. 9C shows LN3 pie charts. FIG. 9D shows spleen pie charts. FIG. 9E shows liver pie charts. FIG. 9F shows pancreas pie charts. FIG. 9G shows lung pie charts. FIG. 9H shows brain pie charts. FIG. 9I shows muscle pie charts.

FIG. 10A is a schematic of an experiment described herein involving: $CD8^+$ T cell isolation from OT-I; Cas9 mice, $CD8^+$ $T_{eff}$ cell, transduction, adoptive transfer into E0771-mCh-cOVA tumor-bearing $Rag1^{-/-}$ mice, $CD8^+$ $T_{eff}$ cell survival and infiltration analysis in draining lymph nodes, non-draining lymph node, spleen, and tumor of E0771-mCh-cOVA tumor-bearing $Rag1^{-/-}$ mice by FACS. FIGS. 10B-10E are a series of FACS plots showing data from adoptively transferred $T_{eff}$ cells in draining LNs (dLN) (FIG. 10B), non-draining LNs (ndLN) (FIG. 10C), spleen (FIG. 10D), and tumors (TILs) from E0771-mCh-cOVA tumor-bearing $Rag1^{-/-}$ mice (FIG. 10E). MKO is the genome-scale T cell knockout CRISPR library and the empty vector; numbers indicate percentage of total. Top rows are FACS plots from PBS-treated mice. Middle rows are FACS plots from mice treated with vector-infected OT-I; Cas9 $CD8^+$ T cells. Bottom rows are FACS plots from mice treated with MKO-infected OT-I; Cas9 $CD8^+$ T cells. FIG. 10F is a growth curve of subcutaneously transplanted E0771-mCh-cOVA tumors in $Rag1^{-/-}$ mice following different treatments. PBS control (n=1), adoptive transfer of OT-I; Cas9 $CD8^+$ $T_{eff}$ cells infected with vector (n=3), and adoptive transfer of OT-I; Cas9 $CD8^+$ $T_{eff}$ cells infected with MKO (n=5). Read arrow indicates the time of adoptive transfer of MKO or vector transduced OT-I; Cas9 $CD8^+$ $T_{eff}$ cells. Data are shown as mean±s.e.m.

FIG. 11A is a heatmap of pairwise Pearson correlations of sgRNA library representation across all samples. Correlations were calculated based on $\log_2$ rpm values. Cell and plasmid samples were most correlated with each other, while organ and tumor samples were most correlated with other organ or tumor samples. FIG. 11B is a bar plot of the number of detected sgRNAs for all cell (orange, n=3) and organ/tumor (blue, n=25) samples. The number of detected sgRNAs is depicted on a $\log_{10}$ scale. The number of detected sgRNAs in cell samples was several magnitudes higher than in organ/tumor (average $\log_{10}$ sgRNA count=4.91 and 2.73, respectively). FIG. 11C is a bar plot of number of significantly enriched sgRNAs for all organ samples, grouped by sample type (tumor, dLN, ndLN, spleen or lung). Statistical significance of sgRNA enrichment was determined by comparison to NTCs, with a threshold of FDR<0.2%. FIG. 11D is a bar plot of the number of genes with 0, 1, or 2 independent sgRNAs that were significantly enriched in at least one organ sample (FDR<0.2%). 13 genes were found to have 2 independent enriched sgRNAs (yellow box). No genes in this experiment were found to have 3 enriched sgRNAs.

" FIG. 12A shows dLN pie charts. FIG. 12B shows ndLN pie charts. FIG. 12C shows spleen pie charts. FIG. 12D shows tumor pie charts. FIG. 12E shows lung pie charts.

FIG. 13 is a table showing results from a t-test of GTC vs NTC in OT-I; Cas9 $CD8^+$ $T_{eff}$ cell minipool assay for in vivo survival in wildtype mice.

FIGS. 14A-14E show gene identifiers of vectors used in the present study. 14A shows gene identifiers for vector pSC017_pLKO-U6-sgBsmBI-EFS-Thy11CO-spA (SEQ ID NO:129,213). FIG. 14B shows gene identifiers for vector pSC008_pLKO-U6-BsmBI-chRNA(+85)-EFS-Thy11 (SEQ ID NO: 129,214). FIG. 14C shows gene identifiers for vector pSC021_pLKO-U6-sgBsmBI-PGK-Thy11CO-spA.sbd (SEQ ID NO:129,215). FIGS. 14D-14E show gene identifiers for vector pMD02: lenti-pLKO-U6-sgBsmBI-EFS-mCherry-2A-cOVA (SEQ ID NO:129,216).

FIG. 15A is a histogram of initial plasmid library sequencing as library QC. The library was sequenced to ensure high coverage. For at least 94.1% of the whole library (121,608/129,209), unique sgRNAs were cloned into the plasmid, covering 98% of all the annotated genes (22,786) designed in the library. The representation showed a tight log-normal distribution, with 97.6% of sgRNAs within 2 orders of magnitude (O.M.), and 99.9% within 3 O.M. FIG. 15B shows the distribution of cloned sgRNA per gene in the MKO plasmid library. Most (17,330) genes were still covered by 6/6 sgRNAs; 20,653 genes have 4 or more sgRNAs; 393 genes have no sgRNAs (loss in cloning, thus not screenable with this plasmid library). FIG. 15C is a schematic of an experiment comprising: virus production, $CD8^+$ T cell isolation and infection with a genome-scale CRISPR library (MKO), Thy1.1 surface staining, and FACS analysis. FIG. 15D show FACS plots of naive OT-I; Cas9 $CD8^+$ T cell infection with multiple dilutions of MKO lentivirus (Thy1.1 gating) using two batches of viruses collected at different time points. FIG. 15E shows quantification of MKO lentivirus from two batches of virus by surface staining of Thy1.1-infected $CD8^+$ T cells. Data were shown as the geometric mean of MFI. FIG. 15F shows quantification of MKO lentivirus from two batches of virus by surface staining of Thy1.1-infected $CD8^+$ T cells. Data were shown as % Thy1.1$^+$ $CD8^+$ T cells.

FIG. 16A is a box-dot plot of overall sgRNA library representation in all samples, including plasmid library (n=1), cellular libraries of pre-injection library-infected naive $CD8^+$ T cells (n=3), and various organs containing $CD8^+$ $T_{eff}$ cells from multiple mice 7 days post-injection (n=7 mice, 62 total samples). SgRNA representation is depicted in terms of $\log_2$ reads per million (rpm). Analyzed tissues include the lymph node (LN), spleen, brain, liver, lung, muscle, and pancreas. FIG. 16B shows correlation analyses between two replicate mice. Average sgRNA representation across all organs for each mouse was plotted against another mouse. Pearson correlation value were noted on the plots. Full correlation plot was in FIG. 1. FIG. 16C shows a correlation analysis between two types of host as recipient mice. Average sgRNA representation across all mice for the B6 recipient group was plotted that of Cas9 host. Pearson correlation value was noted on the plot. FIG. 16D is a Venn diagram showing overlap of sgRNA hits between the $CD8^+$ $T_{eff}$ cells survival and trafficking screens using B6 and Cas9 recipients. Hypergeometric test, p<1e-5.

FIG. 17A, left panel is a Venn diagram comparing the significantly enriched sgRNAs (FDR<0.2%) in lymphoid vs. non-lymphoid organs. A total of 1,566 sgRNAs were enriched in at least one lymphoid sample, while 1,332 sgRNAs were enriched in at least one non-lymphoid sample. Of these, 761 sgRNAs were enriched in both lymphoid and non-lymphoid samples (significance of overlap, p≈0 by hypergeometric test). Right panel: Venn diagram comparing the significantly enriched sgRNAs in lymph node vs. spleen. A total of 1,426 sgRNAs were found to be enriched in at least one lymph node, while 360 sgRNAs were enriched in at least one spleen sample. Of these, 220 sgRNAs were enriched in both lymph node and spleen samples (significance of overlap, p≈0 by hypergeometric test). FIG. 17B is a 5-way Venn diagram of enriched sgRNAs in non-lymphoid tissues (brain, liver, lung, muscle, pancreas). A total of 83 sgRNAs were enriched in all 5 non-lymphoid organs. FIG. 17C shows minipool validation of highly enriched sgRNAs in T cell survival and trafficking in vivo. SgRNA abundance across all organs were plotted. Statistical comparisons were made against control sgRNA group co-injected in the same minipool. *=$p<0.05$, two sided t-test.

FIG. 18A is a schematic of an experiment: cross OT-I mouse to Cas9 mouse, naive $CD8^+$ T cell isolation from OT-I; Cas9 mice, $CD8^+$ T cell transduction, adoptive transfer into mice, and MKO-transduced OT-I; Cas9 $CD8^+$ $T_{eff}$ cell survival analysis in organs by high-throughput sgRNA sequencing. Organs collected include the liver, pancreas, lung, muscle and brain as representative non-lymphoid organs, and the spleen and several types of lymph nodes (sLNs, cLNs and aLNs). FIG. 18B is a waterfall plot of the top sgRNAs across all organs ranked by number of organs being enriched in (FDR<0.5%). A total of 27 sgRNAs were found to be significant in ≥20% of samples. FIG. 18C is a barplot of the number of genes with 0, 1, or 2 independent sgRNAs that were significantly enriched in at least one organ sample (FDR<0.5%). A total of 4 genes were found to have 2 independent sgRNAs enriched. Cd247, Bpifb3, and Tsc2 were found to have 3 independent enriched sgRNAs. FIG. 18D is a Venn diagram of the three enrichment criteria to identify the top gene hits (≥2% read abundance in one sample (n=99), significant in ≥20% of samples (considering all associated sgRNAs) (n=27), and ≥2 independent enriched sgRNAs (n=4)). Noted that the sets of ≥20% of samples and ≥2 independent enriched sgRNAs were contained in the set of ≥2% read abundance in one sample. A total of 3 genes satisfied all three criteria. These genes were Pdcd1, Slc35c1, and Stradb. FIG. 18E is a Venn diagram comparing the hits from the diverse TCR screen and from the clonal TCR screen. 17 genes were found to be significant in ≥2 samples from both datasets. These included 3830406C13Rik, BC055111, Cd247, Gm6927, Hacvr2, Lrp6, Nf1, Olfr1158, Opn3, Pdcd1, Serping1, Slc2a7, Slc35c1, Son, Tsc2, Tspan4, and 4.82. FIG. 18F illustrates donor T cell and recipient host effect analysis. Heatmap of pairwise Pearson correlations of sgRNA library representation in all mice, with all organs averaged, from the genome-scale screen for trafficking and survival in $CD8^+$ T cells with either diverse or clonal TCR (Cas9 vs. OT-I; Cas9), and with wildtype (B6) or syngeneic host (Cas9). FIG. 18G shows organ patterns of genome-scale CRISPR T cell screen. Dimensional reduction plot with t-SNE method showing the clustering patterns based on MKO library screening. Each dot is the sgRNA library representation in an organ color coded according to the legend (brain, liver, LN, lung, muscle, pancreas and spleen). There is a large cluster containing virtually all organ types (k0), while there are 8 smaller clusters (k1-k8) that each consist of 4 to 6 organ types, with several organs as outliers.

FIG. 19A is a Heatmap of pairwise Pearson correlations of sgRNA library representation across all samples in the second WT screen using OT-I; Cas9 $CD8^+$ T cells. Samples were from various organs containing $CD8^+$ $T_{eff}$ cells from multiple mice 7 days post-injection (n=10 mice, 70 total samples). Correlations were calculated based on $\log_2$ rpm values. FIG. 19B is a box-dot plot overall sgRNA library representation in all samples from various organs containing $CD8^+$ $T_{eff}$ cells from multiple mice 7 days post-injection (n=10 mice, 70 total samples). sgRNA representation is depicted in terms of $\log_2$ reads per million (rpm). Analyzed tissues include various lymph nodes (LN), spleen, liver, pancreas, and lung.

FIGS. 20A-20C are a series of images illustrating protein domain and conservation analysis of representative hits. FIG. 20A shows domain structure prediction of human DHX37 protein, which contains an HrpA domain that can be subdivided into 4 subdomains (DEXDc, P-loop NTPase, HELICc and HA2). Representative alignments of regions in DEXDc and HELICc domains that are conserved between multiple mammalian species are shown below (SEQ ID NOs: 140,683-140,746). FIG. 20B shows domain structure prediction of human LRP6 protein, which contains 5 predicted domains (NHL, overlapping LDLRb, LY, FXaI and LDLa). Representative alignments of regions in NHL and LY domains that are conserved between multiple mammalian species are shown below (SEQ ID NOs: 140,747-140,826). FIG. 20C shows domain structure prediction of human SLC35C1 protein, which contains 2 predicted domains (TPT, and overlapping EamA). Representative alignments of a region in EamA/TPT domain that is conserved between multiple mammalian species were shown below (SEQ ID NOs: 140,827-140,863).

FIG. 21A is a growth curve of subcutaneous tumors from transplanted E0771-mCh-cOVA cells in $Rag1^{-/-}$ mice following different treatments. PBS control (n=1), adoptive transfer of OT-I; Cas9 $CD8^+$ $T_{eff}$ cells infected with vector (n=3), and adoptive transfer of OT-I; Cas9 $CD8^+$ $T_{eff}$ cells infected with MKO (n=5). Arrow indicates the time of adoptive transfer of MKO or vector transduced OT-I; Cas9 $CD8^+$ $T_{eff}$ cells. Error bars for certain data points were invisible because the errors were small. Data are shown as mean±s.e.m. FIG. 21B shows full-slide and high-power histology sections stained by hematoxylin and eosin of tumors derived from E0771 cells expressing cOVA antigen in $Rag1^{-/-}$ mice after different treatment conditions. Top group: tumors in mice that were injected with PBS. Middle group: tumors in mice after adoptive transfer of vector-treated activated OT-I; Cas9 $CD8^+$ $T_{eff}$ cells. Bottom group: tumors in mice after adoptive transfer of MKO mutagenized activated OT-I; Cas9 $CD8^+$ $T_{eff}$ cells. In PBS group, tumors were devoid of lymphocytes and showed signatures of rapid proliferation and little cell death. In adoptive transfer groups, tumors were infiltrated by lymphocytes and showed signatures of cell death in large areas. Low magnification image scale bar: 1 mm; high magnification image scale bar: 200 μm. FIG. 21C shows representative FACS plots of adoptively transferred $T_{eff}$ cells in draining and non-draining LNs (dLN and ndLN, respectively), spleen, lung, and tumor (TILs) from E0771-mCh-cOVA tumor-bearing $Rag1^{-/-}$ mice. MKO is the genome-scale T cell CRISPR library. Numbers indicate percentage of total cells. Top row: FACS plots from PBS-treated mice. Middle row: FACS plots from mice treated with vector-infected OT-I; Cas9 $CD8^+$ T cells. Bottom row: FACS plots from mice treated with MKO-infected OT-I; Cas9 $CD8^+$ T cells. FIG. 21D shows correlation analysis of genome-scale CRISPR perturbation of OT-I; Cas9 $CD8^+$ tumor-infiltrating lymphocytes into $Rag1^{-/-}$ mice with E0771-cOVA tumors. Heatmap of pairwise Pearson correlations of sgRNA library representation across 3 cell libraries prior to injection, and all samples in the tumor infiltration screen (n=10 mice, 10 tumors). Correlations were calculated based on $\log_2$ rpm values. E0771-cOVA cells were transplanted subcutaneously for mice 1-5, and into the mammary fat pad for mice 6-10. FIG. 21E shows clonal consistency analysis of adoptive transfer screen. A minipool screen is analyzed between two clones expressing different levels of cOVA (E0771-mChOva cl.3 and cl.5). The sgRNA representation for one clone was plotted against another. Pearson correlation value was noted on the plot. FIG. 21F shows clonal consistency analysis of adoptive transfer screen. A minipool screen is analyzed between two cell lines from different cancer types (breast and lung) expressing the same cOVA construct (E0771-mChOva and LCC-mChOva). The sgRNA representation for one clone was plotted against another. Pearson correlation value was noted on the plot.

FIG. 22A is a schematic of an experiment: Naive OT-I; Cas9 $CD8^+$ T cells were isolated and transduced with MKO lentiviral library, co-cultured with SIINFEKL peptide pulsed E0771 cells (0 or 1 ng/ml), and stained for CD8 and CD107a for $CD8^+$ $T_{eff}$ undergoing active degranulation. Stained cells were analyzed, and the top 5% $CD107a^+$ cells were sorted, and subjected to genomic DNA extraction, CRISPR library readout, and screen data analysis. FIG. 22B shows titration of SIINFEKL peptide for MHC-I presentation in E0771 cells. E0771 cells were pulsed with different concentrations of SIINFEKL peptide, and the MHC-I—peptide complex (SIINFEKL:H-$K2^b$) was measured by mean fluorescent intensity (MFI) of surface staining using FACS. FIG. 22C is a histogram showing $CD107a^+$ T cells analyzed from the co-culture of OT-I; Cas9 $CD8^+$ T cells and E0771 cancer cells. The top 5% $CD107a^+$ cells were sorted. A total of three biological replicates were performed. FIG. 22D is a waterfall plot of the top-ranked sgRNAs across all sorted cell samples (17 sgRNAs significantly enriched in ≥66% of samples, FDR<0.5%). FIG. 22E is a Venn diagram comparing the hits from the in vitro kill assay screen and from the in vivo tumor infiltration study. 3 genes were found to be significant in ≥2 samples from both datasets. These included Dhx37, Lyn, and Odc1. FIG. 22F shows growth curves of mammary fatpad E0771-mCh-cOVA tumors in $Rag1^{-/-}$ mice following different treatments. PBS control (n=4), adoptive transfer of OT-I; Cas9 $CD8^+$ $T_{eff}$ cells infected with vector (n=4), and adoptive transfer of OT-I; Cas9 $CD8^+$ $T_{eff}$ cells infected with sgDhx37 (n=5). Data are shown as mean±s.e.m. PBS and sgDhx37 groups were tested against vector group. PBS group has significantly larger tumors compared to vector indicating the effect of adoptive transfer of OT-I; Cas9 $CD8^+$ $T_{eff}$ cells. The sgDhx37 group significantly reduced tumor burden as compared to vector indicating a gene-specific effect. FIG. 22G illustrates testing the anti-tumor effect of OT-I; Cas9 $CD8^+$ $T_{eff}$ cells with sgPD-1. Tumor growth curves from individual mice were shown. Similar to above, PBS, vector, and sgPdcd1 mice were shown. Data are shown as individual points/curves. 2/5 sgPdcd1 mice have significantly smaller tumors compared to vector, 1/5 is marginal significant, while the remaining 2/5 are not significant. FIG. 22H illustrates testing the anti-tumor effect of OT-I; Cas9 $CD8^+$ $T_{eff}$ cells with sgOdc1. Tumor growth curves from individual mice were shown. Similar to above, PBS, vector, and sgOdc1 mice were shown. Data are shown as individual points/curves. 3/5 sgOdc1 mice have significantly smaller tumors compared to vector, while the remaining 2/5 are not significant. Note: Arrow indicates the time of adoptive transfer of MKO or vector transduced OT-I; Cas9 $CD8^+$ $T_{eff}$ cells. Data from FIGS. 22F-22H were collected together, tumor curves PBS and vector groups from the 3 panels are identical, which were plotted in separation for each gene for comparison and visibility. Statistical comparisons were made against vector group. *=p<0.05, =p<0.01, *=p<0.001, by paired t-test.

FIG. 23A is a schematic of an experiment: adoptive transfer of vector or sgDhx37-infected OT-I; Cas9 $CD8^+$ $T_{eff}$ cells into $Rag1^{-/-}$ mice bearing E0771-mCh-cOVA tumors, tumor harvesting after 50 days of growth, FACS for $CD3^+$ $CD8^+$ T cells, microfluidic-based approach of reverse-transcription and multi-step barcoding library preparation to produce single-cell barcoded DNA droplets, followed by high-throughput sequencing and computational analysis. FIG. 23B shows t-SNE dimensional reduction and visualization of individual tumor-infiltrating $CD8^+$ cells from the mouse TIL scRNAseq. Left panel: visualization by clusters (4 distinct clusters identified); Right panel visualization by experiment groups, i.e. OT-I; Cas9 $CD8^+$ $T_{eff}$ cells treated with either sgDhx37 (n=191 cells) or vector (n=361). FIG. 23C shows differentially expressed genes in sgDhx37-treated $CD8^+$ tumor infiltrating lymphocytes compared to vector-treated. Heatmap of top differentially expressed genes (absolute $\log_2$ fold change≥1) in single $CD8^+$ tumor infiltrating lymphocytes treated with sgDhx37 or vector control. Values shown are in terms of z-scores (scaled by row/gene). FIG. 23D is a Volcano plot of differentially expressed genes in tumor-infiltrating $CD8^+$ cells treated with sgDhx37 compared to vector control. A total of 137 genes were significantly upregulated in sgDhx37 treated cells (Benjamini-Hochberg adjusted p<0.05), while 215 genes were significantly downregulated in sgDhx37 treated cells (adjusted p<0.05). Top upregulated genes included Rgs16, Nr4a2, Tox, Lag3, Rbm3 and Ccl4. Top downregulated genes included Uba52, Hist1h1c, Gm9844, Emp3 and Rps28. FIG. 23E shows gene ontology analysis of significantly upregulated genes in sgDhx37-treated tumor-infiltrating $CD8^+$ cells. Several gene ontology categories were significantly enriched (Bonferroni adjusted p<0.05). These included lymphocyte activation, positive regulation of cytokine production, regulation of cell-cell adhesion, regulation of immune effector process, and positive regulation of interferon-gamma production. FIG. 23F shows gene ontology analysis of significantly downregulated genes in sgDhx37-treated tumor-infiltrating $CD8^+$ cells. Several gene ontology categories were significantly enriched (Bonferroni adjusted p<0.05). These included ribosomal small subunit assembly, ribosomal large subunit biogenesis, regulation of reactive oxygen species metabolic process, regulation of cell migration, positive regulation of leukocyte migration, and apoptotic signaling pathway. FIG. 23G shows differential expression analysis by cluster (sub-population of T cells). mRNA level in individual cells were plotted for NTC and sgDhx37 groups in each of the 4 major clusters (see top panel of b). Violin plots with individual data points were shown. The top up-regulated (Rgs16) and down-regulated (Uba52) genes were shown as examples. For all comparisons between sgDhx37 and control group, FDR adjusted p value<0.05, in all clusters.

FIG. 24A shows Western blot analysis of DHX37 protein in human cells. From left to right, HEK293FT cells with Dhx37 overexpression as a positive control; peripheral blood $CD4^+$ T cells from a healthy donor; peripheral blood $CD8^+$ T cells from a healthy donor; TILs from a tumor biopsy freshly isolated from an NSCLC patient. FIG. 24B shows FACS analysis of intracellular protein level of DHX37 in peripheral blood $CD8^+$ T cells and NSCLC patient TILs. FIG. 24C shows tissue microarray analysis of DHX37 expression across multiple patient samples. Summary level dot plots of $DHX37^+$ cell staining. Each dot represents the total number of $DHX37^+$ cells in one slice of a core biopsy of a patient sample (0.7 mm in diameter, 0.385 $mm^2$ in surface area). Numbers were capped at 1000. Normal brain and glioma samples were on the same array. Breast cancer and melanoma tumor samples were on separate arrays. Normal brain tissues have significantly less $DHX37^+$ cells as compared to glioma tissues (*=p<0.001, by unpaired two-tailed t-test). Matched normal tissues are not available for breast cancer and melanoma for these TMAs. FIG. 24D shows representative images of two patient biopsy samples from tissue microarray analysis. DHX37 staining was found primarily in the nucleus (heavy staining on nuclear membrane). Arrowheads point to representative $DHX37^+$ TILs in glioma, breast cancer and melanoma biopsies. H&E staining was shown for companion samples. FIG. 24**E shows DHX37 in patient prognosis. Top left: Higher DHX37 predicts poorer prognosis in lower grade glioma (LGG). Kaplan-Meier curves of overall survival in High DHX37-high (n=221) vs. DHX37-low (n=223) patients (p=0.0011, hazard ratio=1.899). Bottom left: Higher DHX37 predicts poorer prognosis in hepatocellular carcinoma (LIHC). Kaplan-Meier curves of overall survival in High DHX37-high (n=161) vs. DHX37-low (n=162) patients (p=0.031, hazard ratio=1.522). Top right: Higher DHX37 predicts poorer prognosis in lung adenocarcinoma (LUAD). Kaplan-Meier curves of overall survival in High DHX37-high (n=222) vs. DHX37-low (n=222) patients (p=0.0077, hazard ratio=1.526). Bottom right: Higher DHX37 predicts poorer prognosis in kidney renal cell carcinoma (KIRC). Kaplan-Meier curves of overall survival in High DHX37-high (n=228) vs. DHX37-low (n=228) patients (p=0.047, hazard ratio=1.373).

FIG. 25A shows distribution of DHX37 expression in human peripheral blood T cells, tissue-resident T cells, tumor-normal junction T cells, and tumor-infiltrating T cells in $CD3^+/CD4^+/CD25^-$ helper T cells, $CD3^+/CD8^+$ cytotoxic T cells, and $CD3^+/CD4^+/CD25^+$ regulatory T cells. The number and total percentage of $DHX37^+$ cells is noted on each plot. FIG. 25B is a series of scatter-boxplots of IL12A, ITM2A, RGS16, and STAT1 expression in $DHX37^+$ and $DHX37^-$ $CD3^+/CD8^+$ T cells. Expression of IL12A ($p=7.10*10^{-9}$), ITM2A (p=0.0033), RGS16 ($p=1.23*10^{-7}$), and STAT1 (p=0.0033) was significantly lower in $DHX37^+$ cells. FIG. 25C is a series of scatter-boxplots of PPA1, CISH, TRAP1, and SLC7A6 expression in $DHX37^+$ and $DHX37^-$ $CD3^+/CD8^+$ T cells. Expression of PPA1 (p=0.0002), CISH (p=0.0074), TRAP1 ($p=9.34*10^{-5}$), and SLC7A6 ($p=9.64*10^{-5}$) was significantly higher in $DHX37^+$ cells. FIG. 25D is a set of scatter-boxplots of IKBKE and CPT2 expression in $DHX37^+$ and $DHX37^-$ $CD3^+/CD4^+/CD25^-$ T cells. Expression of IKBKE (p=0.0062) and CPT2 ($p=1.30*10^{-5}$) was significantly lower in $DHX37^+$ cells. FIG. 25E is a set of scatter-boxplots of SLC35E2B and NDFIP 1 expression in $DHX37^+$ and $DHX37^-$ $CD3^+/CD4^+/CD25^-$ T cells. Expression of SLC35E2B ($p=4.75*10^{-5}$) and NDFIP 1 (p=0.0004) was significantly higher in $DHX37^+$ cells. Two-sided Welch's t tests were used in B-E to evaluate statistical significance. Tukey boxplots are shown.

FIG. 26A is a schematics of the design of an AAV-CRISPR T cell knockout vector, which contains an sgRNA expression cassette and a Thy1.1 expression cassette within the two ITR of AAV base vector. FIG. 26B is a schematic of an experiment: Naive OT-I; Cas9 $CD8^+$ T cells were isolated and transduced with AAV-sgRNA-Thy1.1 vector, activated by CD3/CD28, followed by multiple analyses after infection, including indel sequencing, FACS, single cell RNAseq for acute transcriptional regulation, and adoptive transfer for testing anti-tumor activity. FIG. 26C is a plot showing significant downregulation of intracellular Dhx37 level 7 days after AAV-sgDhx37 transduction. Geometric means were shown for each data point. (*, p<0.05, unpaired two sided t test). FIG. 26D shows confirmation of acute knockout of genes by AAV-CRISPR system. Three genes were tested (Mll3, B2m and Dhx37). Representative Illumina targeted amplicon sequencing of the sgRNA target site 5 days after infection with AAV-sgRNA targeting the gene of interest. The top 10 most frequent variants were shown, with the associated variant frequencies in the box to the right (SEQ ID NOs: 140,864-140,896). FIG. 26E shows FACS analysis of Dhx37 knockout. Top, CD107a degranulation assay, where $CD8^+$ $T_{eff}$ cells with AAV-sgDhx37 transduction as compared to vector control showed significant upregulation of surface CD107a (p=0.001). Bottom, $CD8^+$ $T_{eff}$ cells with AAV-sgDhx37 showed significant downregulation of surface CD62L level. Data are shown as mean±s.e.m. Geometric means were shown for each individual data point. Data are also shown as group mean±s.e.m. FIG. 26F shows anti-tumor activity of AAV-CRISPR mediated Dhx37 knockout in $CD8^+$ $T_{eff}$ cells. Growth curves of mammary fatpad E0771-mCh-cOVA tumors in $Rag1^{-/-}$ mice following different treatments. PBS control (n=2), adoptive transfer of OT-I; Cas9 $CD8^+$ $T_{eff}$ cells infected with AAV-vector (n=4), and adoptive transfer of OT-I; Cas9 $CD8^+$ $T_{eff}$ cells infected with AAV-sgDhx37 (n=5). Data are shown as mean±s.e.m. Purple arrow indicates the time of adoptive transfer of viral transduced OT-I; Cas9 $CD8^+$ $T_{eff}$ cells. PBS group mice were not treated and have large tumors early. The AAV-sgDhx37 group significantly reduced tumor burden as compared to AAV-vector indicating a Dhx37 knockout specific effect.

FIGS. 27A-27F are a series of plots and images illustrating molecular interrogation of gene regulation upon acute Dhx37 loss in $CD8^+$ $T_{eff}$ cells. FIG. 27A shows t-SNE dimensional reduction and visualization of single cell transcriptomics of individual OT-I; Cas9 $CD8^+$ $T_{eff}$ cells 6 days after transduction with AAV, colored by experiment groups, i.e. AAV-sgDhx37 or AAV-sgNTC. FIG. 27B shows t-SNE dimensional reduction and visualization of single cell transcriptomics of individual OT-I; Cas9 $CD8^+$ $T_{eff}$ cells 6 days after transduction with AAV, colored by clusters. A total of 6 major clusters were identified as subpopulation of these T cells. FIG. 27C shows cluster-specific population differences between AAV-sgDhx37 or AAV-sgNTC. AAV-sgDhx37 group has more cells in cluster 2, but fewer cells grouped to clusters 4 and 6. FIG. 27D shows gene expression signature of all cells across all 6 major clusters, showing cluster-specific markers for these individual OT-I; Cas9 $CD8^+$ $T_{eff}$ cells. FIG. 27E shows cluster-specific gene regulation between AAV-sgDhx37 or AAV-sgNTC. Top upregulated and downregulated genes upon acute Dhx37 loss by AAV-sgDhx37 transduction were shown for each cluster (k1 to k6). Ccl5 was found to be upregulated across all clusters, while certain genes were found to be differentially upregulated only in specific clusters (e.g. Rgs2 in k1, k2 and k4; Lag3 in k5 and k6, Ifng in k3 only). Rpl35 was found to be downregulated across most clusters (except k4), while certain genes were found to be differentially downregulated only in specific clusters (e.g. Rps29 in k2, k3, k5 and k6; Npm3 in k5 and k6, Ly6c2 in k6 only). FIG. 27F shows violin plots with all data points for mRNA level in individual cells for the most-prevalently differentially up-regulated (Ccl5) and down-regulated (Rpl35) genes upon acute Dhx37 loss by AAV-CRISPR transduction, in each of the 6 major clusters (k1 to k6). For all comparisons between Dhx37 and control group, FDR adjusted p value$<$0.05, in all clusters for Ccl5, and in all clusters except k4 for Rpl35.

FIG. 28A shows cluster-specific differentially expressed genes upon acute Dhx37 loss by AAV-CRISPR transduction. Violin plots with all data points of representative genes in each of the 6 major clusters (k1 to k6) were shown. For all comparisons between Dhx37 and control group, FDR adjusted p value$<$0.05, in all clusters. FIG. 28B shows gene ontology analysis of significantly upregulated genes upon acute Dhx37 loss by AAV-sgDhx37 mediated knockout in $CD8^+$ T cells. Top biological processes were found to be immune related, including inflammatory response, immune response, negative regulation of apoptosis, endopeptidase, immunoglobulin secretion, response to glucose stimulus and T cell co-stimulation. FIG. 28C is a Venn diagram showing the overlap of differentially regulated genes upon Dhx37 loss by three different kinds of mechanisms, lenti-CRISPR mediated perturbation in mouse TILs, AAV-CRISPR mediated acute loss in culture, and naturally low-expression population in human T cells. A total of 24 genes (shown) were found to be significant across all three mechanisms.

DETAILED DESCRIPTION

Definitions

Figure 1A:
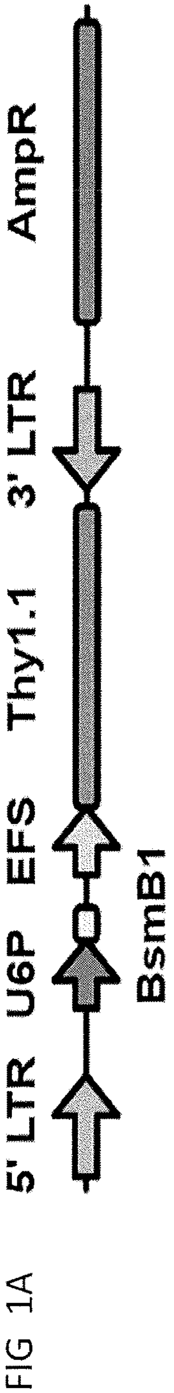
FIGS. 1A-1K are a series of plots and images depicting in vivo analysis of genome-scale CRISPR library mutagenized $CD8^+$ T cells after adoptive transfer into wildtype mice.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

An "adeno-associated virus" or "AAV" as used herein refers to a small non-enveloped virus which infects humans and other primates but does not cause disease. AAV can infect dividing and quiescent cells and exists in an extrachromosomal state without integrating into the host genome. AAVs can be used as vectors for gene delivery to host cells.

As used herein the term "amount" refers to the abundance or quantity of a constituent in a mixture.

As used herein, the term "bp" refers to base pair.

The term "complementary" refers to the degree of anti-parallel alignment between two nucleic acid strands. Complete complementarity requires that each nucleotide be across from its opposite. No complementarity requires that each nucleotide is not across from its opposite. The degree of complementarity determines the stability of the sequences to be together or anneal/hybridize. Furthermore various DNA repair functions as well as regulatory functions are based on base pair complementarity.

The term "CRISPR/Cas" or "clustered regularly interspaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR—associated (Cas) systems that use short RNA to direct degradation of foreign nucleic acids. In bacteria, the CRISPR system provides acquired immunity against invading foreign DNA via. RNA-guided DNA cleavage.

The "CRISPR/Cas9" system or "CRISPR/Cas9-mediated gene editing" refers to a type II CRISPR/Cas system that has been modified for genome editing/engineering. It is typically comprised of a "guide" RNA (gRNA) and a non-specific CRISPR-associated endonuclease (Cas9). "Guide RNA (gRNA)" is used interchangeably herein with "short guide RNA (sgRNA)" or "single guide RNA" (sgRNA). The sgRNA is a short synthetic RNA composed of a "scaffold" sequence necessary for Cas9-binding and a user-defined ~20 nucleotide "spacer" or "targeting" sequence which defines the genomic target to be modified. The genomic target of Cas9 can be changed by changing the targeting sequence present in the sgRNA.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded. cleavage are possible. Double-stranded cleavage can occur as a result of two distinct single-stranded cleavage events. DNA cleavage can result in the production of either blunt ends or staggered ends. In certain embodiments, fusion polypeptides can be used for targeting cleaved double-stranded DNA.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A "mutation" as used herein is a change in a DNA sequence resulting in an alteration from a given reference sequence (which may be, for example, an earlier collected DNA sample from the same subject). The mutation can comprise deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism (subject).

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

A "sample" or "biological sample" as used herein means a biological material from a subject, including but is not limited to organ, tissue, exosome, blood, plasma, saliva, urine and other body fluid. A sample can be any source of material obtained from a subject.

As used herein, the terms "sequencing" or "nucleotide sequencing" refer to determining the order of nucleotides (base sequences) in a nucleic acid sample, e.g. DNA or RNA. Many techniques are available such as Sanger sequencing and high-throughput sequencing technologies (also known as next-generation sequencing technologies) such as Illumina's HiSeq and MiSeq platforms or the GS FLX platform offered by Roche Applied Science.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains, TCRs may exist in α/β and γ/δ forms, which are structurally similar but have distinct anatomical locations and functions. Each chain is composed of two extracellular domains, a variable and constant domain. In some embodiments, the TCR can be modified on any cell comprising a TCR, including, for example, a helper T cell, a cytotoxic cell, a memory T cell, regulatory cell, natural killer T cell, and/or gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides in one aspect compositions and methods for genome-scale editing and screening of T cells. In certain embodiments, the invention provides an sgRNA library for genome-scale mutagenesis of T cells in vitro and/or in vivo. In other embodiments, the invention provides a vector system (comprising a multitude of vectors) enabling multiplexed genome editing in T lymphocytes (T cells), and simultaneously isolate or enrich edited T cells using a surrogate/affinity marker. In yet other embodiments, the invention provides a vector system (comprising a multitude of vectors) enabling expression of model antigens in cancer cells as immunotherapy models. In yet other embodiments, the invention provides a method for high-throughput genetic interrogation of CD8+ T cells in vitro and/or in vivo.

$CD8^+$ T cells are fundamental to the adaptive immune response against intracellular pathogens and tumors. Recent clinical advancements have converged on the theme that $CD8^+$ T cells play a central role in the cancer-immune cycle. Identification of genes modulating T cell function, such as the discovery of the PD-1 gene based on differential gene expression, the anti-tumor effect mediated by CTLA-4 inhibition in mouse model, and many subsequent studies, led to the immunotherapeutic paradigm of checkpoint blockade. Immunotherapy has revolutionized cancer treatments, making late-stage metastatic cancer no longer a death sentence for a fraction of patients suffering from certain cancer types, most pronounced in melanoma and lung cancer. Thus, discovering novel genes in T cells is key to the development of new and more effective cancer therapeutics. Classical genetic studies have further identified individual genes such as 4-1BB, CD27, CD28, ICOS, LAG3, OX-40, TIM3, and VISTA as potential targets for checkpoint modulation. However, an unbiased, global view of genes modulating T cell phenotypes in cancer immunity is lacking, partly due to the technological challenges in performing high-throughput screens in T cells in vivo. Therapeutic targets with the potential to enhance $CD8^+$ T cell function are actively being pursued in pharmaceutical development and the clinic, leading to a new boom of clinical trials testing new checkpoint blockade antibodies and compounds either as monotherapy or in various combinations. Of note, the first-in-human genome editing clinical trials have debut with CRISPR-edited $CD8^+$ T cells infused into cancer patients by adoptive transfer.

The present study uncovered certain genes for T cell trafficking and survival in vivo after adoptive transfer. These new insights can directly influence the conceptualization of new targets for enhancement of chimeric antigen receptor (CAR-T), checkpoint blockade, or combinatorial immunotherapy.

In the present study described herein, a T cell CRISPR knockout vector was generated and a genome-scale knockout library was cloned. The system was utilized to perform two high-throughput genetic screens in $CD8^+$ cytotoxic T cells isolated from both wildtype and TCR-transgenic mice. By adoptively transferring the mutagenized cells into host mice, these screens yielded a global quantitative measurement of the relative abundance of mutant T cells within several lymphoid and non-lymphoid organs in mice. SgRNA enrichment analysis identified various previously undocumented targets that directly influence $CD8^+$ T cell function in vivo upon CRISPR perturbation.

Compositions

In one aspect, the invention includes a vector comprising a 5' long terminal repeat (LTR) sequence, a U6 promoter sequence, a BsmBI restriction site, an EFS sequence or PGK constitutive promoter, an sgRNA expression cassette, a Thy1.1 cassette, a 3' LTR sequence and an ampicillin resistance gene sequence (AmpR). In one embodiment, the vector comprises SEQ ID NO:129,213 (pSC017pLKO-U6-sgBsmBI-EFS-Thy11CO-spA). In another embodiment, the vector comprises SEQ ID NO:129,214. In yet another embodiment, the vector comprises SEQ ID NO:129,215. In certain embodiments, the vector can comprise additional components, such as but not limited to artificial selection markers, fluorescent proteins or a second U6-sgRNA cassette. In certain embodiments, vectors of the present invention enable robust genome editing in T cells.

In another aspect, the invention includes a vector comprising a 5' long terminal repeat (LTR) sequence, a U6 promoter sequence, a BsmB1 restriction site, an EFS sequence, an sgRNA expression cassette, an mCherry sequence, a 2A peptide, a cOVA sequence, a 3' LTR sequence and an ampicillin resistance gene sequence (AmpR). In certain embodiments, this vector enables expression of a model antigen (cOVA) for TCR recognition with transgenic OT-I (CD8+) and OT-II (CD4+) T cells. In one embodiment, this vector comprises SEQ ID NO: 129,216 (pMD02: lenti-pLKO-U6-sgBsmBI-EFS-mCherry-2A-cOVA).

In another aspect, the invention includes an sgRNA library. The library comprises a plurality of vectors, wherein each vector comprises an expression cassette for an sgRNA comprising a nucleotide sequence selected from the group consisting of SEQ ID NOs: 1-129,209. In certain embodiments, each of the plurality of vectors in the sgRNA library comprise a 5' long terminal repeat (LTR) sequence, a U6 promoter sequence, a BsmB1 restriction site, an EFS sequence, an sgRNA expression cassette, a Thy1.1 cassette, a 3' LTR sequence and an ampicillin resistance gene sequence (AmpR).

The invention also provides a kit comprising an sgRNA library. The sgRNA library comprises a plurality of vectors, wherein each vector comprises an expression cassette for an sgRNA comprising a nucleotide sequence selected from the group consisting of SEQ ID NOs: 1-129,209. In certain embodiments, the plurality of vectors comprise a 5' long terminal repeat (LTR) sequence, a U6 promoter sequence, a BsmB1 restriction site, an EFS sequence, an sgRNA expression cassette, a Thy1.1 cassette, a 3' LTR sequence and an ampicillin resistance gene sequence (AmpR). Included in the kits are instructional materials for use thereof. Instructional material can include directions for using the components of the kit as well as instructions or guidance for interpreting the results.

The invention also provides a vector comprising a 5' inverted terminal repeat (ITR) sequence, a U6 promoter sequence, a BbsI restriction site, an sgRNA expression cassette, an EFS sequence, a SB100x cassette, a 3' ITR sequence and an ampicillin resistance gene sequence (AmpR). In one embodiment, the vector comprises SEQ ID NO: 129,217.

```
pLY005SB_pAAV-U6sg(BbsI)-EFS-SB100X
                                                    (SEQ ID NO: 129,217)
   1 cctgcaggca gctgcgcgct cgctcgctca ctgaggccgc ccgggcaaag cccgggcgtc

  61 gggcgacctt tggtcgcccg gcctcagtga gcgagcgagc gcgcagagag ggagtggcca

 121 actccatcac taggggttcc tgcggccgca cgcgttctag actatacagt tgaagtcgga

 181 agtttacata cacttaagtt ggagtcatta aaactcgttt ttcaactact ccacaaattt

 241 cttgttaaca aacaatagtt ttggcaagtc agttaggaca tctactttgt gcatgacaca

 301 agtcattttt ccaacaattg tttacagaca gattatttca cttataattc actgtatcac

 361 aattccagtg ggtcagaagt ttacatacac taagttgact gtgcctttaa acagcttgga

 421 aaattccaga aaatgatgtc atggctttag agaggatccg agggcctatt tcccatgatt

 481 ccttcatatt tgcatatacg atacaaggct gttagagaga taattagaat taatttgact

 541 gtaaacacaa agatattagt acaaaatacg tgacgtagaa agtaataatt tcttgggtag

 601 tttgcagttt taaaattatg ttttaaaatg gactatcata tgcttaccgt aacttgaaag

 661 tatttcgatt tcttggcttt atatatcttg tggaaaggac gaaacaccgg gtcttcgaga

 721 agacctgttt tagagctaga aatagcaagt taaaataagg ctagtccgtt atcaacttga

 781 aaaagtggca ccgagtcggt gctttttttgg ctagctggcc gcgtttaaac gtcgactagg

 841 tcttgaaagg agtgggaatt ggctccggtg cccgtcagtg ggcagagcgc acatcgccca

 901 cagtccccga gaagttgggg ggaggggtcg gcaattgatc cggtgcctag agaaggtggc

 961 gcggggtaaa ctgggaaagt gatgtcgtgt actggctccg cctttttccc gagggtgggg

1021 gagaaccgta tataagtgca gtagtcgccg tgaacgttct ttttcgcaac gggtttgccg

1081 ccagaacaca ggctcgagat gggaaaatca aaagaaatca gccaagacct cagaaaaaga

1141 attgtagacc tccacaagtc tggttcatcc ttgggagcaa tttccaaacg cctggcggta

1201 ccacgttcat ctgtacaaac aatagtacgc aagtataaac accatgggac cacgcagccg

1261 tcataccgct caggaaggag acgcgttctg tctcctagag atgaacgtac tttggtgcga

1321 aaagtgcaaa tcaatcccag aacaacagca aaggaccttg tgaagatgct ggaggaaaca

1381 ggtacaaaag tatctatatc cacagtaaaa cgagtcctat atcgacataa cctgaaaggc

1441 cactcagcaa ggaagaagcc actgctccaa aaccgacata agaaagccag actacggttt

1501 gcaactgcac atggggacaa agatcgtact tttggagaa atgtcctctg gtctgatgaa

1561 acaaaaatag aactgtttgg ccataatgac catcgttatg tttggaggaa gaagggggag

1621 gcttgcaagc cgaagaacac catcccaacc gtgaagcacg gggggtggcag catcatgttg

1681 tgggggtgct ttgctgcagg agggactggt gcacttcaca aaatagatgg catcatggac

1741 gcggtgcagt atgtggatat attgaagcaa catctcaaga catcagtcag gaagttaaag

1801 cttggtcgca aatgggtttt ccaacacgac aatgacccca agcatacttc caaagttgtg

1861 gcaaaatggc ttaaggacaa caaagtcaag gtattggagt ggccatcaca aagccctgac

1921 ctcaatccta tagaaaattt gtgggcagaa ctgaaaaagc gtgtgcgagc aaggaggcct

1981 acaaacctga ctcagttaca ccagctctgt caggaggaat gggccaaaat tcacccaaat

2041 tattgtggga agcttgtgga aggctacccg aaacgtttga cccaagttaa acaatttaaa

2101 ggcaatgcta ccaaatacta ggggccctaa ccgcgggaat aaaagatctt tattttcatt
```

-continued 2161 agatctgtgt gttggttttt tgtgtgaatt cttgagtgta tgtaaacttc tgacccactg 2221 ggaatgtgat gaaagaaata aaagctgaaa tgaatcattc tctctactat tattctgata 2281 tttcacattc ttaaaataaa gtggtgatcc taactgacct aagacaggga atttttacta 2341 ggattaaatg tcaggaattg tgaaaaagtg agtttaaatg tatttggcta aggtgtatgt 2401 aaacttccga cttcaactgt ataggcatgc ggtaaccacg tgcggaccga gcggccgcag 2461 gaacccctag tgatggagtt ggccactccc tctctgcgcg ctcgctcgct cactgaggcc 2521 gggcgaccaa aggtcgcccg acgcccgggc tttgcccggg cggcctcagt gagcgagcga 2581 gcgcgcagct gcctgcaggg gcgcctgatg cggtattttc tccttacgca tctgtgcggt 2641 atttcacacc gcatacgtca aagcaaccat agtacgcgcc ctgtagcggc gcattaagcg 2701 cggcgggtgt ggtggttacg cgcagcgtga ccgctacact tgccagcgcc ctagcgcccg 2761 ctcctttcgc tttcttccct tcctttctcg ccacgttcgc cggctttccc cgtcaagctc 2821 taaatcgggg gctcccttta gggttccgat ttagtgcttt acggcacctc gaccccaaaa 2881 aacttgattt gggtgatggt tcacgtagtg ggccatcgcc ctgatagacg gtttttcgcc 2941 ctttgacgtt ggagtccacg ttctttaata gtggactctt gttccaaact ggaacaacac 3001 tcaaccctat ctcgggctat tcttttgatt tataagggat tttgccgatt tcggcctatt 3061 ggttaaaaaa tgagctgatt taacaaaaat ttaacgcgaa ttttaacaaa atattaacgt 3121 ttacaatttt atggtgcact ctcagtacaa tctgctctga tgccgcatag ttaagccagc 3181 cccgacaccc gccaacaccc gctgacgcgc cctgacgggc ttgtctgctc ccggcatccg 3241 cttacagaca agctgtgacc gtctccggga gctgcatgtg tcagaggttt tcaccgtcat 3301 caccgaaacg cgcgagacga aagggcctcg tgatacgcct atttttatag gttaatgtca 3361 tgataataat ggtttcttag acgtcaggtg gcacttttcg gggaaatgtg cgcggaaccc 3421 ctatttgttt atttttctaa atacattcaa atatgtatcc gctcatgaga caataaccct 3481 gataaatgct tcaataatat tgaaaaagga agagtatgag tattcaacat ttccgtgtcg 3541 cccttattcc cttttttgcg gcattttgcc ttcctgtttt tgctcaccca gaaacgctgg 3601 tgaaagtaaa agatgctgaa gatcagttgg gtgcacgagt gggttacatc gaactggatc 3661 tcaacagcgg taagatcctt gagagttttc gccccgaaga acgttttcca atgatgagca 3721 cttttaaagt tctgctatgt ggcgcggtat tatcccgtat tgacgccggg caagagcaac 3781 tcggtcgccg catacactat tctcagaatg acttggttga gtactcacca gtcacagaaa 3841 agcatcttac ggatggcatg acagtaagag aattatgcag tgctgccata accatgagtg 3901 ataacactgc ggccaactta cttctgacaa cgatcggagg accgaaggag ctaaccgctt 3961 ttttgcacaa catgggggat catgtaactc gccttgatcg ttgggaaccg gagctgaatg 4021 aagccatacc aaacgacgag cgtgacacca cgatgcctgt agcaatggca acaacgttgc 4081 gcaaactatt aactggcgaa ctacttactc tagcttcccg gcaacaatta atagactgga 4141 tggaggcgga taaagttgca ggaccacttc tgcgctcggc ccttccggct ggctggttta 4201 ttgctgataa atctggagcc ggtgagcgtg ggtctcgcgg tatcattgca gcactggggc 4261 cagatggtaa gccctcccgt atcgtagtta tctacacgac ggggagtcag gcaactatgg 4321 atgaacgaaa tagacagatc gctgagatag gtgcctcact gattaagcat tggtaactgt 4381 cagaccaagt ttactcatat atactttaga ttgatttaaa acttcatttt taatttaaaa 4441 ggatctaggt gaagatcctt tttgataatc tcatgaccaa aatcccttaa cgtgagtttt 4501 cgttccactg agcgtcagac cccgtagaaa agatcaaagg atcttcttga gatccttttt 4561 ttctgcgcgt aatctgctgc ttgcaaacaa aaaaaccacc gctaccagcg gtggtttgtt -continued

```
4621 tgccggatca agagctacca actctttttc cgaaggtaac tggcttcagc agagcgcaga
4681 taccaaatac tgtccttcta gtgtagccgt agttaggcca ccacttcaag aactctgtag
4741 caccgcctac atacctcgct ctgctaatcc tgttaccagt ggctgctgcc agtggcgata
4801 agtcgtgtct taccgggttg gactcaagac gatagttacc ggataaggcg cagcggtcgg
4861 gctgaacggg gggttcgtgc acacagccca gcttggagcg aacgacctac accgaactga
4921 gatacctaca gcgtgagcta tgagaaagcg ccacgcttcc cgaagggaga aaggcggaca
4981 ggtatccggt aagcggcagg gtcggaacag gagagcgcac gagggagctt ccagggggaa
5041 acgcctggta tctttatagt cctgtcgggt ttcgccacct ctgacttgag cgtcgatttt
5101 tgtgatgctc gtcagggggg cggagcctat ggaaaaacgc cagcaacgcg gcctttttac
5161 ggttcctggc cttttgctgg ccttttgctc acatgt
```

In another aspect, the invention provides a vector comprising a 5' inverted terminal repeat (ITR) sequence, a U6 promoter sequence, a BbsI restriction site, an sgRNA expression cassette, an EFS sequence, a SB100x cassette, a Thy1.1 cassette, a 3' ITR sequence and an ampicillin resistance gene sequence (AmpR). In one embodiment, the vector comprises SEQ ID NO: 129,218.

```
pLY017SB_pAAV-U6sg(BbsI)-EFS-Thy1
                                                   (SEQ ID NO: 129,218)
   1 cctgcaggca gctgcgcgct cgctcgctca ctgaggccgc ccgggcaaag cccgggcgtc
  61 gggcgacctt tggtcgcccg gcctcagtga gcgagcgagc gcgcagagag ggagtggcca
 121 actccatcac taggggttcc tgcggccgca cgcgttctag actatacagt tgaagtcgga
 181 agtttacata cacttaagtt ggagtcatta aaactcgttt ttcaactact ccacaaattt
 241 cttgttaaca aacaatagtt ttggcaagtc agttaggaca tctactttgt gcatgacaca
 301 agtcattttt ccaacaattg tttacagaca gattatttca cttataattc actgtatcac
 361 aattccagtg ggtcagaagt ttacatacac taagttgact gtgcctttaa acagcttgga
 421 aaattccaga aaatgatgtc atggctttag agaggatccg agggcctatt tcccatgatt
 481 ccttcatatt tgcatatacg atacaaggct gttagagaga taattagaat taatttgact
 541 gtaaacacaa agatattagt acaaaatacg tgacgtagaa agtaataatt tcttgggtag
 601 tttgcagttt taaaattatg ttttaaaatg gactatcata tgcttaccgt aacttgaaag
 661 tatttcgatt tcttggcttt atatatcttg tggaaaggac gaaacaccgg gtcttcgaga
 721 agacctgttt tagagctaga aatagcaagt taaaataagg ctagtccgtt atcaacttga
 781 aaaagtggca ccgagtcggt gctttttttgg ctagctggcc gcgtttaaac gtcgactagg
 841 tcttgaaagg agtgggaatt ggctccggtg cccgtcagtg ggcagagcgc acatcgccca
 901 cagtccccga gaagttgggg ggaggggtcg gcaattgatc cggtgcctag agaaggtggc
 961 gcggggtaaa ctgggaaagt gatgtcgtgt actggctccg cctttttccc gagggtgggg
1021 gagaaccgta tataagtgca gtagtcgccg tgaacgttct ttttcgcaac gggtttgccg
1081 ccagaacaca ggctcgagat gaacccagcc atcagcgtcg ctctcctgct ctcagtcttg
1141 caggtgtccc gagggcagaa ggtgaccagc ctgacagcct gcctggtgaa ccaaaacctt
1201 cgcctggact gccgccatga gaataacacc aaggataact ccatccagca tgagttcagc
1261 ctgacccgag agaagaggaa gcacgtgctc tcaggcaccc ttgggatacc cgagcacacg
1321 taccgctccc gcgtcaccct ctccaaccag ccctatatca aggtccttac cctagccaac
```

-continued 1381 ttcaccacca aggatgaggg cgactacttt tgtgagcttc gcgtgtcggg cgcgaatccc 1441 atgagctcca ataaaagtat cagtgtgtat agagacaagc tggtcaagtg tggcggcata 1501 agcctgctgg ttcagaacac atcctggatg ctgctgctgc tgctttccct ctccctcctc 1561 caagccctgg acttcatttc tctgggcagt ggagagggca gaggaagtct gctaacatgc 1621 ggtgacgtcg aggagaatcc tggcccaatg ggaaaatcaa aagaaatcag ccaagacctc 1681 agaaaaagaa ttgtagacct ccacaagtct ggttcatcct tgggagcaat ttccaaacgc 1741 ctggcggtac cacgttcatc tgtacaaaca atagtacgca agtataaaca ccatgggacc 1801 acgcagccgt cataccgctc aggaaggaga cgcgttctgt ctcctagaga tgaacgtact 1861 ttggtgcgaa aagtgcaaat caatcccaga acaacagcaa aggaccttgt gaagatgctg 1921 gaggaaacag gtacaaaagt atctatatcc acagtaaaac gagtcctata tcgacataac 1981 ctgaaaggcc actcagcaag gaagaagcca ctgctccaaa accgacataa gaaagccaga 2041 ctacggtttg caactgcaca tggggacaaa gatcgtactt tttggagaaa tgtcctctgg 2101 tctgatgaaa caaaaataga actgtttggc cataatgacc atcgttatgt ttggaggaag 2161 aaggggagg cttgcaagcc gaagaacacc atcccaaccg tgaagcacgg gggtggcagc 2221 atcatgttgt gggggtgctt tgctgcagga gggactggtg cacttcacaa aatagatggc 2281 atcatggacg cggtgcagta tgtggatata ttgaagcaac atctcaagac atcagtcagg 2341 aagttaaagc ttggtcgcaa atgggtttc caacacgaca atgaccccaa gcatacttcc 2401 aaagttgtgg caaaatggct taaggacaac aaagtcaagg tattggagtg gccatcacaa 2461 agccctgacc tcaatcctat agaaaatttg tgggcagaac tgaaaaagcg tgtgcgagca 2521 aggaggccta caaacctgac tcagttacac cagctctgtc aggaggaatg ggccaaaatt 2581 cacccaaatt attgtgggaa gcttgtggaa ggctacccga aacgtttgac ccaagttaaa 2641 caatttaaag gcaatgctac caaatactag ggccctaac cgcgggaata aaagatcttt 2701 attttcatta gatctgtgtg ttggtttttt gtgtgaattc ttgagtgtat gtaaacttct 2761 gacccactgg gaatgtgatg aaagaaataa aagctgaaat gaatcattct ctctactatt 2821 attctgatat ttcacattct taaaataaag tggtgatcct aactgaccta agacagggaa 2881 tttttactag gattaaatgt caggaattgt gaaaaagtga gtttaaatgt atttggctaa 2941 ggtgtatgta aacttccgac ttcaactgta taggcatgcg gtaaccacgt gcggaccgag 3001 cggccgcagg aacccctagt gatggagttg gccactccct ctctgcgcgc tcgctcgctc 3061 actgaggccg ggcgaccaaa ggtcgcccga cgcccgggct ttgcccgggc ggcctcagtg 3121 agcgagcgag cgcgcagctg cctgcagggg cgcctgatgc ggtattttct ccttacgcat 3181 ctgtgcggta tttcacaccg catacgtcaa agcaaccata gtacgcgccc tgtagcggcg 3241 cattaagcgc ggcgggtgtg gtggttacgc gcagcgtgac cgctacactt gccagcgccc 3301 tagcgcccgc tcctttcgct ttcttccctt cctttctcgc cacgttcgcc ggctttcccc 3361 gtcaagctct aaatcggggg ctccctttag ggttccgatt tagtgcttta cggcacctcg 3421 accccaaaaa acttgatttg ggtgatggtt cacgtagtgg gccatcgccc tgatagacgg 3481 tttttcgccc tttgacgttg gagtccacgt tctttaatag tggactcttg ttccaaactg 3541 gaacaacact caaccctatc tcgggctatt cttttgattt ataagggatt ttgccgattt 3601 cggcctattg gttaaaaaat gagctgattt aacaaaaatt taacgcgaat tttaacaaaa 3661 tattaacgtt tacaatttta tggtgcactc tcagtacaat ctgctctgat gccgcatagt 3721 taagccagcc ccgacacccg ccaacacccg ctgacgcgcc ctgacgggct tgtctgctcc 3781 cggcatccgc ttacagacaa gctgtgaccg tctccgggag ctgcatgtgt cagaggifit -continued

```
3841 caccgtcatc accgaaacgc gcgagacgaa agggcctcgt gatacgccta tttttatagg
3901 ttaatgtcat gataataatg gtttcttaga cgtcaggtgg cacttttcgg ggaaatgtgc
3961 gcggaacccc tatttgttta tttttctaaa tacattcaaa tatgtatccg ctcatgagac
4021 aataaccctg ataaatgctt caataatatt gaaaaaggaa gagtatgagt attcaacatt
4081 tccgtgtcgc ccttattccc ttttttgcgg cattttgcct tcctgttttt gctcacccag
4141 aaacgctggt gaaagtaaaa gatgctgaag atcagttggg tgcacgagtg ggttacatcg
4201 aactggatct caacagcggt aagatccttg agagttttcg ccccgaagaa cgttttccaa
4261 tgatgagcac ttttaaagtt ctgctatgtg gcgcggtatt atcccgtatt gacgccgggc
4321 aagagcaact cggtcgccgc atacactatt ctcagaatga cttggttgag tactcaccag
4381 tcacagaaaa gcatcttacg gatggcatga cagtaagaga attatgcagt gctgccataa
4441 ccatgagtga taacactgcg gccaacttac ttctgacaac gatcggagga ccgaaggagc
4501 taaccgcttt tttgcacaac atgggggatc atgtaactcg ccttgatcgt tgggaaccgg
4561 agctgaatga agccatacca aacgacgagc gtgacaccac gatgcctgta gcaatggcaa
4621 caacgttgcg caaactatta actggcgaac tacttactct agcttcccgg caacaattaa
4681 tagactggat ggaggcggat aaagttgcag gaccacttct gcgctcggcc cttccggctg
4741 gctggtttat tgctgataaa tctggagccg gtgagcgtgg gtctcgcggt atcattgcag
4801 cactggggcc agatggtaag ccctcccgta tcgtagttat ctacacgacg gggagtcagg
4861 caactatgga tgaacgaaat agacagatcg ctgagatagg tgcctcactg attaagcatt
4921 ggtaactgtc agaccaagtt tactcatata tactttagat tgatttaaaa cttcattttt
4981 aatttaaaag gatctaggtg aagatccttt ttgataatct catgaccaaa atcccttaac
5041 gtgagttttc gttccactga gcgtcagacc ccgtagaaaa gatcaaagga tcttcttgag
5101 atcctttttt tctgcgcgta atctgctgct tgcaaacaaa aaaaccaccg ctaccagcgg
5161 tggtttgttt gccggatcaa gagctaccaa ctctttttcc gaaggtaact ggcttcagca
5221 gagcgcagat accaaatact gtccttctag tgtagccgta gttaggccac cacttcaaga
5281 actctgtagc accgcctaca tacctcgctc tgctaatcct gttaccagtg gctgctgcca
5341 gtggcgataa gtcgtgtctt accgggttgg actcaagacg atagttaccg gataaggcgc
5401 agcggtcggg ctgaacgggg ggttcgtgca cacagcccag cttggagcga acgacctaca
5461 ccgaactgag atacctacag cgtgagctat gagaaagcgc cacgcttccc gaagggagaa
5521 aggcggacag gtatccggta agcggcaggg tcggaacagg agagcgcacg agggagcttc
5581 caggggggaaa cgcctggtat ctttatagtc ctgtcgggtt tcgccacctc tgacttgagc
5641 gtcgattttt gtgatgctcg tcaggggggc ggagcctatg gaaaaacgcc agcaacgcgg
5701 cctttttacg gttcctggcc ttttgctggc cttttgctca catgt
```

In another aspect, the invention provides a vector comprising a 5' inverted terminal repeat (ITR) sequence, a U6 promoter sequence, a BbsI restriction site, an sgRNA expression cassette, a 3' ITR sequence and an ampicillin resistance gene sequence (AmpR). In one embodiment, the vector comprises SEQ ID NO: 129,219.

pSC026b_pAAV-U6sgbbSapI-XD011bb (SEQ ID NO: 129,219)

```
  1 cctgcaggca gctgcgcgct cgctcgctca ctgaggccgc ccgggcaaag cccgggcgtc
 61 gggcgacctt tggtcgcccg gcctcagtga gcgagcgagc gcgcagagag ggagtggcca
121 actccatcac taggggttcc tgcggccgca cgcgttctag aagagggcct atttcccatg
181 attccttcat atttgcatat acgatacaag gctgttagag agataattgg aattaatttg
```

-continued 241 actgtaaaca caaagatatt agtacaaaat acgtgacgta gaaagtaata atttcttggg
301 tagtttgcag ttttaaaatt atgttttaaa atggactatc atatgcttac cgtaacttga
361 aagtatttcg atttcttggc tttatatatc ttGTGGAAAG GACGAAACAC Cggaagagcg
421 agctcttctg ttttagagct aGAAAtagca agttaaaata aggctagtcc gttatcaact
481 tgaaaaagtg gcaccgagtc ggtgcTTTTT Tggtaccgtg cggaccgagc ggccgcagga
541 acccctagtg atggagttgg ccactccctc tctgcgcgct cgctcgctca ctgaggccgg
601 gcgaccaaag gtcgcccgac gcccgggctt tgcccgggcg gcctcagtga gcgagcgagc
661 gcgcagctgc ctgcaggggc gcctgatgcg gtattttctc cttacgcatc tgtgcggtat
721 ttcacaccgc atacgtcaaa gcaaccatag tacgcgccct gtagcggcgc attaagcgcg
781 gcgggtgtgg tggttacgcg cagcgtgacc gctacacttg ccagcgccct agcgcccgct
841 cctttcgctt tcttcccttc ctttctcgcc acgttcgccg gctttccccg tcaagctcta
901 aatcgggggc tccctttagg gttccgattt agtgctttac ggcacctcga ccccaaaaaa
961 cttgatttgg gtgatggttc acgtagtggg ccatcgccct gatagacggt ttttcgccct
1021 ttgacgttgg agtccacgtt ctttaatagt ggactcttgt tccaaactgg aacaacactc
1081 aaccctatct cgggctattc ttttgattta taagggattt tgccgatttc ggcctattgg
1141 ttaaaaaatg agctgattta acaaaaattt aacgcgaatt ttaacaaaat attaacgttt
1201 acaattttat ggtgcactct cagtacaatc tgctctgatg ccgcatagtt aagccagccc
1261 cgacacccgc caacacccgc tgacgcgccc tgacgggctt gtctgctccc ggcatccgct
1321 tacagacaag ctgtgaccgt ctccgggagc tgcatgtgtc agaggttttc accgtcatca
1381 ccgaaacgcg cgagacgaaa gggcctcgtg atacgcctat ttttataggt taatgtcatg
1441 ataataatgg tttcttagac gtcaggtggc acttttcggg gaaatgtgcg cggaacccct
1501 atttgtttat ttttctaaat acattcaaat atgtatccgc tcatgagaca ataaccctga
1561 taaatgcttc aataatattg aaaaaggaag agtatgagta ttcaacattt ccgtgtcgcc
1621 cttattccct tttttgcggc attttgcctt cctgtttttg ctcacccaga aacgctggtg
1681 aaagtaaaag atgctgaaga tcagttgggt gcacgagtgg gttacatcga actggatctc
1741 aacagcggta agatccttga gagttttcgc cccgaagaac gttttccaat gatgagcact
1801 tttaaagttc tgctatgtgg cgcggtatta tcccgtattg acgccgggca agagcaactc
1861 ggtcgccgca tacactattc tcagaatgac ttggttgagt actcaccagt cacagaaaag
1921 catcttacgg atggcatgac agtaagagaa ttatgcagtg ctgccataac catgagtgat
1981 aacactgcgg ccaacttact tctgacaacg atcggaggac cgaaggagct aaccgctttt
2041 ttgcacaaca tgggggatca tgtaactcgc cttgatcgtt gggaaccgga gctgaatgaa
2101 gccataccaa acgacgagcg tgacaccacg atgcctgtag caatggcaac aacgttgcgc
2161 aaactattaa ctggcgaact acttactcta gcttcccggc aacaattaat agactggatg
2221 gaggcggata aagttgcagg accacttctg cgctcggccc ttccggctgg ctggtttatt
2281 gctgataaat ctggagccgg tgagcgtggg tctcgcggta tcattgcagc actggggcca
2341 gatggtaagc cctcccgtat cgtagttatc tacacgacgg ggagtcaggc aactatggat
2401 gaacgaaata gacagatcgc tgagataggt gcctcactga ttaagcattg gtaactgtca
2461 gaccaagttt actcatatat actttagatt gatttaaaac ttcattttta atttaaaagg
2521 atctaggtga agatcctttt tgataatctc atgaccaaaa tcccttaacg tgagttttcg
2581 ttccactgag cgtcagaccc cgtagaaaag atcaaaggat cttcttgaga tectifittt -continued 2641 ctgcgcgtaa tctgctgctt gcaaacaaaa aaaccaccgc taccagcggt ggtttgtttg 2701 ccggatcaag agctaccaac tctifitccg aaggtaactg gcttcagcag agcgcagata 2761 ccaaatactg tccttctagt gtagccgtag ttaggccacc acttcaagaa ctctgtagca 2821 ccgcctacat acctcgctct gctaatcctg ttaccagtgg ctgctgccag tggcgataag 2881 tcgtgtctta ccgggttgga ctcaagacga tagttaccgg ataaggcgca gcggtcgggc 2941 tgaacggggg gttcgtgcac acagcccagc ttggagcgaa cgacctacac cgaactgaga 3001 tacctacagc gtgagctatg agaaagcgcc acgcttcccg aagggagaaa ggcggacagg 3061 tatccggtaa gcggcagggt cggaacagga gagcgcacga gggagcttcc agggggaaac 3121 gcctggtatc tttatagtcc tgtcgggttt cgccacctct gacttgagcg tcgatttttg 3181 tgatgctcgt caggggggcg gagcctatgg aaaaacgcca gcaacgcggc ctttttacgg 3241 ttcctggcct tttgctggcc ttttgctcac atgt In another aspect, the invention provides a vector comprising a 5' inverted terminal repeat (ITR) sequence, a U6 promoter sequence, a BbsI restriction site, an sgRNA expression cassette, an EFS sequence, a Thy1.1 cassette, a 3' ITR sequence and an ampicillin resistance gene sequence (AmpR). In one embodiment, the vector comprises SEQ ID NO: 129,220.

pSC025d_pAAV-U6sgbbSapI-EFS-Thy1

(SEQ ID NO: 129,220)

1 cctgcaggca gctgcgcgct cgctcgctca ctgaggccgc ccgggcaaag cccgggcgtc 61 gggcgacctt tggtcgcccg gcctcagtga gcgagcgagc gcgcagagag ggagtggcca 121 actccatcac taggggttcc tgcggccgca cgcgttctag aagagggcct atttcccatg 181 attccttcat atttgcatat acgatacaag gctgttagag agataattgg aattaatttg 241 actgtaaaca caaagatatt agtacaaaat acgtgacgta gaaagtaata atttcttggg 301 tagtttgcag ttttaaaatt atgttttaaa atggactatc atatgcttac cgtaacttga 361 aagtatttcg atttcttggc tttatatatc ttgtggaaag gacgaaacac cggaagagcg 421 agctcttctg ttttagagct agaaatagca agttaaaata aggctagtcc gttatcaact 481 tgaaaaagtg gcaccgagtc ggtgcttttt tggtacctag gtcttgaaag gagtgggaat 541 tggctccggt gcccgtcagt gggcagagcg cacatcgccc acagtccccg agaagttggg 601 gggaggggtc ggcaattgat ccggtgccta gagaaggtgg cgcggggtaa actgggaaag 661 tgatgtcgtg tactggctcc gcctttttcc cgagggtggg ggagaaccgt atataagtgc 721 agtagtcgcc gtgaacgttc tttttcgcaa cgggtttgcc gccagaacac aggcaccggt 781 tctagacgta cggccaccat gaacccagcc atcagcgtcg ctctcctgct ctcagtcttg 841 caggtgtccc gagggcagaa ggtgaccagc ctgacagcct gcctggtgaa ccaaaacctt 901 cgcctggact gccgccatga gaataacacc aaggataact ccatccagca tgagttcagc 961 ctgacccgag agaagaggaa gcacgtgctc tcaggcaccc ttgggatacc cgagcacacg 1021 taccgctccc gcgtcaccct ctccaaccag ccctatatca aggtccttac cctagccaac 1081 ttcaccacca aggatgaggg cgactacttt tgtgagcttc gcgtaagtgg cgcgaatccc 1141 atgagctcca ataaaagtat cagtgtgtat agagacaagc tggtcaagtg tggcggcata 1201 agcctgctgg ttcagaacac atcctggatg ctgctgctgc tgetttccct ctccctcctc 1261 caagccctgg acttcatttc tctgtgaagc gcttaagaat tcgatatcaa gcttaataaa 1321 agatctttat tttcattaga tctgtgtgtt ggtttttttgt gtggtaacca cgtgcggacc -continued 1381 gagcggccgc aggaacccct agtgatggag ttggccactc cctctctgcg cgctcgctcg 1441 ctcactgagg ccgggcgacc aaaggtcgcc cgacgcccgg gctttgcccg ggcggcctca 1501 gtgagcgagc gagcgcgcag ctgcctgcag gggcgcctga tgcggtattt tctccttacg 1561 catctgtgcg gtatttcaca ccgcatacgt caaagcaacc atagtacgcg ccctgtagcg 1621 gcgcattaag cgcggcgggt gtggtggtta cgcgcagcgt gaccgctaca cttgccagcg 1681 ccctagcgcc cgctcctttc gctttcttcc cttcctttct cgccacgttc gccggctttc 1741 cccgtcaagc tctaaatcgg gggctccctt tagggttccg atttagtgct ttacggcacc 1801 tcgaccccaa aaaacttgat ttgggtgatg gttcacgtag tgggccatcg ccctgataga 1861 cggtttttcg ccctttgacg ttggagtcca cgttctttaa tagtggactc ttgttccaaa 1921 ctggaacaac actcaaccct atctcgggct attcttttga tttataaggg attttgccga 1981 tttcggccta ttggttaaaa aatgagctga tttaacaaaa atttaacgcg aattttaaca 2041 aaatattaac gtttacaatt ttatggtgca ctctcagtac aatctgctct gatgccgcat 2101 agttaagcca gccccgacac ccgccaacac ccgctgacgc gccctgacgg gcttgtctgc 2161 tcccggcatc cgcttacaga caagctgtga ccgtctccgg gagctgcatg tgtcagaggt 2221 tttcaccgtc atcaccgaaa cgcgcgagac gaaagggcct cgtgatacgc ctatttttat 2281 aggttaatgt catgataata atggtttctt agacgtcagg tggcactttt cggggaaatg 2341 tgcgcggaac ccctatttgt ttattifict aaatacattc aaatatgtat ccgctcatga 2401 gacaataacc ctgataaatg cttcaataat attgaaaaag gaagagtatg agtattcaac 2461 atttccgtgt cgcccttatt cccttttttg cggcattttg ccttcctgtt tttgctcacc 2521 cagaaacgct ggtgaaagta aaagatgctg aagatcagtt gggtgcacga gtgggttaca 2581 tcgaactgga tctcaacagc ggtaagatcc ttgagagttt tcgccccgaa gaacgttttc 2641 caatgatgag cacttttaaa gttctgctat gtggcgcggt attatcccgt attgacgccg 2701 ggcaagagca actcggtcgc cgcatacact attctcagaa tgacttggtt gagtactcac 2761 cagtcacaga aaagcatctt acggatggca tgacagtaag agaattatgc agtgctgcca 2821 taaccatgag tgataacact gcggccaact tacttctgac aacgatcgga ggaccgaagg 2881 agctaaccgc ttttttgcac aacatggggg atcatgtaac tcgccttgat cgttgggaac 2941 cggagctgaa tgaagccata ccaaacgacg agcgtgacac cacgatgcct gtagcaatgg 3001 caacaacgtt gcgcaaacta ttaactggcg aactacttac tctagcttcc cggcaacaat 3061 taatagactg gatggaggcg gataaagttg caggaccact tctgcgctcg gcccttccgg 3121 ctggctggtt tattgctgat aaatctggag ccggtgagcg tgggtctcgc ggtatcattg 3181 cagcactggg gccagatggt aagccctccc gtatcgtagt tatctacacg acggggagtc 3241 aggcaactat ggatgaacga aatagacaga tcgctgagat aggtgcctca ctgattaagc 3301 attggtaact gtcagaccaa gtttactcat atatacttta gattgattta aaacttcatt 3361 tttaatttaa aaggatctag gtgaagatcc tttttgataa tctcatgacc aaaatccctt 3421 aacgtgagtt ttcgttccac tgagcgtcag accccgtaga aaagatcaaa ggatcttctt 3481 gagatccttt ttttctgcgc gtaatctgct gcttgcaaac aaaaaaacca ccgctaccag 3541 cggtggtttg tttgccggat caagagctac caactctttt tccgaaggta actggcttca 3601 gcagagcgca gataccaaat actgtccttc tagtgtagcc gtagttaggc caccacttca 3661 agaactctgt agcaccgcct acatacctcg ctctgctaat cctgttacca gtggctgctg 3721 ccagtggcga taagtcgtgt cttaccgggt tggactcaag acgatagtta ccggataagg -continued

```
3781 cgcagcggtc gggctgaacg gggggttcgt gcacacagcc cagcttggag cgaacgacct
3841 acaccgaact gagataccta cagcgtgagc tatgagaaag cgccacgctt cccgaaggga
3901 gaaaggcgga caggtatccg gtaagcggca gggtcggaac aggagagcgc acgagggagc
3961 ttccaggggg aaacgcctgg tatctttata gtcctgtcgg gtttcgccac ctctgacttg
4021 agcgtcgatt tttgtgatgc tcgtcagggg ggcggagcct atggaaaaac gccagcaacg
4081 cggccttttt acggttcctg gccttttgct ggccttttgc tcacatgt
```

In another aspect, the invention provides a vector comprising a 5' inverted terminal repeat (ITR) sequence, a U6 promoter sequence, a BbsI restriction site, an sgRNA expression cassette, an EFS sequence, a SB100x cassette, a GFP-NLS fusion cassette, a 3' ITR sequence and an ampicillin resistance gene sequence (AmpR). In one embodiment, the vector comprises SEQ ID NO: 129,221.

pSC031_pAAV-U6sgbbSapI-EFS-GFP-NLS (SEQ ID NO: 129,221)

```
   1 cctgcaggca gctgcgcgct cgctcgctca ctgaggccgc ccgggcaaag cccgggcgtc
  61 gggcgacctt tggtcgcccg gcctcagtga gcgagcgagc gcgcagagag ggagtggcca
 121 actccatcac taggggttcc tgcggccgca cgcgttctag aagagggcct atttcccatg
 181 attccttcat atttgcatat acgatacaag gctgttagag agataattgg aattaatttg
 241 actgtaaaca caaagatatt agtacaaaat acgtgacgta gaaagtaata atttcttggg
 301 tagtttgcag ttttaaaatt atgttttaaa atggactatc atatgcttac cgtaacttga
 361 aagtatttcg atttcttggc tttatatatc ttgtggaaag gacgaaacac cggaagagcg
 421 agctcttctg ttttagagct agaaatagca agttaaaata aggctagtcc gttatcaact
 481 tgaaaaagtg gcaccgagtc ggtgcttttt tggtacctag gtcttgaaag gagtgggaat
 541 tggctccggt gcccgtcagt gggcagagcg cacatcgccc acagtccccg agaagttggg
 601 gggaggggtc ggcaattgat ccggtgccta gagaaggtgg cgcggggtaa actgggaaag
 661 tgatgtcgtg tactggctcc gcctttttcc cgagggtggg ggagaaccgt atataagtgc
 721 agtagtcgcc gtgaacgttc tttttcgcaa cgggtttgcc gccagaacac aggaccggtt
 781 ctagacgtac ggccaccatg gtgagcaagg gcgaggagct gttcaccggg gtggtgccca
 841 tcctggtcga gctggacggc gacgtaaacg gccacaagtt cagcgtgtcc ggcgagggcg
 901 agggcgatgc cacctacggc aagctgaccc tgaagttcat ctgcaccacc ggcaagctgc
 961 ccgtgccctg gcccaccctc gtgaccaccc tgacctacgg cgtgcagtgc ttcagccgct
1021 accccgacca catgaagcag cacgacttct tcaagtccgc catgcccgaa ggctacgtcc
1081 aggagcgcac catcttcttc aaggacgacg gcaactacaa gacccgcgcc gaggtgaagt
1141 tcgagggcga caccctggtg aaccgcatcg agctgaaggg catcgacttc aaggaggacg
1201 gcaacatcct ggggcacaag ctggagtaca actacaacag ccacaacgtc tatatcatgg
1261 ccgacaagca gaagaacggc atcaaggtga acttcaagat ccgccacaac atcgaggacg
1321 gcagcgtgca gctcgccgac cactaccagc agaacacccc catcggcgac ggccccgtgc
1381 tgctgcccga caaccactac ctgagcaccc agtccgccct gagcaaagac cccaacgaga
1441 agcgcgatca catggtcctg ctggagttcg tgaccgccgc cgggatcact ctcggcatgg
1501 acgagctgta caagaagcgt cctgctgcta ctaagaaagc tggtcaagct aagaaaaaga
1561 aataagaatt cgatatcaag cttaataaaa gatctttatt ttcattagat ctgtgtgttg
1621 gtttttttgtg tggtaaccac gtgcggaccg agcggccgca ggaacccta gtgatggagt
```

-continued 1681 tggccactcc ctctctgcgc gctcgctcgc tcactgaggc cgggcgacca aaggtcgccc 1741 gacgcccggg ctttgcccgg gcggcctcag tgagcgagcg agcgcgcagc tgcctgcagg 1801 ggcgcctgat gcggtatttt ctccttacgc atctgtgcgg tatttcacac cgcatacgtc 1861 aaagcaacca tagtacgcgc cctgtagcgg cgcattaagc gcggcgggtg tggtggttac 1921 gcgcagcgtg accgctacac ttgccagcgc cctagcgccc gctcctttcg ctttcttccc 1981 ttcctttctc gccacgttcg ccggctttcc ccgtcaagct ctaaatcggg ggctcccttt 2041 agggttccga tttagtgctt tacggcacct cgaccccaaa aaacttgatt tgggtgatgg 2101 ttcacgtagt gggccatcgc cctgatagac ggtttttcgc cctttgacgt tggagtccac 2161 gttctttaat agtggactct tgttccaaac tggaacaaca ctcaacccta tctcgggcta 2221 ttcttttgat ttataaggga ttttgccgat ttcggcctat tggttaaaaa atgagctgat 2281 ttaacaaaaa tttaacgcga attttaacaa aatattaacg tttacaattt tatggtgcac 2341 tctcagtaca atctgctctg atgccgcata gttaagccag ccccgacacc cgccaacacc 2401 cgctgacgcg ccctgacggg cttgtctgct cccggcatcc gcttacagac aagctgtgac 2461 cgtctccggg agctgcatgt gtcagaggtt ttcaccgtca tcaccgaaac gcgcgagacg 2521 aaagggcctc gtgatacgcc tatttttata ggttaatgtc atgataataa tggtttctta 2581 gacgtcaggt ggcacttttc ggggaaatgt gcgcggaacc cctatttgtt tatttttcta 2641 aatacattca aatatgtatc cgctcatgag acaataaccc tgataaatgc ttcaataata 2701 ttgaaaaagg aagagtatga gtattcaaca tttccgtgtc gcccttattc ccttttttgc 2761 ggcattttgc cttcctgttt ttgctcaccc agaaacgctg gtgaaagtaa aagatgctga 2821 agatcagttg ggtgcacgag tgggttacat cgaactggat ctcaacagcg gtaagatcct 2881 tgagagtttt cgccccgaag aacgttttcc aatgatgagc acttttaaag ttctgctatg 2941 tggcgcggta ttatcccgta ttgacgccgg gcaagagcaa ctcggtcgcc gcatacacta 3001 ttctcagaat gacttggttg agtactcacc agtcacagaa aagcatctta cggatggcat 3061 gacagtaaga gaattatgca gtgctgccat aaccatgagt gataacactg cggccaactt 3121 acttctgaca acgatcggag gaccgaagga gctaaccgct tttttgcaca acatggggga 3181 tcatgtaact cgccttgatc gttgggaacc ggagctgaat gaagccatac caaacgacga 3241 gcgtgacacc acgatgcctg tagcaatggc aacaacgttg cgcaaactat taactggcga 3301 actacttact ctagcttccc ggcaacaatt aatagactgg atggaggcgg ataaagttgc 3361 aggaccactt ctgcgctcgg cccttccggc tggctggttt attgctgata aatctggagc 3421 cggtgagcgt gggtctcgcg gtatcattgc agcactgggg ccagatggta agccctcccg 3481 tatcgtagtt atctacacga cggggagtca ggcaactatg gatgaacgaa atagacagat 3541 cgctgagata ggtgcctcac tgattaagca ttggtaactg tcagaccaag tttactcata 3601 tatactttag attgatttaa aacttcattt ttaatttaaa aggatctagg tgaagatcct 3661 ttttgataat ctcatgacca aaatccctta acgtgagttt tcgttccact gagcgtcaga 3721 ccccgtagaa aagatcaaag gatcttcttg agatcctttt tttctgcgcg taatctgctg 3781 cttgcaaaca aaaaaaccac cgctaccagc ggtggtttgt ttgccggatc aagagctacc 3841 aactcttttt ccgaaggtaa ctggcttcag cagagcgcag ataccaaata ctgtccttct 3901 agtgtagccg tagttaggcc accacttcaa gaactctgta gcaccgccta catacctcgc 3961 tctgctaatc ctgttaccag tggctgctgc cagtggcgat aagtcgtgtc ttaccgggtt 4021 ggactcaaga cgatagttac cggataaggc gcagcggtcg ggctgaacgg ggggttcgtg -continued

```
4081 cacacagccc agcttggagc gaacgaccta caccgaactg agatacctac agcgtgagct

4141 atgagaaagc gccacgcttc ccgaagggag aaaggcggac aggtatccgg taagcggcag

4201 ggtcggaaca ggagagcgca cgagggagct tccaggggga aacgcctggt atctttatag

4261 tcctgtcggg tttcgccacc tctgacttga gcgtcgattt ttgtgatgct cgtcaggggg

4321 gcggagccta tggaaaaacg ccagcaacgc ggccttttta cggttcctgg ccttttgctg

4381 gccttttgct cacatgt
```

In certain embodiments, any of the vectors of the present invention may comprise an sgRNA expression cassette that expresses an sgRNA comprising a nucleotide sequence selected from the group consisting of SEQ ID NOs: 1-129, 209. In other embodiments, any one of the vectors may comprise an sgRNA expression cassette the expresses an sgRNA comprising a nucleotide sequence selected from the group consisting of SEQ ID NOs: 129,222-140,680. In certain embodiments, any of the vectors of the present invention may comprise an sgRNA expression cassette that expresses an sgRNA consisting of a nucleotide sequence selected from the group consisting of SEQ ID NOs: 1-129, 209. In other embodiments, any one of the vectors may comprise an sgRNA expression cassette that expresses an sgRNA consisting of a nucleotide sequence selected from the group consisting of SEQ ID NOs: 129,222-140,680.

Methods

In one aspect, the invention includes a method of genome editing and screening of a T cell in vitro. The method comprises contacting the T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 1-129,209. The contacting causes the T cell to undergo genome editing. The T cell is then screened in vitro.

In another aspect, the invention includes a method of genome editing and screening of a T cell in vitro. The method comprises contacting the T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 129, 222-140,680. The contacting causes the T cell to undergo genome editing. The T cell is then screened in vitro.

Another aspect of the invention includes a method of genome editing and screening of a T cell in vivo. The method comprises contacting an isolated T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 1-129,209. The contacting causes the T cell to undergo genome editing, thus yielding a modified T cell. The modified T cell is then administered to an animal, and the modified T cell is screened in vivo.

Yet another aspect of the invention includes a method of genome editing and screening of a T cell in vivo. The method comprises contacting an isolated T cell with Cas9 and an sgRNA library. The sgRNA library comprises a plurality of vectors, wherein each vector comprises an expression cassette for an sgRNA comprising a nucleotide sequence selected from the group consisting of SEQ ID NOs: 1-129,209. The contacting causes the T cell to undergo genome editing, thus yielding a modified T cell. The modified T cell is then administered to an animal, and the modified T cell is screened in vivo.

The T cell can be any type of T lymphocyte including but not limited to: a CD8+ cell, a CD4+ cell, or a T regulatory (Treg) cell, a Th1 cell, a Th2 cell, a Th17 cell, a follicular helper T cell (Tfh), a T memory cell, a T effector cell, a T effector memory cell, an engineered T cell, and a CAR T cell. The methods of the invention can further comprise isolating and or enriching the T cells.

In certain embodiments of the invention, the animal has a condition, which can include any condition related to or affected by T cells. Examples of such conditions can include, but are not limited to, (1) Primary immune deficiencies such as Severe Combined Immunodeficiency (SCID), DiGeorge syndrome, Hyperimmunoglobulin E syndrome (also known as Job's Syndrome), Common variable immunodeficiency (CVID) (B-cell levels are normal in circulation but with decreased production of IgG throughout the years, so it is the only primary immune disorder that presents onset in the late teens years), Chronic granulomatous disease (CGD—a deficiency in NADPH oxidase enzyme, which causes failure to generate oxygen radicals. Classical recurrent infection from catalase positive bacteria and fungi), Wiskott-Aldrich syndrome (WAS), Autoimmune lymphoproliferative syndrome (ALPS), Hyper IgM syndrome (X-linked disorder that causes a deficiency in the production of CD40 ligand on activated T-cells. This increases the production and release of IgM into circulation. The B-cell and T-cell numbers are within normal limits. Increased susceptibility to extracellular bacteria and opportunistic infections), Leukocyte adhesion deficiency (LAD), NF-κB Essential Modifier (NEMO) Mutations, Selective immunoglobulin A deficiency (the most common defect of the humoral immunity, characterized by a deficiency of IgA. Produces repeating sinopulmonary and gastrointestinal infections), X-linked agammaglobulinemia (XLA; also known as Bruton type agammaglobulinemia: characterized by a deficiency in tyrosine kinase enzyme that blocks B-cell maturation in the bone marrow. No B-cells are produced to circulation and thus, there are no immunoglobulin classes, although there tends to be a normal cell-mediated immunity), X-linked lymphoproliferative disease (XLP), Ataxia-telangiectasia; (2) Secondary immune deficiencies such as HIV/AIDS; (3) Other internal immune disorders such as immune-mediated inflammatory diseases, autoimmune disease, transplantation rejection, Graft versus Host Disease (GVHD); (4) Infections such as viral infections, bacterial infections, and parasitic infections; (5) Cancers such leukemia, liver cancer, lung cancer, melanoma, Non-Hodgkin lymphoma, pancreatic cancer, prostate cancer, and thyroid cancer.

In certain embodiments, screening T cells after the sgRNA library has been administered to the animal provides information about the specific genes involved in a condition the animal has. Screening T cells can comprise any method commonly known to one of ordinary skill in the art including but not limited to methods of nucleotide sequencing, sgRNA PCR, and/or flow cytometry.

Nucleotide sequencing or "sequencing", as it is commonly known in the art, can be performed by standard methods commonly known to one of ordinary skill in the art. In certain embodiments of the invention, sequencing is performed by targeted capture sequencing. Targeted captured sequencing can be performed as described herein, or by methods commonly performed by one of ordinary skill in the art. In certain embodiments of the invention sequencing is performed via next-generation sequencing. Next-generation sequencing (NGS), also known as high-throughput sequencing, is used herein to describe a number of different modern sequencing technologies that allow to sequence DNA and RNA much more quickly and cheaply than the previously used Sanger sequencing (Metzker, 2010, Nature Reviews Genetics 11.1: 31-46). It is based on micro- and nanotechnologies to reduce the size of sample, the reagent costs, and to enable massively parallel sequencing reactions. It can be highly multiplexed which allows simultaneous sequencing and analysis of millions of samples. NGS includes first, second, third as well as subsequent Next Generations Sequencing technologies. Data generated from NGS can be analyzed via a broad range of computational tools. The wide variety of analysis can be appreciated and performed by those skilled in the art.

Genome editing can include introducing mutations throughout the genome of the cell. The mutations introduced can be any combination of insertions or deletions, including but not limited to a single base insertion, a single base deletion, a frameshift, a rearrangement, and an insertion or deletion of 2, 3, 4, 5, 6, 7, 8, 9, 10, 15, 20, 25, 30, 40, 50, 60, 70, 80, 90, 100, 150, 200, 250, 300, any and all numbers in between, bases. The mutation can occur in a gene or in a non-coding region.

In certain embodiments of the invention, the animal is a mouse. Other animals that can be used include but are not limited to rats, rabbits, dogs, cats, horses, pigs, cows and birds. In certain embodiments, the animal is a human. The sgRNA library can be administered to an animal by any means standard in the art. For example the vectors can be injected into the animal. The injections can be intravenous, subcutaneous, intraperitoneal, or directly into a tissue or organ. In certain embodiments, the sgRNA library is adoptively transferred to the animal.

CRISPR/Cas9

The CRISPR/Cas9 system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/Cas9 system can thereby be engineered to cleave virtually any DNA sequence by redesigning the gRNA in cell lines (such as 293T cells), primary cells, and CART cells. The CRISPR/Cas9 system can simultaneously target multiple genomic loci by co-expressing a single Cas9 protein with two or more gRNAs, making this system uniquely suited for multiple gene editing or synergistic activation of target genes.

The Cas9 protein and guide RNA form a complex that identifies and cleaves target sequences. Cas9 is comprised of six domains: REC I, REC II, Bridge Helix, PAM interacting, HNK and RuvC. The RecI domain binds the guide RNA, while the Bridge helix binds to target DNA. The HNH and RuvC domains are nuclease domains. Guide RNA is engineered to have a 5' end that is complementary to the target DNA sequence. Upon binding of the guide RNA to the Cas9 protein, a conformational change occurs activating the protein. Once activated, Cas9 searches for target DNA by binding to sequences that match its protospacer adjacent motif (PAM) sequence, A PAM is a two or three nucleotide base sequence within one nucleotide downstream of the region complementary to the guide RNA. In one non-limiting example, the PAM sequence is 5'-NGG-3'. When the Cas9 protein finds its target sequence with the appropriate PAM, it melts the bases upstream of the PAM and pairs them with the complementary region on the guide RNA. Then the RuvC and HNH nuclease domains cut the target DNA after the third nucleotide base upstream of the PAM.

One non-limiting example of a CRISPR/Cas system used to inhibit gene expression, CRISPRi, is described in U.S. Patent Appl. Publ. No. US20140068797. CRISPRi induces permanent gene disruption that utilizes the RNA-guided Cas9 endonuclease to introduce DNA double stranded breaks which trigger error-prone repair pathways to result in frame shift mutations. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR/Cas system comprises an expression vector, such as, but not limited to, an pAd5F35-CRISPR vector. In other embodiments, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combinations thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

In certain embodiments, guide RNA(s) and Cas9 can be delivered to a cell as a ribonucleoprotein (RNP) complex. RNPs are comprised of purified Cas9 protein complexed with gRNA and are well known in the art to be efficiently delivered to multiple types of cells, including but not limited to stem cells and immune cells (Addgene, Cambridge, MA, Minis Bio LLC, Madison, WI).

The guide RNA is specific for a genomic region of interest and targets that region for Cas endonuclease-induced double strand breaks. The target sequence of the guide RNA sequence may be within a loci of a gene or within a non-coding region of the genome. In certain embodiments, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as a DNA or a RNA polynucleotide. In certain embodiments, a target sequence is located in the nucleus or cytoplasm of a cell. In other embodiments, the target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional.

In certain embodiments, one or more vectors driving expression of one or more elements of a CRISPR system are introduced into a host cell, such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in U.S. Patent Appl. Publ. No. US20110059502, incorporated herein by reference. In certain embodiments, a tagged CRISPR enzyme is used to identify the location of a target sequence.

Conventional viral and non-viral based gene transfer methods can be used to introduce nucleic acids in mammalian and non-mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu, et al., 1994, Gene Therapy 1:13-26).

In certain embodiments, the CRISPR/Cas is derived from a type II CRISPR/Cas system. In other embodiments, the CRISPR/Cas system is derived from a Cas9 protein. The Cas9 protein can be from *Streptococcus pyogenes, Streptococcus thermophilus*, or other species.

In general, Cas proteins comprise at least one RNA recognition and/or RNA binding domain. RNA recognition and/or RNA binding domains interact with the guiding RNA. Cas proteins can also comprise nuclease domains (i.e., DNase or RNase domains), DNA binding domains, helicase domains, RNAse domains, protein-protein interaction domains, dimerization domains, as well as other domains. The Cas proteins can be modified to increase nucleic acid binding affinity and/or specificity, alter an enzymatic activity, and/or change another property of the protein. In certain embodiments, the Cas-like protein of the fusion protein can be derived from a wild type Cas9 protein or fragment thereof. In other embodiments, the Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek, et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 and 5,589,466, incorporated by reference herein in their entireties).

Further, the vector may be provided to a cell in the form of a viral vector. Viral vector technology is well known in the art and is described, for example, in Sambrook et al. ($4^{th}$ Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

It should be understood that the method and compositions that would be useful in the present invention are not limited to the particular formulations set forth in the examples. The following examples are put forth so as to provide those of ordinary skill in the art with a complete disclosure and description, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook et al. (2012) Molecular Cloning, Cold Spring Harbor Laboratory); "Oligonucleotide Synthesis" (Gait, M. J. (1984). Oligonucleotide synthesis. IRL press); "Culture of Animal Cells" (Freshney, R. (2010). Culture of animal cells. Cell Proliferation, 15(2.3), 1); "Methods in Enzymology" "Weir's Handbook of Experimental Immunology" (Wiley-Blackwell; 5 edition (Jan. 15, 1996); "Gene Transfer Vectors for Mammalian Cells" (Miller and Carlos, (1987) Cold Spring Harbor Laboratory, New York); "Short Protocols in Molecular Biology" (Ausubel et al., Current Protocols; 5 edition (Nov. 5, 2002)); "Polymerase Chain Reaction: Principles, Applications and Troubleshooting", (Babar, M., VDM Verlag Dr. Müller (Aug. 17, 2011)); "Current Protocols in Immunology" (Coligan, John Wiley & Sons, Inc. Nov. 1, 2002).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Mice: Various strains of mice between the ages of 6-12 weeks of age were used for the present study described. OT-I TCR transgenic mice (OT-I mice) were described by Hogquist et al., Cell 76, 17-27 (1994). Constitutive Cas9-2A-EGFP mice (Cas9 mice) were described by Platt et al., Cell 159, 440-455 (2014). OT-I; Cas9 mice were generated by breeding OT-I and Cas9 mice and genotyped according to Jackson Lab protocol. Naive $CD8^+$ T cells were isolated from OT-I mice, Cas9 mice, and OT-I; Cas9 mice. All animals were housed in standard individually ventilated, pathogen-free conditions, with 12 h:12 h or 13 h:11 h light cycle, room temperature (21-23° C.) and 40-60% relative humidity. When a cohort of animals were receiving multiple treatments, animals were randomized by 1) randomly assign animals to different groups using littermates, 2) random mixing of females prior to treatment, maximizing the evenness or representation of mice from different cages in each group, and/or 3) random assignment of mice to each group, in order to minimize the effect of gender, litter, small difference in age, cage, housing position, where applicable.

Generation of a T cell CRISPR vector (sgRNA-Thy1.1 Expression Vector): A lentiviral T cell CRISPR vector, lenti-pLKO-U6-sgRNA(BsmBI)-EFS-Thy1.1CO-spA, was generated by codon-optimizing and subcloning Thy1.1 and sgRNA expression cassette into a lentiviral vector via Gibson Assembly. Three versions of the vector were generated to enable robust genome editing in T cells.

```
pSC017_pLKO-U6-sgBsmBI-EFS-Thy11CO-spA (SEQ ID NO: 129,213):
ttaatgtagtcttatgcaatactcttgtagtcttgcaacatggtaacgatgagttagcaacatgccttac

aaggagagaaaaagcaccgtgcatgccgattggtggaagtaaggtggtacgatcgtgccttattaggaag

gcaacagacgggtctgacatggattggacgaaccactgaattgccgcattgcagagatattgtatttaag

tgcctagctcgatacataaacgggtctctctggttagaccagatctgagcctgggagctctctggctaac

tagggaacccactgcttaagcctcaataaagcttgccttgagtgcttcaagtagtgtgtgcccgtctgtt

gtgtgactctggtaactagagatccctcagacccttttagtcagtgtggaaaatctctagcagtggcgcc

cgaacagggacttgaaagcgaaagggaaaccagaggagctctctcgacgcaggactcggcttgctgaagc

gcgcacggcaagaggcgaggggcggcgactggtgagtacgccaaaaattttgactagcggaggctagaag

gagagagatgggtgcgagagcgtcagtattaagcgggggagaattagatcgcgatgggaaaaaattcggt

taaggccagggggaaagaaaaaatataaattaaaacatatagtatgggcaagcagggagctagaacgatt

cgcagttaatcctggcctgttagaaacatcagaaggctgtagacaaatactgggacagctacaaccatcc

cttcagacaggatcagaagaacttagatcattatataatacagtagcaaccctctattgtgtgcatcaaa

ggatagagataaaagacaccaaggaagctttagacaagatagaggaagagcaaaacaaaagtaagaccac

cgcacagcaagcggccgctgatcttcagacctggaggaggagatatgagggacaattggagaagtgaatt

atataaatataaagtagtaaaaattgaaccattaggagtagcacccaccaaggcaaagagaagagtggtg

cagagagaaaaaagagcagtgggaataggagctttgttccttgggttcttgggagcagcaggaagcacta

tgggcgcagcgtcaatgacgctgacggtacaggccagacaattattgtctggtatagtgcagcagcagaa

caatttgctgagggctattgaggcgcaacagcatctgttgcaactcacagtctggggcatcaagcagctc

caggcaagaatcctggctgtggaaagatacctaaaggatcaacagctcctggggatttggggttgctctg

gaaaactcatttgcaccactgctgtgccttggaatgctagttggagtaataaatctctggaacagatttg

gaatcacacgacctggatggagtgggacagagaaattaacaattacacaagcttaatacactccttaatt

gaagaatcgcaaaaccagcaagaaaagaatgaacaagaattattggaattagataaatgggcaagtttgt

ggaattggtttaacataacaaattggctgtggtatataaaattattcataatgatagtaggaggcttggt

aggtttaagaatagtttttgctgtactttctatagtgaatagagttaggcagggatattcaccattatcg

tttcagacccacctcccaaccccgaggggacccagagagggcctatttcccatgattccttcatatttgc

atatacgatacaaggctgttagagagataattagaattaatttgactgtaaacacaaagatattagtaca

aaatacgtgacgtagaaagtaataatttcttgggtagtttgcagttttaaaattatgttttaaaatggac

tatcatatgcttaccgtaacttgaaagtatttcgatttcttggctttatatatcttGTGGAAAGGACGAA

ACACCgGAGACGgaCGTCTCtgttttagagctaGAAAtagcaagttaaaataaggctagtccgttatcaa

cttgaaaaagtggcaccgagtcggtgcTTTTTTaagcttggcgtaactagatcttgagacaaatggcagt

attcatccacaattttaaaagaaaaggggggattggggggtacagtgcaggggaaagaatagtagacata

atagcaacagacatacaaactaaagaattacaaaaacaaattacaaaaattcaaaattttcgggtttatt

acagggacagcagagatccactttggcgccggctcgagggggcccggggaattcgctagctaggtcttga

aaggagtgggaattggctccggtgcccgtcagtgggcagagcgcacatcgcccacagtccccgagaagtt
```

-continued gggggggaggggtcggcaattgatccggtgcctagagaaggtggcgcggggtaaactgggaaagtgatgtc
gtgtactggctccgcctttttcccgagggtgggggagaaccgtatataagtgcagtagtcgccgtgaacg
ttctttttcgcaacgggtttgccgccagaacacaggaccggttctagacgtacggccaccATGAACCCAG
CCATCAGCGTCGCTCTCCTGCTCTCAGICTTGCAGGTGTCCCGAGGGCAGAAGGTGACCAGCCTGACAGC
CTGCCTGGTGAACCAAAACCTTCGCCTGGACTGCCGCCATGAGAATAACACCAAGGATAACTCCATCCAG
CATGAGTTCAGCCTGACCCGAGAGAAGAGGAAGCACGTGCTCTCAGGCACCCTTGGGATACCCGAGCACA
CGTACCGCTCCCGCGTCACCCTCTCCAACCAGCCCTATATCAAGGTCCTTACCCTAGCCAACTTCACCAC
CAAGGATGAGGGCGACTACTTTTGTGAGCTTCGCGTAAGTGGCGCGAATCCCATGAGCTCCAATAAAAGT
ATCAGTGTGTATAGAGACAAGCTGGTCAAGTGTGGCGGCATAAGCCTGCTGGTTCAGAACACATCCTGGA
TGCTGCTGCTGCTGCTTTCCCTCTCCCTCCTCCAAGCCCTGGACTTCATTTCTCTGTGAagcgctAATAA
AAGATCTTTATTTTCATTAGATCTGTGTGTTGGTTTTTTGTGTGacgtgcggtcgactttaagaccaatg
acttacaaggcagctgtagatcttagccactttttaaaagaaaaggggggactggaagggctaattcact
cccaacgaagacaagatctgctttttgcttgtactgggtctctctggttagaccagatctgagcctggga
gctctctggctaactagggaacccactgcttaagcctcaataaagcttgccttgagtgcttcaagtagtg
tgtgcccgtctgttgtgtgactctggtaactagagatccctcagacccttttagtcagtgtggaaaatct
ctagcagtacgtatagtagttcatgtcatcttattattcagtatttataacttgcaaagaaatgaatatc
agagagtgagaggaacttgtttattgcagcttataatggttacaaataaagcaatagcatcacaaatttc
acaaataaagcatttttttcactgcattctagttgtggtttgtccaaactcatcaatgtatcttatcatg
tctggctctagctatcccgcccctaactccgcccatcccgcccctaactccgcccagttccgcccattct
ccgccccatggctgactaattttttttatttatgcagaggccgaggccgcctcggcctctgagctattcc
agaagtagtgaggaggcttttttggaggcctagggacgtacccaattcgccctatagtgagtcgtattac
gcgcgctcactggccgtcgttttacaacgtcgtgactgggaaaaccctggcgttacccaacttaatcgcc
ttgcagcacatcccccttcgccagctggcgtaatagcgaagaggcccgcaccgatcgcccttcccaaca
gttgcgcagcctgaatggcgaatgggacgcgccctgtagcggcgcattaagcgcggcgggtgtggtggtt
acgcgcagcgtgaccgctacacttgccagcgccctagcgcccgctcctttcgctttcttcccttcctttc
tcgccacgttcgccggctttccccgtcaagctctaaatcgggggctccctttagggttccgatttagtgc
tttacggcacctcgaccccaaaaaacttgattagggtgatggttcacgtagtgggccatcgccctgatag
acggtttttcgccctttgacgttggagtccacgttctttaatagtggactcttgttccaaactggaacaa
cactcaaccctatctcggtctattcttttgatttataagggattttgccgatttcggcctattggttaaa
aaatgagctgatttaacaaaaatttaacgcgaattttaacaaaatattaacgcttacaatttaggtggca
cttttcggggaaatgtgcgcggaacccctatttgtttatttttctaaatacattcaaatatgtatccgct
catgagacaataaccctgataaatgcttcaataatattgaaaaaggaagagtatgagtattcaacatttc
cgtgtcgcccttattcccttttttgcggcattttgccttcctgtttttgctcacccagaaacgctggtga
aagtaaaagatgctgaagatcagttgggtgcacgagtgggttacatcgaactggatctcaacagcggtaa
gatccttgagagttttcgccccgaagaacgttttccaatgatgagcacttttaaagttctgctatgtggc
gcggtattatcccgtattgacgccgggcaagagcaactcggtcgccgcatacactattctcagaatgact
tggttgagtactcaccagtcacagaaaagcatcttacggatggcatgacagtaagagaattatgcagtgc
tgccataaccatgagtgataacactgcggccaacttacttctgacaacgatcggaggaccgaaggagcta
accgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaac
tggcgaactacttactctagcttcccggcaacaattaatagactggatggaggcggataaagttgcagga -continued ccacttctgcgctcggcccttccggctggctggtttattgctgataaatctggagccggtgagcgtgggt ctcgcggtatcattgcagcactggggccagatggtaagccctcccgtatcgtagttatctacacgacggg gagtcaggcaactatggatgaacgaaatagacagatcgctgagataggtgcctcactgattaagcattgg taactgtcagaccaagtttactcatatatactttagattgatttaaaacttcatttttaatttaaaagga tctaggtgaagatcctttttgataatctcatgaccaaaatcccttaacgtgagttttcgttccactgagc gtcagaccccgtagaaaagatcaaaggatcttcttgagatcctttttttctgcgcgtaatctgctgcttg caaacaaaaaaaccaccgctaccagcggtggtttgtttgccggatcaagagctaccaactctttttccga aggtaactggcttcagcagagcgcagataccaaatactgttcttctagtgtagccgtagttaggccacca cttcaagaactctgtagcaccgcctacatacctcgctctgctaatcctgttaccagtggctgctgccagt ggcgataagtcgtgtcttaccgggttggactcaagacgatagttaccggataaggcgcagcggtcgggct gaacggggggttcgtgcacacagcccagcttggagcgaacgacctacaccgaactgagatacctacagcg tgagctatgagaaagcgccacgcttcccgaagggagaaaggcggacaggtatccggtaagcggcagggtc ggaacaggagagcgcacgagggagcttccagggggaaacgcctggtatctttatagtcctgtcgggtttc gccacctctgacttgagcgtcgatttttgtgatgctcgtcaggggggcggagcctatggaaaaacgccag caacgcggcctttttacggttcctggccttttgctggccttttgctcacatgttctttcctgcgttatcc cctgattctgtggataaccgtattaccgcctttgagtgagctgataccgctcgccgcagccgaacgaccg agcgcagcgagtcagtgagcgaggaagcggaagagcgcccaatacgcaaaccgcctctccccgcgcgttg gccgattcattaatgcagctggcacgacaggtttcccgactggaaagcgggcagtgagcgcaacgcaatt aatgtgagttagctcactcattaggcaccccaggctttacactttatgcttccggctcgtatgttgtgtg gaattgtgagcggataacaatttcacacaggaaacagctatgaccatgattacgccaagcgcgcaattaa ccctcactaaagggaacaaaagctggagctgcaagc pSC008_pLKO-U6-BsmBI-chRNA(+85)-EFS-Thy11 (SEQ ID NO: 129,214):

1 ttaatgtagt cttatgcaat actcttgtag tcttgcaaca tggtaacgat gagttagcaa 61 catgccttac aaggagagaa aaagcaccgt gcatgccgat tggtggaagt aaggtggtac 121 gatcgtgcct tattaggaag gcaacagacg ggtctgacat ggattggacg aaccactgaa 181 ttgccgcatt gcagagatat tgtatttaag tgcctagctc gatacataaa cgggtctctc 241 tggttagacc agatctgagc ctgggagctc tctggctaac tagggaaccc actgcttaag 301 cctcaataaa gcttgccttg agtgcttcaa gtagtgtgtg cccgtctgtt gtgtgactct 361 ggtaactaga gatccctcag acccttttag tcagtgtgga aaatctctag cagtggcgcc 421 cgaacaggga cttgaaagcg aaagggaaac cagaggagct ctctcgacgc aggactcggc 481 ttgctgaagc gcgcacggca agaggcgagg ggcggcgact ggtgagtacg ccaaaaattt 541 tgactagcgg aggctagaag gagagagatg ggtgcgagag cgtcagtatt aagcggggga 601 gaattagatc gcgatgggaa aaaattcggt taaggccagg gggaaagaaa aaatataaat 661 taaaacatat agtatgggca agcagggagc tagaacgatt cgcagttaat cctggcctgt 721 tagaaacatc agaaggctgt agacaaatac tgggacagct acaaccatcc cttcagacag 781 gatcagaaga acttagatca ttatataata cagtagcaac cctctattgt gtgcatcaaa 841 ggatagagat aaaagacacc aaggaagctt tagacaagat agaggaagag caaaacaaaa 901 gtaagaccac cgcacagcaa gcggccgctg atcttcagac ctggaggagg agatatgagg 961 gacaattgga gaagtgaatt atataaatat aaagtagtaa aaattgaacc attaggagta 1021 gcacccacca aggcaaagag aagagtggtg cagagagaaa aaagagcagt gggaatagga 1081 gctttgttcc ttgggttctt gggagcagca ggaagcacta tgggcgcagc gtcaatgacg -continued

```
1141 ctgacggtac aggccagaca attattgtct ggtatagtgc agcagcagaa caatttgctg
1201 agggctattg aggcgcaaca gcatctgttg caactcacag tctggggcat caagcagctc
1261 caggcaagaa tcctggctgt ggaaagatac ctaaaggatc aacagctcct ggggatttgg
1321 ggttgctctg gaaaactcat ttgcaccact gctgtgcctt ggaatgctag ttggagtaat
1381 aaatctctgg aacagatttg gaatcacacg acctggatgg agtgggacag agaaattaac
1441 aattacacaa gcttaataca ctccttaatt gaagaatcgc aaaaccagca agaaaagaat
1501 gaacaagaat tattggaatt agataaatgg gcaagtttgt ggaattggtt taacataaca
1561 aattggctgt ggtatataaa attattcata atgatagtag gaggcttggt aggtttaaga
1621 atagtttttg ctgtactttc tatagtgaat agagttaggc agggatattc accattatcg
1681 tttcagaccc acctcccaac cccgagggga cccagagagg gcctatttcc catgattcct
1741 tcatatttgc atatacgata caaggctgtt agagagataa ttagaattaa tttgactgta
1801 aacacaaaga tattagtaca aaatacgtga cgtagaaagt aataatttct tgggtagttt
1861 gcagttttaa aattatgttt taaaatggac tatcatatgc ttaccgtaac ttgaaagtat
1921 ttcgatttct tggctttata tatcttGTGG AAAGGACGAA ACACCgGAGA CGgaCGTCTC
1981 tgttttagag ctaGAAAtag caagttaaaa taaggctagt ccgttatcaa cttgaaaaag
2041 tggcaccgag tcggtgcTTT TTTaagcttg gcgtaactag atcttgagac aaatggcagt
2101 attcatccac aattttaaaa gaaaaggggg gattgggggg tacagtgcag gggaaagaat
2161 agtagacata atagcaacag acatacaaac taaagaatta caaaaacaaa ttacaaaaat
2221 tcaaaatttt cgggtttatt acagggacag cagagatcca ctttggcgcc ggctcgaggg
2281 ggcccgggga attcgctagc taggtcttga aaggagtggg aattggctcc ggtgcccgtc
2341 agtgggcaga gcgcacatcg cccacagtcc ccgagaagtt ggggggaggg gtcggcaatt
2401 gatccggtgc ctagagaagg tggcgcgggg taaactggga aagtgatgtc gtgtactggc
2461 tccgcctttt tcccgagggt gggggagaac cgtatataag tgcagtagtc gccgtgaacg
2521 ttctttttcg caacgggttt gccgccagaa cacaggaccg gttctagacg tacggccacc
2581 ATGAACCCAG CCATCAGCGT CGCTCTCCTG CTCTCAGTCT TGCAGGTGTC CCGAGGGCAG
2641 AAGGTGACCA GCCTGACAGC CTGCCTGGTG AACCAAAACC TTCGCCTGGA CTGCCGCCAT
2701 GAGAATAACA CCAAGGATAA CTCCATCCAG CATGAGTTCA GCCTGACCCG AGAGAAGAGG
2761 AAGCACGTGC TCTCAGGCAC CCTTGGGATA CCCGAGCACA CGTACCGCTC CCGCGTCACC
2821 CTCTCCAACC AGCCCTATAT CAAGGTCCTT ACCCTAGCCA ACTTCACCAC CAAGGATGAG
2881 GGCGACTACT TTTGTGAGCT TCGCGTCTCG GGCGCGAATC CCATGAGCTC CAATAAAAGT
2941 ATCAGTGTGT ATAGAGACAA GCTGGTCAAG TGTGGCGGCA TAAGCCTGCT GGTTCAGAAC
3001 ACATCCTGGA TGCTGCTGCT GCTGCTTTCC CTCTCCCTCC TCCAAGCCCT GGACTTCATT
3061 TCTCTGTGAa gcgctAATAA AAGATCTTTA TTTTCATTAG ATCTGTGTGT TGGTTTTTTG
3121 TGTggtaaCT CGAGacgtgc ggtcgacttt aagaccaatg acttacaagg cagctgtaga
3181 tcttagccac tttttaaaag aaaagggggg actggaaggg ctaattcact cccaacgaag
3241 acaagatctg ctttttgctt gtactgggtc tctctggtta gaccagatct gagcctggga
3301 gctctctggc taactaggga acccactgct taagcctcaa taaagcttgc cttgagtgct
3361 tcaagtagtg tgtgcccgtc tgttgtgtga ctctggtaac tagagatccc tcagaccctt
3421 ttagtcagtg tggaaaatct ctagcagtac gtatagtagt tcatgtcatc ttattattca
3481 gtatttataa cttgcaaaga aatgaatatc agagagtgag aggaacttgt ttattgcagc
```

-continued

```
3541 ttataatggt tacaaataaa gcaatagcat cacaaatttc acaaataaag catttttttc
3601 actgcattct agttgtggtt tgtccaaact catcaatgta tcttatcatg tctggctcta
3661 gctatcccgc ccctaactcc gcccatcccg cccctaactc cgcccagttc cgcccattct
3721 ccgccccatg gctgactaat tttttttatt tatgcagagg ccgaggccgc ctcggcctct
3781 gagctattcc agaagtagtg aggaggcttt tttggaggcc tagggacgta cccaattcgc
3841 cctatagtga gtcgtattac gcgcgctcac tggccgtcgt tttacaacgt cgtgactggg
3901 aaaaccctgg cgttacccaa cttaatcgcc ttgcagcaca tccccctttc gccagctggc
3961 gtaatagcga agaggcccgc accgatcgcc cttcccaaca gttgcgcagc ctgaatggcg
4021 aatgggacgc gccctgtagc ggcgcattaa gcgcggcggg tgtggtggtt acgcgcagcg
4081 tgaccgctac acttgccagc gccctagcgc ccgctccttt cgctttcttc ccttcctttc
4141 tcgccacgtt cgccggcttt ccccgtcaag ctctaaatcg ggggctccct ttagggttcc
4201 gatttagtgc tttacggcac ctcgacccca aaaaacttga ttagggtgat ggttcacgta
4261 gtgggccatc gccctgatag acggtttttc gccctttgac gttggagtcc acgttcttta
4321 atagtggact cttgttccaa actggaacaa cactcaaccc tatctcggtc tattcttttg
4381 atttataagg gattttgccg atttcggcct attggttaaa aaatgagctg atttaacaaa
4441 aatttaacgc gaattttaac aaaatattaa cgcttacaat ttaggtggca cttttcgggg
4501 aaatgtgcgc ggaaccccta tttgtttatt tttctaaata cattcaaata tgtatccgct
4561 catgagacaa taaccctgat aaatgcttca ataatattga aaaaggaaga gtatgagtat
4621 tcaacatttc cgtgtcgccc ttattccctt ttttgcggca ttttgccttc ctgtttttgc
4681 tcacccagaa acgctggtga aagtaaaaga tgctgaagat cagttgggtg cacgagtggg
4741 ttacatcgaa ctggatctca acagcggtaa gatccttgag agttttcgcc ccgaagaacg
4801 ttttccaatg atgagcactt ttaaagttct gctatgtggc gcggtattat cccgtattga
4861 cgccgggcaa gagcaactcg gtcgccgcat acactattct cagaatgact tggttgagta
4921 ctcaccagtc acagaaaagc atcttacgga tggcatgaca gtaagagaat tatgcagtgc
4981 tgccataacc atgagtgata acactgcggc caacttactt ctgacaacga tcggaggacc
5041 gaaggagcta accgcttttt tgcacaacat gggggatcat gtaactcgcc ttgatcgttg
5101 ggaaccggag ctgaatgaag ccataccaaa cgacgagcgt gacaccacga tgcctgtagc
5161 aatggcaaca acgttgcgca aactattaac tggcgaacta cttactctag cttcccggca
5221 acaattaata gactggatgg aggcggataa agttgcagga ccacttctgc gctcggccct
5281 tccggctggc tggtttattg ctgataaatc tggagccggt gagcgtgggt ctcgcggtat
5341 cattgcagca ctggggccag atggtaagcc ctcccgtatc gtagttatct acacgacggg
5401 gagtcaggca actatggatg aacgaaatag acagatcgct gagataggtg cctcactgat
5461 taagcattgg taactgtcag accaagttta ctcatatata ctttagattg atttaaaact
5521 tcatttttaa tttaaaagga tctaggtgaa gatccttttt gataatctca tgaccaaaat
5581 cccttaacgt gagttttcgt tccactgagc gtcagacccc gtagaaaaga tcaaaggatc
5641 ttcttgagat cctttttttc tgcgcgtaat ctgctgcttg caaacaaaaa aaccaccgct
5701 accagcggtg gtttgtttgc cggatcaaga gctaccaact ctttttccga aggtaactgg
5761 cttcagcaga gcgcagatac caaatactgt tcttctagtg tagccgtagt taggccacca
5821 cttcaagaac tctgtagcac cgcctacata cctcgctctg ctaatcctgt taccagtggc
5881 tgctgccagt ggcgataagt cgtgtcttac cgggttggac tcaagacgat agttaccgga
5941 taaggcgcag cggtcgggct gaacgggggg ttcgtgcaca cagcccagct tggagcgaac
```

-continued

```
6001 gacctacacc gaactgagat acctacagcg tgagctatga gaaagcgcca cgcttcccga
6061 agggagaaag gcggacaggt atccggtaag cggcagggtc ggaacaggag agcgcacgag
6121 ggagcttcca gggggaaacg cctggtatct ttatagtcct gtcgggtttc gccacctctg
6181 acttgagcgt cgatttttgt gatgctcgtc aggggggcgg agcctatgga aaaacgccag
6241 caacgcggcc tttttacggt tcctggcctt ttgctggcct tttgctcaca tgttctttcc
6301 tgcgttatcc cctgattctg tggataaccg tattaccgcc tttgagtgag ctgataccgc
6361 tcgccgcagc cgaacgaccg agcgcagcga gtcagtgagc gaggaagcgg aagagcgccc
6421 aatacgcaaa ccgcctctcc ccgcgcgttg gccgattcat taatgcagct ggcacgacag
6481 gtttcccgac tggaaagcgg gcagtgagcg caacgcaatt aatgtgagtt agctcactca
6541 ttaggcaccc caggctttac actttatgct tccggctcgt atgttgtgtg gaattgtgag
6601 cggataacaa tttcacacag gaaacagcta tgaccatgat tacgccaagc gcgcaattaa
6661 ccctcactaa agggaacaaa agctggagct gcaagc
```

pSC021_pLKO-U6-sgBsmBI-PGK-Thy11CO-spA.sbd (SEQ ID NO: 129,215):

```
   1 ttaatgtagt cttatgcaat actcttgtag tcttgcaaca tggtaacgat gagttagcaa
  61 catgccttac aaggagagaa aaagcaccgt gcatgccgat tggtggaagt aaggtggtac
 121 gatcgtgcct tattaggaag gcaacagacg ggtctgacat ggattggacg aaccactgaa
 181 ttgccgcatt gcagagatat tgtatttaag tgcctagctc gatacataaa cgggtctctc
 241 tggttagacc agatctgagc ctgggagctc tctggctaac tagggaaccc actgcttaag
 301 cctcaataaa gcttgccttg agtgcttcaa gtagtgtgtg cccgtctgtt gtgtgactct
 361 ggtaactaga gatccctcag acccttttag tcagtgtgga aaatctctag cagtggcgcc
 421 cgaacaggga cttgaaagcg aaagggaaac cagaggagct ctctcgacgc aggactcggc
 481 ttgctgaagc gcgcacggca agaggcgagg ggcggcgact ggtgagtacg ccaaaaattt
 541 tgactagcgg aggctagaag gagagagatg ggtgcgagag cgtcagtatt aagcggggga
 601 gaattagatc gcgatgggaa aaaattcggt taaggccagg gggaaagaaa aaatataaat
 661 taaaacatat agtatgggca agcagggagc tagaacgatt cgcagttaat cctggcctgt
 721 tagaaacatc agaaggctgt agacaaatac tgggacagct acaaccatcc cttcagacag
 781 gatcagaaga acttagatca ttatataata cagtagcaac cctctattgt gtgcatcaaa
 841 ggatagagat aaaagacacc aaggaagctt tagacaagat agaggaagag caaaacaaaa
 901 gtaagaccac cgcacagcaa gcggccgctg atcttcagac ctggaggagg agatatgagg
 961 gacaattgga gaagtgaatt atataaatat aaagtagtaa aaattgaacc attaggagta
1021 gcacccacca aggcaaagag aagagtggtg cagagagaaa aaagagcagt gggaatagga
1081 gctttgttcc ttgggttctt gggagcagca ggaagcacta tgggcgcagc gtcaatgacg
1141 ctgacggtac aggccagaca attattgtct ggtatagtgc agcagcagaa caatttgctg
1201 agggctattg aggcgcaaca gcatctgttg caactcacag tctggggcat caagcagctc
1261 caggcaagaa tcctggctgt ggaaagatac ctaaaggatc aacagctcct ggggatttgg
1321 ggttgctctg gaaaactcat ttgcaccact gctgtgcctt ggaatgctag ttggagtaat
1381 aaatctctgg aacagatttg gaatcacacg acctggatgg agtgggacag agaaattaac
1441 aattacacaa gcttaataca ctccttaatt gaagaatcgc aaaaccagca agaaaagaat
1501 gaacaagaat tattggaatt agataaatgg gcaagtttgt ggaattggtt taacataaca
1561 aattggctgt ggtatataaa attattcata atgatagtag gaggcttggt aggtttaaga
1621 atagtttttg ctgtactttc tatagtgaat agagttaggc agggatattc accattatcg
```

-continued 1681 tttcagaccc acctcccaac cccgagggga cccagagagg gcctatttcc catgattcct 1741 tcatatttgc atatacgata caaggctgtt agagagataa ttagaattaa tttgactgta 1801 aacacaaaga tattagtaca aaatacgtga cgtagaaagt aataatttct tgggtagttt 1861 gcagttttaa aattatgttt taaaatggac tatcatatgc ttaccgtaac ttgaaagtat 1921 ttcgatttct tggctttata tatcttGTGG AAAGGACGAA ACACCgGAGA CGgaCGTCTC 1981 tgttttagag ctaGAAAtag caagttaaaa taaggctagt ccgttatcaa cttgaaaaag 2041 tggcaccgag tcggtgcTTT TTTaagcttg gcgtaactag atcttgagac aaatggcagt 2101 attcatccac aattttaaaa gaaaaggggg gattgggggg tacagtgcag gggaaagaat 2161 agtagacata atagcaacag acatacaaac taaagaatta caaaaacaaa ttacaaaaat 2221 tcaaaatttt cgggtttatt acagggacag cagagatcca ctttggcgcc ggctcgaggg 2281 ggcccgggga attcgctagc gtctgaagag gagtttacgt ccagccaagc ttaggatctc 2341 gacctcgaaa ttctaccggg taggggaggc gcttttccca aggcagtctg gagcatgcgc 2401 tttagcagcc ccgctggcac ttggcgctac acaagtggcc tctggcctcg cacacattcc 2461 acatccaccg gtagcgccaa ccggctccgt tctttggtgg ccccttcgcg ccaccttcta 2521 ctcctcccct agtcaggaag ttcccccccg ccccgcagct cgcgtcgtgc aggacgtgac 2581 aaatggaagt agcatgtcac actagtctcg tgcagatgga cagcaccgct gagcaatgga 2641 agcgggtagg cctttggggc agcggccaat agcagctttg ctccttcgct ttctgggctc 2701 agcagctggg aagggtgggt ccgggggcgg gctcaggggc gggctcaggg gcggggcggg 2761 cgcccgaagg tcctccggag gcccggcatt ctgcacgctt caaaagcgca cgtctgccgc 2821 gctgttctcc tcttcctcat ctccgggcct ttcgacctgc atccatctag atctcgagca 2881 gctgaagctt aaccggttct agacgtacgg ccaccATGAA CCCAGCCATC AGCGTCGCTC

2941 TCCTGCTCTC AGTCTTGCAG GTGTCCCGAG GGCAGAAGGT GACCAGCCTG ACAGCCTGCC

3001 TGGTGAACCA AAACCTTCGC CTGGACTGCC GCCATGAGAA TAACACCAAG GATAACTCCA

3061 TCCAGCATGA GTTCAGCCTG ACCCGAGAGA AGAGGAAGCA CGTGCTCTCA GGCACCCTTG

3121 GGATACCCGA GCACACGTAC CGCTCCCGCG TCACCCTCTC CAACCAGCCC TATATCAAGG

3181 TCCTTACCCT AGCCAACTTC ACCACCAAGG ATGAGGGCGA CTACTTTTGT GAGCTTCGCG

3241 TAAGTGGCGC GAATCCCATG AGCTCCAATA AAAGTATCAG TGTGTATAGA GACAAGCTGG

3301 TCAAGTGTGG CGGCATAAGC CTGCTGGTTC AGAACACATC CTGGATGCTG CTGCTGCTGC

3361 TTTCCCTCTC CCTCCTCCAA GCCCTGGACT TCATTTCTCT GTGAagcgct AATAAAAGAT

3421 CTTTATTTTC ATTAGATCTG TGTGTTGGTT TTTTGTGTGa cgtgcggtcg actttaagac 3481 caatgactta caaggcagct gtagatctta gccacttttt aaaagaaaag gggggactgg 3541 aagggctaat tcactcccaa cgaagacaag atctgctttt tgcttgtact gggtctctct 3601 ggttagacca gatctgagcc tgggagctct ctggctaact agggaaccca ctgcttaagc 3661 ctcaataaag cttgccttga gtgcttcaag tagtgtgtgc ccgtctgttg tgtgactctg 3721 gtaactagag atccctcaga cccttttagt cagtgtggaa aatctctagc agtacgtata 3781 gtagttcatg tcatcttatt attcagtatt tataacttgc aaagaaatga atatcagaga 3841 gtgagaggaa cttgtttatt gcagcttata atggttacaa ataaagcaat agcatcacaa 3901 atttcacaaa taaagcattt ttttcactgc attctagttg tggtttgtcc aaactcatca 3961 atgtatctta tcatgtctgg ctctagctat cccgccccta actccgccca tcccgcccct 4021 aactccgccc agttccgccc attctccgcc ccatggctga ctaatttttt ttatttatgc -continued 4081 agaggccgag gccgcctcgg cctctgagct attccagaag tagtgaggag gctttttttgg 4141 aggcctaggg acgtacccaa ttcgccctat agtgagtcgt attacgcgcg ctcactggcc 4201 gtcgttttac aacgtcgtga ctgggaaaac cctggcgtta cccaacttaa tcgccttgca 4261 gcacatcccc ctttcgccag ctggcgtaat agcgaagagg cccgcaccga tcgcccttcc 4321 caacagttgc gcagcctgaa tggcgaatgg gacgcgccct gtagcggcgc attaagcgcg 4381 gcgggtgtgg tggttacgcg cagcgtgacc gctacacttg ccagcgccct agcgcccgct 4441 cctttcgctt tcttcccttc ctttctcgcc acgttcgccg gctttccccg tcaagctcta 4501 aatcgggggc tccctttagg gttccgattt agtgctttac ggcacctcga ccccaaaaaa 4561 cttgattagg gtgatggttc acgtagtggg ccatcgccct gatagacggt ttttcgccct 4621 ttgacgttgg agtccacgtt ctttaatagt ggactcttgt tccaaactgg aacaacactc 4681 aaccctatct cggtctattc ttttgattta taagggattt tgccgatttc ggcctattgg 4741 ttaaaaaatg agctgattta acaaaaattt aacgcgaatt ttaacaaaat attaacgctt 4801 acaatttagg tggcactttt cggggaaatg tgcgcggaac ccctatttgt ttatttttct 4861 aaatacattc aaatatgtat ccgctcatga gacaataacc ctgataaatg cttcaataat 4921 attgaaaaag gaagagtatg agtattcaac atttccgtgt cgcccttatt cccttttttg 4981 cggcattttg ccttcctgtt tttgctcacc cagaaacgct ggtgaaagta aaagatgctg 5041 aagatcagtt gggtgcacga gtgggttaca tcgaactgga tctcaacagc ggtaagatcc 5101 ttgagagttt tcgccccgaa gaacgttttc caatgatgag cacttttaaa gttctgctat 5161 gtggcgcggt attatcccgt attgacgccg ggcaagagca actcggtcgc cgcatacact 5221 attctcagaa tgacttggtt gagtactcac cagtcacaga aaagcatctt acggatggca 5281 tgacagtaag agaattatgc agtgctgcca taaccatgag tgataacact gcggccaact 5341 tacttctgac aacgatcgga ggaccgaagg agctaaccgc ttttttgcac aacatggggg 5401 atcatgtaac tcgccttgat cgttgggaac cggagctgaa tgaagccata ccaaacgacg 5461 agcgtgacac cacgatgcct gtagcaatgg caacaacgtt gcgcaaacta ttaactggcg 5521 aactacttac tctagcttcc cggcaacaat taatagactg gatggaggcg gataaagttg 5581 caggaccact tctgcgctcg gcccttccgg ctggctggtt tattgctgat aaatctggag 5641 ccggtgagcg tgggtctcgc ggtatcattg cagcactggg gccagatggt aagccctccc 5701 gtatcgtagt tatctacacg acggggagtc aggcaactat ggatgaacga aatagacaga 5761 tcgctgagat aggtgcctca ctgattaagc attggtaact gtcagaccaa gtttactcat 5821 atatacttta gattgattta aaacttcatt tttaatttaa aaggatctag gtgaagatcc 5881 tttttgataa tctcatgacc aaaatccctt aacgtgagtt ttcgttccac tgagcgtcag 5941 accccgtaga aaagatcaaa ggatcttctt gagatccttt ttttctgcgc gtaatctgct 6001 gcttgcaaac aaaaaaacca ccgctaccag cggtggtttg tttgccggat caagagctac 6061 caactctttt tccgaaggta actggcttca gcagagcgca gataccaaat actgttcttc 6121 tagtgtagcc gtagttaggc caccacttca agaactctgt agcaccgcct acatacctcg 6181 ctctgctaat cctgttacca gtggctgctg ccagtggcga taagtcgtgt cttaccgggt 6241 tggactcaag acgatagtta ccggataagg cgcagcggtc gggctgaacg gggggttcgt 6301 gcacacagcc cagcttggag cgaacgacct acaccgaact gagataccta cagcgtgagc 6361 tatgagaaag cgccacgctt cccgaaggga gaaaggcgga caggtatccg gtaagcggca 6421 gggtcggaac aggagagcgc acgagggagc ttccaggggg aaacgcctgg tatctttata 6481 gtcctgtcgg gtttcgccac ctctgacttg agcgtcgatt tttgtgatgc tcgtcagggg -continued

```
6541 ggcggagcct atggaaaaac gccagcaacg cggccttttt acggttcctg gccttttgct
6601 ggccttttgc tcacatgttc tttcctgcgt tatcccctga ttctgtggat aaccgtatta
6661 ccgcctttga gtgagctgat accgctcgcc gcagccgaac gaccgagcgc agcgagtcag
6721 tgagcgagga agcggaagag cgcccaatac gcaaaccgcc tctccccgcg cgttggccga
6781 ttcattaatg cagctggcac gacaggtttc ccgactggaa agcgggcagt gagcgcaacg
6841 caattaatgt gagttagctc actcattagg caccccaggc tttacacttt atgcttccgg
6901 ctcgtatgtt gtgtggaatt gtgagcggat aacaatttca cacaggaaac agctatgacc
6961 atgattacgc caagcgcgca attaaccctc actaaaggga acaaaagctg gagctgcaag
7021 c
```

Genome-scale mouse T cell CRISPR library cloning: The original mouse CRISPR knockout library, in two sub-libraries (mGeCKOa and mGeCKOb) was from Sanjana et al., Nat Methods 11, 783-784 (2014). mGeCKOa and mGeCKOb were sub-cloned in equal molar, by Gibson assembly and electroporation, into the T cell CRISPR vector to generate the Genome-scale mouse T cell CRISPR library (MKO), with a total of 129,209 sgRNAs including 1,000 non-targeting controls (NTCs). An estimated library coverage of >50× (~$7\times10^6$ total colonies) was achieved in electroporation. The library was subsequently sequence-verified by Illumina sequencing. At least 94.1% (121,608/129,209) of unique sgRNAs the whole library cloned, targeting 98.3% (22,375/22,768) of all protein coding genes and microRNAs in the mouse genome, with a tight log-normal distribution representing the vast majority of all designed sgRNAs (90% within 2 orders of magnitude, 99% within 3 orders of magnitude).

Viral library production: The MKO library plasmid was transfected into low-passage HEK293FT cells at 80% confluency in 15 cm tissue culture plates. Viral supernatant was collected at 48 h and 72 h post-transfection, filtered via a 0.45 μm filtration unit (Fisher/VWR), and concentrated using AmiconUltra 100 kD ultracentrifugation units (Millipore), aliquoted and stored in −80° C. until use. Virus for empty vector was produced in a similar manner.

T cell isolation and culture: Spleens and mesenteric lymph nodes (mLNs) were isolated from various indicated mouse strains, and placed in ice-cold 2% FBS [FBS (Sigma)+RPMI-1640 (Lonza)]. Organs were prepared by mashing organs through a 100 μm filter. Lymphocytes were suspended in 2% FBS. RBCs were lysed with 1 ml of ACK Lysis Buffer (Lonza) per spleen, incubated for 2 mins at room temperature, and washed with 2% FBS. Lymphocytes were filtered through a 40 μm filter and resuspended with MACS Buffer (PBS+0.5% BSA+2 μM EDTA). Naive $CD8^+$ T cells were isolated using the protocol and kit established by Miltenyi. Naive $CD8^+$ T cells were resuspended with cRPMI (RPMI-1640+10% FBS+2 mM L-Glutamine+100 U Pen/Strep (Fisher)+49 nM β-mercaptoethanol (Sigma)) to a final concentration of $1\times10^6$ cells/ml. Medium for in vivo experiments was supplemented with 2 ng/ml IL-2+2.5 ng/ml IL-7+50 ng/ml IL-15+1 μg/ml anti-CD28. Medium for in vitro experiments was supplemented with 2 ng/ml IL-2+2 ng/ml IL-12p70+1 μg/ml anti-CD28. Cells were cultured on plates pretreated with 5 μg/ml anti-CD3 and incubated at 37° C. Various cytokines and antibodies were purchased from BD, Biolegend and eBiosciences.

T cell transduction, virus titration: T cells were infected in culture immediately after isolation by directly adding concentrated virus into the media. 3 days after infection, T cells were stained for Thy1.1 expression and analyzed on FACS. Viral titer was determined for each batch by the number of $Thy1.1^+$ T cells normalized to total T cells divided by the volume of virus used. At least 3 doses of viruses with experimental duplicates were used for determining viral titer.

Antibody and Flow Cytometry: Infectivity of $CD8^+$ T cells was assessed via surface staining with anti-CD3ε APC, anti-CD8α FITC, and anti-Thy1.1 PE. Biolegend antibodies used in experiments include anti-CD3ε PE/Cy7, anti-CD8α APC, anti-CD16/32, CD62L PE, CD107a PE, anti-GranzymeA PE, anti-SIINFEKL:H-$2K^b$ PE, and anti-Thy1.1 PE. Anti-human/mouse DHX37/Dhx37 was purchased from Novus Biologicals. Anti-rabbit IgG AF594 was purchased from cell signaling. For surface stains, cells were stained on ice for 30 mins. Samples were collected on a BD FACSAria cell sorter with 3 lasers, and analyzed using FlowJo software 9.9.4 (Treestar, Ashland, OR) on a MAC® workstation.

Library-scale viral transduction of T cells: T cells were isolated and cultured as described herein. With the viral titer information, for each infection replicate, a total of $>1\times10^8$ Cas9 or naive OT-I; Cas9 $CD8^+$ T cells were transduced at a MOI of 1 with concentrated lentivirus containing the MKO library described above, to achieve an initial library coverage of >700×. Transduction with the virus containing the empty vector was performed in parallel with a total of $>1\times10^7$ naive $CD8^+$ T cells. Unlike cancer cell screens, pooled screens in primary cells often use relatively high MOI (Chen et al., (2014) Immunity 41, 325-338; Zhou et al., (2014) Nature 506, 52-57), as sufficient infectivity is necessary to reach sufficient on-target efficiency in these cells. Multiple computational strategies were used to generate quantitative ranked list of genes and to distinguish mis-association or false-positives from potential true hits with strong selection, including usage of independent infection replicates, different mice, independent screens, different TCRs, and independent sgRNAs. In each experiment, 3 infection replicates were applied for generation of T cell library unless otherwise noted.

Adoptive transfer of viral library infected T cells and tissue processing: At day 0 of the culture, naive $CD8^+$ T cells were infected with the lentiviral MKO library, and incubated at 37° C. for 3 days. On day 3 of culture, T cells were collected, washed with ice-cold PBS, and resuspended to a final concentration of $5\times10^7$ cells/ml. $1\times10^7$ cells were injected intravenously into each mouse. C57BL/6 (B6), B6.129, B6.129.Fvb, Cas9, or $Rag1^{-/-}$ mice were used as recipient mice in respective experiments. All adoptive cell transfer experiments in this study were done without lymphodepletion unless otherwise noted. On 7-day post-transfer, mice were sacrificed, and relevant organs were isolated. Skin draining lymph nodes were comprised of inguinal, popliteal, axillary, and brachial lymph nodes. Cervical lymph nodes isolated entailed the 6 superficial cervical lymph nodes. Abdominal lymph nodes included the mesenteric and pancreatic lymph nodes. Other relevant organs isolated were the spleen, liver, pancreas, lung, muscle and brain.

Generation of a neoantigen expression vector (mCherry-cOVA Expression Vector): A lentiviral mCherry-cOVA (mCh-cOVA) vector, lenti-pLKO-U6-sg(BsmBI)-EF S-mCherry-2A-cOVA, was generated by subcloning cOVA into a mCherry lentiviral vector via Gibson Assembly.

```
pMD02: lenti-pLKO-U6-sgBsmBI-EFS-mCherry-2A-cOVA (SEQ ID NO: 129,216):
     1 ttaatgtagt cttatgcaat actcttgtag tcttgcaaca tggtaacgat gagttagcaa

    61 catgccttac aaggagagaa aaagcaccgt gcatgccgat tggtggaagt aaggtggtac

   121 gatcgtgcct tattaggaag gcaacagacg ggtctgacat ggattggacg aaccactgaa

   181 ttgccgcatt gcagagatat tgtatttaag tgcctagctc gatacataaa cgggtctctc

   241 tggttagacc agatctgagc ctgggagctc tctggctaac tagggaaccc actgcttaag

   301 cctcaataaa gcttgccttg agtgcttcaa gtagtgtgtg cccgtctgtt gtgtgactct

   361 ggtaactaga gatccctcag acccttttag tcagtgtgga aaatctctag cagtggcgcc

   421 cgaacaggga cttgaaagcg aaagggaaac cagaggagct ctctcgacgc aggactcggc

   481 ttgctgaagc gcgcacggca agaggcgagg ggcggcgact ggtgagtacg ccaaaaattt

   541 tgactagcgg aggctagaag gagagagatg ggtgcgagag cgtcagtatt aagcggggga

   601 gaattagatc gcgatgggaa aaaattcggt taaggccagg gggaaagaaa aaatataaat

   661 taaaacatat agtatgggca agcagggagc tagaacgatt cgcagttaat cctggcctgt

   721 tagaaacatc agaaggctgt agacaaatac tgggacagct acaaccatcc cttcagacag

   781 gatcagaaga acttagatca ttatataata cagtagcaac cctctattgt gtgcatcaaa

   841 ggatagagat aaaagacacc aaggaagctt tagacaagat agaggaagag caaaacaaaa

   901 gtaagaccac cgcacagcaa gcggccgctg atcttcagac ctggaggagg agatatgagg

   961 gacaattgga gaagtgaatt atataaatat aaagtagtaa aaattgaacc attaggagta

  1021 gcacccacca aggcaaagag aagagtggtg cagagagaaa aaagagcagt gggaatagga

  1081 gctttgttcc ttgggttctt gggagcagca ggaagcacta tgggcgcagc gtcaatgacg

  1141 ctgacggtac aggccagaca attattgtct ggtatagtgc agcagcagaa caatttgctg

  1201 agggctattg aggcgcaaca gcatctgttg caactcacag tctggggcat caagcagctc

  1261 caggcaagaa tcctggctgt ggaaagatac ctaaaggatc aacagctcct ggggatttgg

  1321 ggttgctctg gaaaactcat ttgcaccact gctgtgcctt ggaatgctag ttggagtaat

  1381 aaatctctgg aacagatttg gaatcacacg acctggatgg agtgggacag agaaattaac

  1441 aattacacaa gcttaataca ctccttaatt gaagaatcgc aaaaccagca agaaaagaat

  1501 gaacaagaat tattggaatt agataaatgg gcaagtttgt ggaattggtt taacataaca

  1561 aattggctgt ggtatataaa attattcata atgatagtag gaggcttggt aggtttaaga

  1621 atagtttttg ctgtactttc tatagtgaat agagttaggc agggatattc accattatcg

  1681 tttcagaccc acctcccaac cccgagggga cccagagagg gcctatttcc catgattcct

  1741 tcatatttgc atatacgata caaggctgtt agagagataa ttagaattaa tttgactgta

  1801 aacacaaaga tattagtaca aaatacgtga cgtagaaagt aataatttct tgggtagttt

  1861 gcagttttaa aattatgttt taaaatggac tatcatatgc ttaccgtaac ttgaaagtat

  1921 ttcgatttct tggctttata tatcttGTGG AAAGGACGAA ACACCgGAGA CGgaCGTCTC

  1981 tgttttagag ctaGAAAtag caagttaaaa taaggctagt ccgttatcaa cttgaaaaag

  2041 tggcaccgag tcggtgcTTT TTTaagcttg gcgtaactag atcttgagac aaatggcagt

  2101 attcatccac aattttaaaa gaaaaggggg gattgggggg tacagtgcag gggaaagaat

  2161 agtagacata atagcaacag acatacaaac taaagaatta caaaaacaaa ttacaaaaat
```

-continued 2221 tcaaaatttt cgggtttatt acagggacag cagagatcca ctttggcgcc ggctcgaggg
2281 ggcccgggtg caaagatgga taaagtttta aacagagagg aatctttgca gctaatggac
2341 cttctaggtc ttgaaaggag tgggaattgg ctccggtgcc cgtcagtggg cagagcgcac
2401 atcgcccaca gtccccgaga agttgggggg aggggtcggc aattgatccg gtgcctagag
2461 aaggtggcgc ggggtaaact gggaaagtga tgtcgtgtac tggctccgcc tttttcccga
2521 gggtggggga gaaccgtata taagtgcagt agtcgccgtg aacgttcttt ttcgcaacgg
2581 gtttgccgcc agaacacagg taagtgccgt gtgtggttcc cgcgggcctg gcctctttac
2641 gggttatggc ccttgcgtgc cttgaattac ttccactggc tgcagtacgt gattcttgat
2701 cccgagcttc gggttggaag tgggtgggag agttcgaggc cttgcgctta aggagcccct
2761 tcgcctcgtg cttgagttga ggcctggcct gggcgctggg gccgccgcgt gcgaatctgg
2821 tggcaccttc gcgcctgtct cgctgctttc gataagtctc tagccattta aaatttttga
2881 tgacctgctg cgacgctttt tttctggcaa gatagtcttg taaatgcggg ccaagatctg
2941 cacactggta tttcggtttt tggggccgcg ggcggcgacg gggcccgtgc gtcccagcgc
3001 acatgttcgg cgaggcgggg cctgcgagcg cggccaccga gaatcggacg ggggtagtct
3061 caagctggcc ggcctgctct ggtgcctggc ctcgcgccgc cgtgtatcgc cccgccctgg
3121 gcggcaaggc tggcccggtc ggcaccagtt gcgtgagcgg aaagatggcc gcttcccggc
3181 cctgctgcag ggagctcaaa atggaggacg cggcgctcgg gagagcgggc gggtgagtca
3241 cccacacaaa ggaaaagggc ctttccgtcc tcagccgtcg cttcatgtga ctccacggag
3301 taccgggcgc cgtccaggca cctcgattag ttctcgagct tttggagtac gtcgtcttta
3361 ggttgggggg aggggtttta tgcgatggag tttccccaca ctgagtgggt ggagactgaa
3421 gttaggccag cttggcactt gatgtaattc tccttggaat ttgccctttt tgagtttgga
3481 tcttggttca ttctcaagcc tcagacagtg gttcaaagtt tttttcttcc atttcaggtg
3541 tcgtgacgta cggccaccat gGTGAGCAAG GGCGAGGAGG ATAACATGGC CATCATCAAG
3601 GAGTTCATGC GCTTCAAGGT GCACATGGAG GGCTCCGTGA ACGGCCACGA GTTCGAGATC
3661 GAGGGCGAGG GCGAGGGCCG CCCCTACGAG GGCACCCAGA CCGCCAAGCT GAAGGTGACC
3721 AAGGGTGGCC CCCTGCCCTT CGCCTGGGAC ATCCTGTCCC CTCAGTTCAT GTACGGCTCC
3781 AAGGCCTACG TGAAGCACCC CGCCGACATC CCCGACTACT TGAAGCTGTC CTTCCCCGAG
3841 GGCTTCAAGT GGGAGCGCGT GATGAACTTC GAGGACGGCG GCGTGGTGAC CGTGACCCAG
3901 GACTCCTCCC TGCAGGACGG CGAGTTCATC TACAAGGTGA AGCTGCGCGG CACCAACTTC
3961 CCCTCCGACG GCCCCGTAAT GCAGAAGAAG ACCATGGGCT GGGAGGCCTC CTCCGAGCGG
4021 ATGTACCCCG AGGACGGCGC CCTGAAGGGC GAGATCAAGC AGAGGCTGAA GCTGAAGGAC
4081 GGCGGCCACT ACGACGCTGA GGTCAAGACC ACCTACAAGG CCAAGAAGCC CGTGCAGCTG
4141 CCCGGCGCCT ACAACGTCAA CATCAAGTTG GACATCACCT CCCACAACGA GGACTACACC
4201 ATCGTGGAAC AGTACGAACG CGCCGAGGGC CGCCACTCCA CCGGCGGCAT GGACGAGCTG
4261 TACAAGGGCA GTGGAGAGGG CAGAGGAAGT CTGCTAACAT GCGGTGACGT CGAGGAGAAT
4321 CCTGGCCCAA TGGGCTCCAT CGGCGCAGCA AGCATGGAAT TTTGTTTTGA TGTATTCAAG
4381 GAGCTCATCA ATTCCTGGGT AGAAAGTCAG ACAAATGGAA TTATCAGAAA TGTCCTTCAG
4441 CCAAGCTCCG TGGATTCTCA AACTGCAATG GTTCTGGTTA ATGCCATTGT CTTCAAAGGA
4501 CTGTGGGAGA AAACATTTAA GGATGAAGAC ACACAAGCAA TGCCTTTCAG AGTGACTGAG
4561 CAAGAAAGCA AACCTGTGCA GATGATGTAC CAGATTGGTT TATTTAGAGT GGCATCAATG -continued

4621 GCTTCTGAGA AAATGAAGAT CCTGGAGCTT CCATTTGCCA GTGGGACAAT GAGCATGTTG

4681 GTGCTGTTGC CTGATGAAGT CTCAGGCCTT GAGCAGCTTG AGAGTATAAT CAACTTTGAA

4741 AAACTGACTG AATGGACCAG TTCTAATGTT ATGGAAGAGA GGAAGATCAA AGTGTACTTA

4801 CCTCGCATGA AGATGGAGGA AAAATACAAC CTCACATCTG TCTTAATGGC TATGGGCATT

4861 ACTGACGTGT TTAGCTCTTC AGCCAATCTG TCTGGCATCT CCTCAGCAGA GAGCCTGAAG

4921 ATATCTCAAG CTGTCCATGC AGCACATGCA GAAATCAATG AAGCAGGCAG AGAGGTGGTA

4981 GGGTCAGCAG AGGCTGGAGT GGATGCTGCA AGCGTCTCTG AAGAATTTAG GGCTGACCAT

5041 CCATTCCTCT TCTGTATCAA GCACATCGCA ACCAACGCCG TTCTCTTCTT TGGCAGATGT

5101 GTTTCCCCTT AAacgcgtta agtcgacaat caacctctgg attacaaaat ttgtgaaaga 5161 ttgactggta ttcttaacta tgttgctcct tttacgctat gtggatacgc tgctttaatg 5221 cctttgtatc atgctattgc ttcccgtatg gctttcattt tctcctcctt gtataaatcc 5281 tggttgctgt ctctttatga ggagttgtgg cccgttgtca ggcaacgtgg cgtggtgtgc 5341 actgtgtttg ctgacgcaac ccccactggt tggggcattg ccaccacctg tcagctcctt 5401 tccgggactt tcgctttccc cctccctatt gccacggcgg aactcatcgc cgcctgcctt 5461 gcccgctgct ggacaggggc tcggctgttg ggcactgaca attccgtggt gttgtcgggg 5521 aaatcatcgt cctttccttg gctgctcgcc tgtgttgcca cctggattct gcgcgggacg 5581 tccttctgct acgtcccttc ggccctcaat ccagcggacc ttccttcccg cggcctgctg 5641 ccggctctgc ggcctcttcc gcgtcttcgc cttcgccctc agacgagtcg gatctccctt 5701 tgggccgcct ccccgcgtcg actttaagac caatgactta caaggcagct gtagatctta 5761 gccacttttt aaaagaaaag gggggactgg aagggctaat tcactcccaa cgaagacaag 5821 atctgctttt tgcttgtact gggtctctct ggttagacca gatctgagcc tgggagctct 5881 ctggctaact agggaaccca ctgcttaagc ctcaataaag cttgccttga gtgcttcaag 5941 tagtgtgtgc ccgtctgttg tgtgactctg gtaactagag atccctcaga cccttttagt 6001 cagtgtggaa aatctctagc agtacgtata gtagttcatg tcatcttatt attcagtatt 6061 tataacttgc aaagaaatga atatcagaga gtgagaggaa cttgtttatt gcagcttata 6121 atggttacaa ataaagcaat agcatcacaa atttcacaaa taaagcattt ttttcactgc 6181 attctagttg tggtttgtcc aaactcatca atgtatctta tcatgtctgg ctctagctat 6241 cccgccccta actccgccca tcccgcccct aactccgccc agttccgccc attctccgcc 6301 ccatggctga ctaatttttt ttatttatgc agaggccgag gccgcctcgg cctctgagct 6361 attccagaag tagtgaggag gcttttttgg aggcctaggg acgtacccaa ttcgccctat 6421 agtgagtcgt attacgcgcg ctcactggcc gtcgttttac aacgtcgtga ctgggaaaac 6481 cctggcgtta cccaacttaa tcgccttgca gcacatcccc ctttcgccag ctggcgtaat 6541 agcgaagagg cccgcaccga tcgcccttcc caacagttgc gcagcctgaa tggcgaatgg 6601 gacgcgccct gtagcggcgc attaagcgcg gcgggtgtgg tggttacgcg cagcgtgacc 6661 gctacacttg ccagcgccct agcgcccgct cctttcgctt tcttcccttc ctttctcgcc 6721 acgttcgccg gctttccccg tcaagctcta aatcgggggc tccctttagg gttccgattt 6781 agtgctttac ggcacctcga ccccaaaaaa cttgattagg gtgatggttc acgtagtggg 6841 ccatcgccct gatagacggt ttttcgccct ttgacgttgg agtccacgtt ctttaatagt 6901 ggactcttgt tccaaactgg aacaacactc aaccctatct cggtctattc ttttgattta 6961 taagggattt tgccgatttc ggcctattgg ttaaaaaatg agctgattta acaaaaattt 7021 aacgcgaatt ttaacaaaat attaacgctt acaatttagg tggcactttt cggggaaatg -continued

```
7081 tgcgcggaac ccctatttgt ttatttttct aaatacattc aaatatgtat ccgctcatga
7141 gacaataacc ctgataaatg cttcaataat attgaaaaag gaagagtatg agtattcaac
7201 atttccgtgt cgcccttatt cccttttttg cggcattttg ccttcctgtt tttgctcacc
7261 cagaaacgct ggtgaaagta aaagatgctg aagatcagtt gggtgcacga gtgggttaca
7321 tcgaactgga tctcaacagc ggtaagatcc ttgagagttt tcgccccgaa gaacgttttc
7381 caatgatgag cacttttaaa gttctgctat gtggcgcggt attatcccgt attgacgccg
7441 ggcaagagca actcggtcgc cgcatacact attctcagaa tgacttggtt gagtactcac
7501 cagtcacaga aaagcatctt acggatggca tgacagtaag agaattatgc agtgctgcca
7561 taaccatgag tgataacact gcggccaact tacttctgac aacgatcgga ggaccgaagg
7621 agctaaccgc ttttttgcac aacatggggg atcatgtaac tcgccttgat cgttgggaac
7681 cggagctgaa tgaagccata ccaaacgacg agcgtgacac cacgatgcct gtagcaatgg
7741 caacaacgtt gcgcaaacta ttaactggcg aactacttac tctagcttcc cggcaacaat
7801 taatagactg gatggaggcg gataaagttg caggaccact tctgcgctcg gcccttccgg
7861 ctggctggtt tattgctgat aaatctggag ccggtgagcg tgggtctcgc ggtatcattg
7921 cagcactggg gccagatggt aagccctccc gtatcgtagt tatctacacg acggggagtc
7981 aggcaactat ggatgaacga aatagacaga tcgctgagat aggtgcctca ctgattaagc
8041 attggtaact gtcagaccaa gtttactcat atatacttta gattgattta aaacttcatt
8101 tttaatttaa aaggatctag gtgaagatcc tttttgataa tctcatgacc aaaatccctt
8161 aacgtgagtt ttcgttccac tgagcgtcag accccgtaga aaagatcaaa ggatcttctt
8221 gagatccttt ttttctgcgc gtaatctgct gcttgcaaac aaaaaaacca ccgctaccag
8281 cggtggtttg tttgccggat caagagctac caactctttt tccgaaggta actggcttca
8341 gcagagcgca gataccaaat actgttcttc tagtgtagcc gtagttaggc caccacttca
8401 agaactctgt agcaccgcct acatacctcg ctctgctaat cctgttacca gtggctgctg
8461 ccagtggcga taagtcgtgt cttaccgggt tggactcaag acgatagtta ccggataagg
8521 cgcagcggtc gggctgaacg gggggttcgt gcacacagcc cagcttggag cgaacgacct
8581 acaccgaact gagataccta cagcgtgagc tatgagaaag cgccacgctt cccgaaggga
8641 gaaaggcgga caggtatccg gtaagcggca gggtcggaac aggagagcgc acgagggagc
8701 ttccaggggg aaacgcctgg tatctttata gtcctgtcgg gtttcgccac ctctgacttg
8761 agcgtcgatt tttgtgatgc tcgtcagggg ggcggagcct atggaaaaac gccagcaacg
8821 cggccttttt acggttcctg gccttttgct ggccttttgc tcacatgttc tttcctgcgt
8881 tatcccctga ttctgtggat aaccgtatta ccgcctttga gtgagctgat accgctcgcc
8941 gcagccgaac gaccgagcgc agcgagtcag tgagcgagga agcggaagag cgcccaatac
9001 gcaaaccgcc tctccccgcg cgttggccga ttcattaatg cagctggcac gacaggtttc
9061 ccgactggaa agcgggcagt gagcgcaacg caattaatgt gagttagctc actcattagg
9121 caccccaggc tttacacttt atgcttccgg ctcgtatgtt gtgtggaatt gtgagcggat
9181 aacaatttca cacaggaaac agctatgacc atgattacgc caagcgcgca attaaccctc
9241 actaaaggga acaaaagctg gagctgcaag c
```

Generation of stably transfected mCherry-cOVA expressing cell line: E0771 murine breast cancer cells were transduced with mCh-cOVA-expressing lentivirus. After 3 days post-transduction, transduced E0771 cells were cultured individually in 96-well plates by resuspending cells to 10 cells/ml and culturing 100 μl of cell suspension in each well. Two weeks later, clonal $mCh^+$E0771 clones were identified by fluorescence microscopy. $mCh^+$E0771 clones were stained with established anti-mouse [H-2$K^b$ bound to SIINFEKL] antibody (Porgador et al., Immunity 6, 715-726

(1997)) to determine cOVA expression. Different $mCh^+$ $cOVA^+$ clones were selected based on cOVA expression. E0771 cells were pulsed with varying concentrations of SIINFEKL peptide for 4 hours at 37° C., and subsequently stained with an the established antibody described elsewhere herein. $mCh^+cOVA^+$E0771 clones were compared to SIINFEKL-pulsed cells. Clone 3 was chosen for in vivo experiments because of its low, uniform expression of cOVA to select for genes with stronger phenotypes. In addition, a LCC-mChcOVA cell line was generated by transducing a mouse lung cancer cell line.

Transplantation of cancer cells into $Rag1^{-/-}$ mice and tissue processing: $5\times10^6$ $mCh^+cOVA^+$E0771 cells were injected either subcutaneously or into the intra-mammary fat pad of $Rag1^{-/-}$ mice. Ten days post-transplantation, viral library infected T cells, were intravenously injected in tumor-bearing $Rag1^{-/-}$ mice. After 7 days, draining lymph nodes, non-draining lymph nodes, spleens, lungs, and tumors were isolated. Samples were prepared for DNA extraction or FACS analysis.

Spleens and lymph nodes were prepared as described elsewhere herein. Tumors were broken down into smaller fragments, about the size of lentils. Tumors were then dissociated with 1 μg/ml Collagenase IV for 30 minutes using GentleMacs Octo dissociator from Miltenyi, and cell suspensions were passed through 100 μm filter twice before staining.

Degranulation (kill) assay in genome-scale CRISPR screening and validation: Experiments were first optimized by pulsing E0771 cells with varying concentrations of SIINFEKL peptide for 4 hours at 37° C., and subsequently stained with the anti-mouse [SIINFEKL:H-$2K^b$] antibody and analyzed by flow cytometry. The dose of 1 ng/ml was chosen as it represents the maximum concentration tested without being detected by anti-(SIINFEKL:H-$2K^b$). Naive OT-I; Cas9 $CD8^+$ T cells were isolated and transduced with MKO lentiviral library described herein. Infected OT-I; Cas9 $CD8^+$ T cells were incubated on plates pretreated with 5 μg/ml anti-CD3ε in cRPMI supplemented with 2 ng/ml IL-2+2 ng/ml IL-12p70+1 μg/ml anti-CD28 for 6 days. 12 hours before assay, infected OT-I; Cas9 $CD8^+$ T cells were incubated on untreated plates in the presence of 2 ng/ml IL-2+2 ng/ml IL-12p70 to rest the cells. On day 6, 12 hours before the assay, $1\times10^7$ E0771 cells were also plated on 10 cm plate in D10 media (DMEM+10% FBS+100 U Pen/Strep). The following day, E0771 cells were incubated with warm D10 media supplemented with either 0 or 1 ng/ml SIINFEKL peptide for 4 hours. Meanwhile, infected OT-I; Cas9 $CD8^+$ T cells were resuspended to a final concentration $1\times10^6$ cells/ml with cRPMI+2 nM monensin+anti-CD107a PE antibody, and added to E0771 cells at a T cell: seeding cancer cell ratio=1:1. Cells were coincubated at 37° C. for 2 hours. Cells were then stained with anti-CD8 APC for 30 minutes on ice, and cells were sorted via BD FACSAria. A total of $1\times10^7$ T cells were analyzed, and the top 5% $CD107a^+$ cells were sorted, and subjected to genomic DNA extraction, CRISPR library readout, and screen data analysis. A total of three biological replicates were performed.

In validation experiments, both T cells and E0771 cells were scaled down accordingly, while maintaining T cell: seeding cancer cell ratio=1:1. Briefly, cells were infected and cultured at 37° C. for 7 days. On day 6, T cells were rested overnight and E0771 cells were plated in 12-well plates at $5\times10^5$ cells/ml/well. E0771 cells were then incubated with 10 ng/ml SIINFEKL for 4 hours in D10 media. $5\times10^5$ OT-I; Cas9 $CD8^+$ T cells were added to the pulsed E0771 cells. During co-culture, IL-2, IL-12, anti-CD107a-PE (1:400), and monensin was added. After 2 hours of incubation, cells were isolated, stained, and run on flow cytometry.

Genomic DNA extraction from cells and mouse tissues: For gDNA extraction, three methods were used. Method 1: for samples with a total number of less than or equal to $1\times10^5$ cells, 100 μl of QuickExtract solution (Epicentre) was directly added to cells and incubated at 65° C. for 30 to 60 minutes until the cell pellets were completely dissolved. Method 2: for cellular samples with a total number of $1\times10^5$ to $2\times10^6$ cells, or tissue samples from mouse lymph nodes, samples were subjected to QIAamp Fast DNA Tissue Kit (Qiagen) following the manufacturer's protocol. Method 3: for cellular samples with a total number of greater than $2\times10^6$ cells, or tissue samples from mouse organs such as spleen, lung, liver, brain, pancreas, colon, or tumor samples, a custom Puregene protocol was used.

Briefly, 50-200 mg of frozen ground tissue were resuspended in 6 ml of Lysis Buffer (50 mM Tris, 50 mM EDTA, 1% SDS, pH 8) in a 15 ml conical tube, and 30 μl of 20 mg/ml Proteinase K (Qiagen) were added to the tissue/cell sample and incubated at 55° C. overnight. The next day, 30 μl of 10 mg/ml RNAse A (Qiagen) was added to the lysed sample, which was then inverted 25 times and incubated at 37° C. for 30 minutes. Samples were cooled on ice before addition of 2 ml of pre-chilled 7.5M ammonium acetate (Sigma) to precipitate proteins. The samples were vortexed at high speed for 20 seconds and then centrifuged at ≥4,000×g for 10 minutes. Then, a tight pellet was visible in each tube and the supernatant was carefully decanted into a new 15 ml conical tube. Then 6 ml 100% isopropanol was added to the tube, inverted 50 times and centrifuged at ≥4,000×g for 10 minutes. Genomic DNA was visible as a small white pellet in each tube. The supernatant was discarded, 6 ml of freshly prepared 70% ethanol was added, the tube was inverted 10 times, and then centrifuged at ≥4,000×g for 1 minute. The supernatant was discarded by pouring; the tube was briefly spun, and remaining ethanol was removed using a P200 pipette. After air-drying for 10-30 minutes, the DNA changed appearance from a milky white pellet to slightly translucent. Then, 500 μl of $ddH_2O$ was added, the tube was incubated at 65° C. for 1 hour and at room temperature overnight to fully resuspend the DNA. The next day, the gDNA samples were vortexed briefly. The gDNA concentration was measured using a Nanodrop (Thermo Scientific).

SgRNA library readout by deep sequencing: The sgRNA library readout was performed using a two-steps PCR strategy, where the first PCR includes enough genomic DNA to preserve full library complexity and the second PCR adds appropriate sequencing adapters to the products from the first PCR.

For PCR #1, a region containing sgRNA cassette was amplified using primers specific to the T cell CRISPR vector:

```
Forward
                              (SEQ ID NO: 129,211)
CCCGAGGGGACCCAGAGAG

Reverse
                              (SEQ ID NO: 129,212)
CAATTCCCACTCCTTTCAAGAC
```

PCR was performed using Phusion Flash High Fidelity Master Mix (PF) or DreamTaq Green PCR Master Mix (DT) (ThermoFisher). For reactions using PF, in PCR #1, the thermocycling parameters were: 98° C. for 2 min, 18-24 cycles of (98° C. for 1 s, 62° C. for 5 s, 72° C. for 30 s), and 72° C. for 2 minutes. For reactions using DT, the thermocycling parameters were adjusted according to manufacturer's protocol. In each PCR #1 reaction, 3 μg of total gDNA was used. For each sample, the appropriate number of PCR #1 reactions was used to capture the full representation of the screen. For example, at ~200× coverage of the 129,209 MKO sgRNA library, gDNA from $2.5\times10^7$ cells was used. Assuming 6.6 pg of gDNA per cell, ~160 μg of gDNA was used per sample, in approximately 50 PCR #1 reactions (with ~3 μg of gDNA per reaction).

PCR #1 products for each biological sample were pooled and used for amplification with barcoded second PCR primers. For each sample, at least 4 PCR #2 reactions were performed using 2 μl of the pooled PCR #1 product per PCR #2 reaction. Second PCR products were pooled and then normalized for each biological sample before combining uniquely barcoded separate biological samples. The pooled product was then gel purified from a 2% E-gel EX (Life Technologies) using the QiaQuick kit (Qiagen). The purified pooled library was then quantified with a gel-based method using the Low-Range Quantitative Ladder Life Technologies, dsDNA High-Sensitivity Qubit (Life Technologies), BioAnalyzer (Agilent) and/or qPCR. Diluted libraries with 5-20% PhiX were sequenced with MiSeq, HiSeq 2500 or HiSeq 4000 systems (Illumina).

Demultiplexing and read preprocessing: Raw single-end fastq read files were filtered and demultiplexed using Cutadapt (Martin et al., EMBnet.journal 17, 10-12 (2011)). To remove extra sequences downstream (i.e. 3' end) of the sgRNA spacer sequences, the following settings were used: cutadapt --discard-untrimmed -a GTTTTAGAGCTAGAAATGGC (SEQ ID NO: 140,897). As the forward PCR primers used to readout sgRNA representation were designed to have a variety of barcodes to facilitate multiplexed sequencing, these filtered reads were then demultiplexed with the following settings: cutadapt -g file: fbc.fasta --no-trim, where fbc.fasta contained the 12 possible barcode sequences within the forward primers. Finally, to remove extra sequences upstream (i.e. 5' end) of the sgRNA spacers, the following settings were used: cutadapt --discard-untrimmed -g GTGGAAAGGACGAAACACCG (SEQ ID NO: 140,898). Through this procedure, the raw fastq read files could be pared down to the 20 bp sgRNA spacer sequences.

Mapping of sgRNA spacers and quantitation of sgRNAs: Having extracted the 20 bp sgRNA spacer sequences from each demulitplexed sample, the sgRNA spacers were then mapped to the MKO library from which they originated (mGeCKO). A bowtie index of either sgRNA library was generated using the bowtie-build command in Bowtie 1.1.2 (Langmead et al., Genome Biol 10, R25 (2009). Using these bowtie indexes, the filtered fastq read files were mapped using the following settings: bowtie -v 1 --suppress 4,5,6,7 --chunkmbs 2000 -best. Using the resultant mapping output, the number of reads that had mapped to each sgRNA within the library were quantitated. To generate sgRNA representation barplots, a detection threshold of 1 read was set, and the number of unique sgRNAs present in each sample was counted.

Normalization and summary-level analysis of sgRNA abundances: The number of reads in each sample was normalized by converting raw sgRNA counts to reads per million (rpm). The rpm values were then subject to $\log_2$ transformation for certain analyses. To generate correlation heatmaps, the NMF R package was used (Gaujoux et al., BMC Bioinformatics 11, 367 (2010)) and the Pearson correlations between individual samples calculated using $\log_2$ rpm counts. To calculate the cumulative distribution function for each sample group, the normalized sgRNA counts were first averaged across all samples within a given group. Then the ecdfplot function in the latticeExtra R package was used to generate empirical cumulative distribution plots.

Enrichment analysis of sgRNAs: Three criteria were used to identify the top candidate genes: 1) if an sgRNA comprised≥2% of the total reads in at least one organ sample; 2) if an sgRNA was deemed statistically significantly enriched in ≥25% of all organ samples using a false-discovery rate (FDR) threshold of 2% based on the abundances of all non-targeting controls; or 3) if ≥2 independent sgRNAs targeting the same gene were each found to be statistically significant at FDR<2% in at least one sample. For the first and second criteria, individual sgRNA hits were collapsed to genes to facilitate comparisons with the hits from the third criteria.

Heatmap of sgRNA library representation: Heatmaps of the top enriched sgRNAs were generated using the aheatmap function with default setting (NMF R package). Only sgRNAs with a $\log_2$ rpm≥1 were included for visualization in the heatmaps.

Overlap and significance analysis of enriched sgRNAs: To generate Venn diagrams of enriched sgRNAs, all sgRNAs were considered that were found to be significantly enriched across different statistical calling algorithms, different T cells, or different experiments.

Additional CRISPR screen T cell survival analysis by organ: Enrichment analysis was first performed for each organ as a sample to call significant sgRNAs passing specific FDR cutoff. Sets of significant sgRNAs were compared against each other. In addition, the whole library representation was used as input for dimensional reduction analysis using t-SNE as in single-cell RNA-seq analysis, to find clusters of organs.

Minipool screen validation: SgRNA minipools were generated by pooling a selection of genes from the primary screen and cloned into the same T cell CRISPR vector. Viral production, transduction, and adoptive transfer was done similar to the screen with 1e6 T cells per transfer.

Pathway enrichment analysis of enriched sgRNAs: SgRNAs that were significantly enriched in each tissue type were determined. To convert these sgRNAs to their target genes, the resultant gene sets for DAVID functional annotation analysis were used (Huang da et al., Nucleic Acids Res 37, 1-13 (2009)). A GO category was considered statistically significant if the enrichment p value is less than 0.01, and Benjamini-Hochberg adjusted p-value was less than 0.1.

Gene ontology and pathway enrichment analysis: Various gene sets were used for gene ontology and pathway enrichment analysis using DAVID functional annotation analysis. For sgRNA set, sgRNAs were converted to their target genes and then the resultant genes were used for analysis.

Testing anti-tumor function of T cells with sgRNAs targeting individual genes by adoptive transfer: SgRNAs targeting individual genes were cloned into the T cell CRISPR vector. Two independent sgRNAs targeting each gene (e.g. Dhx37) were used. Virus prep and T cell infection were performed as described herein. $5\times10^6$ $mCh^+cOVA^+$ E0771 cells were injected either subcutaneously or into the intra-mammary fat pad of $Rag1^{-/-}$ mice. 7 days post-transplantation, freshly isolated naive OT-I; Cas9 $CD8^+$ T cells were plated on plates pretreated with 5 μg/ml anti-CD3ε in cRPMI supplemented with 2 ng/ml IL-2+2.5 ng/mL IL-7+50 ng/mL IL-15+1 μg/ml anti-CD28, infected with these sgRNA-containing lentiviruses (at MOI of ~≤1) as described herein, and cultured for 3 days. 10 days post-transplantation, $5\times10^6$ virally infected T cells were intravenously injected in tumor-bearing $Rag1^{-/-}$ mice (T cell: initial cancer cell ratio=1:1). PBS and empty vector infected T cells were used as adoptive transfer controls. Tumor sizes were measured by caliper once to twice per week. 6 weeks after adoptive transfer, tumors were dissected, and samples were subjected to molecular, cellular, histology analysis, or single-cell RNA-seq. For statistical comparison of tumor growth curves, multiple t-tests were performed (Benjamini, Krieger and Yekutieli FDR method) on each time point.

Tumor Infiltration Lymphocyte (TIL) Isolation for single cell RNA-seq: Tumor bearing mice were euthanized at designated time points, and their tumors were collected and kept in ice cold 2% FBS. Tumors were minced into 1-3 mm size pieces using scalpel and then digested in 1 μg/ml Collagenase IV for 30-60 min using Miltenyi GentleMACS™ Octo Dissociator. Tumor suspensions were filtered twice through 100 μm cell strainer, and again through 40 μm cell strainer to remove large bulk. Subsequently, tumor suspensions were carefully layered onto Ficoll-Paque™ media (GE Healthcare) and centrifuged at 400 g for 30 min to enrich lymphocytes at the bilayer interface. Cells at the interface were carefully collected, and washed twice with 2% FBS, counted, and stained with indicated antibodies for 30 minutes on ice. $CD3^+CD8^+$ TILs were then sorted on BD FACSAria™. A total of $3\times10^3$ to $2\times10^4$ TILs were collected per tumor.

Mouse TIL single cell RNA-seq (scRNAseq): TILs sorted from freshly isolated tumors were subjected to single-cell RNAseq library preparation, according to manufacturer's protocol (10× Genomics). In brief, Single Cell Master Mix was prepared fresh containing RT reagent mix, RT primer, additive A, and RT enzyme mix. A Single Cell 3' Chip was placed in a 10×™ Chip Holder. 50% glycerol solution was added to each unused well accordingly, TIL solution at ~100 cell/ul was added together with the master mix. The Single Cell 3' Gel Bead Strip was placed into a 10×™ Vortex Adapter and vortex for 30 sec. Then, Single Cell 3' Gel Bead suspension and Partitioning Oil were dispensed into the bottom of the wells in the specified rows. The fully loaded chip was then inserted into Chromium™ Controller to generate emulsion. The emulsion was then transferred to a 96-well PCR plate for GEM-RT reaction, RT clean up, cDNA amplification, cDNA clean up, quantification and QC, and subjected to Illumina library construction. In library construction, clean input cDNA was then subjected to fragmentation, end repair & A-tailing. After that, double sided size selection was performed using SPRI Select, followed by adaptor ligation, clean up, and sample indexing PCR, pooling and PCR cleanup, resulting a single-cell RNA-seq library. Enzymatic Fragmentation and Size Selection were used to optimize the cDNA amplicon size prior to library construction per manufacturer's protocols. R1 (read 1 primer sequence) are added to the molecules during GEM incubation. P5, P7, a sample index and R2 (read 2 primer sequence) are added during library construction via end repair, A-tailing, adaptor ligation and PCR. The Single Cell 3' Protocol produces Illumina-ready sequencing libraries contain the P5 and P7 primers used in Illumina bridge amplification. This final library was then QC'ed and quantified using BioAnalyzer, and loaded on a Hiseq 2500 RapidRun for standard Illumina paired-end sequencing, where Barcode and 10 bp randomer (UMI) was encoded in Read 1, while Read 2 was used to sequence the cDNA fragment. Sample index sequences were incorporated as the i7 index read.

scRNA-seq data processing: TIL scRNA-seq fastq data was pre-processed using established and custom pipelines. Briefly, raw Illumina data files were subjected to Cell Ranger, which used cellranger mkfastq to wrap Illumina's bcl2fastq to correctly demultiplex Chromium-prepared sequencing samples and to convert barcode and read data to FASTQ files. Then, cellranger count was used to take FASTQ files and perform alignments to the mouse genome (mm10), filtering, and UMI counting. Raw sequencing output was first preprocessed by Cell Ranger 1.3 (10× Genomics) (Zheng et al., 2017b) using cellranger mkfastq, count, and aggr (no normalization mode). Cells passed the initial quality control metrics imposed by the Cell Ranger pipeline were further filtered using a variety of criteria (Lun et al., (2016) F1000Res 5, 2122): 1) All cells with a total library count (i.e. # of UMIs) that was ≥4 standard deviations below the mean were excluded; 2) All cells with library diversity (i.e. # of detected genes/features) that was ≥4 standard deviations below the mean were excluded; and 3) All cells in which mitochondrial genes disproportionately comprised the total % of the library (≥4 standard deviations above the mean) were excluded. After applying these 3 filters, a final set of cells was retained for further analysis. The 27,998 genes/features were additionally filtered the using a flat cutoff metric: genes with low variance were excluded. Finally, the data was normalized by library size using the scran R package (Lun et al., (2016) F1000Res 5, 2122).

scRNA-seq t-SNE dimension reduction and visualization: Using the final normalized and processed dataset (described above), t-SNE dimension reduction was performed using the Rtsne R package with default settings (Maaten, (2014) J Mach Learn Res 15, 3221-3245; Maaten and Hinton, (2008) J Mach Learn Res 9, 2579-2605). Individual data points were colored based on the treatment condition for each cell.

scRNA-seq differential expression analysis: Using the final normalized and processed dataset (described above), differential expression analysis was performed using the edgeR R package (Robinson et al., (2010) Bioinformatics 26, 139-14). In brief, edgeR first estimates the negative binomial dispersion parameter to model the variance between cells from the same treatment group. A generalized linear model is then fitted to determine differentially expressed genes between treatment conditions. Multiple hypothesis correction was performed by the Benjamini-Hochberg method. Significantly differentially expressed genes were defined as having a Benjamini-Hochberg adjusted $p<0.05$, with upregulated genes having a positive log fold change and downregulated genes having a negative log fold change. Volcano plots were generated using edgeR output statistics. Gene ontology enrichment analyses on differentially expressed genes were performed using the PANTHER classification system (Mi et al., (2013) Nat Protoc 8, 1551-1566). The statistical overrepresentation test was used to identify enriched GO (biological process) categories among the differentially expressed genes. Bonferroni multiple hypothesis correction was performed.

scRNA-seq heatmap of differentially expressed genes: To generate an overall view of the top differentially expressed genes, each row of the dataset (i.e. by gene) was scaled to obtain z-scores. Heatmaps were generated using the NMF R package (Gaujoux and Seoighe, (2010) BMC Bioinformatics 11, 367).

Analysis of human T cell scRNA-seq data: Human T cell scRNA-seq data from liver cancer patients (Zheng et al., (2017) Cell 169, 1342-1356 e1316) were retrieved from GEO (GSE98638). Cells were classified according to the original definitions: peripheral blood, tissue-resident, tumor-normal junction, and tumor-infiltrating T cells; $CD3^+/CD4^+/CD25^-$ T cells, $CD3^+/CD8^+$ T cells, and $CD3^+/CD4^+/CD25^+$ T cells. Stratification of subpopulation of cells that express relative higher level of DHX37 ($DHX37^+$ T cells) and as compared to those expressing lower or undetectable level ($DHX37^-$ T cells) was done by a cutoff of 1 $log_2(cpm)$ normalized expression. Analysis of differentially expressed genes was done by comparing $DHX37^+$ and $DHX37^-$ groups using two-sided unpaired Welch's t test assuming unequal variance.

DHX37 overexpression: A Dhx37 cDNA was cloned into a lentiviral vector using standard molecular biology techniques, and was used to transfect or transduce cells to overexpress the protein.

Analysis of human DHX37 expression by western blot: Human PB $CD4^+$, $CD8^+$ T cells, as well as patient TILs were analyzed for DHX37 protein expression by western blot with a rabit polyclonal antibody (Novus, NBP2-13922).

Analysis of human DHX37 expression by FACS: Intracellular DHX37 expression was analyzed for human PB $CD8^+$ T cells, as well as patient TILs with a rabit polyclonal antibody (Novus, NBP2-13922).

Analysis of human DHX37 using tissue microarray (TMA): All work involving human samples was approved by institutional IRB. Human tissue samples were collected with existing IRB protocols in place. TMAs from several cancer types were retrieved from biospecimen bank for the following cancer types: glioma, breast cancer and melanoma, with normal and tumor biopsies for brain origin. IHC for DHX37 was done with a rabit polyclonal antibody (Novus, NBP2-13922). H&E and IHC slides were scanned using Leica slidescanners and scored manually for lymphocytes and DHX37+ cells.

Generation of an AAV T cell knockout vector: An adeno-associated virus (AAV) knockout vector, pAAV-U6-sgBbsI-EFS-Thy1.1-PolyA, was generated by subcloning Thy1.1 and sgRNA expression cassette into a AAV vector via Gibson Assembly (NEB). For individual gene targeting, the AAV knockout vector was digested with BbsI. Oligonucleotides encoding sgRNAs for MlI3, B2m, and mDhx37 were ligated into the digested AAV knockout vector using T4 ligase (NEB).

AAV virus production: The AAV knockout plasmid vector (AAV-vector), AAV-MlI3, AAV-B2m, and AAV-mDhx37 were subjected to AAV9 production and chemical purification. Briefly, HEK293FT cells (ThermoFisher) were transiently transfected with transfer (AAV-plasmids), serotype (AAV9) and packaging (pDF6) plasmids using polyethyleneimine (PEI). Approximately 72 h post-transfection, cells were dislodged and transferred to a conical tube in sterile PBS. 1/10 volume of pure chloroform was added to the mixture and incubated at 37° C. for 1 h. NaCl was added to a final concentration of 1 M. The mixture was subsequently shaken until dissolved and then pelleted at 20,000 gx at 4° C. for 15 min. The chloroform layer was discarded while the aqueous layer was transferred to another tube. PEG8000 was added to 10% (w/v) and shaken until dissolved. The mixture was incubated at 4° C. for 1 h and spun at 20,000 gx at 4° C. for 15 min. After the supernatant was discarded, the pellet was resuspended in $DPBS+MgCl_2$, treated with benzonase (Sigma), and then incubated at 37° C. for 30 min. Chloroform (1:1 volume) was then added, shaken and spun down at 12,000 g at 4° C. for 15 min. The aqueous layer was isolated and passed through a 100-kDa MWCO (Millipore). The concentrated solution was washed with PBS and the filtration process was repeated. Virus was titered by qPCR using custom Taqman assays (ThermoFisher).

AAV viral transduction: T cell pellets were directly transduced with indicated AAV-virus. 3 days after infection, T cells were stained for Thy1.1 expression and analyzed on FACS.

Determining cutting efficiency: DNA from cells was extracted by incubating cells with Epicentre QuickExtract for 65° C. for 30 minutes, and subsequently incubated at 98° C. for 5 minutes. gDNA from samples was amplified by PCR. Purified PCR product was subjected to both T7 endonuclease surveyor (NEB) and Nextera sequencing according to Illumina protocol.

Acute deletion and gene expression analysis of mouse CD8 T cells: OT-I; Cas9 $CD8^+$ T cells were transduced with AAV-sgDhx37 or AAV-sgNTC, activated and cultured in vitro for 6 days, and then subjected to 10x Genomics single-cell RNAseq library prep. The initial scRNAseq data processing was done as above.

Single cell RNAseq analysis with Seurat: Raw UMI-based 10x count matrices were analyzed using Seurat (Butler and Satija, (2017) bioRxiv) with recommended settings. Counts were normalized by UMIs per cell, and log transformed for downstream analysis. Graph-based clustering was performed to identify subpopulations across the entire dataset. Subsequently, differential expression analysis comparing sgDhx37 and NTC samples was performed by non-parametric Wilcoxon test.

Nuclear staining: Nuclear staining was performed using FoxP3 staining kit and protocol from eBioscience. Prior to nuclear staining, primary antibodies were pre-adsorbed for at least 30 minutes on ice. Serum used for pre-adsorption varied depending on species of samples stained. 5% human serum was used to pre-adsorb antibodies for human T cell staining. 5% normal mouse and 5% normal rat serum was used to pre-adsorb antibodies for murine T cell staining. Cells were stained with primary stain overnight at 4° C., and subsequently stained with secondary antibody for 1 h at room temperature.

Endosomal staining: Endosomal staining was performed using BD Cytofix/Cytoperm staining kit and protocol. Prior to endosomal staining, cells were incubated with anti-CD16/32 to neutralize FcγRII/III, and subsequently stained with endosomal stain for 30 minutes on ice.

Blinding statement: Investigators were blinded for sequencing data analysis, but not blinded for tumor engraftment, adoptive transfer, organ dissection and flow cytometry.

The results of the experiments are now described.

Figure 15B:
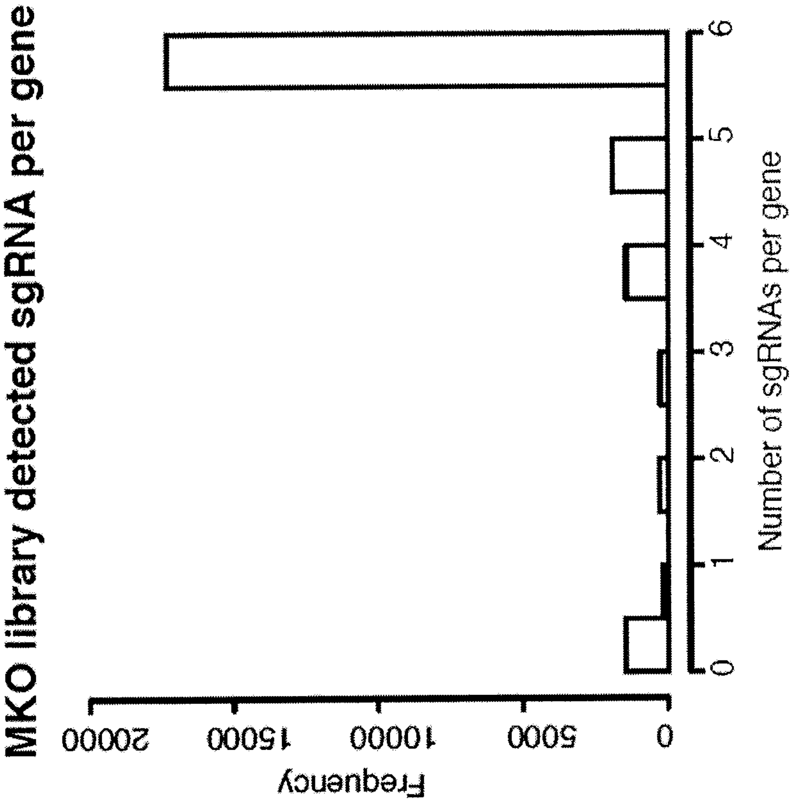
FIGS. 15A-15F are a series of plots and images illustrating generation, QC, and titration of a genome-scale T cell CRISPR library (MKO) for screening.
Figure 15A:
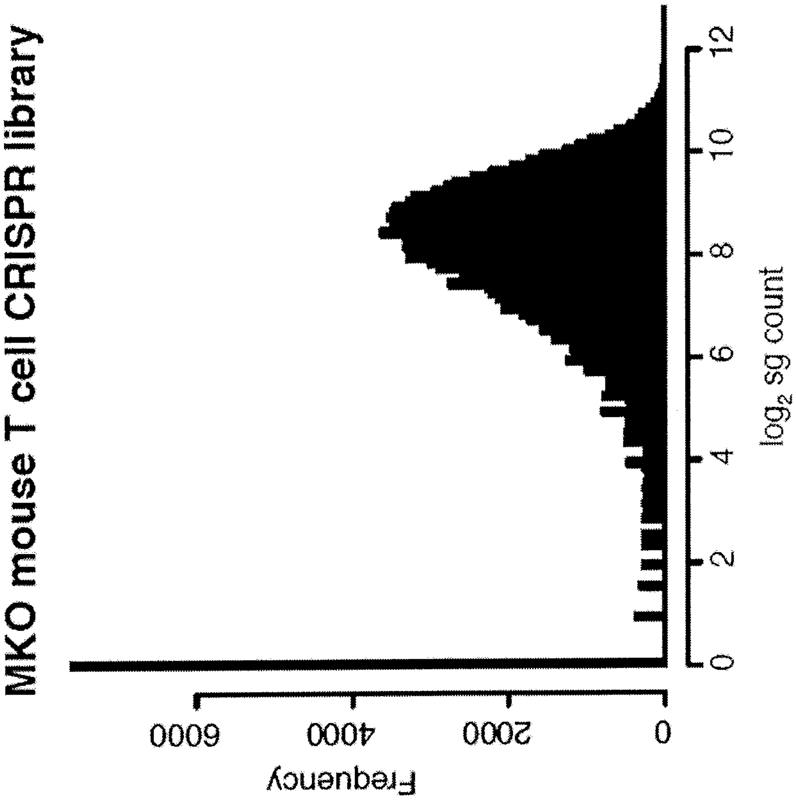

Example 1: Design, Construction and Production of T Cell Crispr Vector and Genome-Scale Library To enable efficient genome editing and isolation of $CD8^+$ T cells, a T cell CRISPR vector was designed and generated. This vector contained an sgRNA expression cassette enabling genome editing in conjunction with Cas9, and a cassette that expresses a congenic variant of Thy1 protein (Thy1.1), enabling the specific identification and single-cell isolation of transduced $CD8^+$ T cells (FIG. 1A). To enable large-scale genetic manipulation and thus high-throughput screening, a genome-scale sgRNA library containing a total of 129,209 sgRNAs (SEQ ID NOs: 1-129,209) including 1,000 non-targeting controls (NTCs), was cloned into this vector at an estimated library coverage of >50x (~$7×10^6$ total colonies). The successful cloning of the library was verified by Illumina sequencing: (1) tight log-normal distribution of designed sgRNAs with 97.6% of sgRNAs within 2 orders of magnitude (O.M.), and 99.9% within 3 O. M, (2) covering 98.3% targeted genes (FIGS. 15A-15B).

Figure 1B:
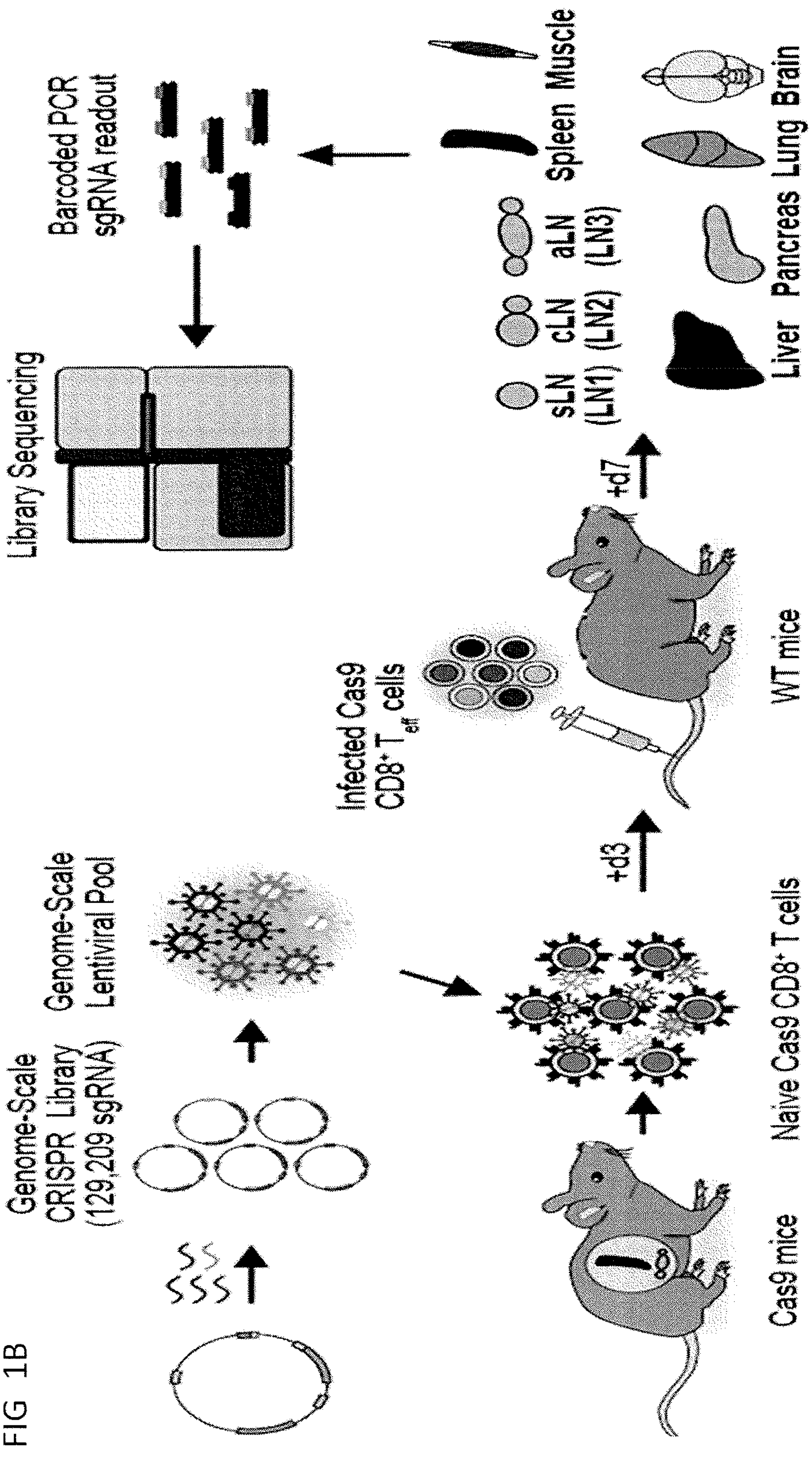
Figure 7A:
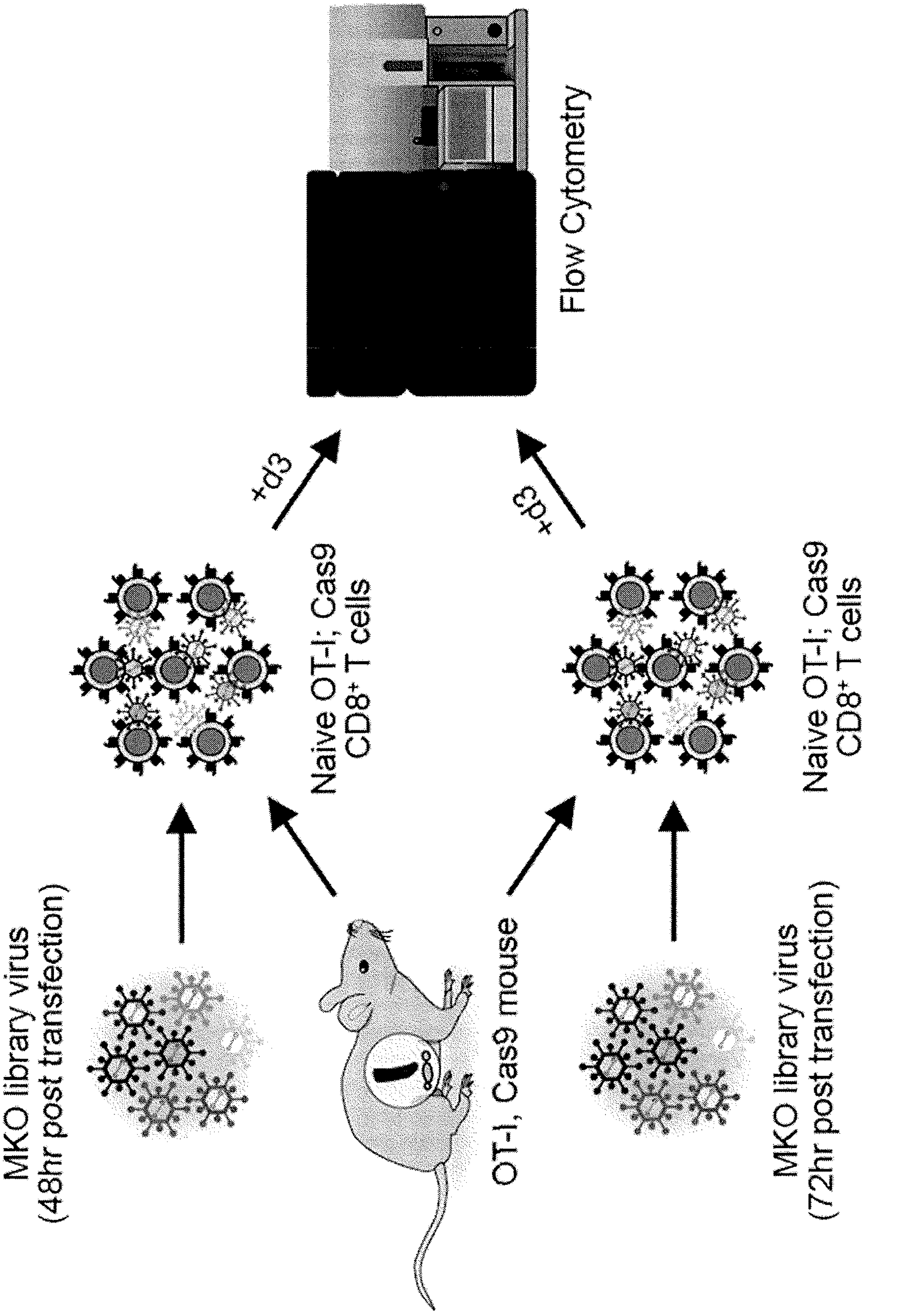
FIGS. 7A-7E are a series of plots and images illustrating FACS data for setup experiments of OT-I; Cas9 $CD8^+$ T cell survival in WT mice.
Figure 7B:
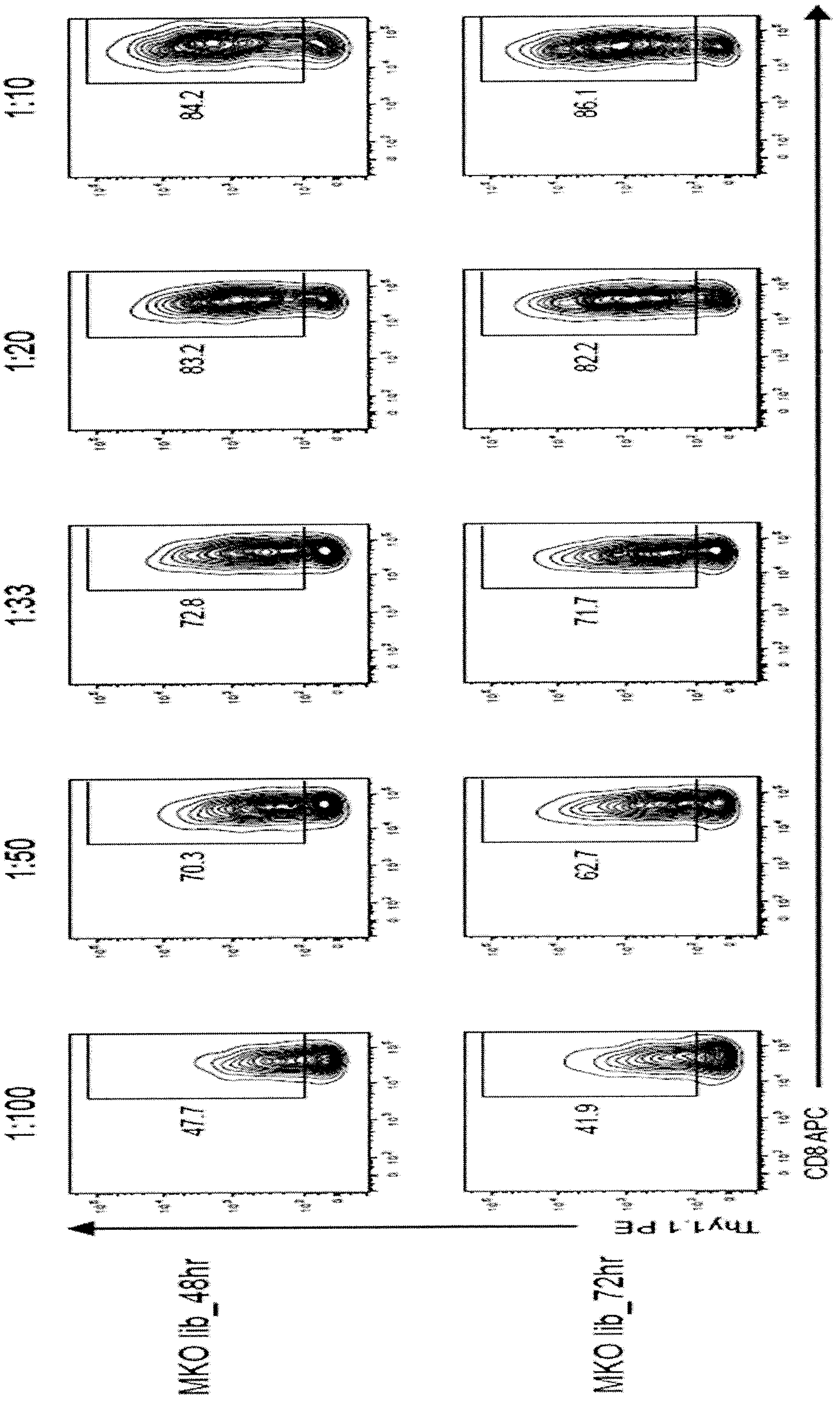
Figure 7C:
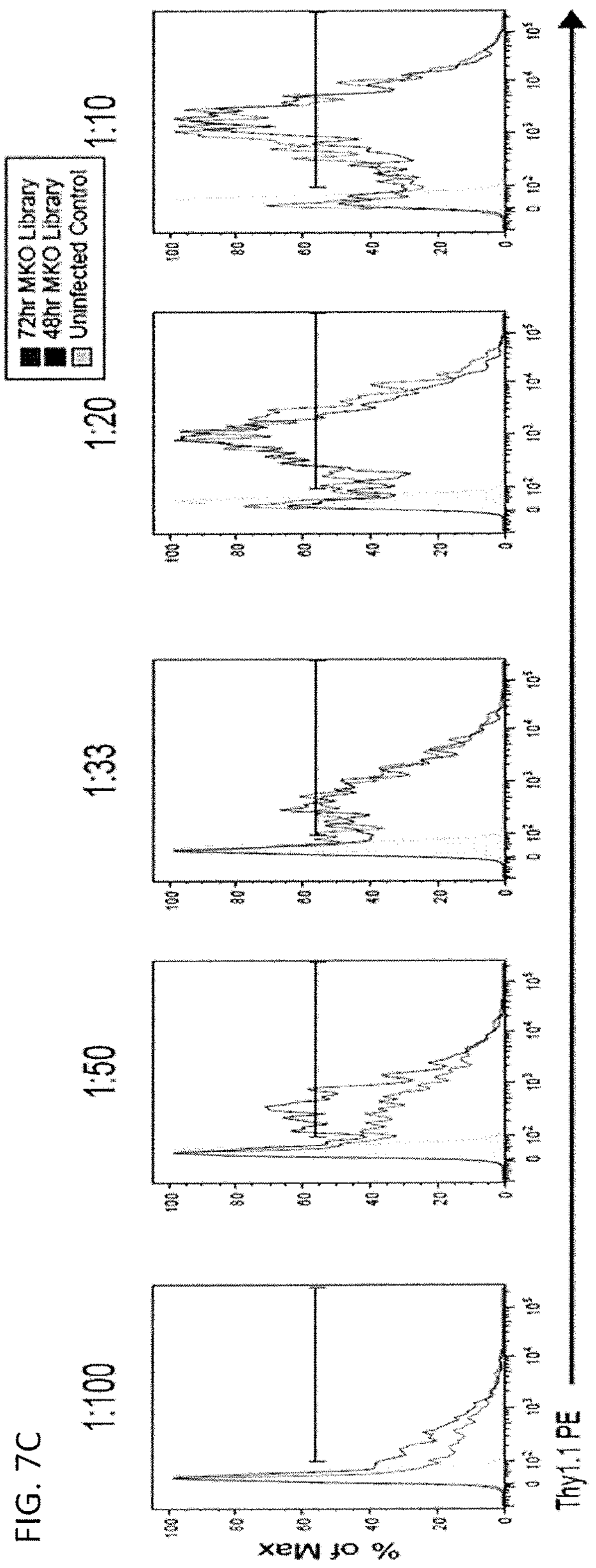
Figure 7D:
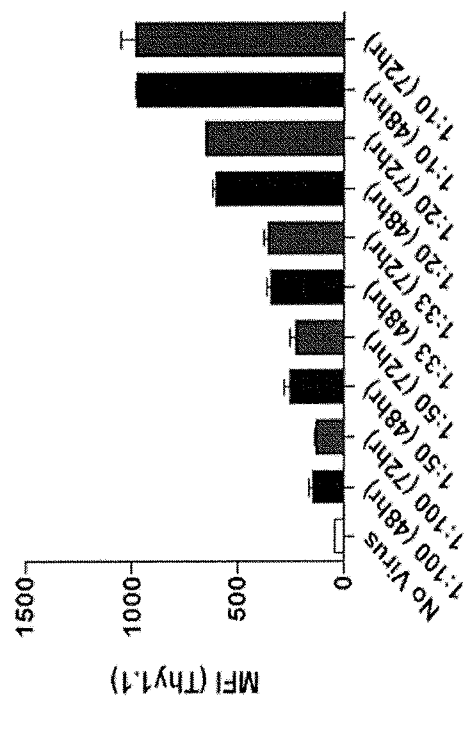
Figure 7E:
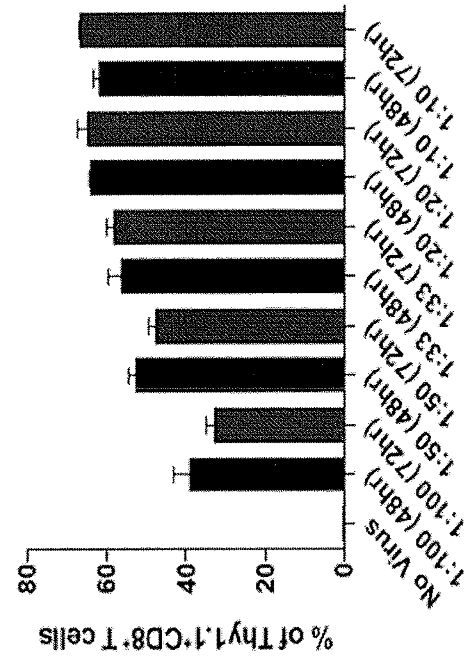
Figure 15C:
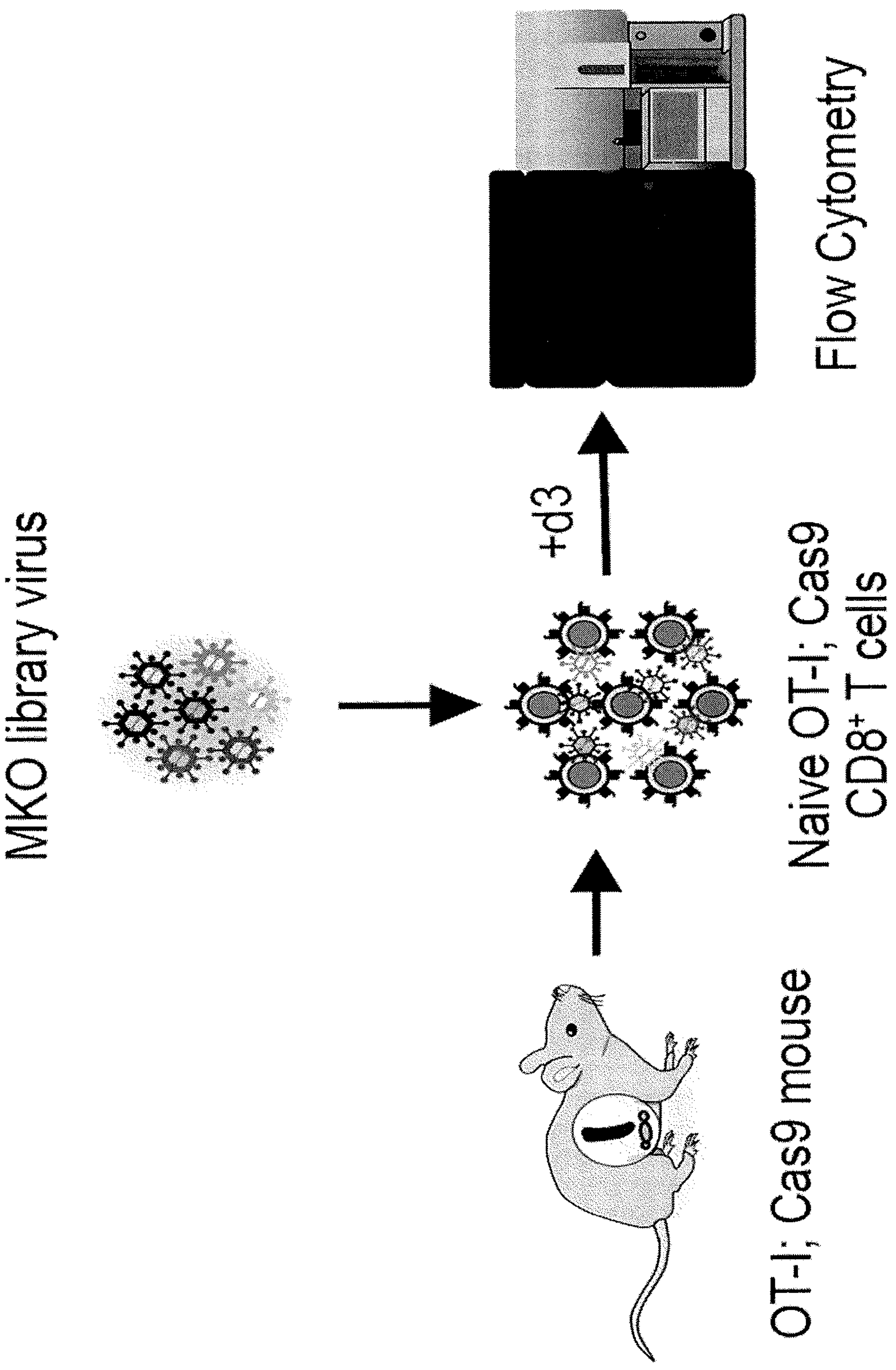
Figure 15D:
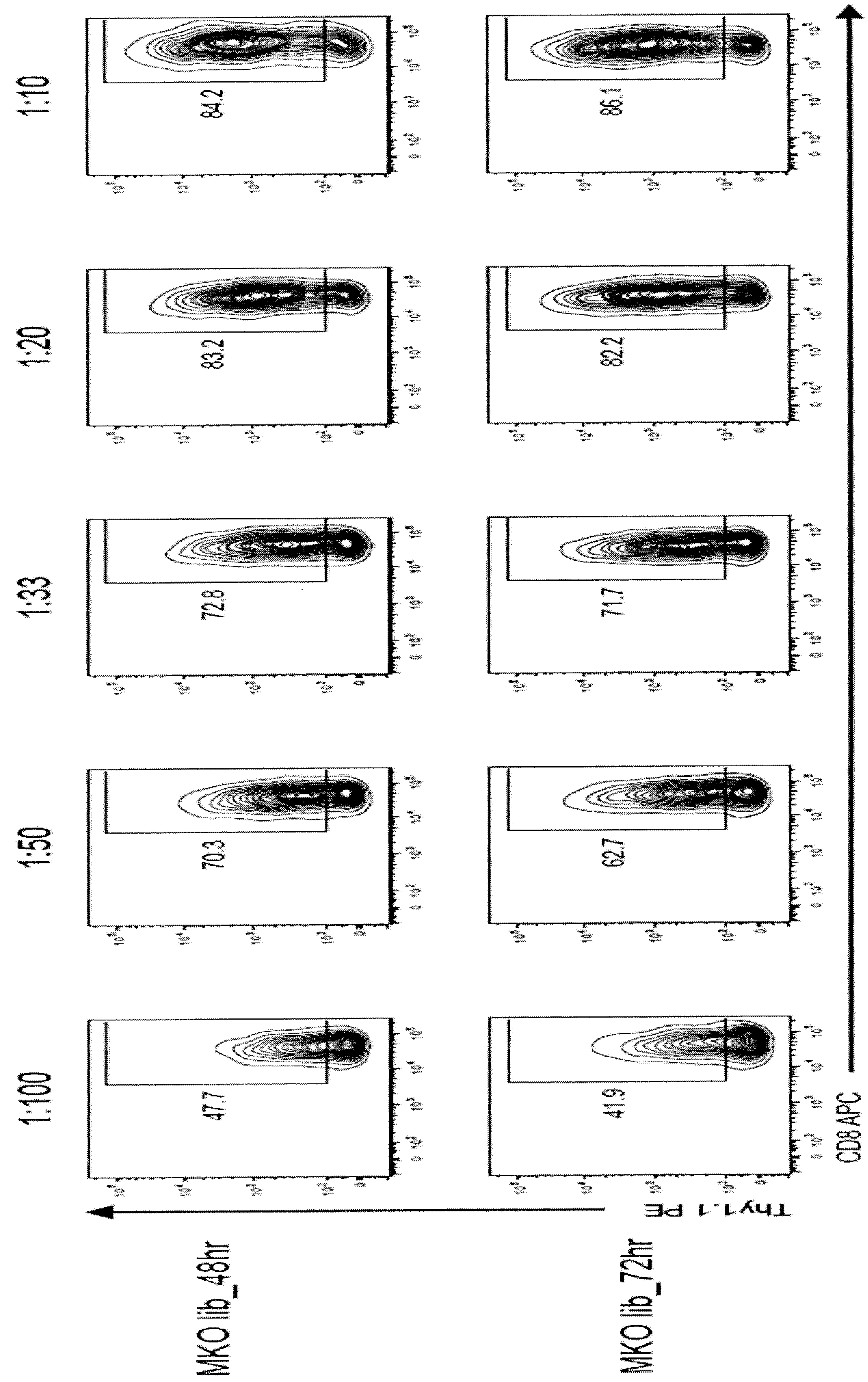
Figure 15E:
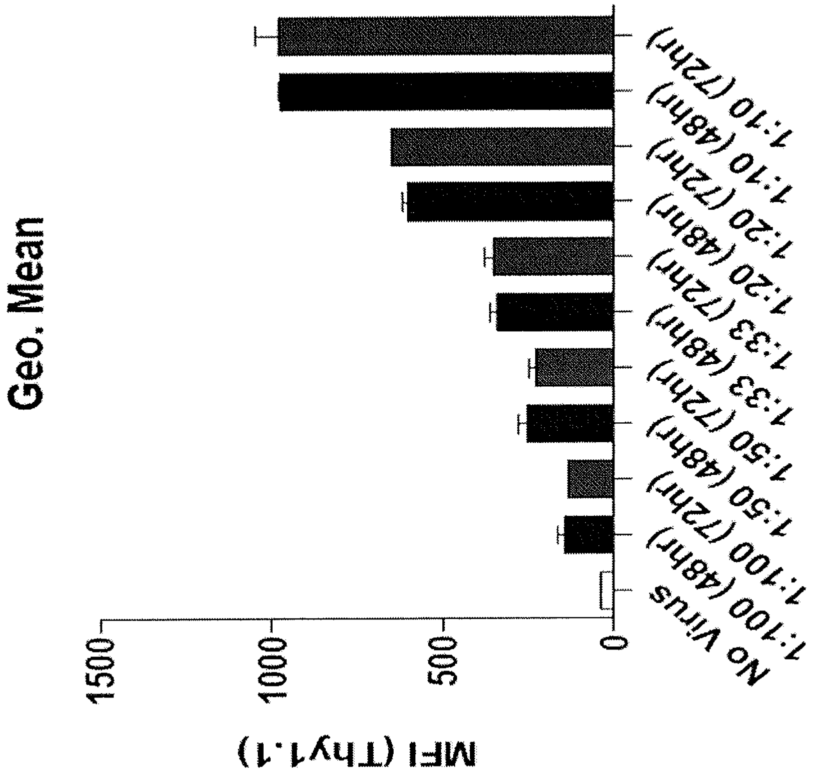
Figure 15F:
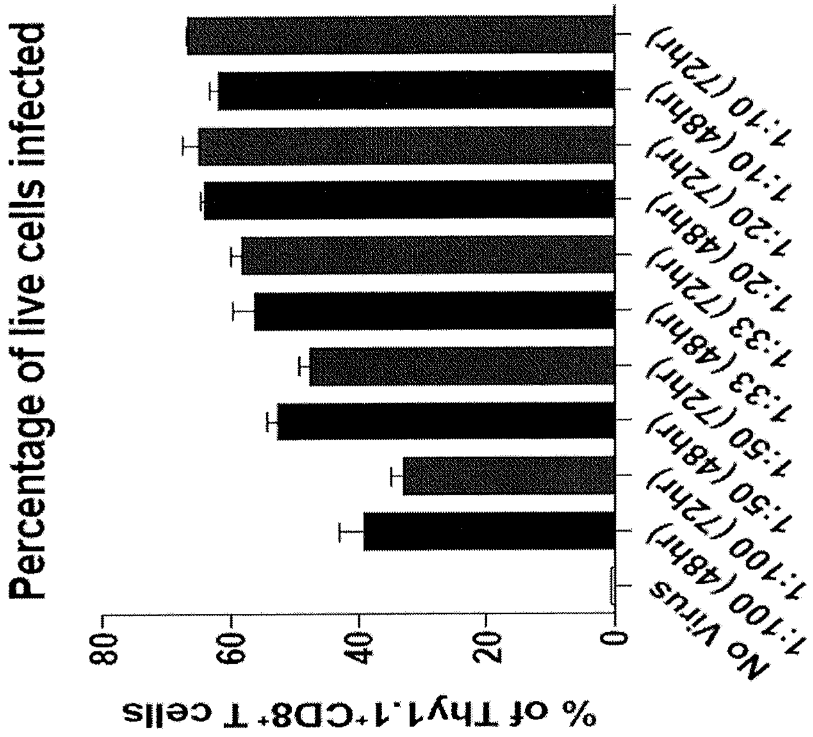

High-titer lentivirus was generated from the mouse genome-scale sgRNA library (termed MKO thereafter), and tested for efficient virus transduction of cytotoxic T cells. Naive $CD8^+$ T cells were isolated from mice that constitutively express Cas9, enabling genetic perturbations upon delivery of sgRNA, transduced with various concentrations of MKO virus, and analyzed for expression of the Thy1.1 surface marker via flow cytometry three days post-infection (FIG. 1B, FIG. 7A, FIG. 15C). Efficient transduction of $CD8^+$ T cells was achieved with various concentrations of MKO virus, starting at a 1:100 dilution of the original virus concentrate (FIG. 1C, FIGS. 7B-7E, FIG. 15D-15F).

Example 2: Genome-Scale Mutagenesis of $CD8^+$ T Cells and Adoptive Transfer

Figure 1C:
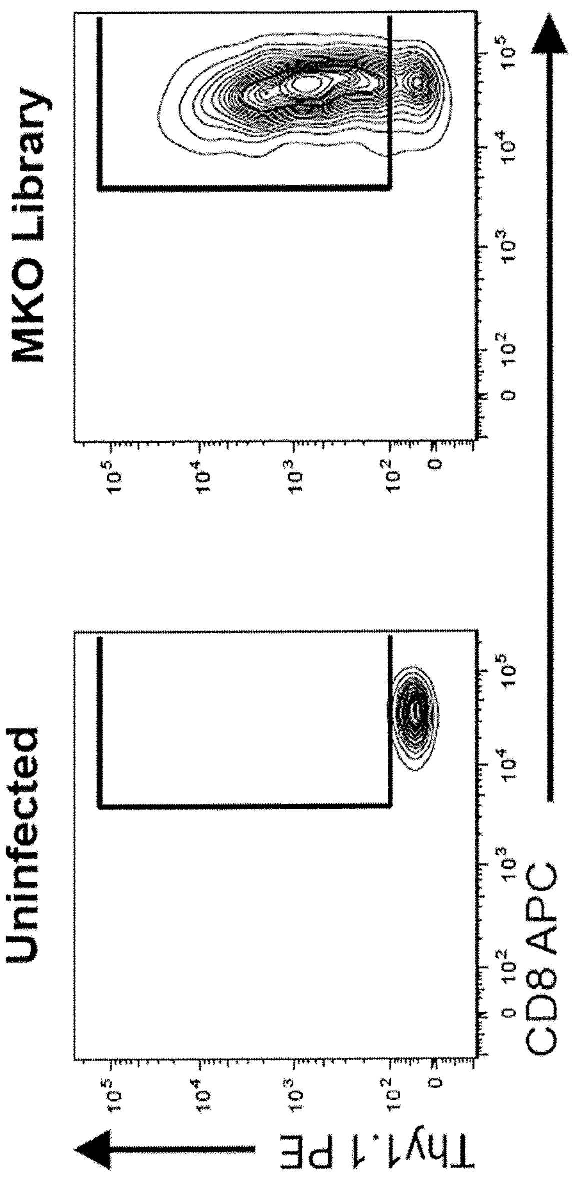

To map the genetic factors modulating the trafficking and survival of diverse T cell populations in vivo, the MKO library was used to interrogate the survival of adoptively transferred mutant T cells after trafficking to relevant organs (FIG. 1B). First, freshly isolated naive Cas9 $CD8^+$ T cells were mutagenized by transducing with the MKO lentiviral sgRNA library to achieve an initial coverage of >700× for each infection replicate (n=3). Three days after transduction, the MKO-infected mutant pool of $CD8^+$ T cells (MKO T cell library) was adoptively transferred into wildtype C57BL/6 (B6) recipient mice (n=7) (FIG. 1B), without lymphodepletion or any other immune modulation. After adoptive transfer, T cells in circulation traffick to lymphoid and non-lymphoid organs in which they either survive or undergo apoptosis. In order to systematically examine whether T cells trafficked to these organs and persisted within the in vivo tissue microenvironment, the relative abundance of surviving mutants was assessed seven days after adoptive transfer. The mice were sacrificed and various lymphoid and non-lymphoid organs isolated to investigate the surviving MKO T cells in each organ by sequencing the sgRNA representation. The liver, pancreas, lung, muscle and brain were collected and surveyed as representative non-lymphoid organs, and the spleen and several types of lymph nodes (LNs) as lymphoid organs (FIG. 1C). The LNs collected included three groups: LN1—skin draining lymph nodes (sLNs) comprised of inguinal, popliteal, axillary, and brachial lymph nodes; LN2—cervical lymph nodes (cLNs) that entailed the 6 superficial lymph nodes; and LN3—abdominal lymph nodes (aLNs) that included the mesenteric and the pancreatic lymph nodes (FIG. 1B).

Figure 1D:
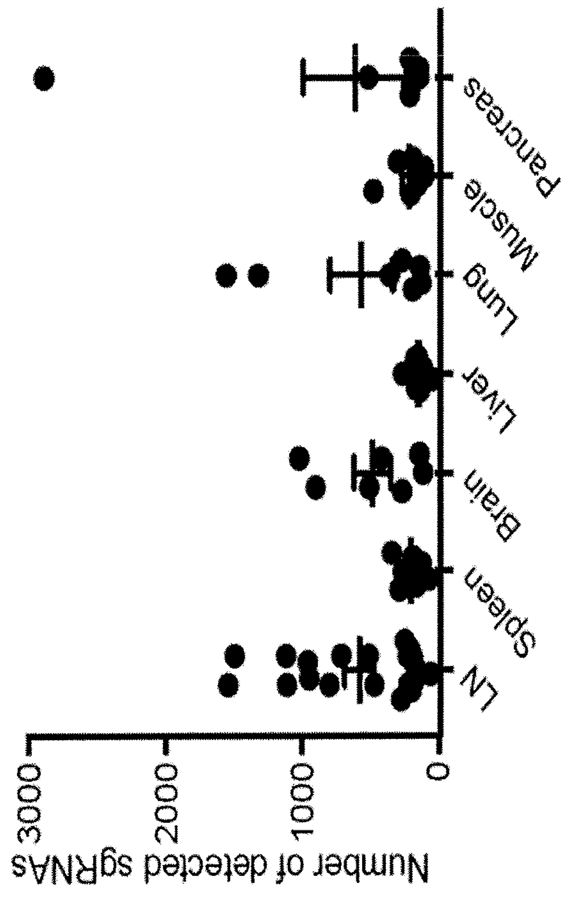
Figure 1E:
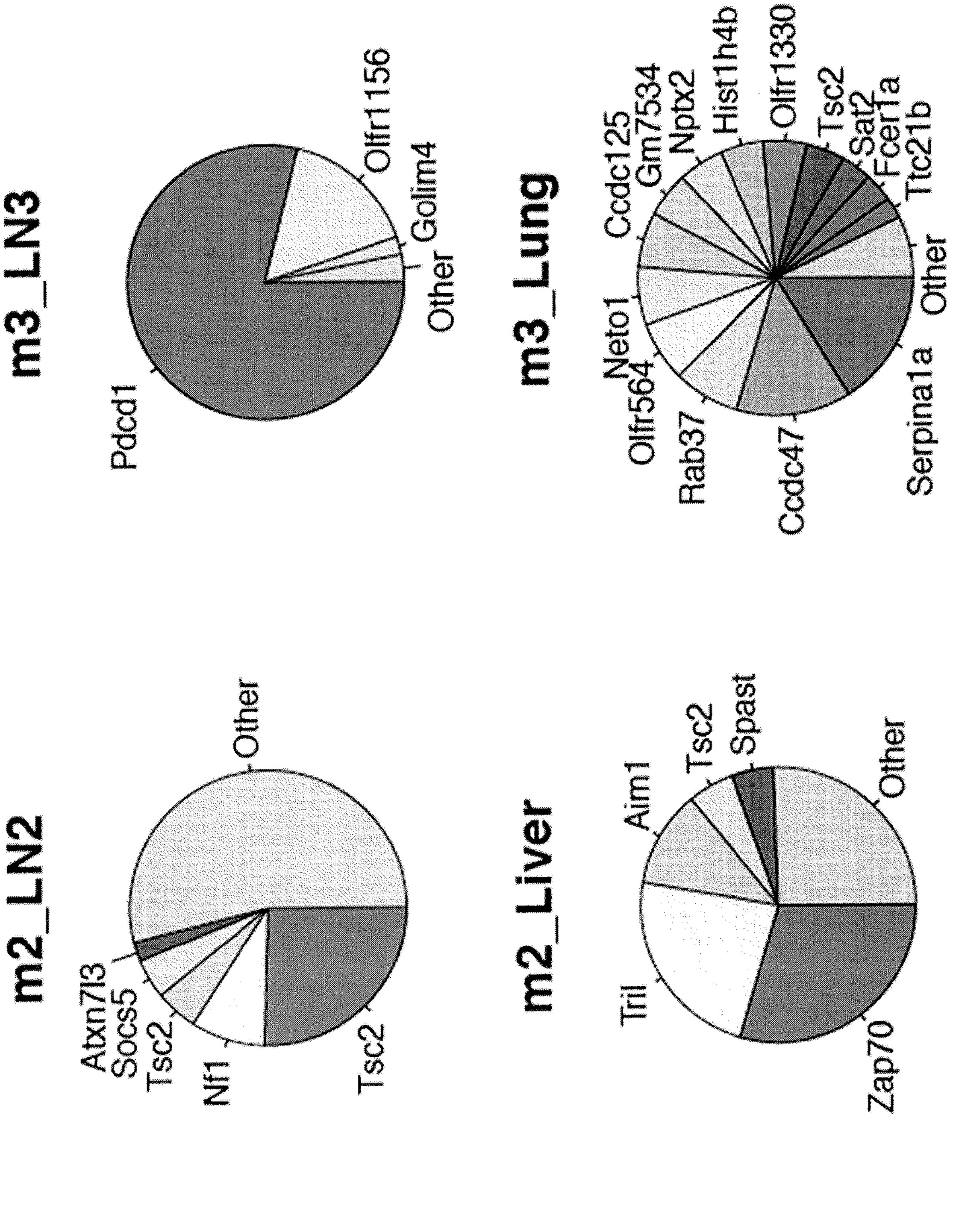
Figure 1F:
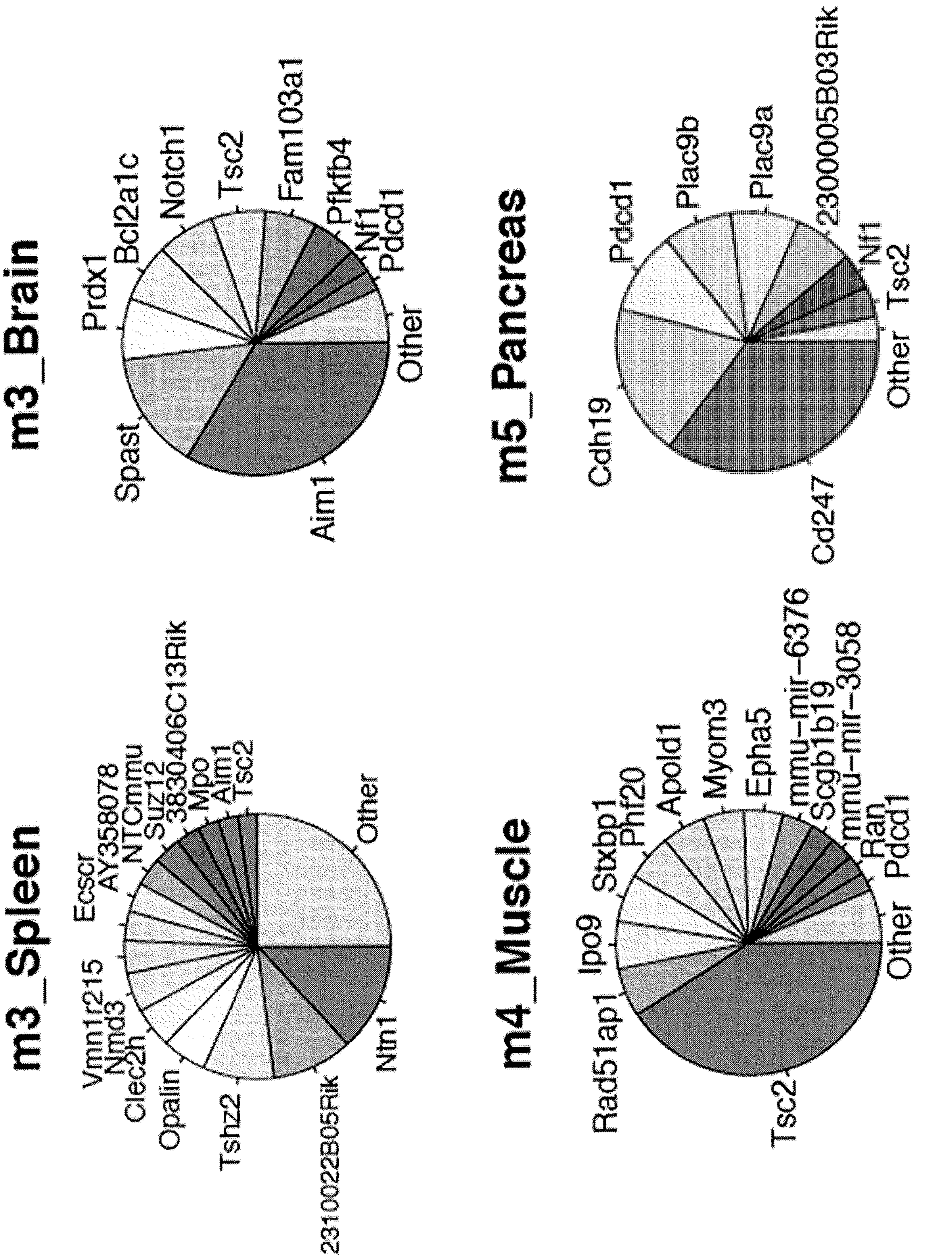
Figure 1G:
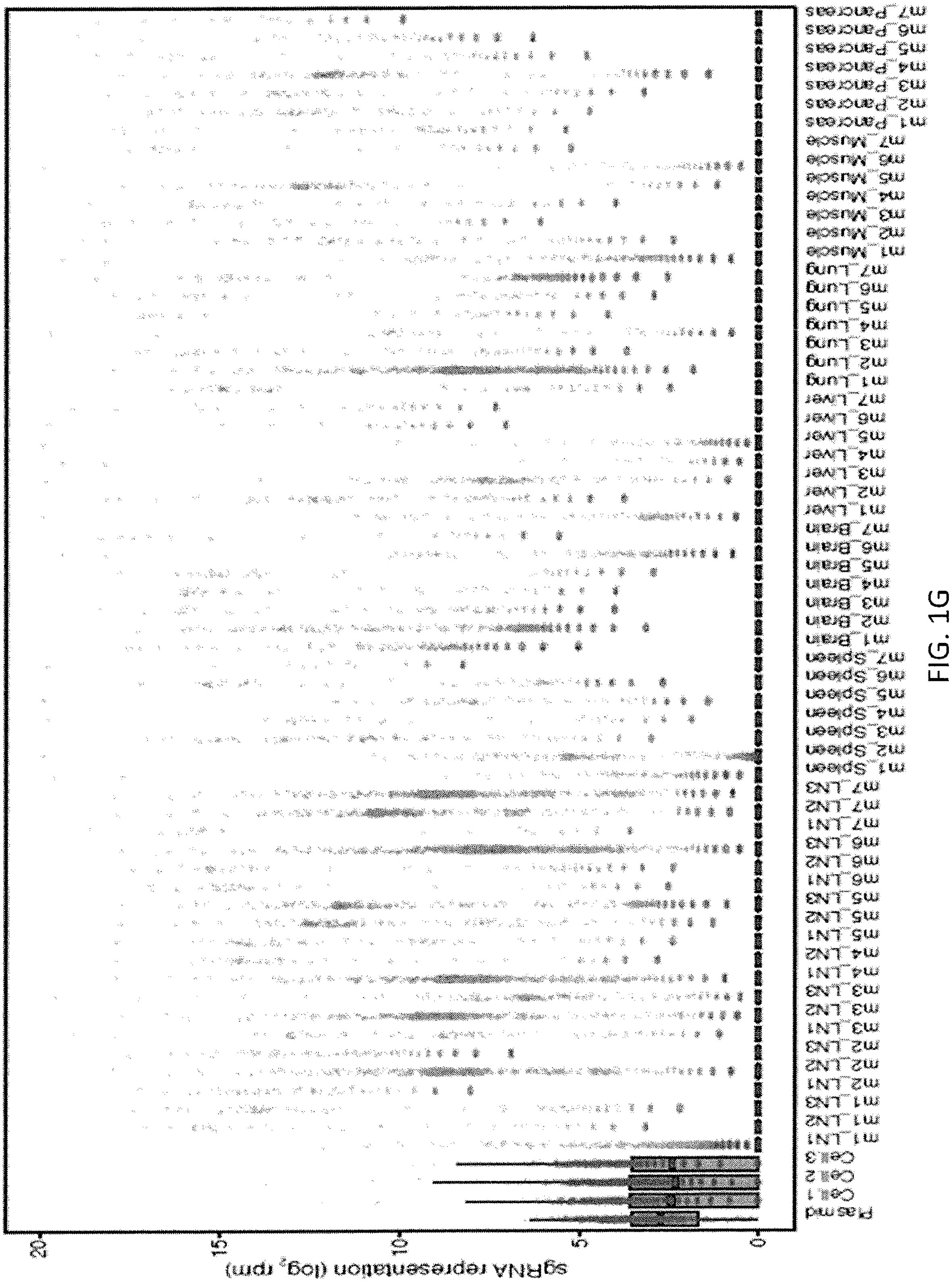
Figure 1H:
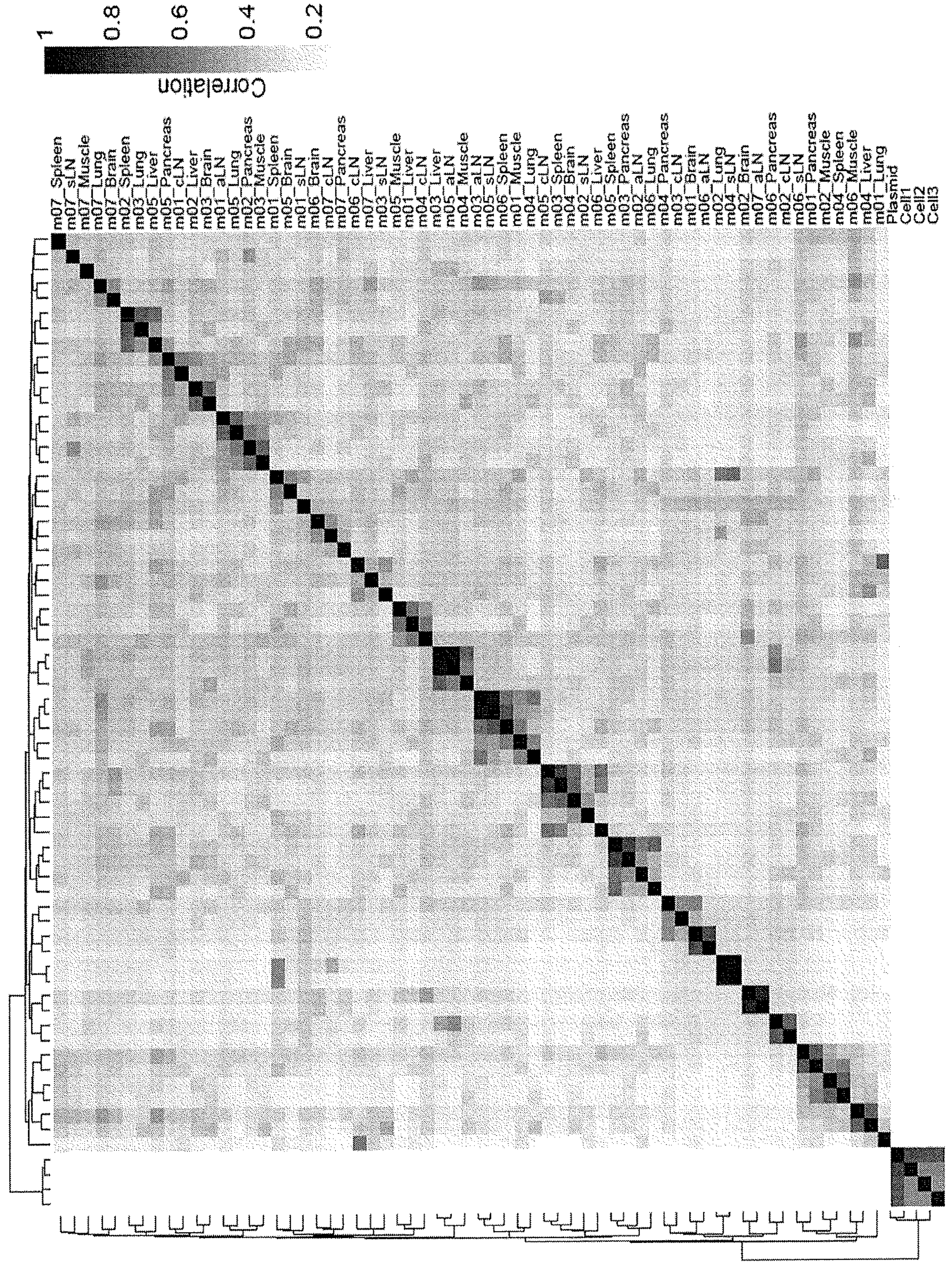
Figure 8A:
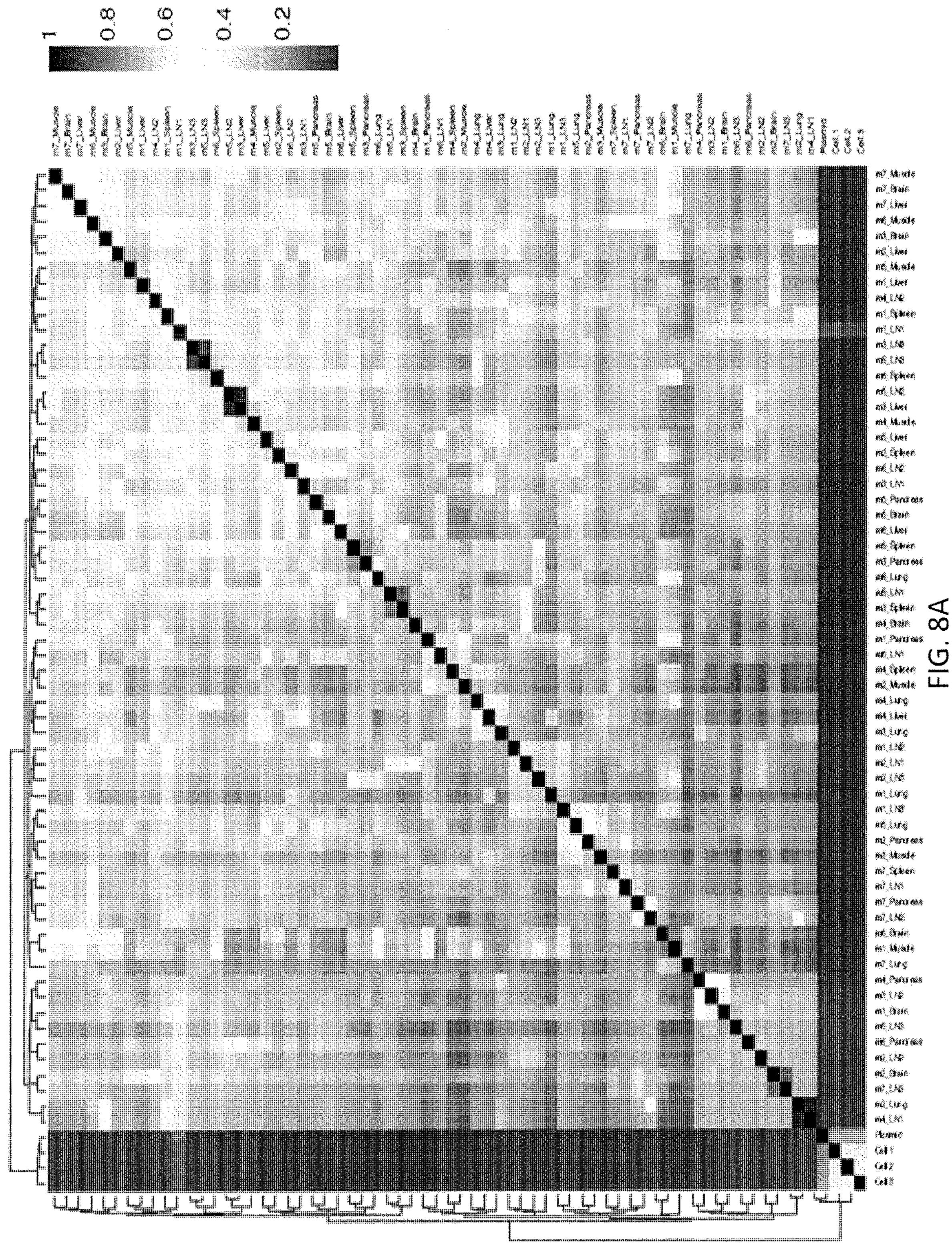
Figure 8B:
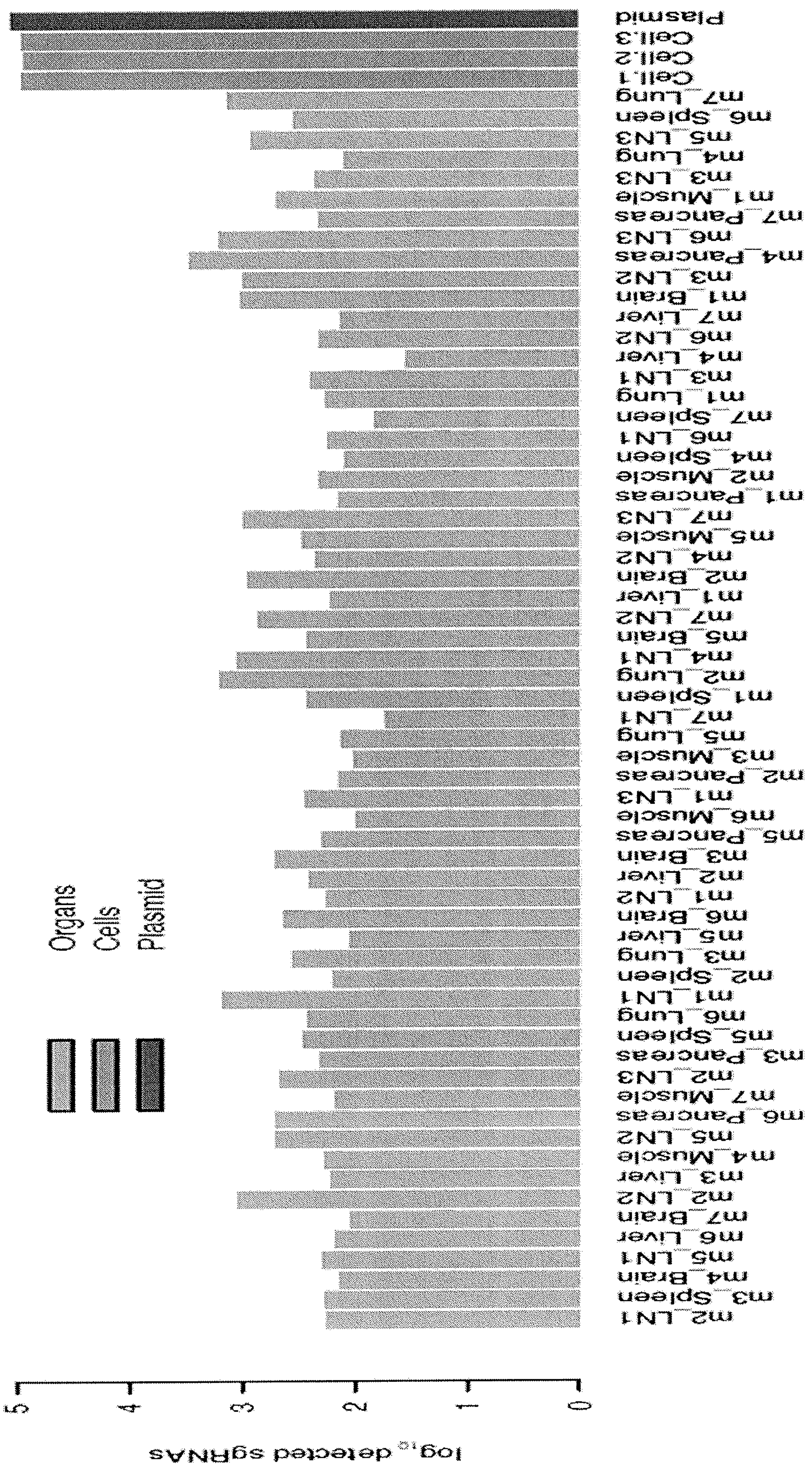

Example 3: In Vivo Analysis of Genome-Scale T Cell Mutants for Representation in Mouse Organs after $CD8^+$ $T_{eff}$ Cell Trafficking Illumina sequencing was performed and the sgRNA library representation of the $CD8^+$ T cells in all organs, as well as three representative pools of pre-injected MKO-transduced T cells, were successfully readout. As shown in FIGS. 1E-1F, different organs can display highly dynamic compositions of sgRNAs. While an organ can be dominated by one or a few T cell mutants (e.g. a $CD8^+$ T cell clone with an sgRNA targeting Program cell death protein 1 (PD-1/Pdcd1) dominated the LN sample in mouse 3) (FIG. 1E), a given organ can also consist of multiple highly abundant, but non-dominating clones (FIGS. 1E-1F, FIGS. 9A-9I). Monoclonal (one major clone), oligoclonal (2 to 10 major clones each with ≥2% of total reads) and polyclonal (more than 10 clones with 2% or more reads) compositions of T cell variants exist in both lymphoid and non-lymphoid organs (FIGS. 1E-1G, FIGS. 9A-9I). The library representation in all three replicates of uninfected T cells closely clustered with each other and the MKO plasmid library, whereas the library representation of all organs clustered together (FIG. 1H, FIG. 8A). On average, a total of 86,277±536 (78.34%±0.49% of plasmid) sgRNAs were detected in the initial T cell population (mean±s.e.m. (standard error of the mean), n=3) (FIG. 8B), whereas only a small fraction of sgRNAs (435±62, or 0.39%±0.06% of plasmid)) were detected in internal organs, indicating a low diversity of T cell mutants in these organs (FIG. 8B). Across all organ types, the LN group had the most detected sgRNAs (578±106 (mean±s.e.m.), n=20) whereas liver had the least (142±25, n=7) (FIG. 1D, FIG. 8B). These data suggest that, after trafficking in vivo for 7 days, only a small fraction of the adoptively transferred $CD8^+$ T cell variants survived in the destination organs.

Figure 8C:
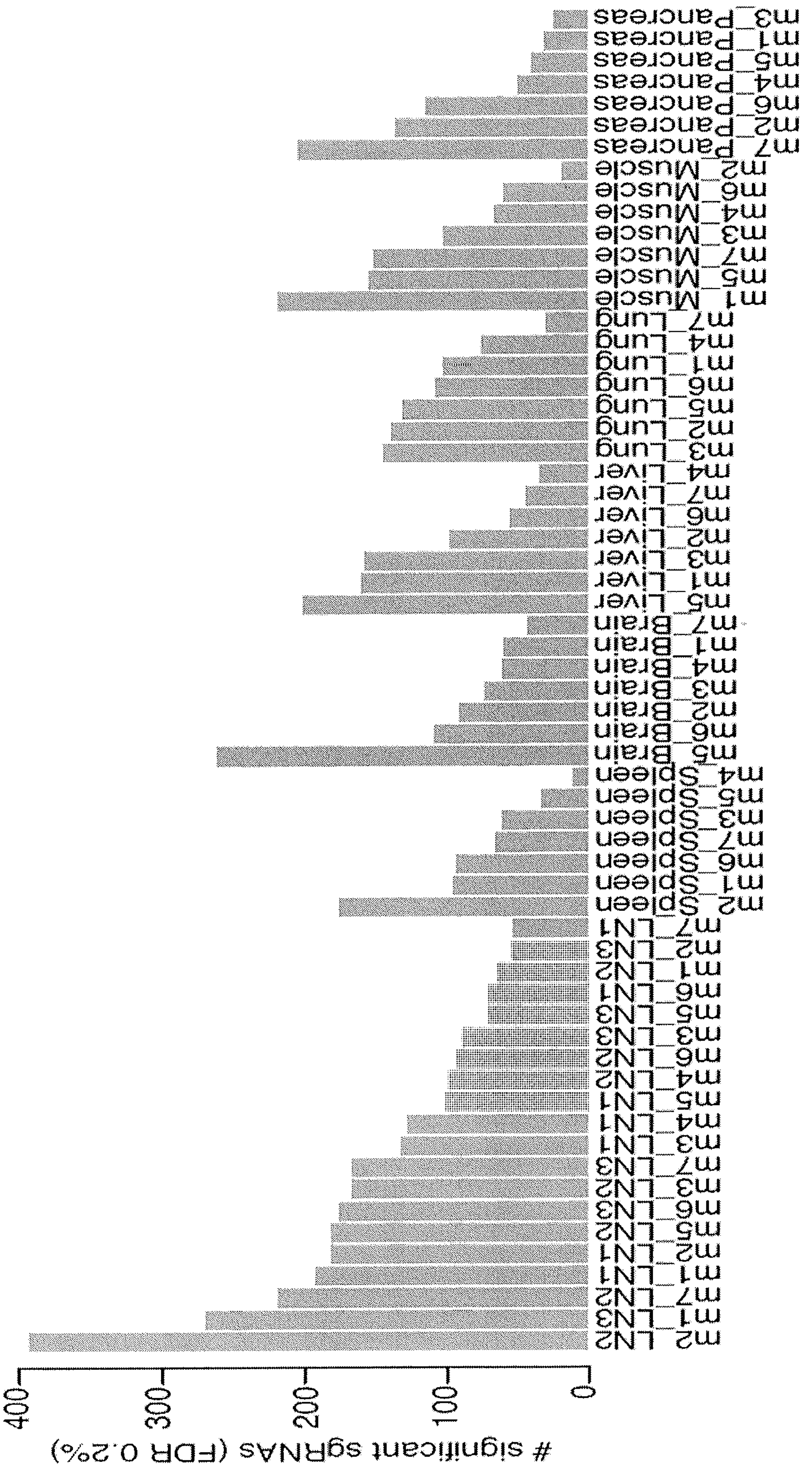
Figure 8D:
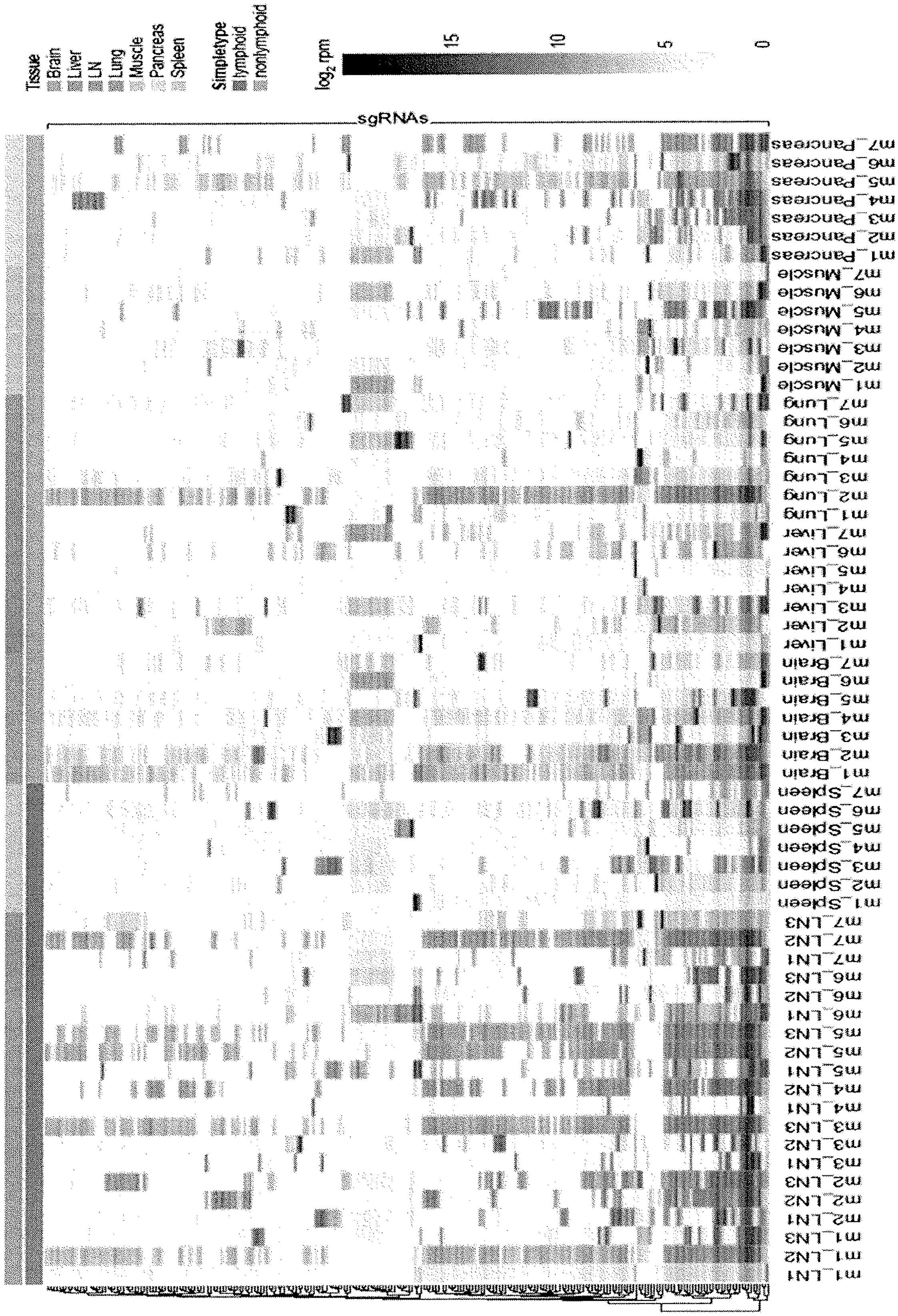
Figure 9A:
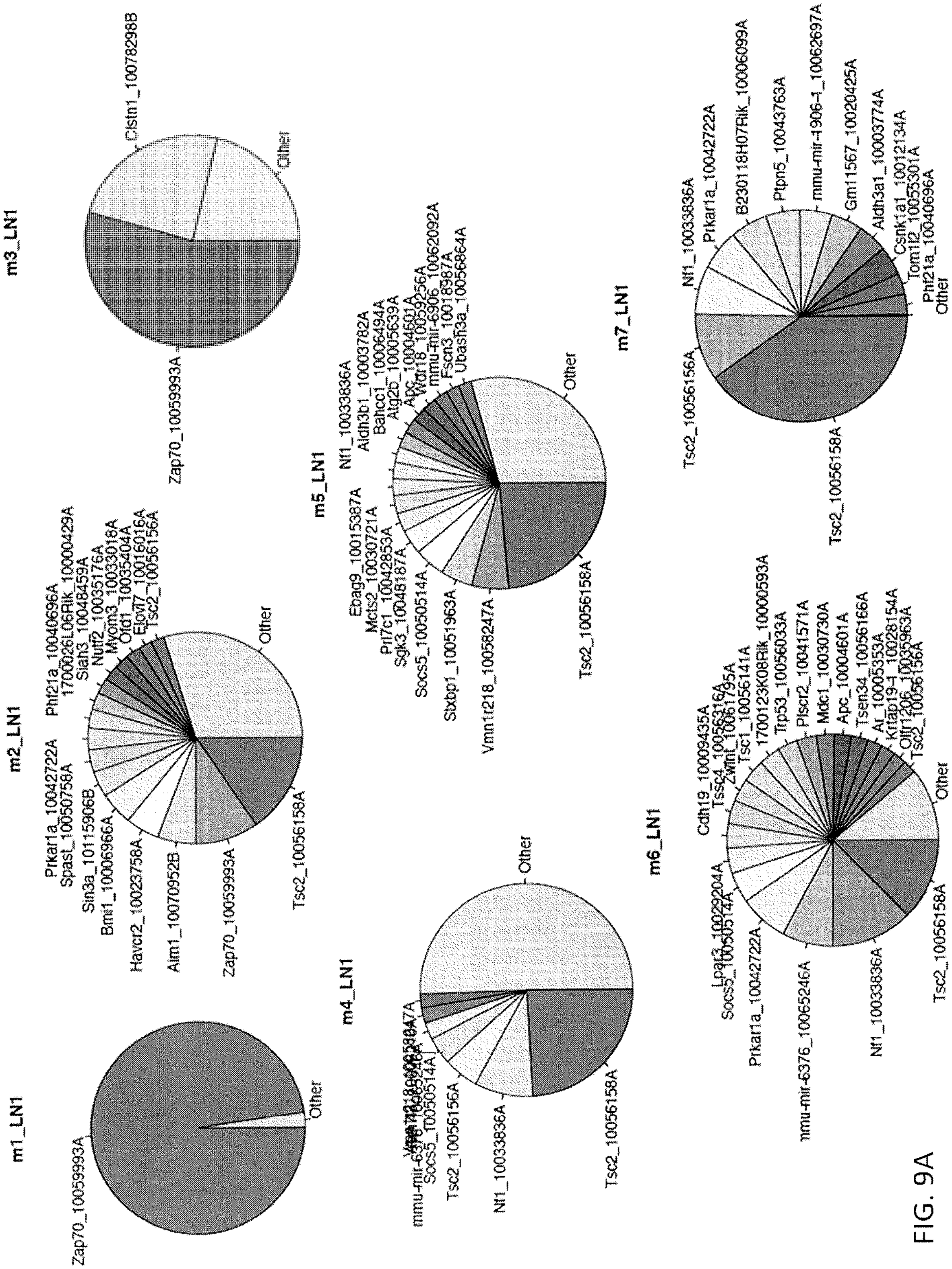
FIGS. 9A-9I are a series of pie charts showing results from analysis of genome-scale CRISPR screen of naive Cas9 $CD8^+$ $T_{eff}$ cell survival in WT mice (in 3 pages). All pie charts of sgRNA compositions in organ samples. SgRNAs that comprised≥2% of total reads for each sample are shown, with the remaining reads classified as "Other.
Figure 9B:
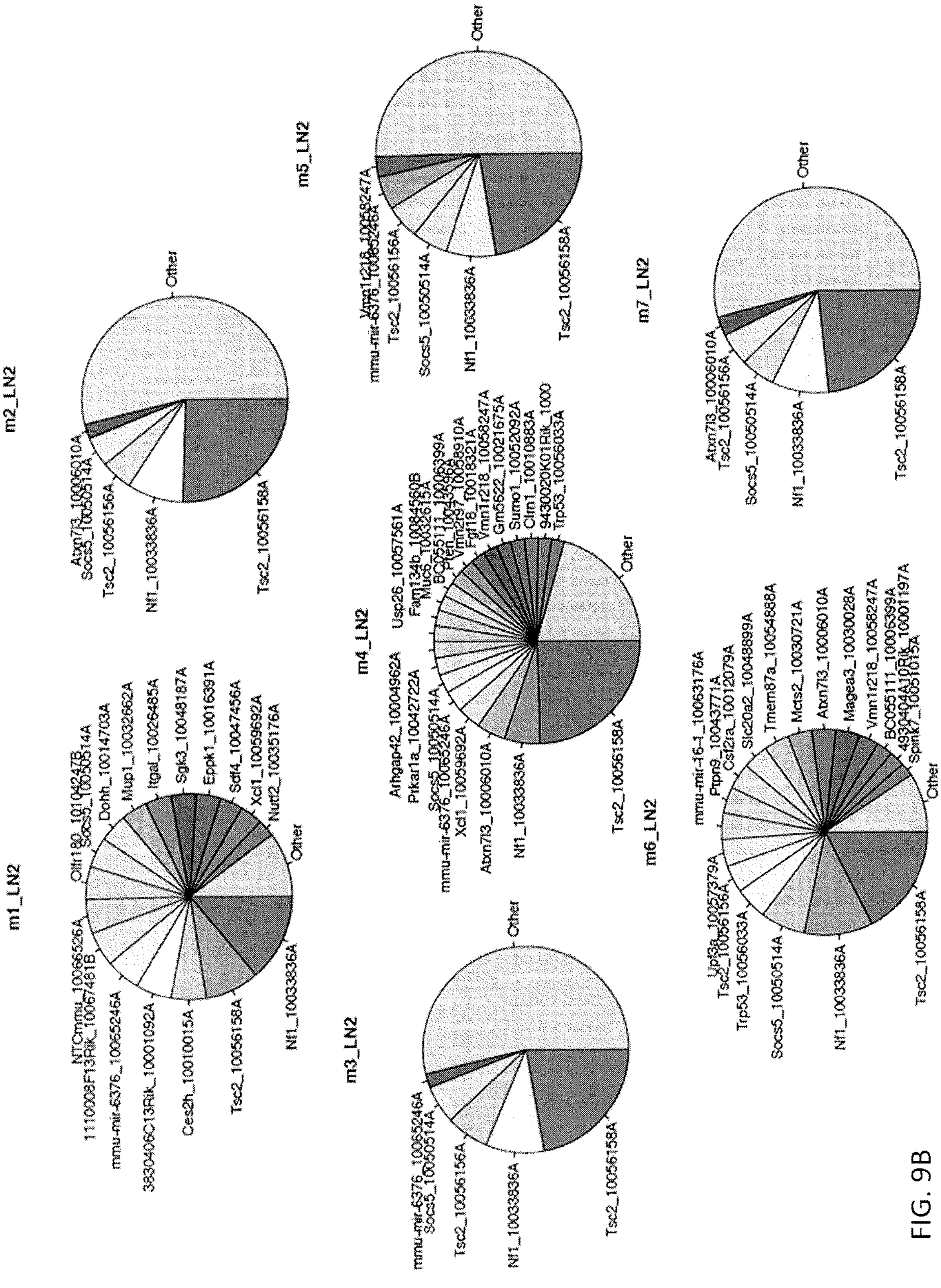
Figure 9C:
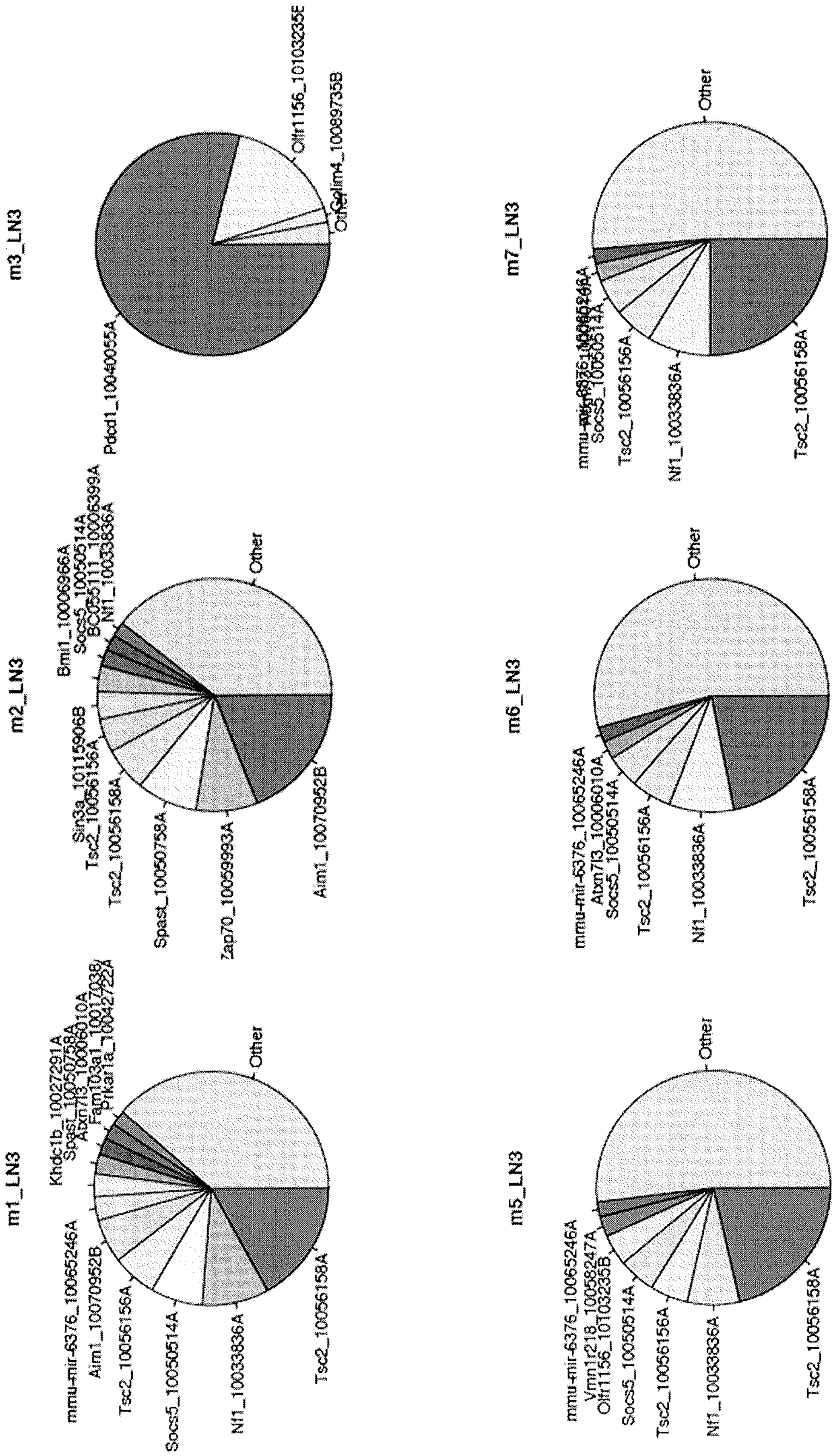
Figure 9D:
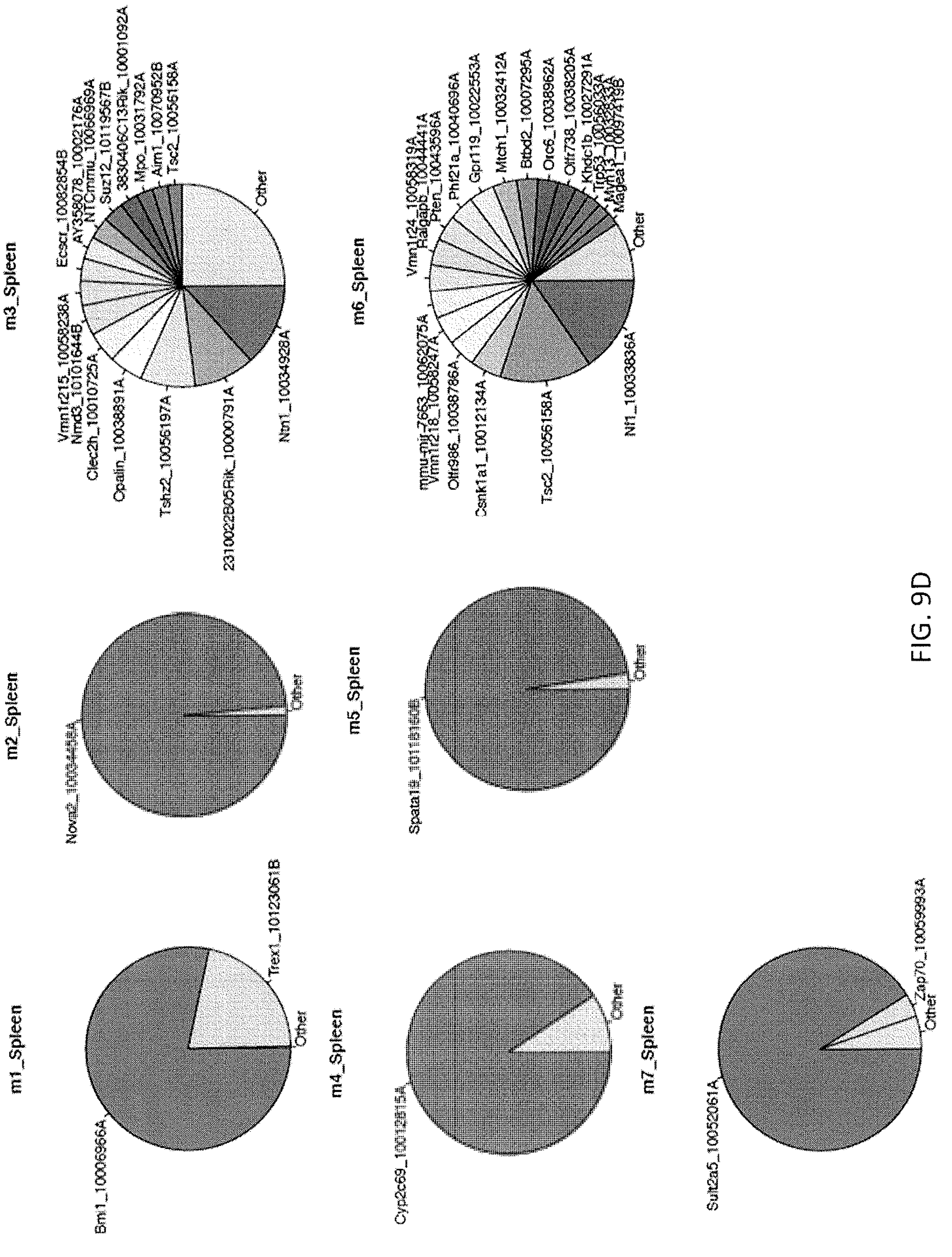
Figure 9E:
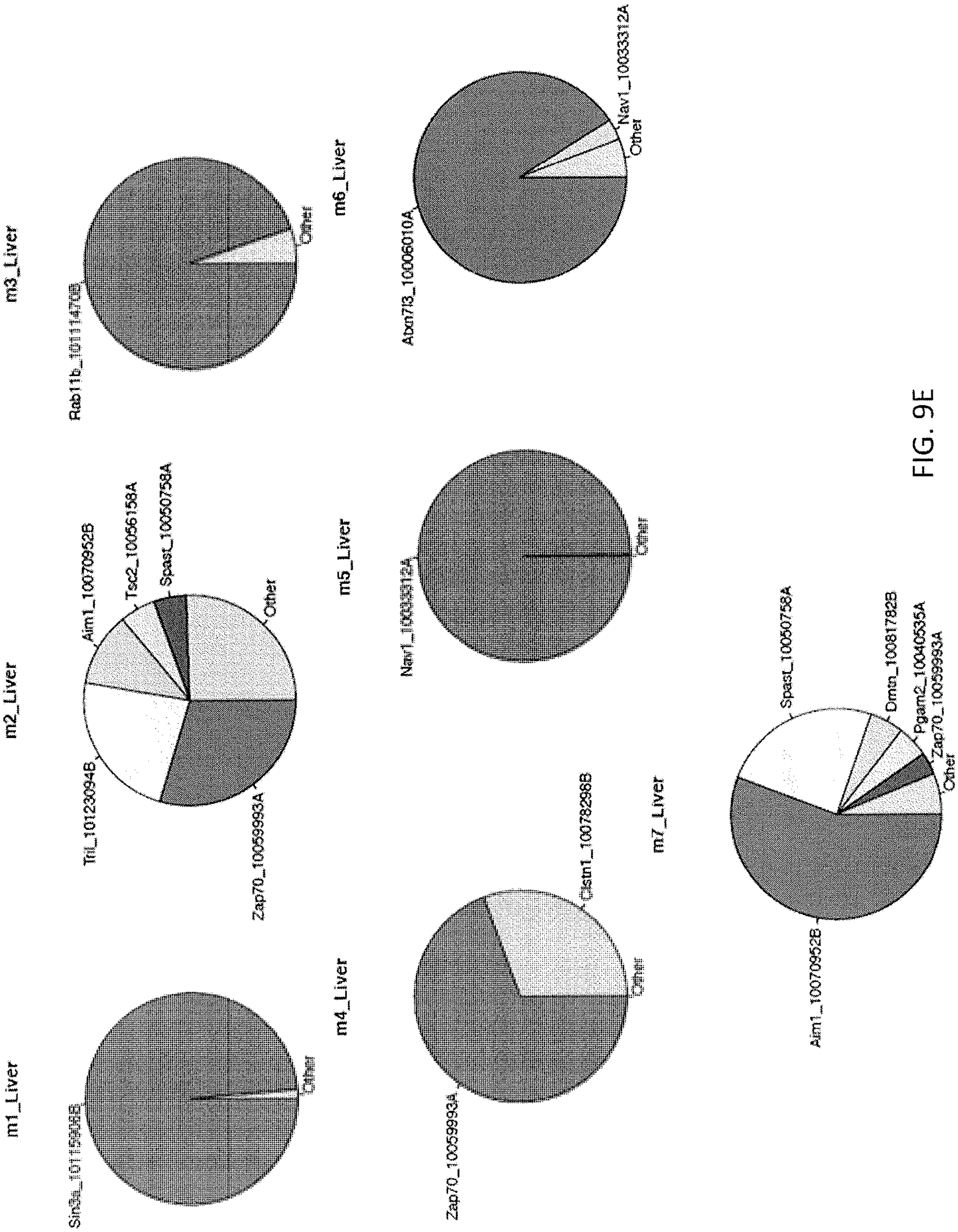
Figure 9F:
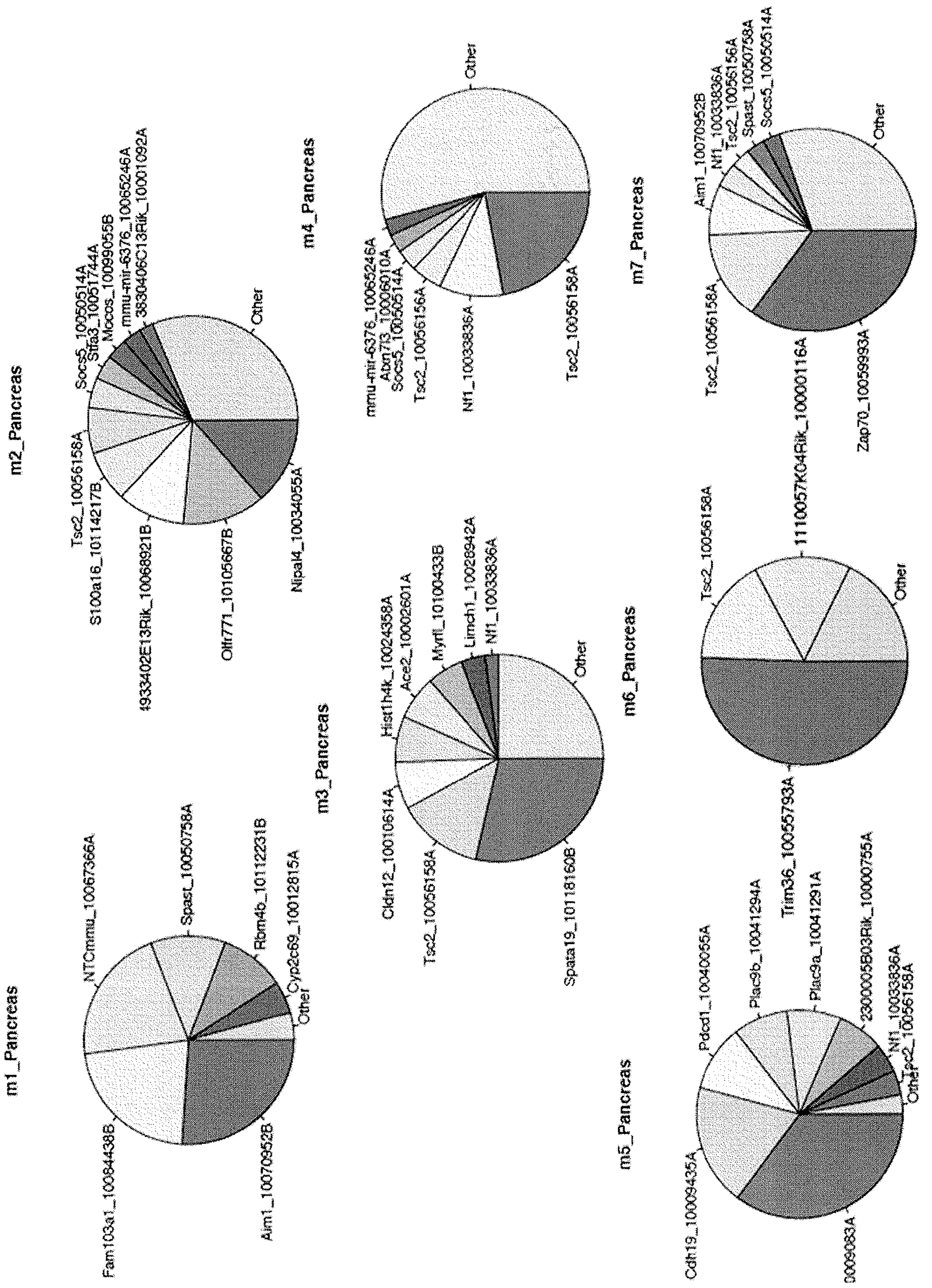
Figure 9G:
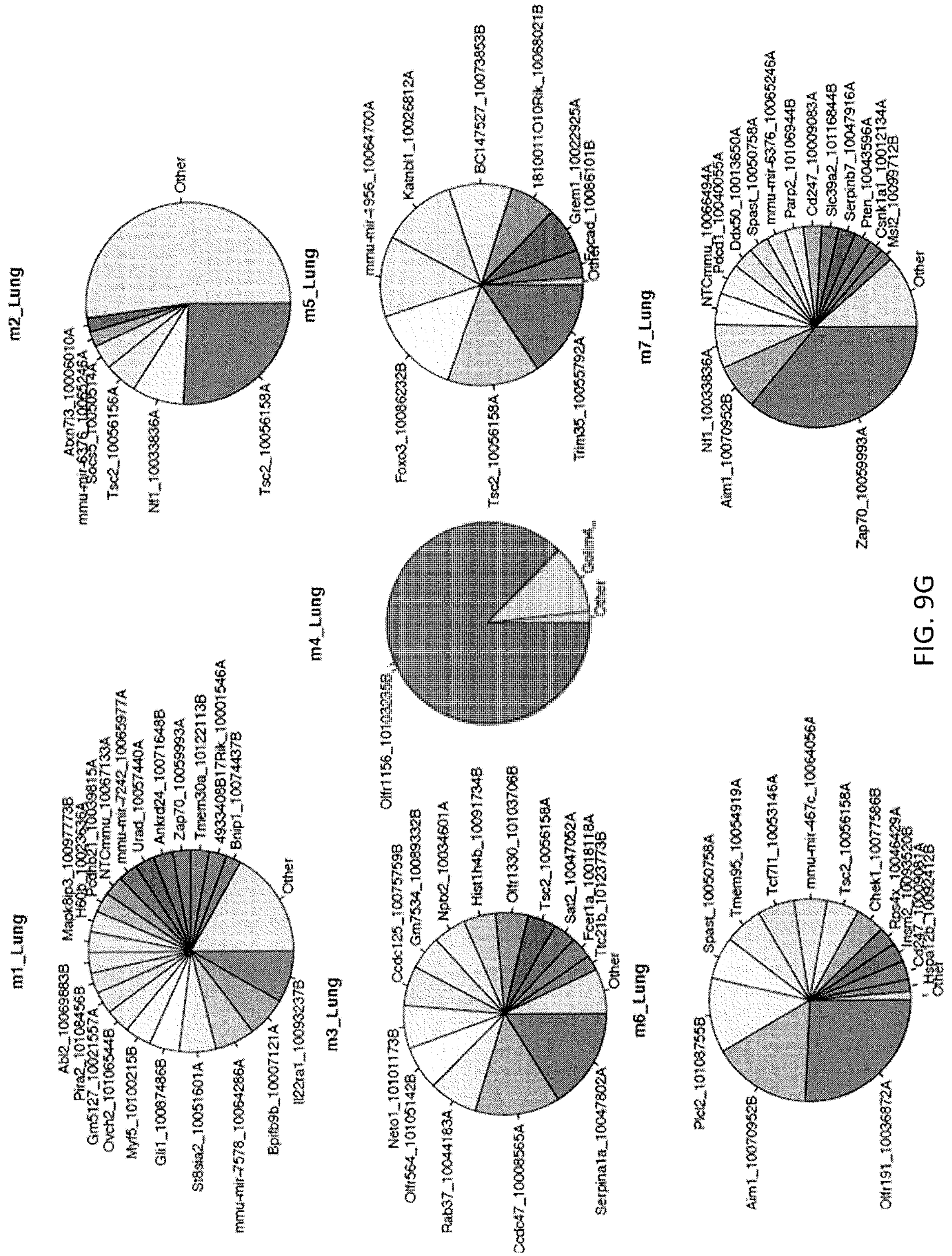
Figure 9H:
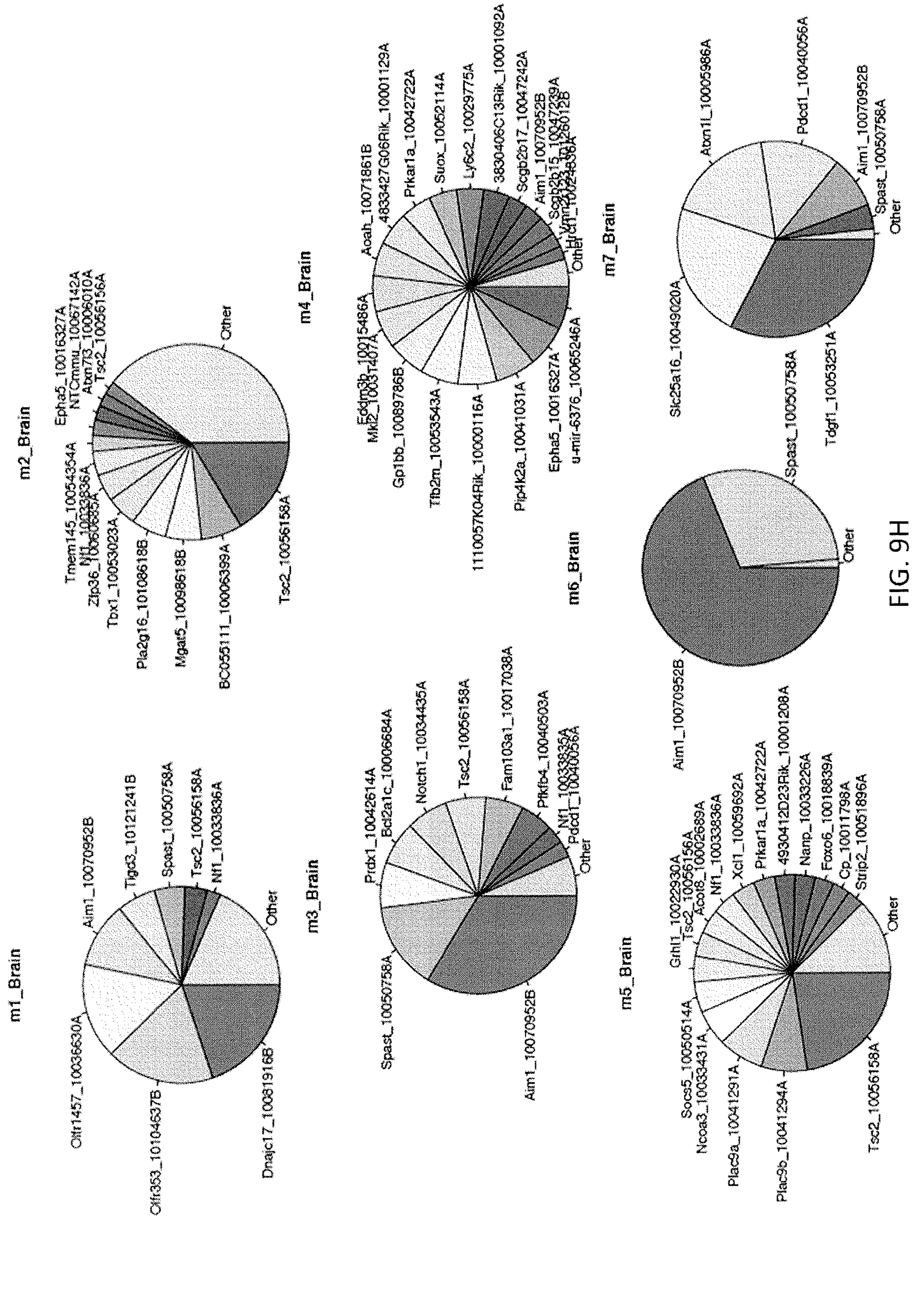
Figure 9I:
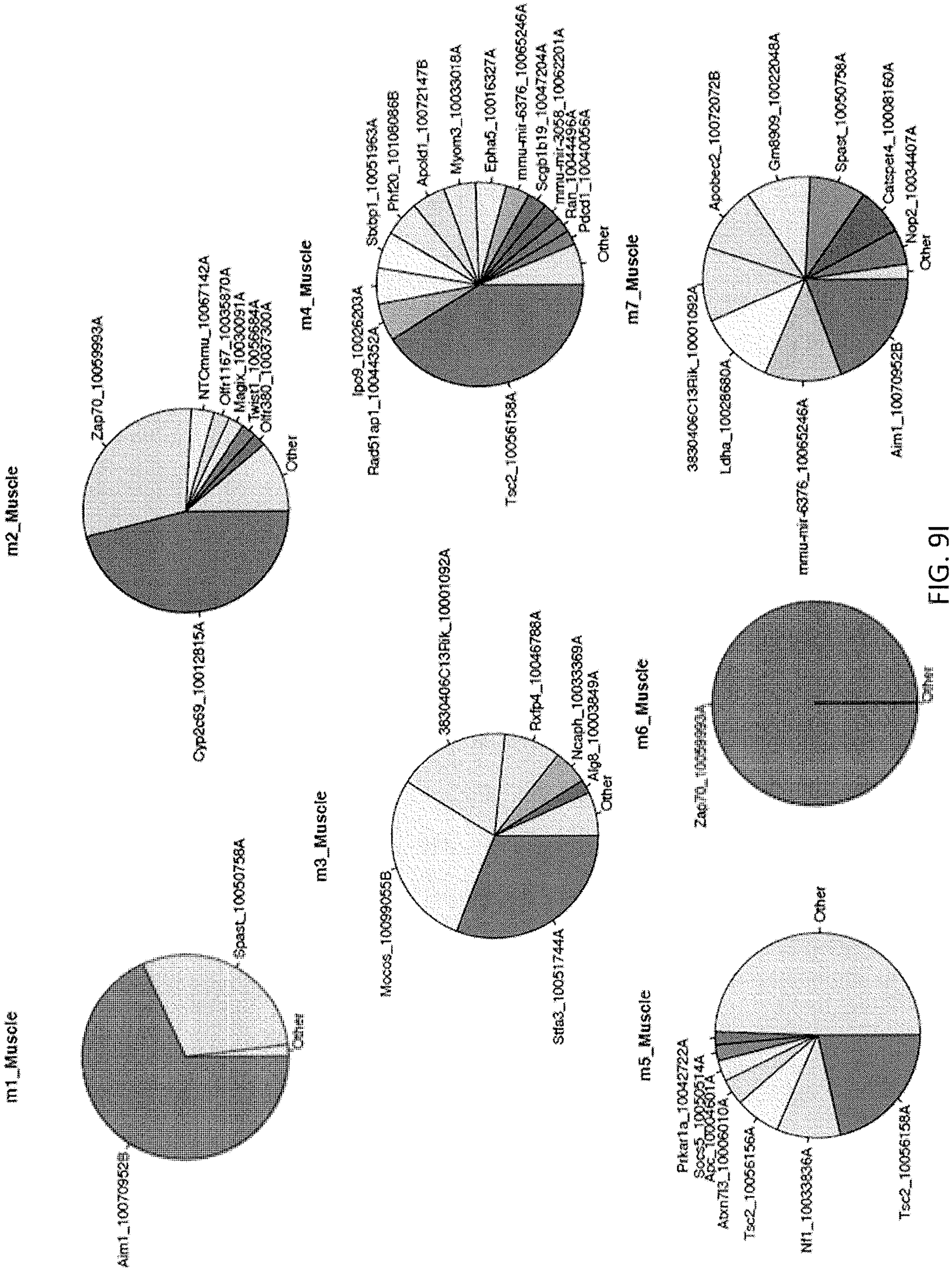
Figure 16A:
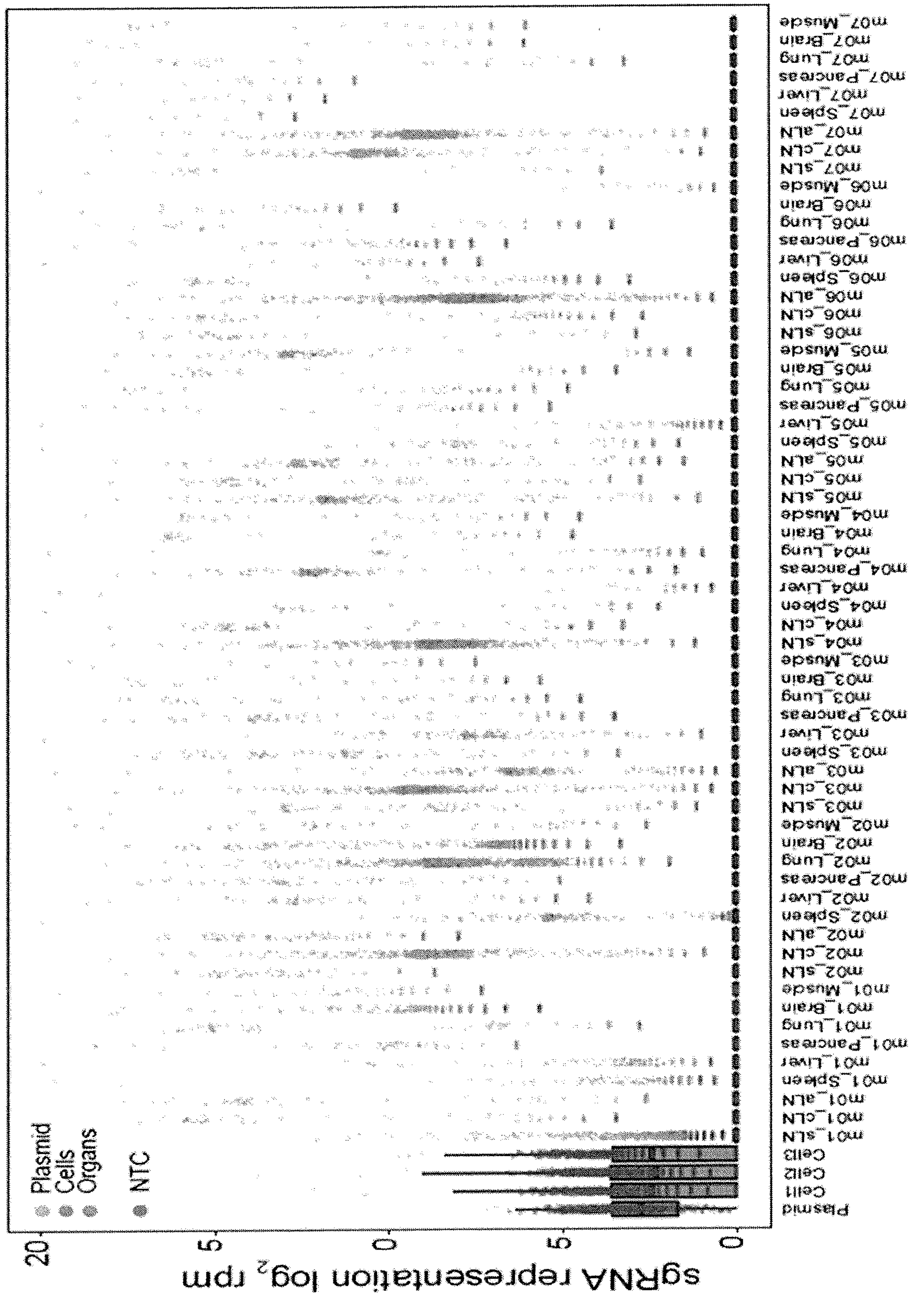
FIGS. 16A-16D are a series of plots illustrating additional analysis of genome-scale CRISPR $CD8^+$ T cell survival screens.
Figure 16B:
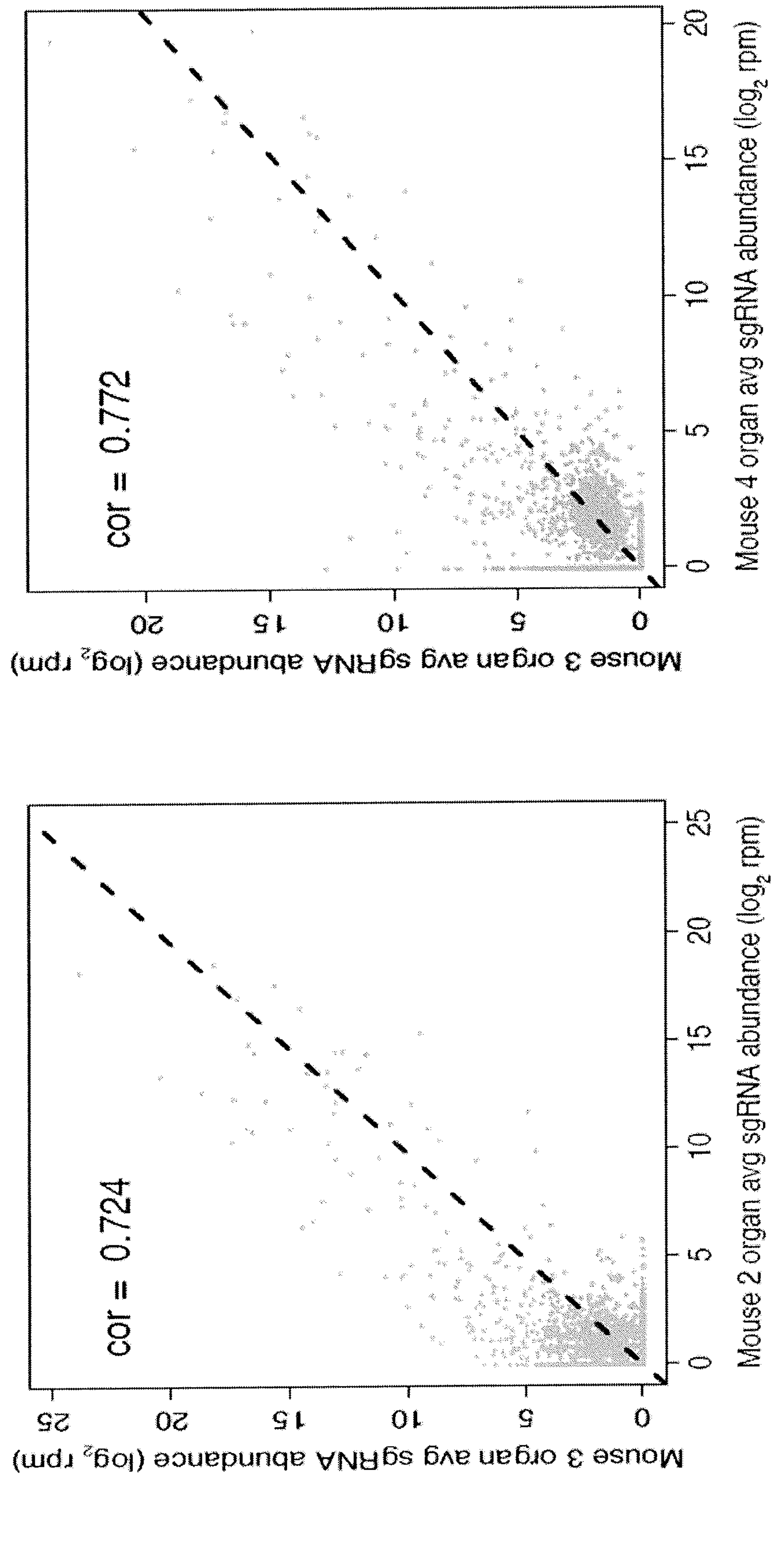

While the library representation of infected, pre-injected T cells followed a log-normal distribution for both gene-targeting sgRNAs (GTS) and NTCs, the sgRNA representation in organs was characterized by the dominance of a small fraction of sgRNAs (FIGS. 1E-1G, FIGS. 9A-9I, FIG. 16A), a signature of clonal expansion of a subset of targeted T cells. While an organ can be dominated by one or a few T cell mutants (e.g. a $CD8^+$ T cell clone with an sgRNA targeting Program cell death protein 1 (PD-1/Pdcd1) dominated LN3 sample in mouse 3) (FIG. 1E), it can also consist of multiple highly abundant, but not dominating clones (FIG. 1E, FIGS. 9A-9I). Monoclonal (one major clone with >=90% of total reads), oligoclonal (3 to 10 major clones each with >=2% of total reads) and polyclonal (more than 10 clones with 2% or more reads) compositions of T cell variants existed in both lymphoid and non-lymphoid organs (FIG. 1E, FIGS. 9A-9I). At the individual mouse level, the sgRNA representation between different mice were correlated with each other (FIG. 16B). All these enriched sgRNAs across all 62 organ samples showed a highly heterogeneous landscape of enrichment pattern, with many sgRNAs shared between multiple organs (FIG. 8D). These data revealed a global landscape of organ survival for mutant $CD8^+$ T cells with a diverse TCR repertoire, and showed that a small subset of the variants from the MKO $CD8^+$ T cell pool became enriched in vivo after trafficking and survival in a new host for 7 days.

Figure 2B:
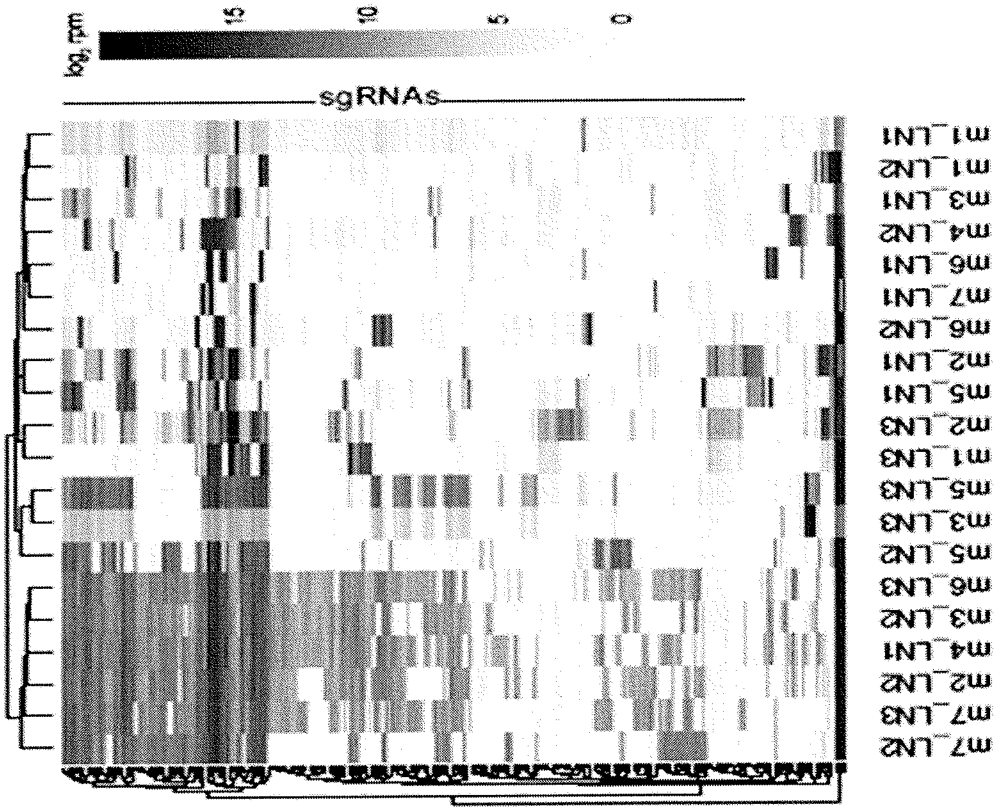
FIGS. 2A-2G are a series of plots and images illustrating significantly enriched sgRNAs and genes of MKO infected CD8+ T cells in wildtype mice.
Figure 2A:
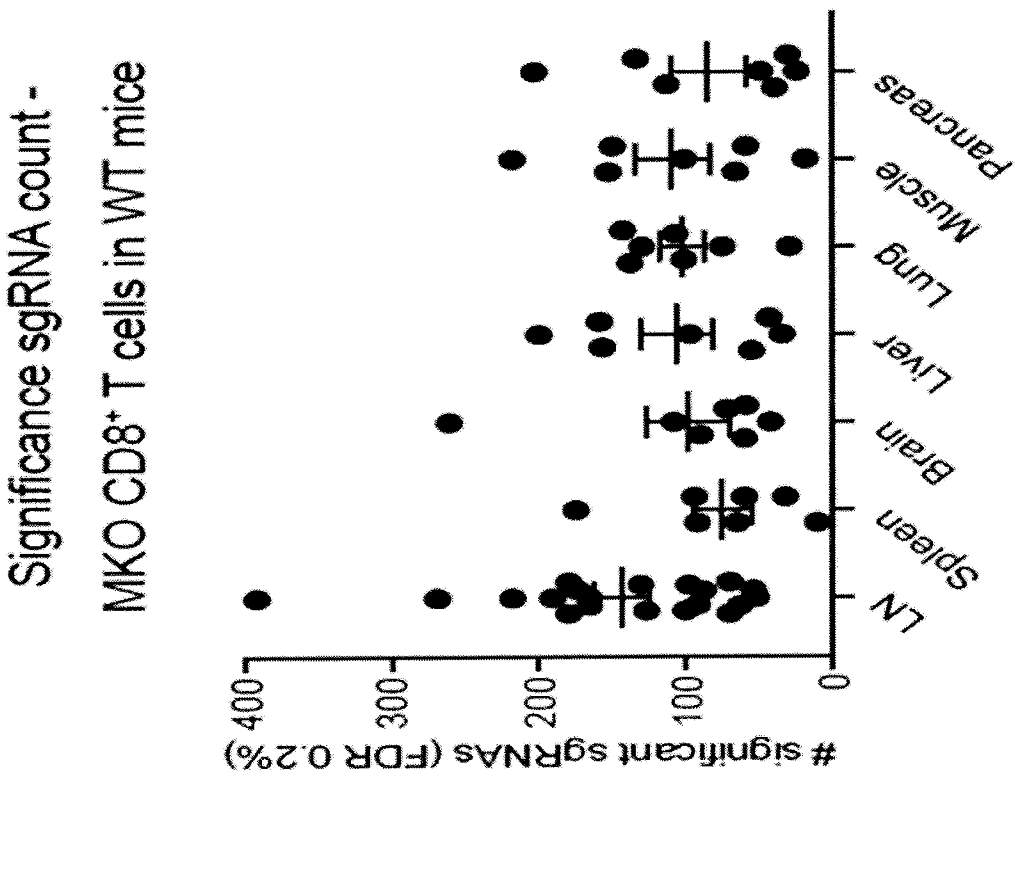

The library representation within each sample was analyzed to find enriched sgRNAs compared to the 1,000 NTC sgRNAs. To identify genes whose perturbation might result in enhanced ability of $CD8^+$ $T_{eff}$ cells to survive in differential organs in vivo, the sgRNAs and genes represented in the MKO library were ranked using multiple statistical metrics. At a false discovery rate (FDR) of 0.5% or lower, a set of significantly enriched sgRNAs were identified in each organ (FIG. 2A, FIG. 8C). In all 62 organs across 7 mice surveyed, an average of 112±9 (mean±s.e.m.) sgRNAs were found as significantly enriched (FIG. 8D). Although the numbers of significant sgRNAs were largely similar between organs, LNs on average (96±9) had the highest number compared to all other organs (two-sided unpaired t-test, p=0.03) (FIG. 2A, FIG. 8D). All these enriched sgRNAs across all 62 organ samples showed a highly heterogeneous landscape of enrichment pattern (FIG. 2B, FIG. 8D). These data revealed a highly dynamic map of mutant $CD8^+$ T cell clonal selection within internal organs after adoptive transfer.

Figure 1I:
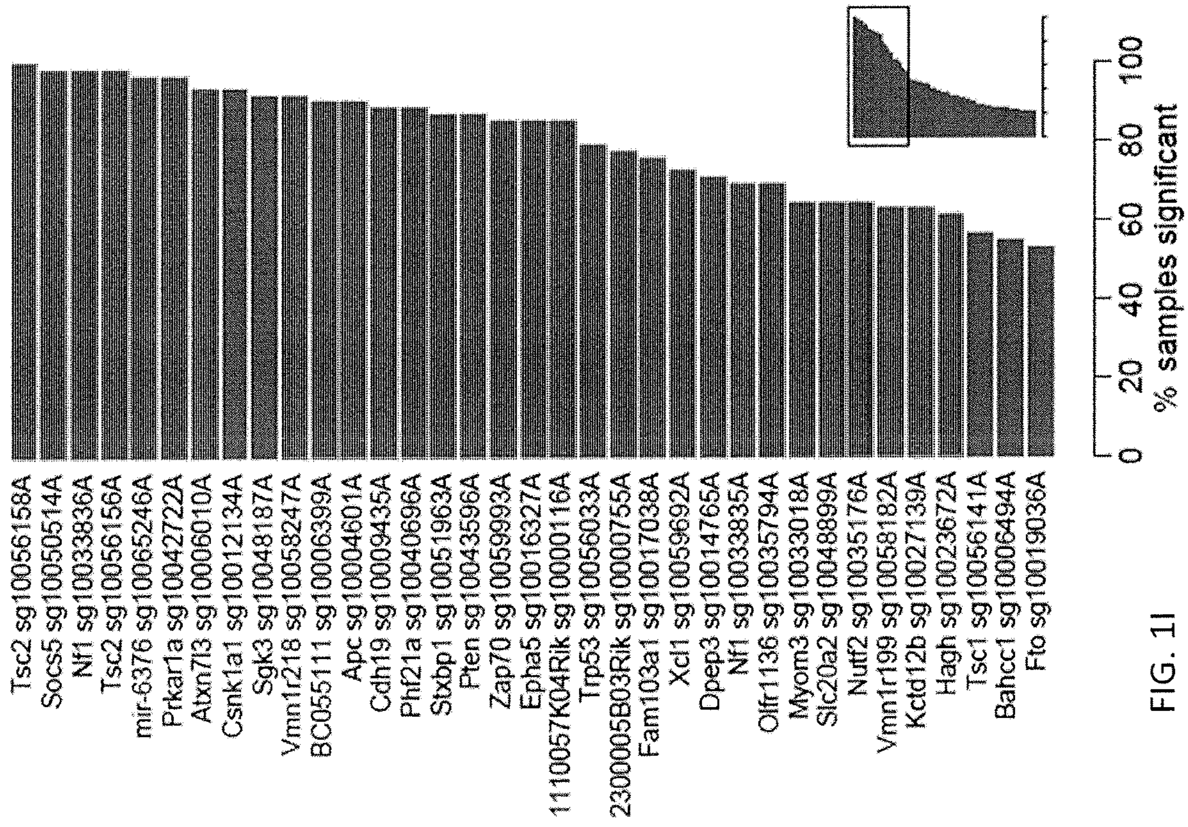
Figure 1J:
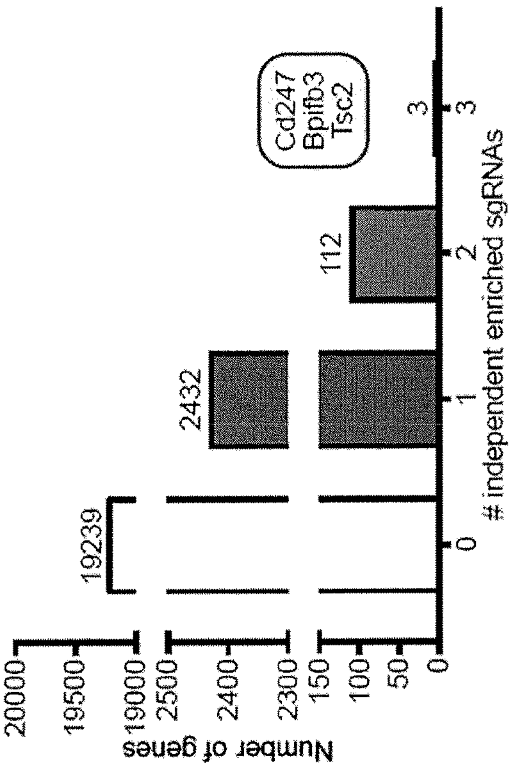
Figure 1K:
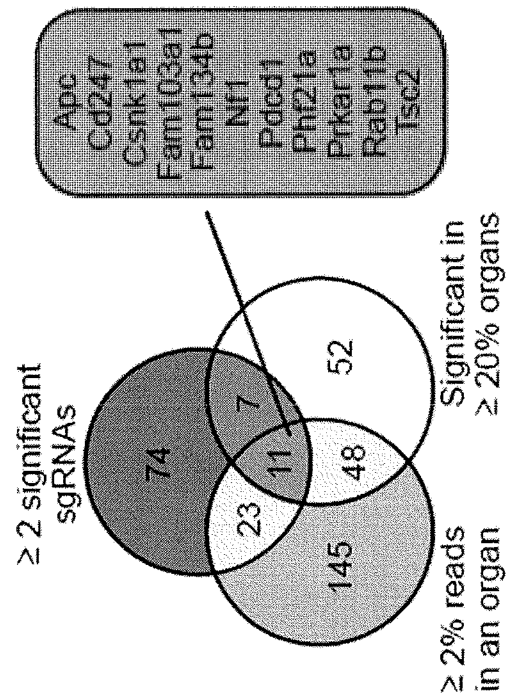
Figure 2C:
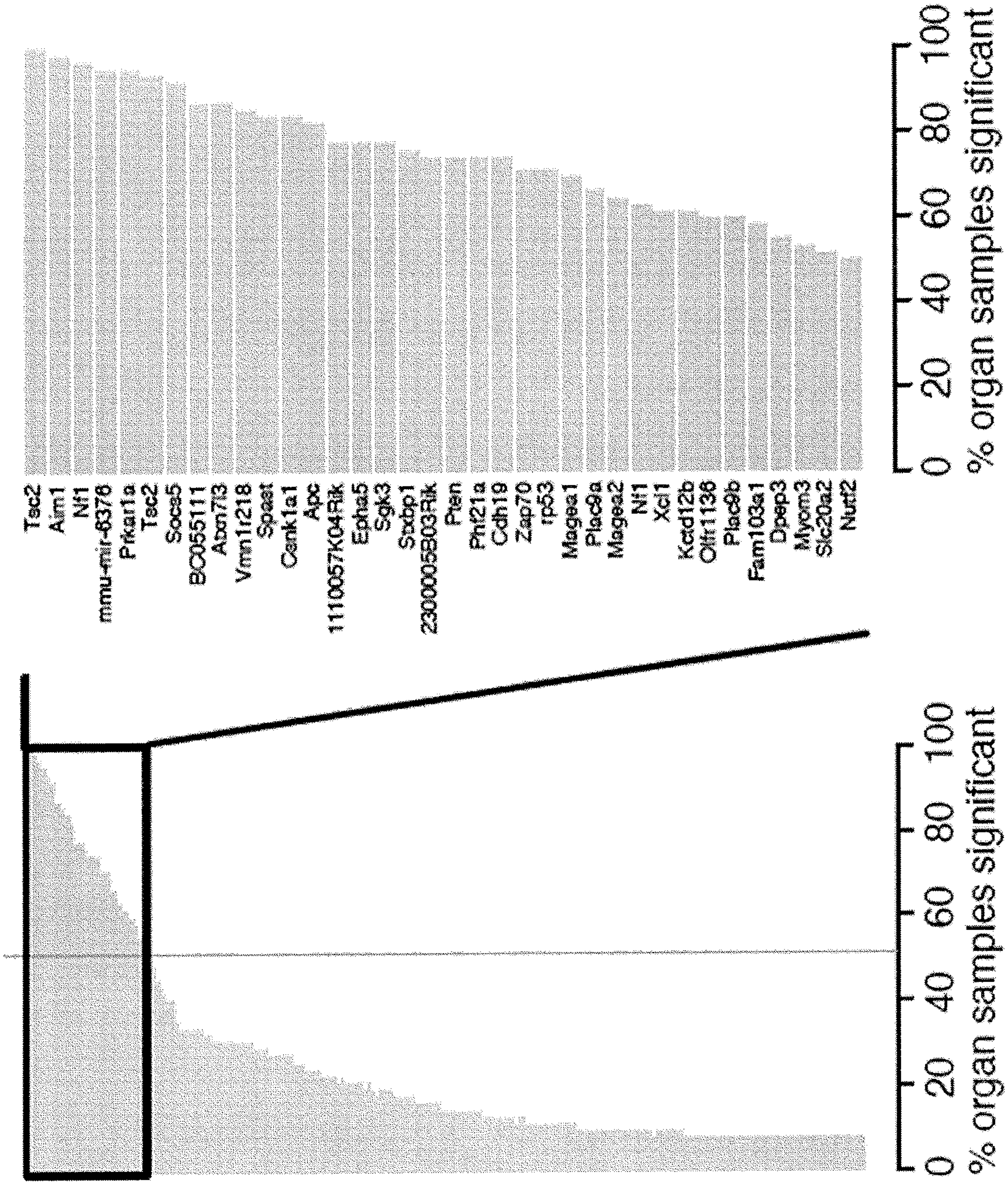
Figure 2E:
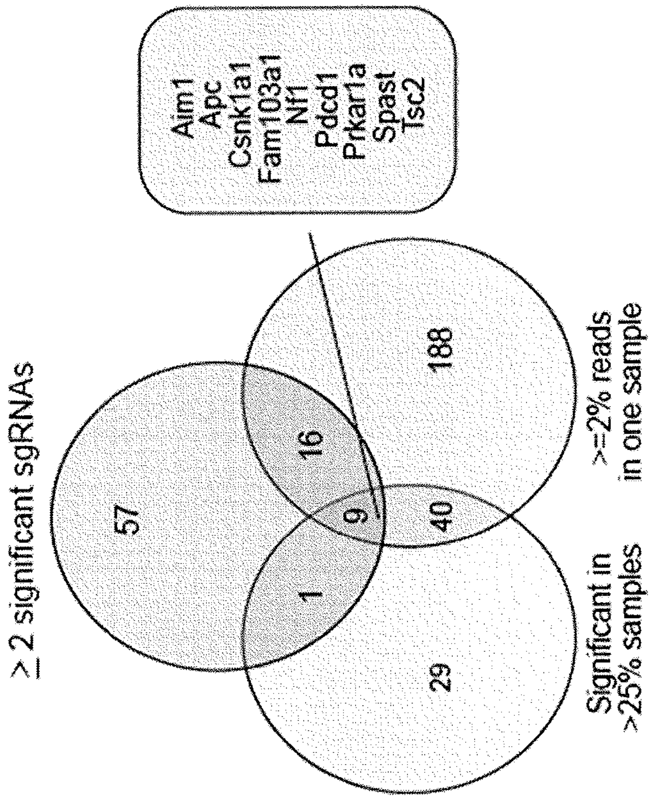
Figure 2D:
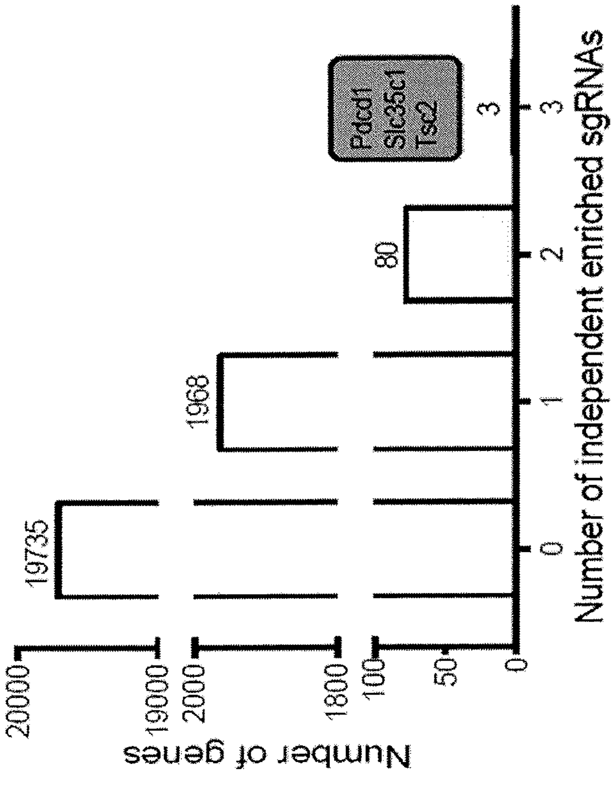
Figure 2G:
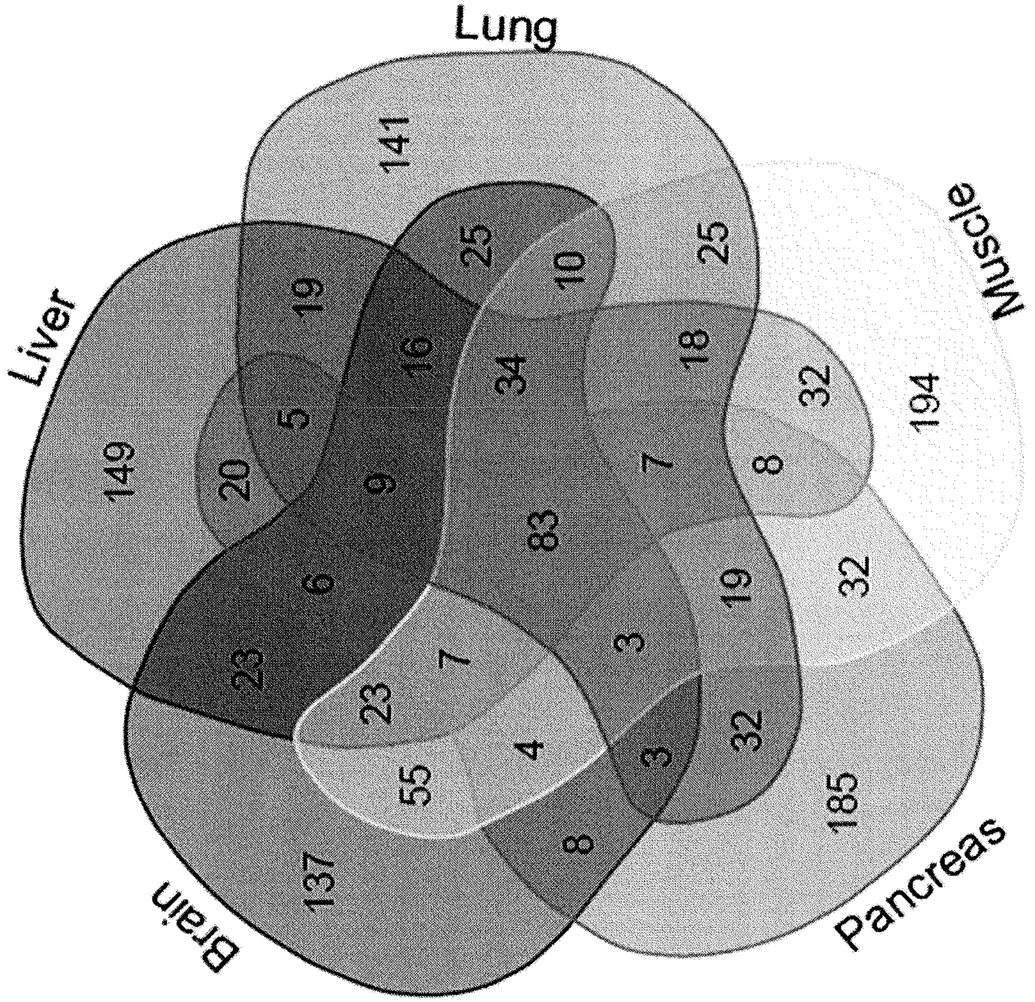
Figure 2F:
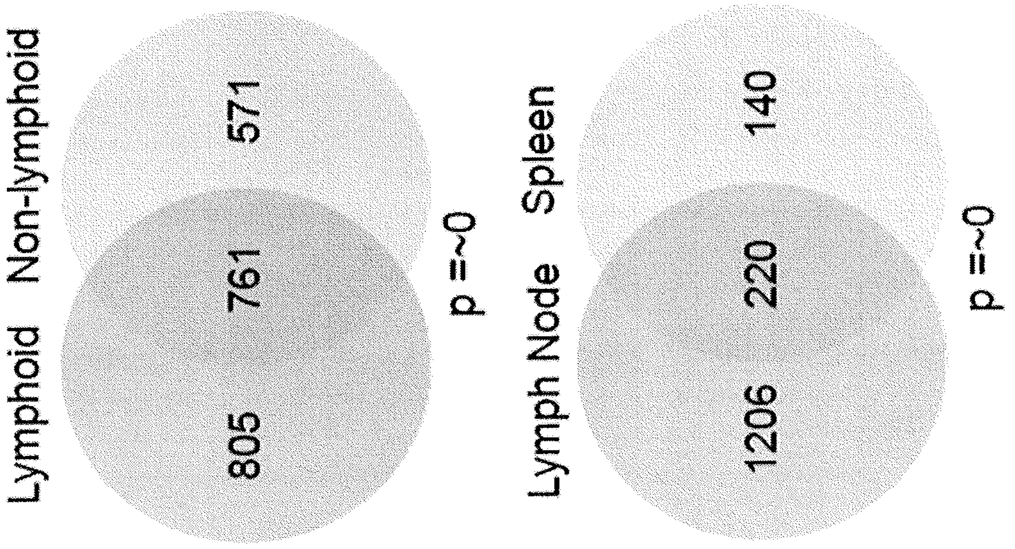
Figure 17A:
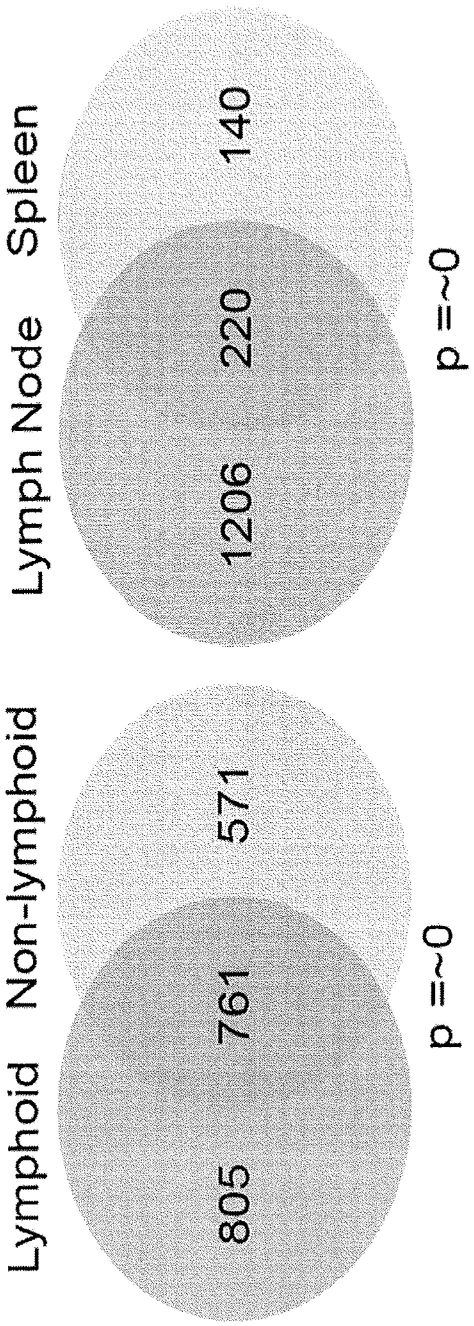
FIGS. 17A-17C are as series of plots and images illustrating analysis of sgRNA library representation by organ types.
Figure 17B:
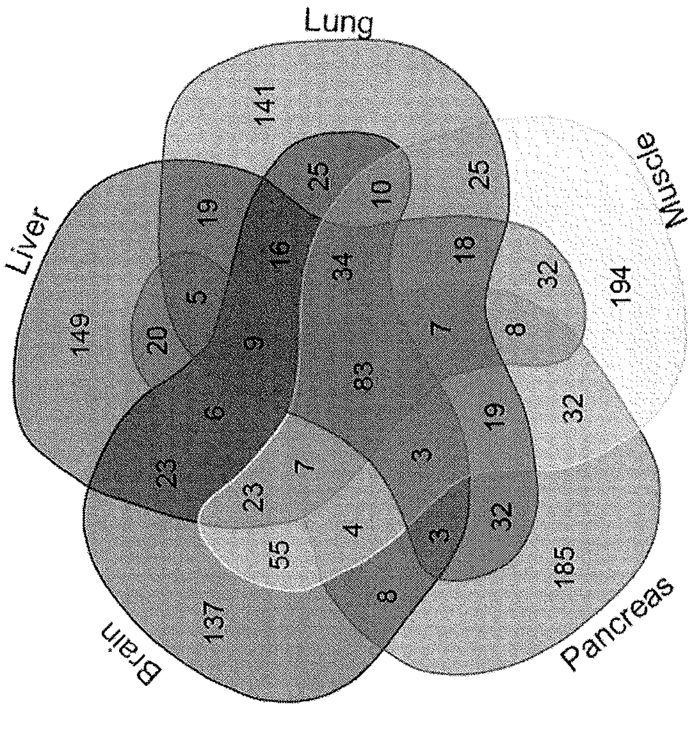
Figure 17C:
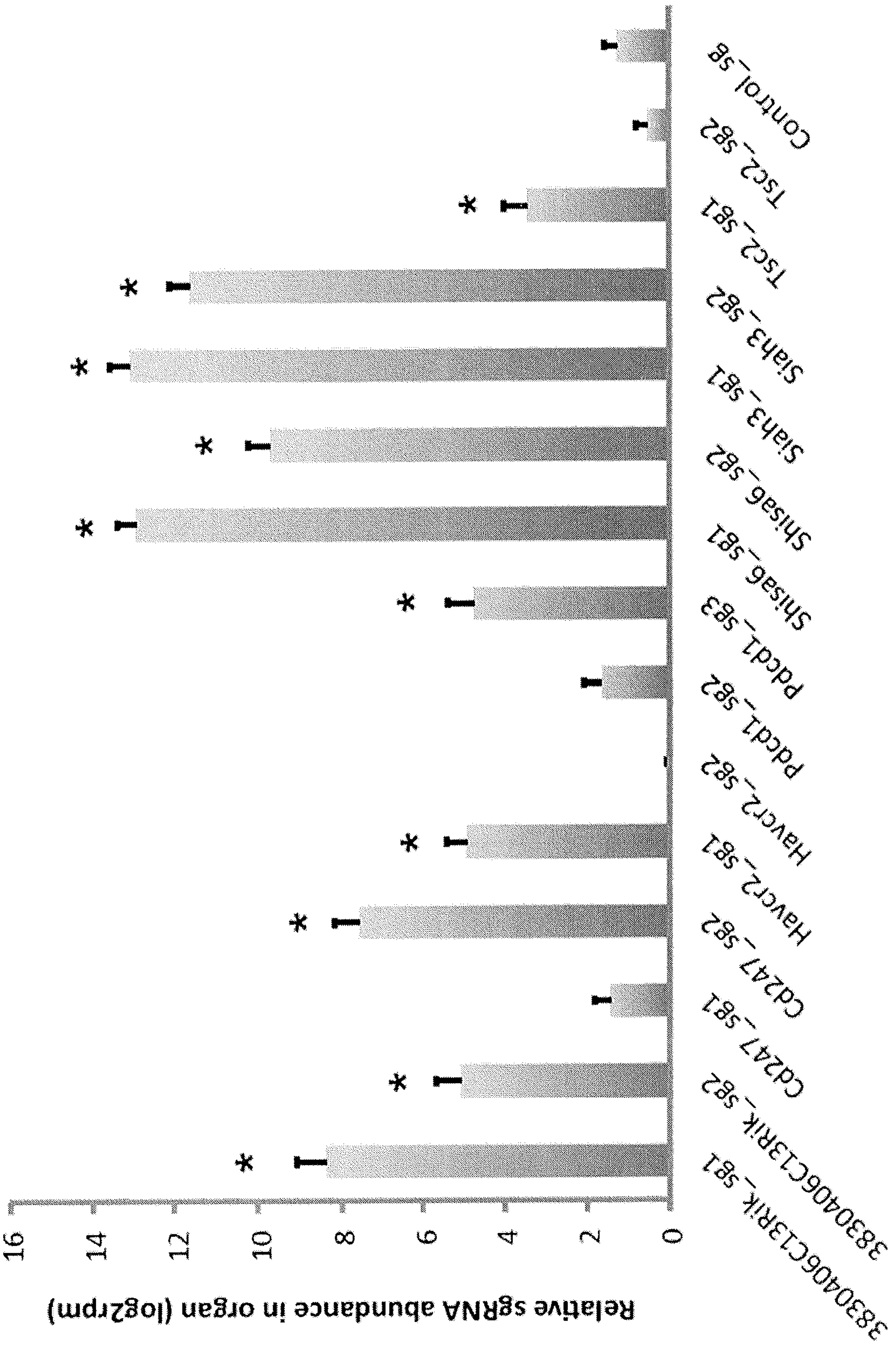

Example 4: Significantly Enriched sgRNAs Targeted Immune Genes and Genes with Diverse Functions To identify genes whose perturbation might result in enhanced ability of $CD8^+$ $T_{eff}$ cell to survive in differential organs in vivo, the sgRNAs and genes represented in the MKO library were ranked using multiple statistical metrics. By comparing the set of enriched sgRNAs between organs, it was discovered that lymphoid organs significantly overlapped with non-lymphoid organs (hypergeometric test, $p\approx0$) (FIG. 17A), although there are substantial sets of sgRNAs unique to each organ type (FIG. 17A), reflected by the set of significantly differentially enriched sgRNAs in lymphoid compared to non-lymphoid organs. Among lymphoid organs, LNs and spleen also significantly overlapped ($p\approx0$) (FIG. 17A). Within non-lymphoid organs, the set of all significant sgRNAs in each of the five organs (brain, liver, lung, muscle and pancreas) significantly overlapped with each other ($p<1\times10^{-5}$ for all pairwise comparisons) (FIG. 17B). Ranking sgRNAs by their prevalence (frequency of being enriched in an organ) (FIG. 1I), or by their overall average abundance in organs as compared to cells (FIG. 8E), revealed dominant signatures of three types of genes: (1) immune genes (such as Lexm/BC055111, Socs5, Zap70), consistent with their role in T cells; (2) genes regulating general cell growth and proliferation (e.g. tumor suppressor genes such as Tsc2, Nf1, Aim1, Pten, and Trp53); as well as (3) genes with undocumented functions in $CD8^+$ T cells or largely uncharacterized genes (such as Sgk3, Fam103a, Phf21a, and 1110057K04Rik) (FIG. 2C, FIG. 8E, FIG. 1I). Ranking sgRNAs by the number of independent enriched sgRNAs also revealed these three types of genes, with the top three genes representing three different categories (Cd247—immune, Tsc2—growth, and Bpifb3—unknown) (FIG. 1J). In conjunction with a third criteria, in which a given sgRNA must comprise≥2% of the reads in a single sample, a total of 11 genes are significantly enriched across all three criteria, again representing immune (Pdcd1, Cd247), growth (Apc, Nf1, Tsc2) and unknown (Csnk1a1, Fam103a1, Fam134b, Phf21a, Prkar1a, and Rab11b) genes (FIG. 1K). Pdcd1, also known as PD-1, is a well-established immune checkpoint regulator expressed on T cells, and a major target of checkpoint blockade. The fact that Pdcd1 passed all three criteria and emerged as a robust hit provided strong evidence for the validity of this approach. Many of the significantly enriched genes are membrane proteins involved in the immune system. Minipool validation experiments were performed, and as a result, 10/14 sgRNAs (71.4%), covering all 7/7 genes (100%), were validated in the in vivo minipool survival experiment. Specific gene-targeting sgRNAs were more abundant as compared to NTC in organs, including those targeting 3830406C13Rik, Cd247, Havcr2, PD-1, Shisa6, Siah3 and Tsc2 (FIG. 17C). Together, these data suggest that perturbation of these genes by CRISPR allows $CD8^+$ $T_{eff}$ cells to better survive in lymphoid and non-lymphoid organs in vivo.

Figure 18A:
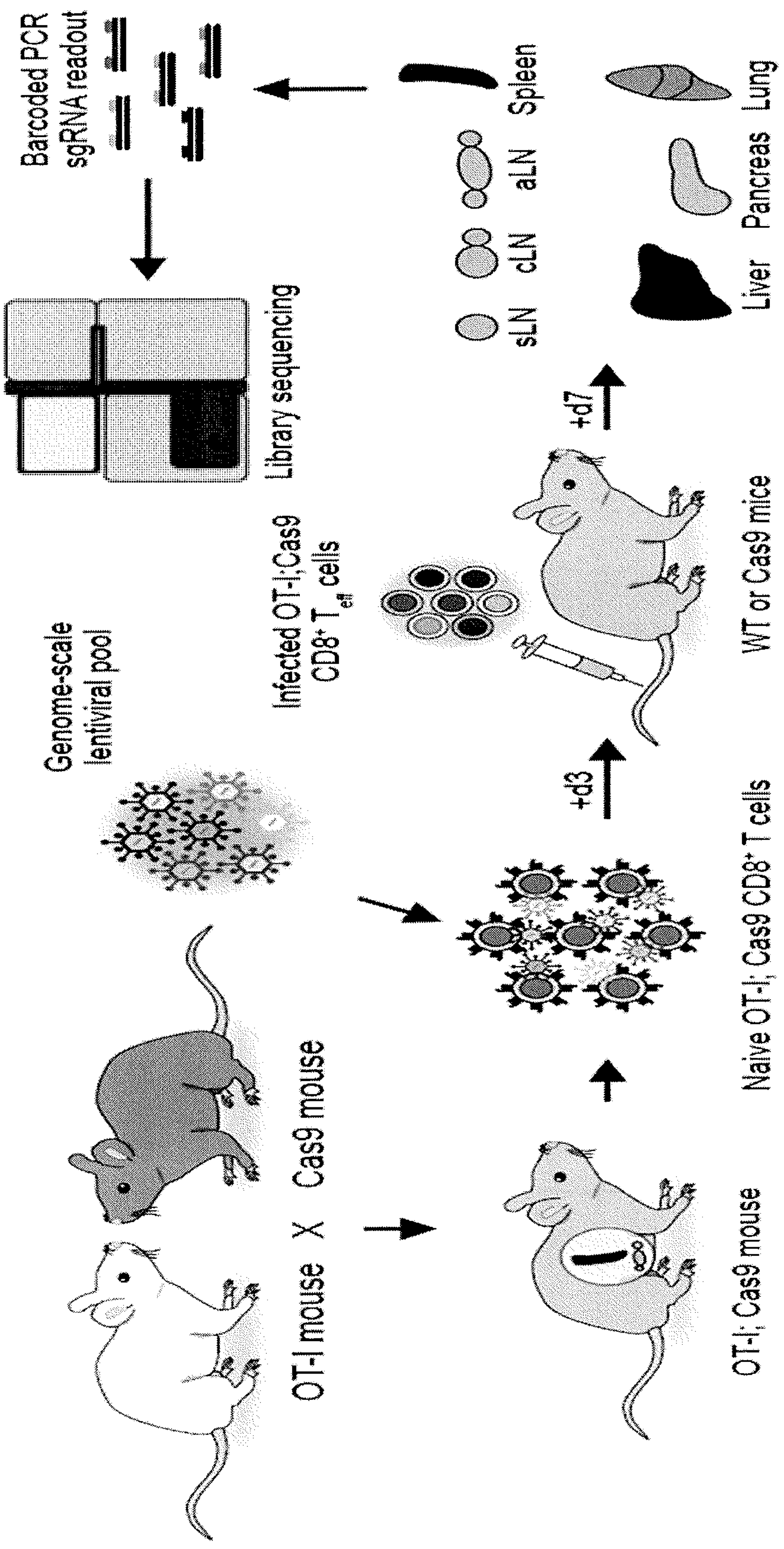
FIGS. 18A-18G are a series of plots and images illustrating a genome-scale screen for trafficking and survival with effector CD8+ T cells with transgenic, clonal TCR.
Figure 19A:
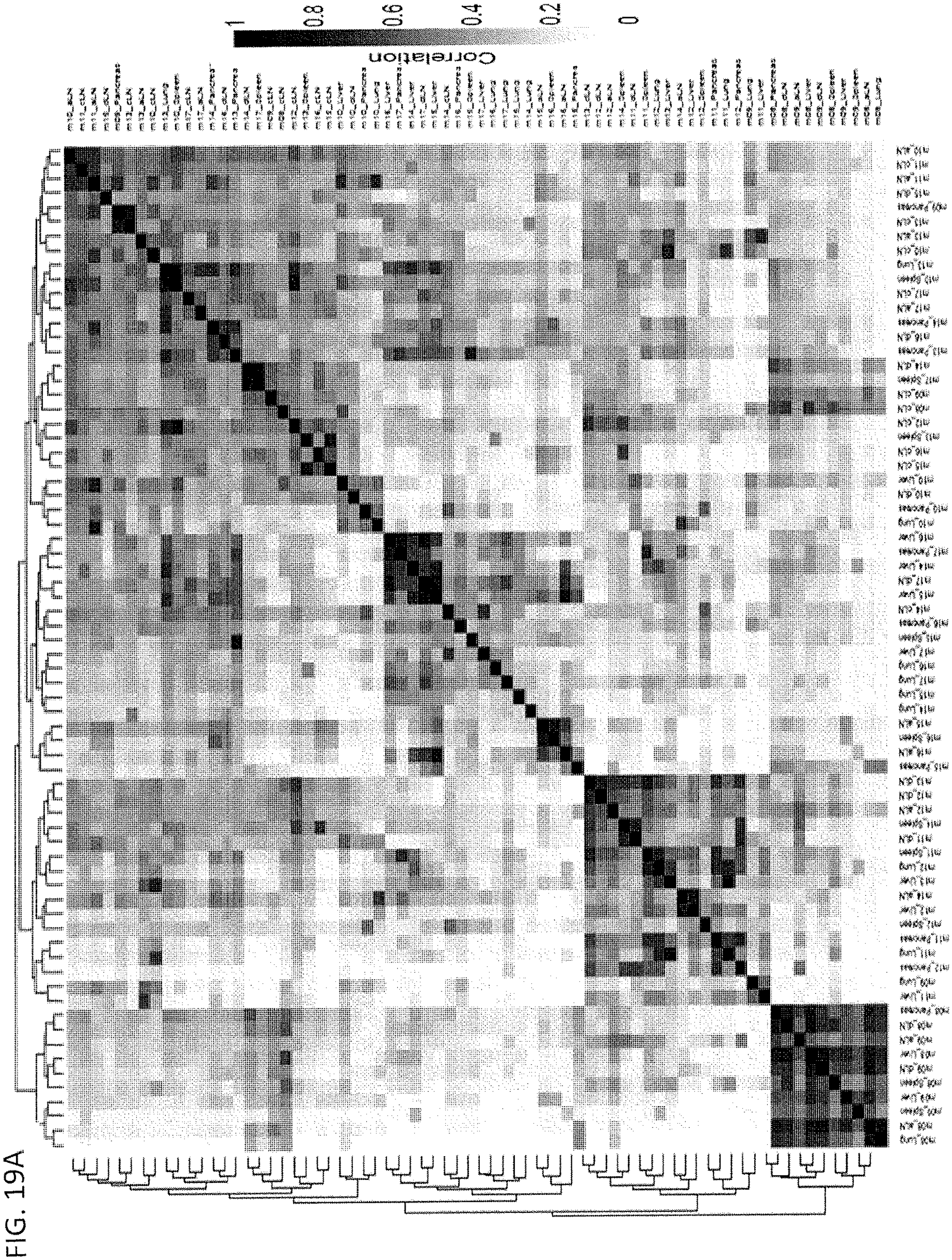
FIGS. 19A-19B are a set of plots illustrating analysis of genome-scale CRISPR CD8+ T cell survival screens with OT-I; Cas9 CD8+ T cells.
Figure 19B:
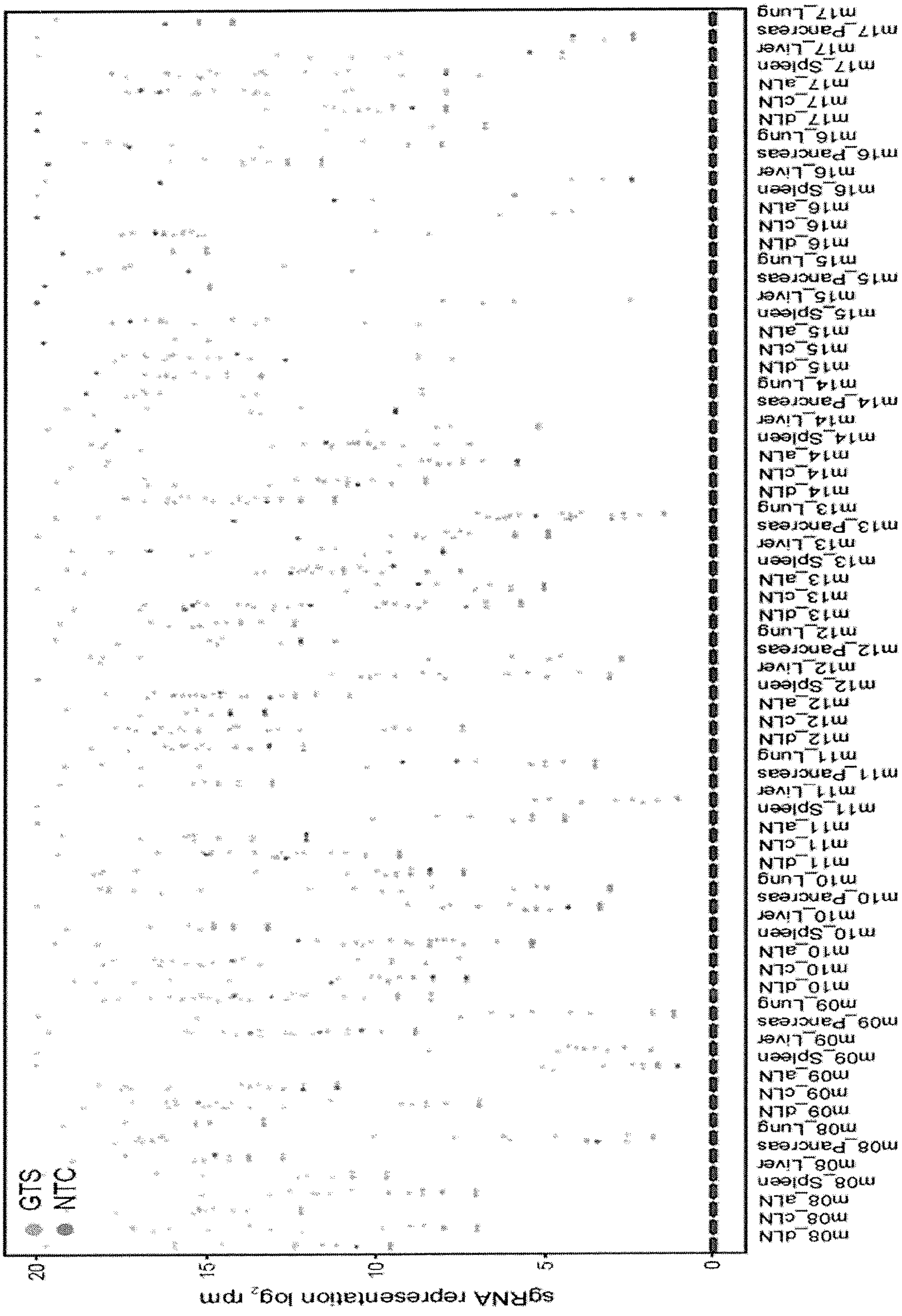

Example 5: Genome-Scale Screen for Trafficking and Survival with Effector $CD8^+$ T Cells with Transgenic, Clonal TCR Due to the diversity of the TCR repertoire in Cas9 mice, certain genetic effects may be masked by the heterogeneity of the TCR pool. To address this issue and thereby provide a parallel picture in an isogenic setting, the genome-scale CRISPR screen was repeated with a homogenous pool of $CD8^+$ $T_{eff}$ cells that expressed the transgenic OT-I TCR, which specifically recognizes the SIINFEKL peptide of chicken ovalbumin (cOVA) presented on $H\text{-}2K^b$, a haplotype of MHC-I. Through genetic crosses, a mouse strain (OT-I; Cas9 mice) was generated that expresses both Cas9 and the OT-I transgenic TCRs (FIG. 18A). With these mice, the aim was to identify genes whose perturbation might result in enhanced ability of $T_{eff}$ cells to survive in different organs in vivo following trafficking starting from clonal TCRs. Similarly, naive OT-I; Cas9 $CD8^+$ T cells were isolated, the MKO lentiviral library introduced with 3 infection replicates, and adoptively transferred into wildtype B6 (n=5) or Cas9 (n=5) recipient mice (n=10 total) (FIG. 18A). Seven days post adoptive transfer, the mice were euthanized and relevant lymphoid and non-lymphoid organs collected. Illumina sequencing was performed to readout the sgRNA library representation. The sgRNA library representation revealed a global landscape of organ survival for mutant $T_{eff}$ cells with clonal TCR in vivo (FIGS. 19A-19B).

Figure 18C:
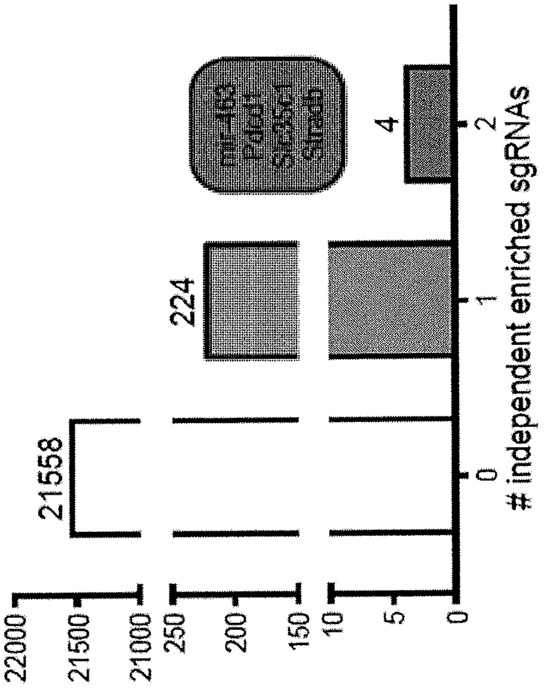
Figure 18D:
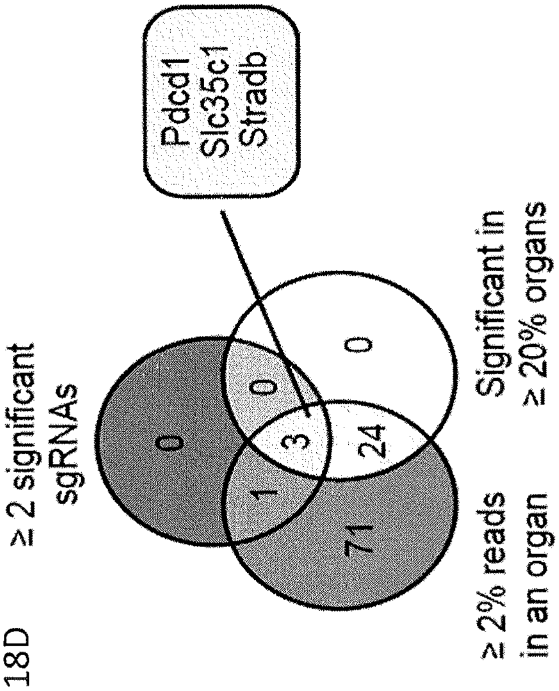
Figure 18B:
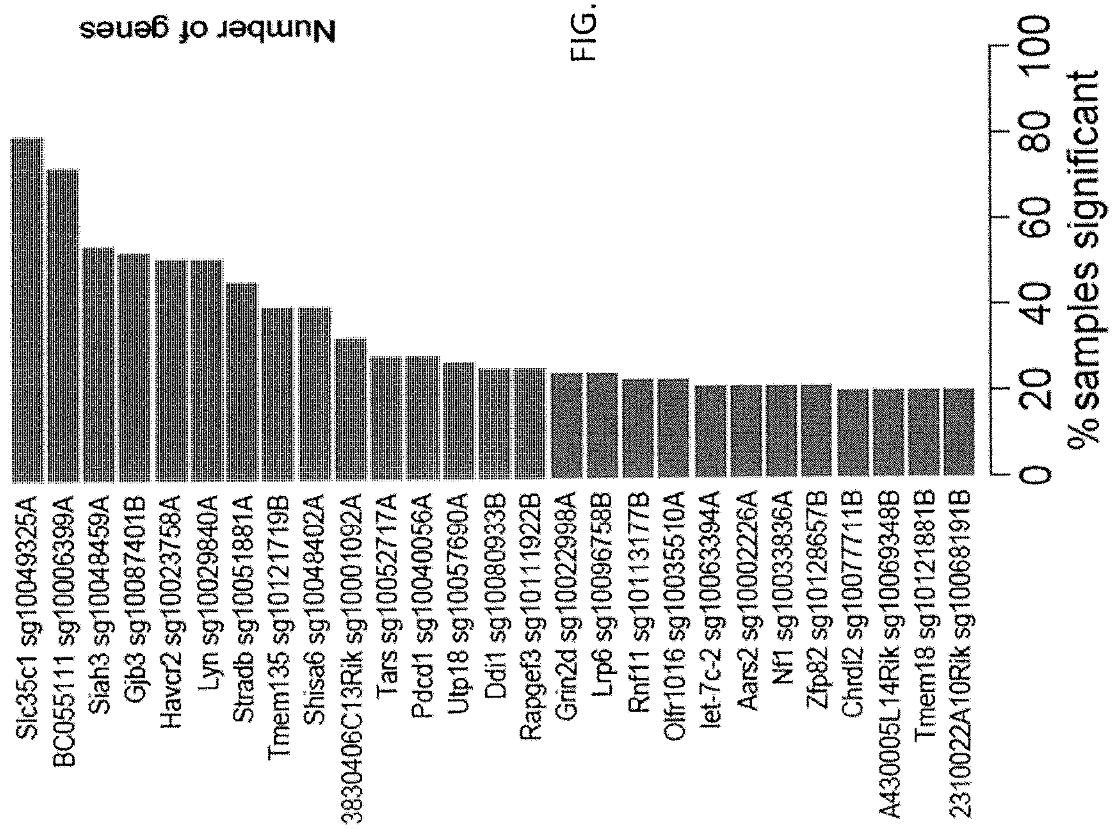
Figure 18F:
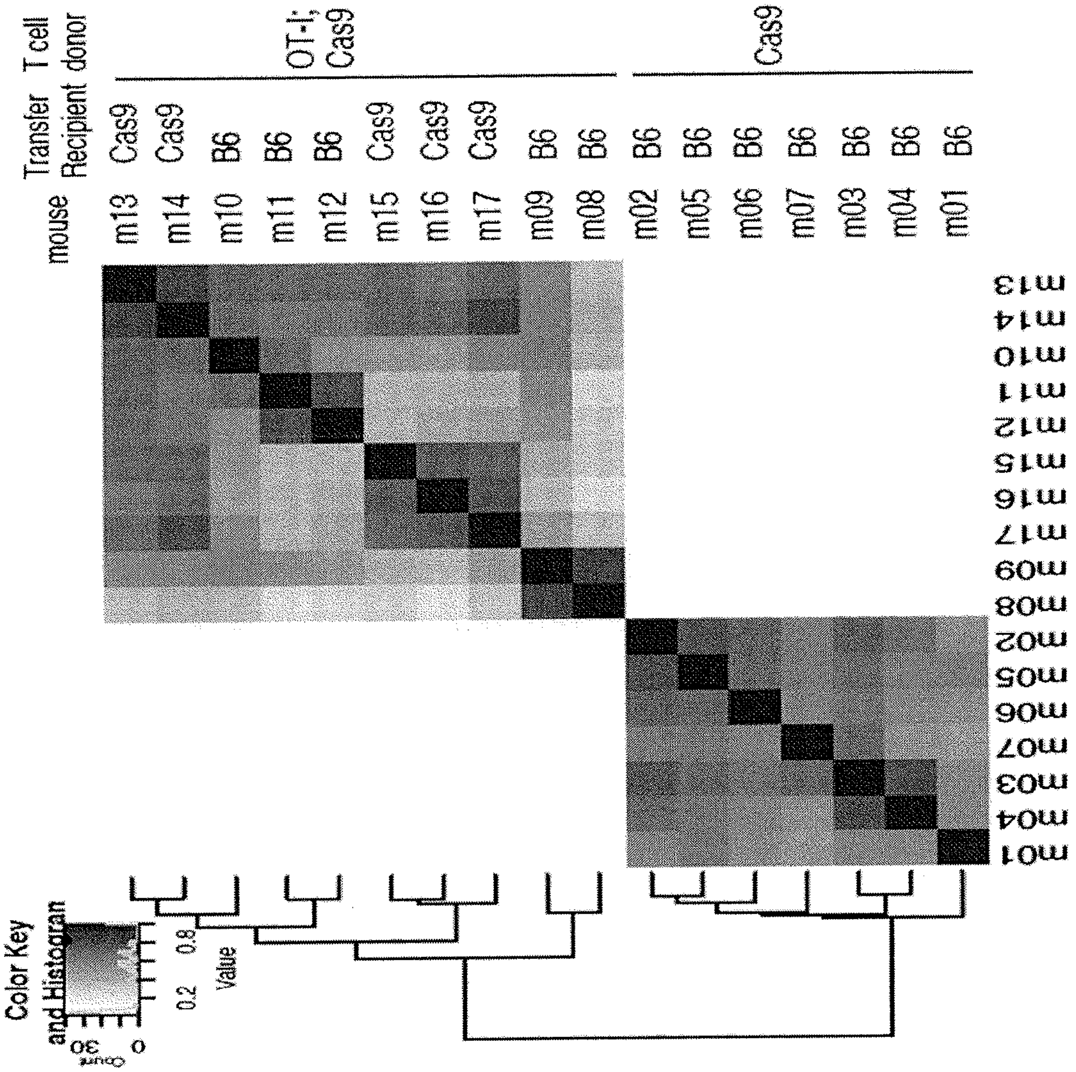

To identify genes modulating trafficking and survival of OT-I; Cas9 $CD8^+$ $T_{eff}$ cells, sgRNAs and genes represented in the MKO library were ranked using multiple statistical metrics. Ranking sgRNAs by their prevalence (frequency of being enriched in an organ) (FIG. 2*b*) again revealed dominant signatures of three types of genes: (1) immune genes (e.g. BC055111, Hacvr2, Lyn and Pdcd1); (2) growth regulators (e.g. Nf1), although fewer compared to the previous screen; as well as (3) genes with undocumented functions in $CD8^+$ T cells or largely uncharacterized genes (e.g. Slc35c1, Siah3, Gjb3, Tmem135 and Shisa6) (FIG. 18B). Havcr2, also known as Tim-3, is a well-established immune checkpoint regulator expressed on T cells, and currently an active target for immunomodulation. Ranking sgRNAs by the number of independent enriched sgRNAs revealed 4 genes with multiple enriched sgRNAs (mir-463, Pdcd1, Slc35c1, and Stradb) (FIG. 18C). In conjunction with the sgRNA abundance criteria (≥2% of total reads in a sample) a total of 3 genes are significantly enriched across all three criteria (Pdcd1, Slc35c1, and Stradb) (FIG. 18D). These data together suggest that the CRISPR targeting of these genes allows TCR-clonal OT-I; $CD8^+$ $T_{eff}$ cells to better survive in lymphoid and non-lymphoid organs in vivo.

Figure 16C:
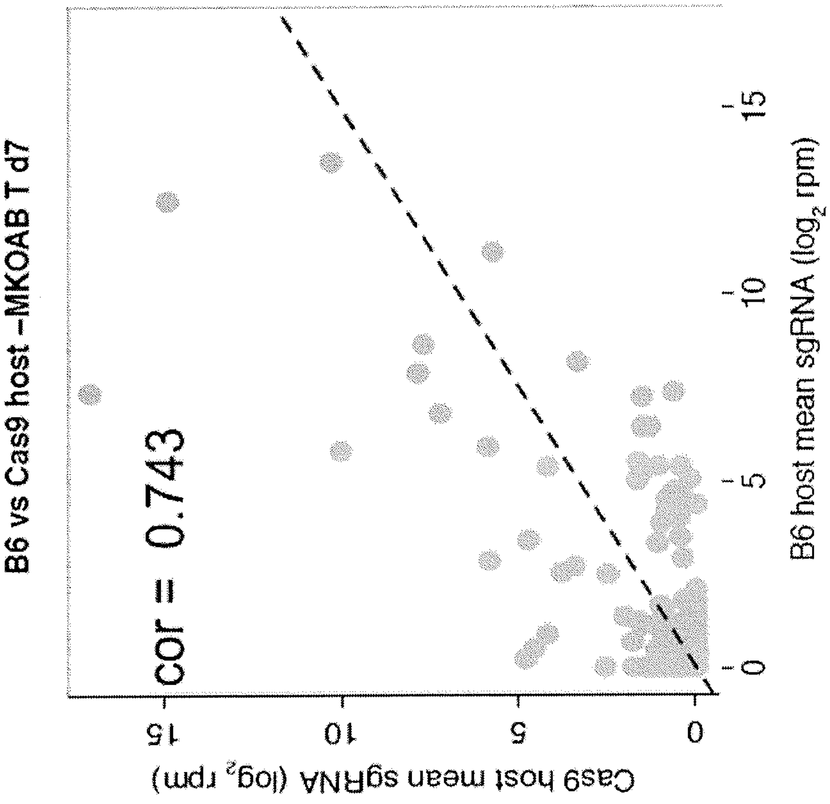
Figure 16D:
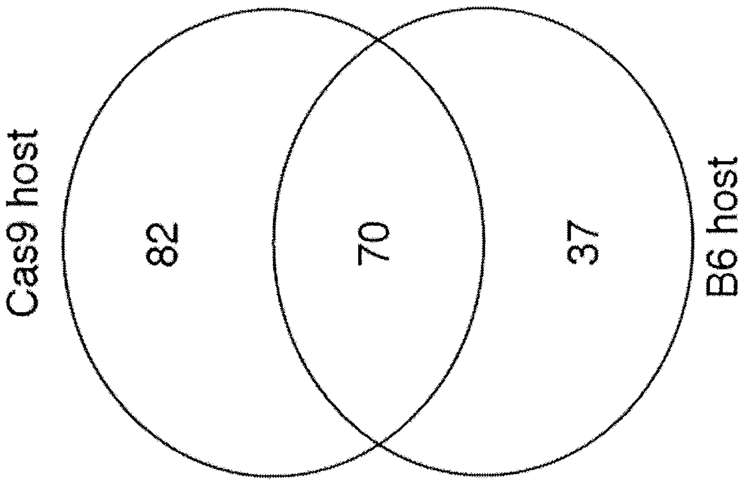
Figure 18E:
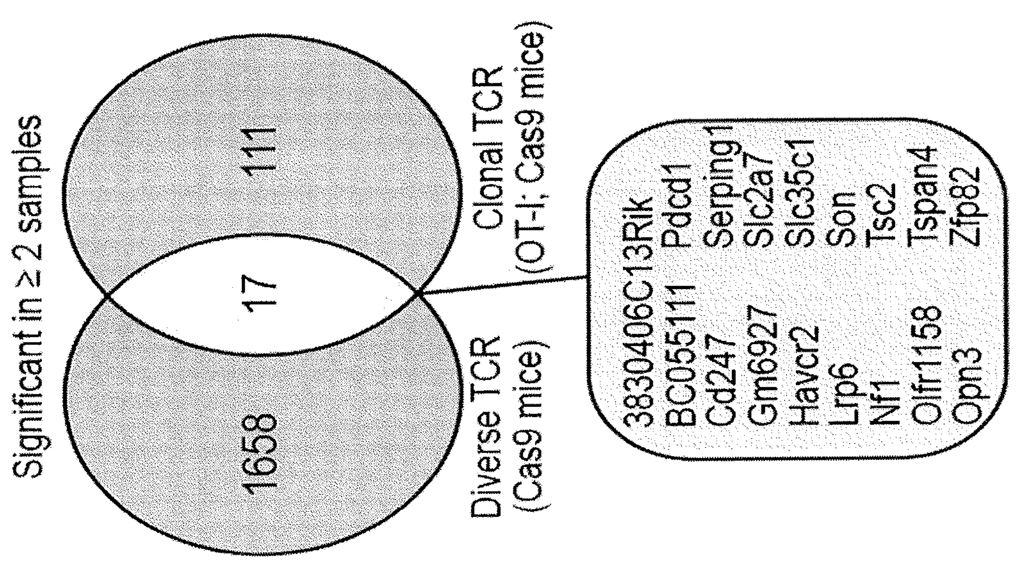
Figure 20B:
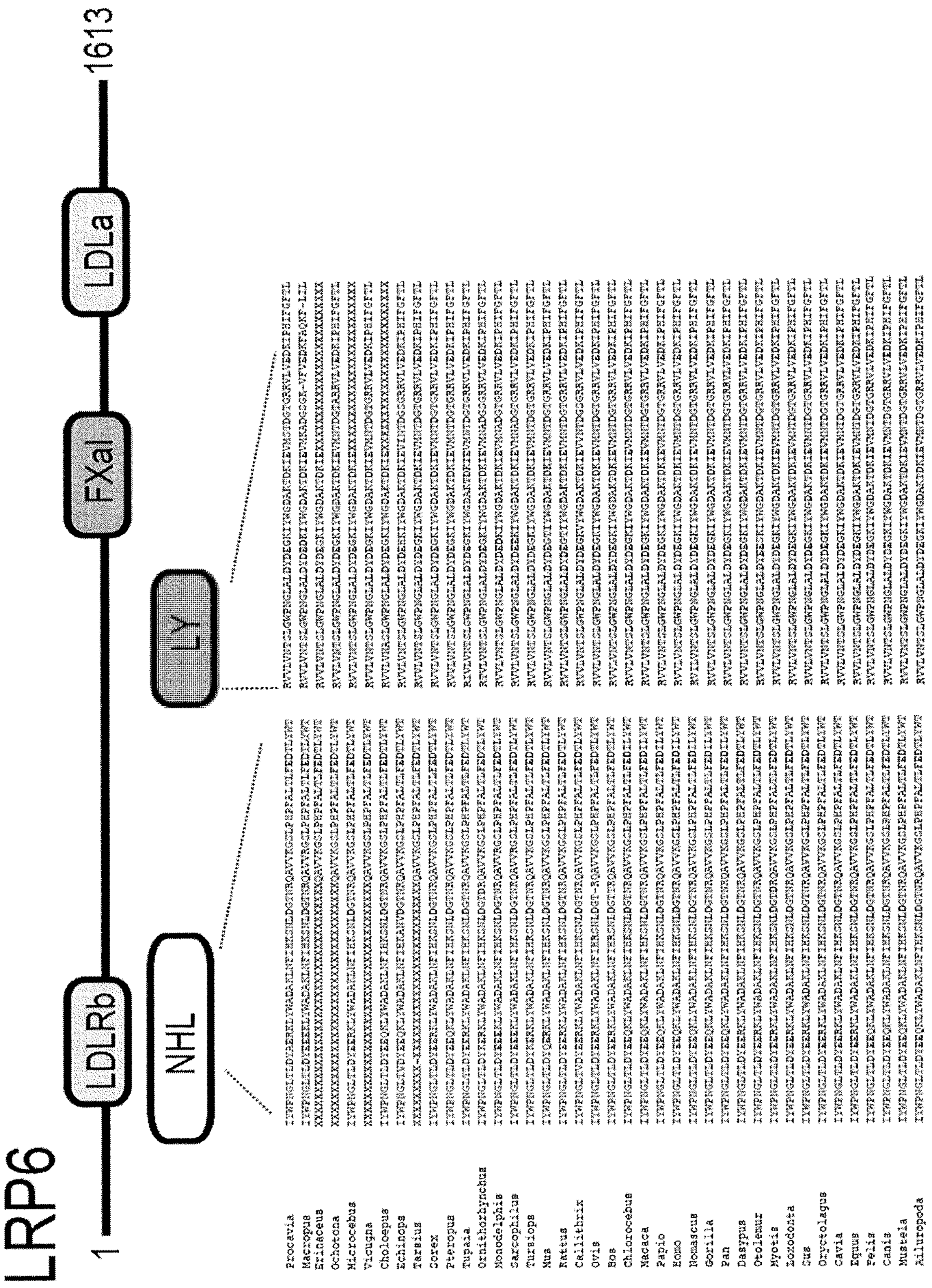

An integrated analysis was performed using both screens with diverse TCR and clonal TCR settings as a whole. To find which candidate genes can modulate T cell function in both diverse (Cas9 $CD8^+$ T cells) and clonal TCR (OT-I; Cas9 $CD8^+$ T cells), the gene sets from these two screens were directly compared. A total of 17 genes were identified in both screen as common hits (FIG. 18E), which again included immune genes (BC055111, Cd247, Hacvr2, and Pdcd1), tumor suppressors (Nf1 and Tsc2), and unknown or uncharacterized genes in T cells (e.g. Gm6927, Slc35c1, Slc2a7, Lrp6, and 4.82). Several of these shared hits encode highly conserved surface proteins, which are either well-established immune regulators/immunotherapy targets (Cd247, Hacvr2, Pdcd1), or are potentially directly targetable with monoclonal antibodies (Slc35c1, Slc2a7, Lrp6). These proteins have highly conserved functional domains across multiple mammalian species (FIGS. 20A-20C). Between the two recipient hosts, C57BL/6 or Cas9 syngeneic, the overall sgRNA representations significantly correlated with each other (FIG. 16C), and screens in both share a large set of hits (p<1e5) (FIG. 16D). Thus, in this case, host choice did not affect the result of the in vivo survival screen.

Figure 18G:
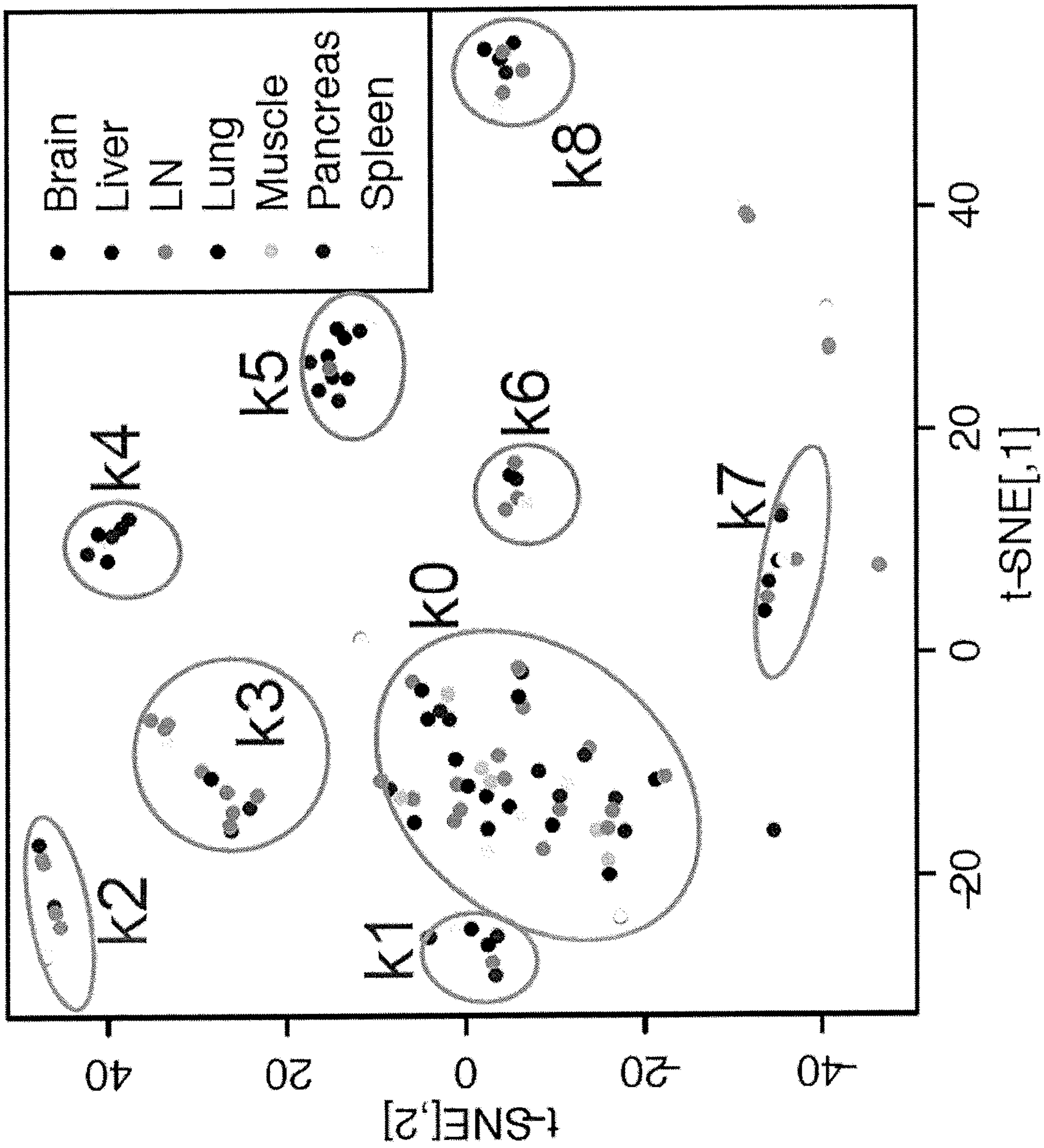

Using dimension reduction methods such as t-SNE, clustering patterns of samples were observed purely based on the sgRNA representations in the tissue-infiltrated T cell population (FIG. 18G). There was a large cluster (k0) containing virtually all organ types (including brain, liver, LN, lung, muscle, pancreas and spleen), while there were 8 smaller clusters (k1-k8) that each consisted of 4 to 6 organ types, with several organs as outliers (FIG. 18G). The emergence of multiple immune genes as mutual top hits, in both diverse TCR and clonal TCR settings, further validated the rigor of this approach, gaining higher confidence for the phenotypes of the unknown genes or those previously not associated with T cell function.

Figure 3A:
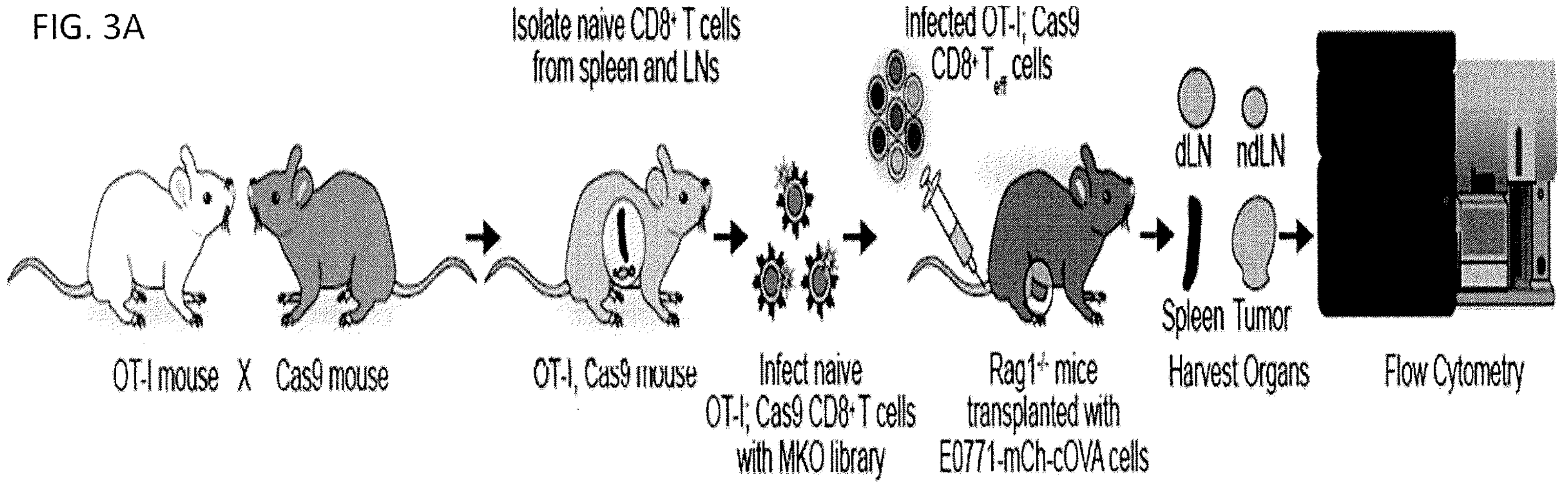
FIGS. 3A-3F are a series of plots and images illustrating flow cytometry analysis of in vivo survival of MKO mutagenized OT-I; Cas9 $CD8^+$ $T_{eff}$ cells in $Rag1^{-/-}$ mice with transplanted tumors expressing cOVA antigen.
Figure 3B:
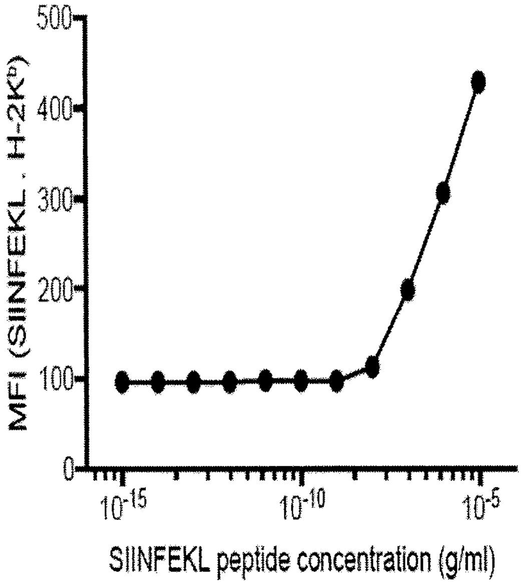
Figure 3C:
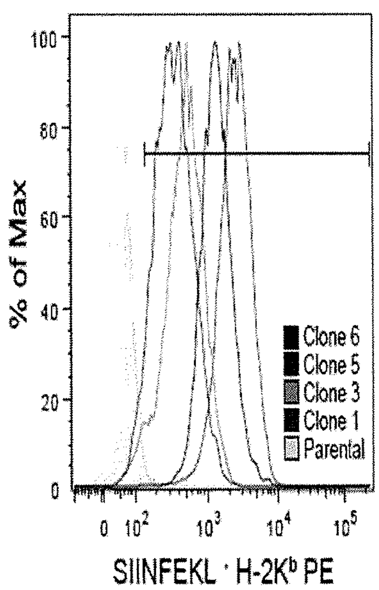

Example 6: In Vivo Genome-Scale Analysis of TCR-Engineered Effector $T_{eff}$ Cells in Mice with Tumors Expressing a Model Antigen In order to analyze in vivo $CD8^+$ $T_{eff}$ cell trafficking and survival in the context of antigen-recognition, an engineered TCR that specifically recognized a well-characterized model antigen, chicken ovalbumin (cOVA), was utilized. Through genetic crosses, a mouse strain (OT-I; Cas9 mice) was generated that expresses both Cas9 and the OT-I transgenic TCRs specific for an 8 amino acid peptide epitope (SIINFEKL) (SEQ ID NO: 129,210) of cOVA (FIGS. 3A and 10A-10F). Breast cancer cell line E0771 was pulsed with various concentrations of SIINFEKL peptides, and a dose-dependent antigen presentation on cell surface by MHC-I was observed using immunostaining for the peptide-protein complex (FIG. 3B). Clonal cell lines that present cOVA were generated, and it was confirmed that the antigenic SIINFEKL peptide was presented on surface $H\text{-}2K^b$, the haplotype of MHC-I recognized by OT-I TCR (FIG. 3C). Clone 3 of E0771-mCherry-cOVA (E0771-mCh-cOVA for short) cell lines presented SIINFEKL on $H\text{-}2K^b$ at a level similar to pulsing cells with $1\times10^{-5}$ g/ml peptide, and was chosen for in vivo study. This clonal cell line was transplanted into $Rag1^{-/-}$ mice with $5\times10^6$ cells per mouse, which subsequently grew as tumors within 10 days (FIGS. 3A, 3D, 10A, and 10F).

Figure 3D:
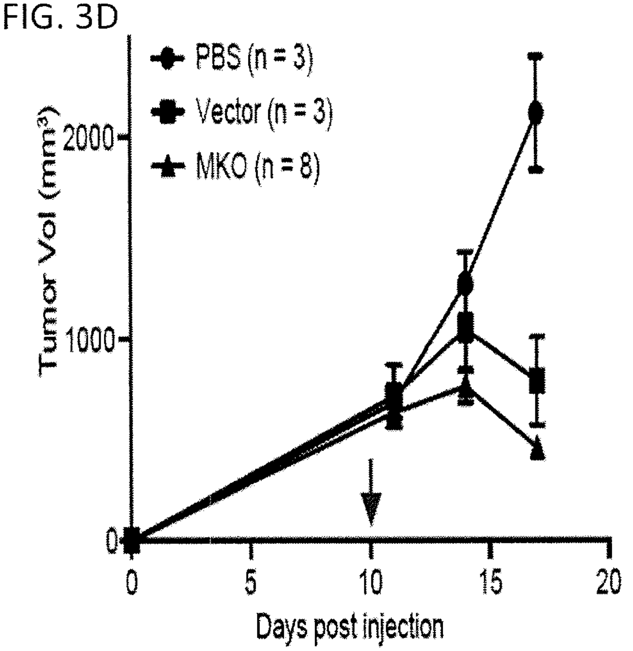
Figure 3E:
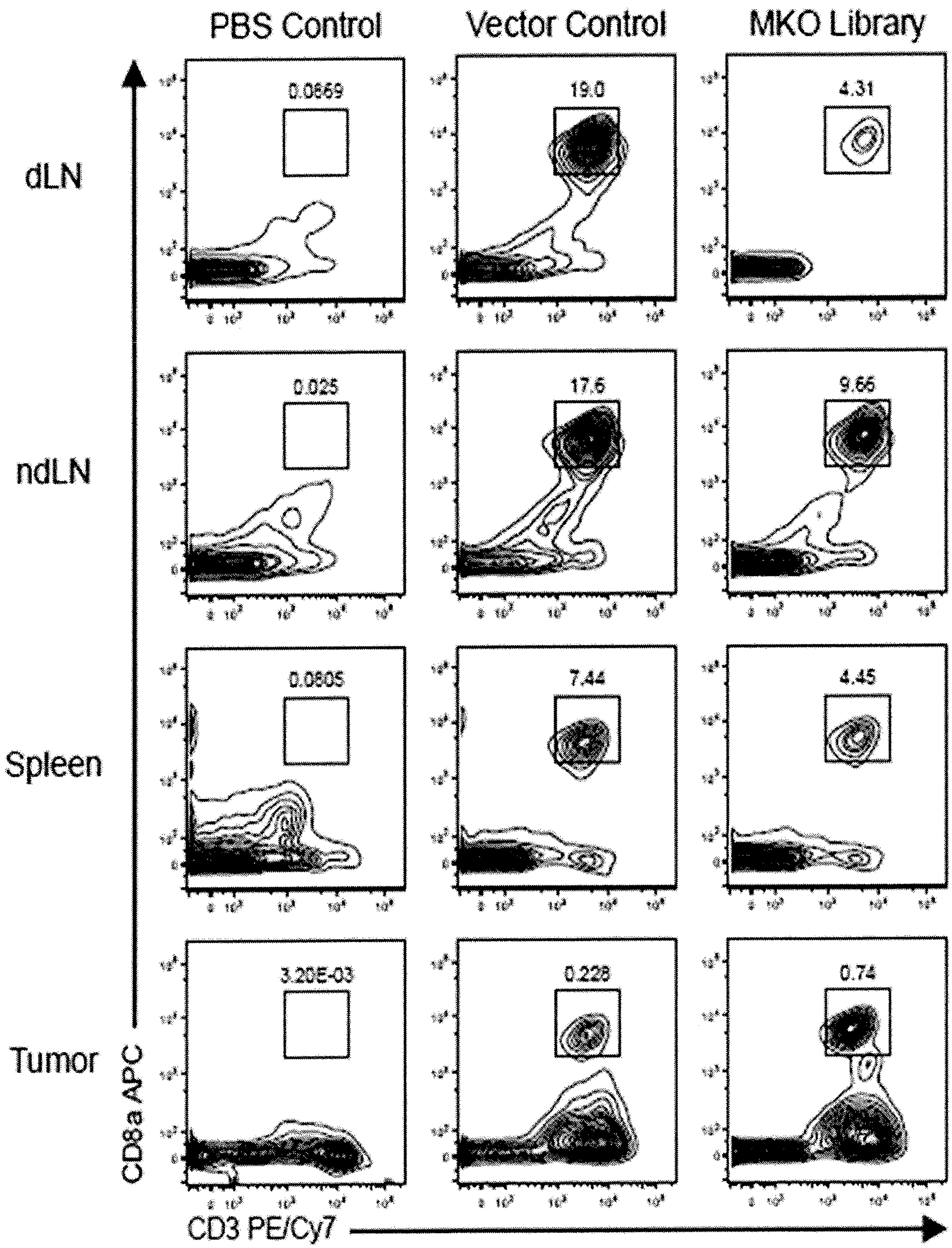
Figure 3F:
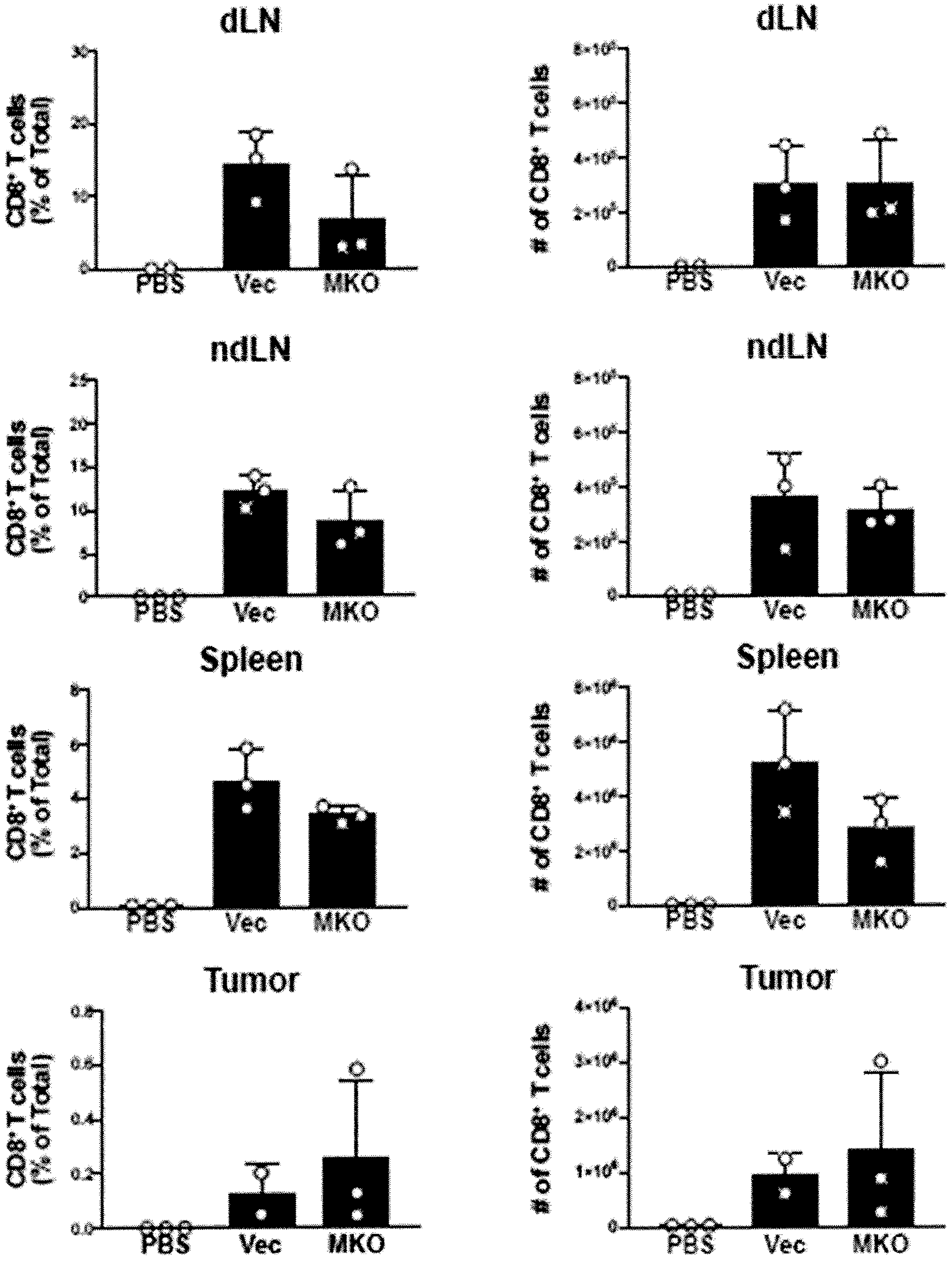
Figure 4A:
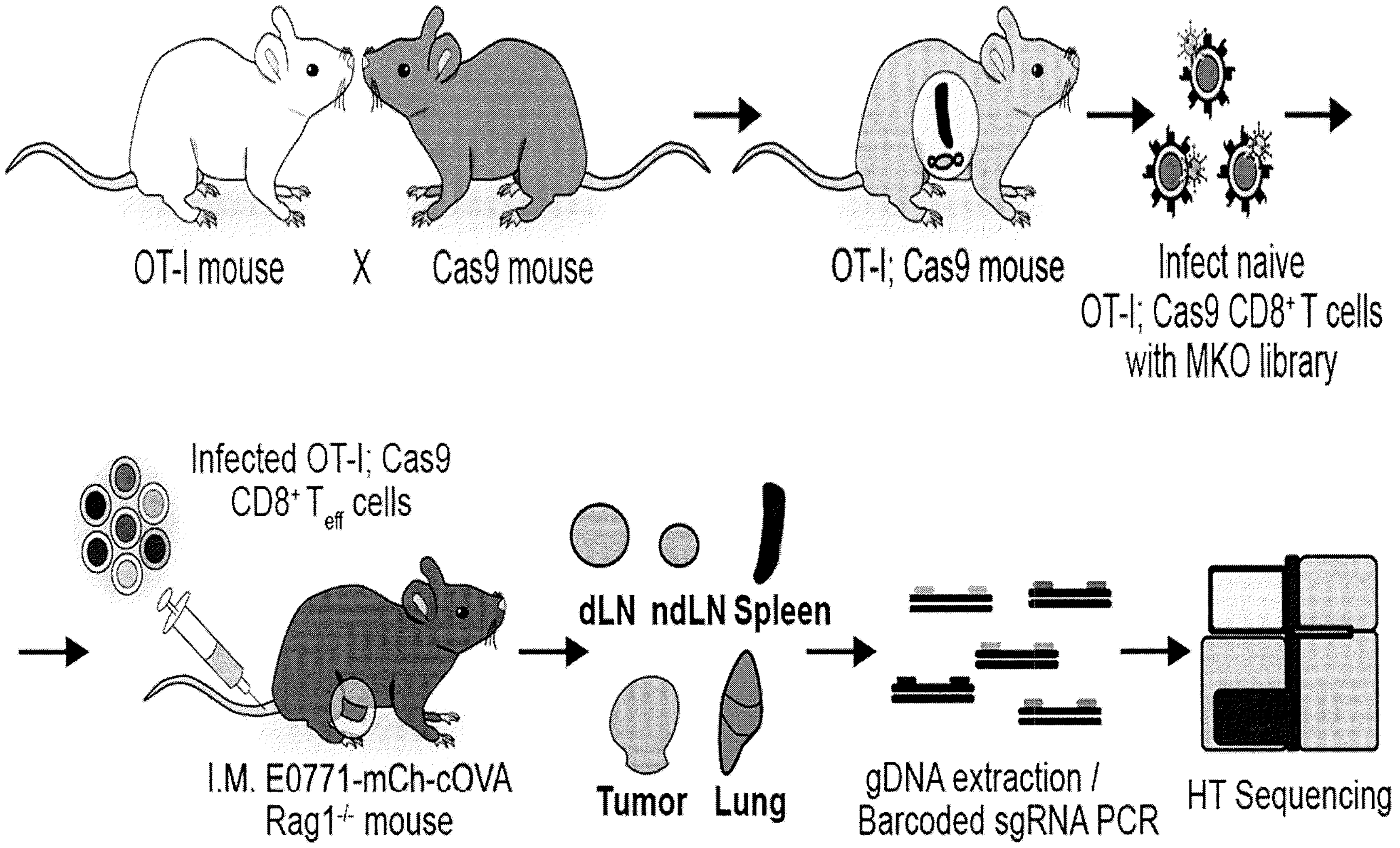
FIGS. 4A-4J are a series of plots and images illustrating sgRNA library sequencing analysis of in vivo survival of MKO mutagenized OT-I; Cas9 $CD8^+$ $T_{eff}$ cells in $Rag1^{-/-}$ mice with transplanted tumors expressing cOVA antigen.
Figure 10A:
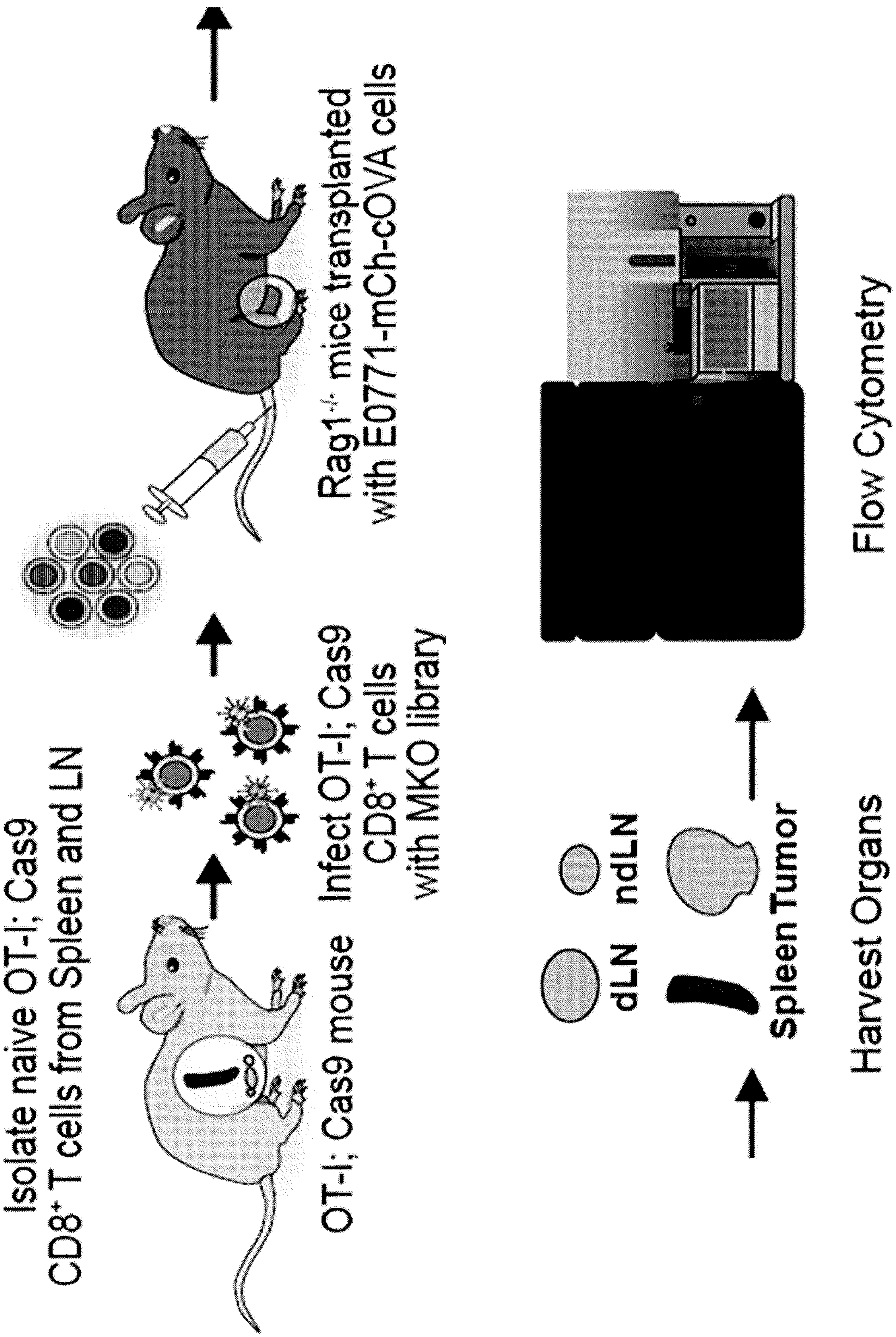
FIGS. 10A-10F are a series of plots and images depicting FACS data for setup experiments of MKO mutagenized activated OT-I; Cas9 $CD8^+$ $T_{eff}$ cells in $Rag1^{-/-}$ mice with transplanted tumors expressing cOVA antigen.
Figure 10B:
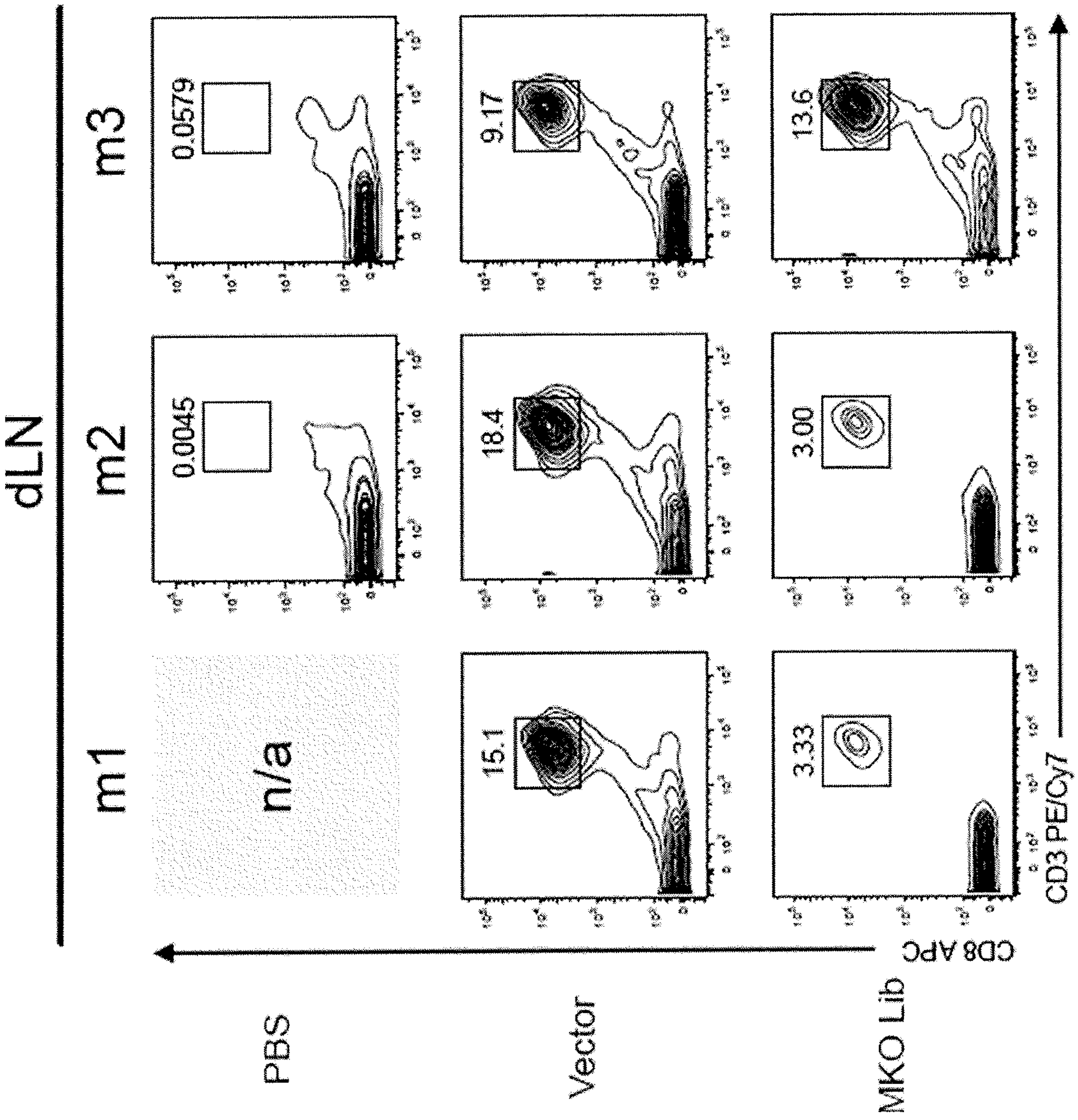
Figure 10C:
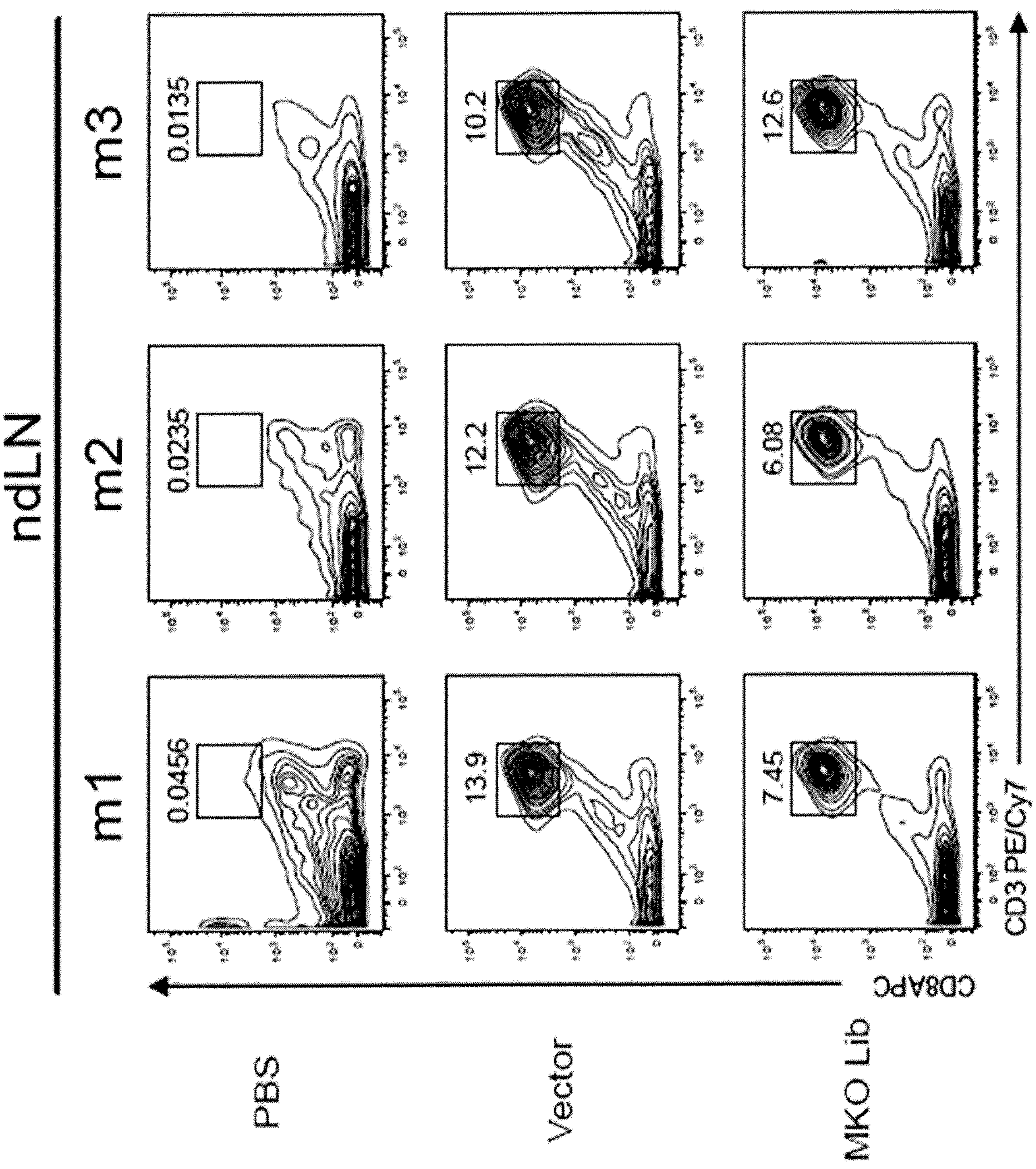
Figure 10D:
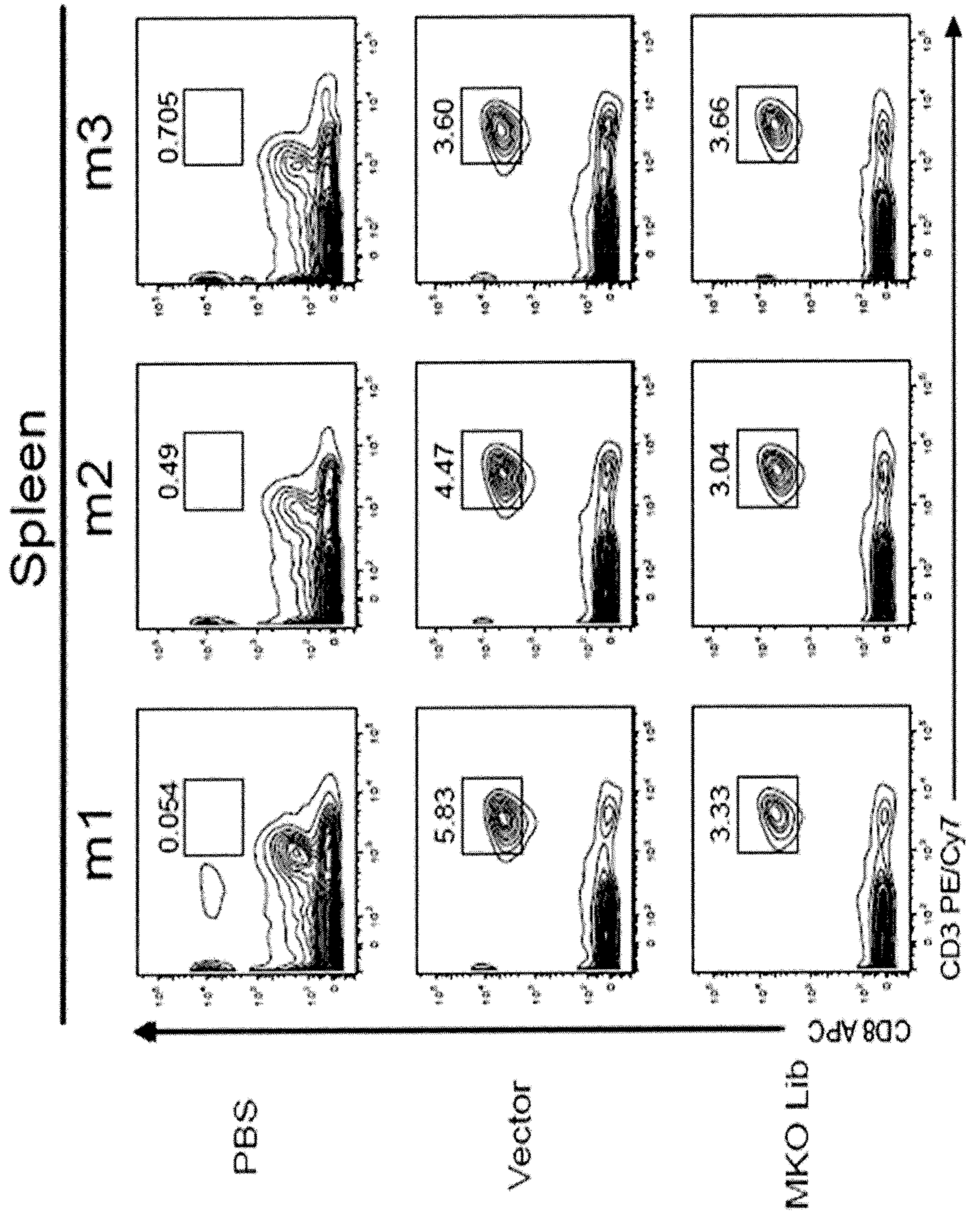
Figure 10E:
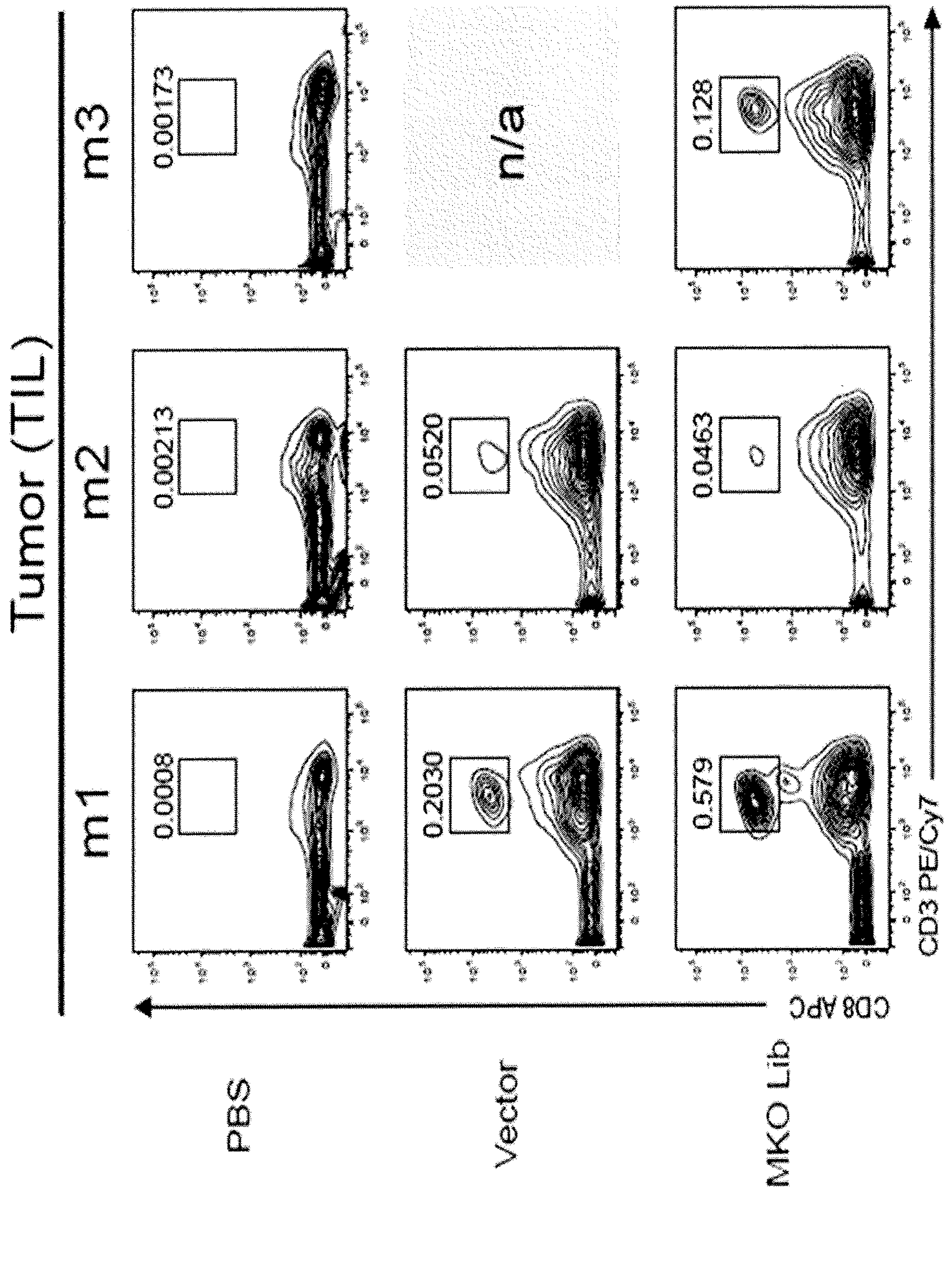
Figure 10F:
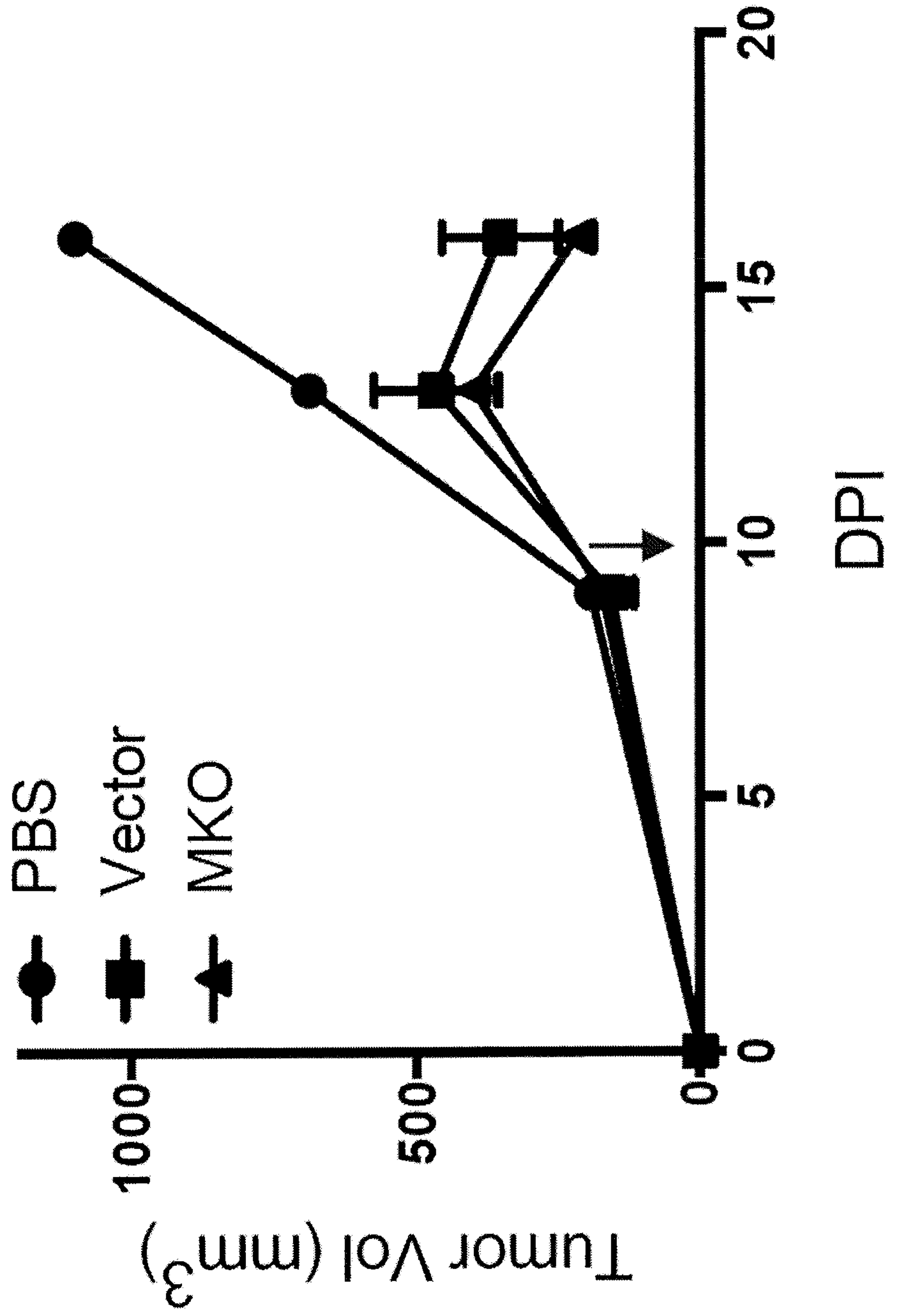
Figure 21A:
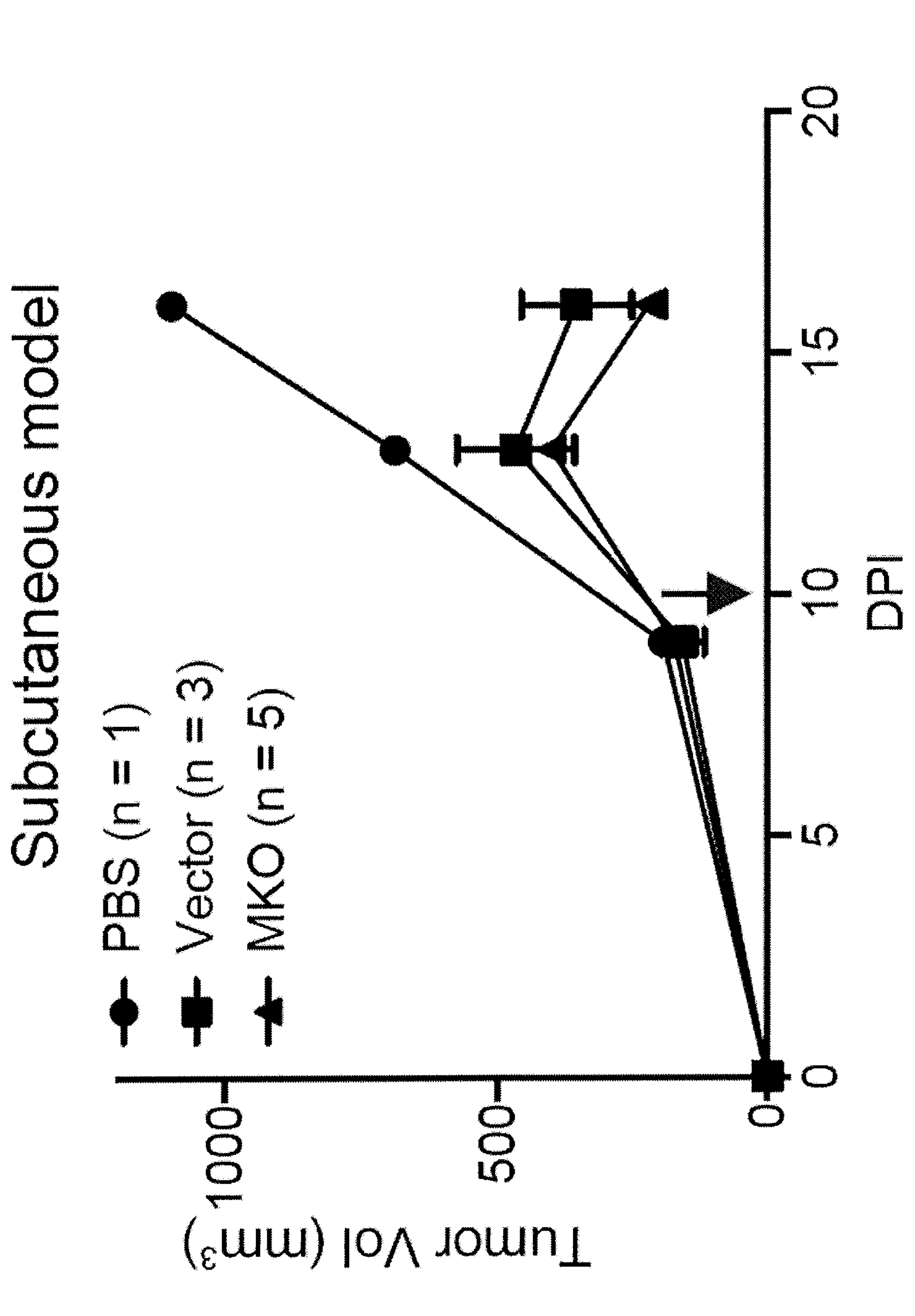
FIGS. 21A-21F are a series of plots and images illustrating additional experiments for adoptive transfer tumor infiltration screen.
Figure 21B:
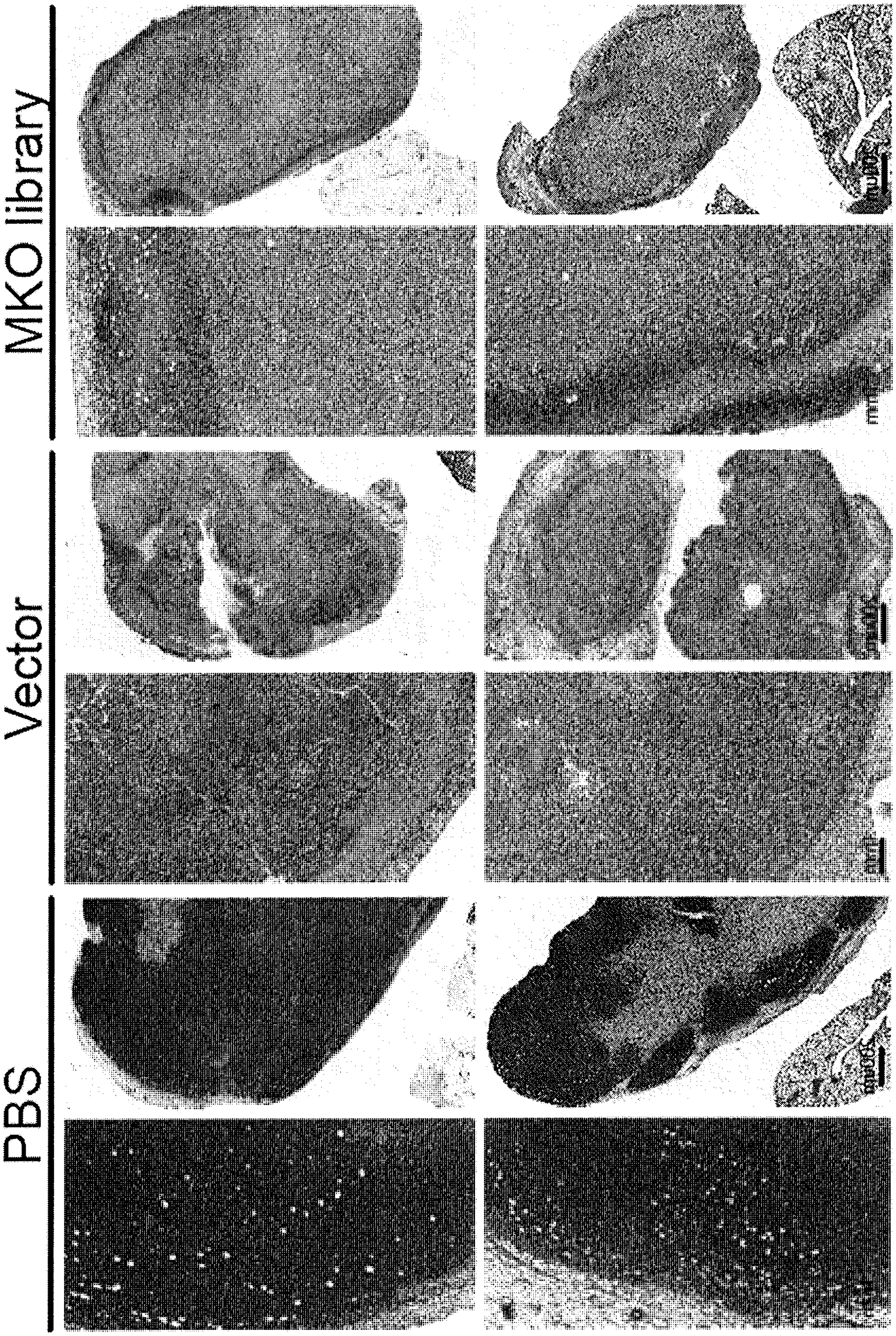
Figure 21C:
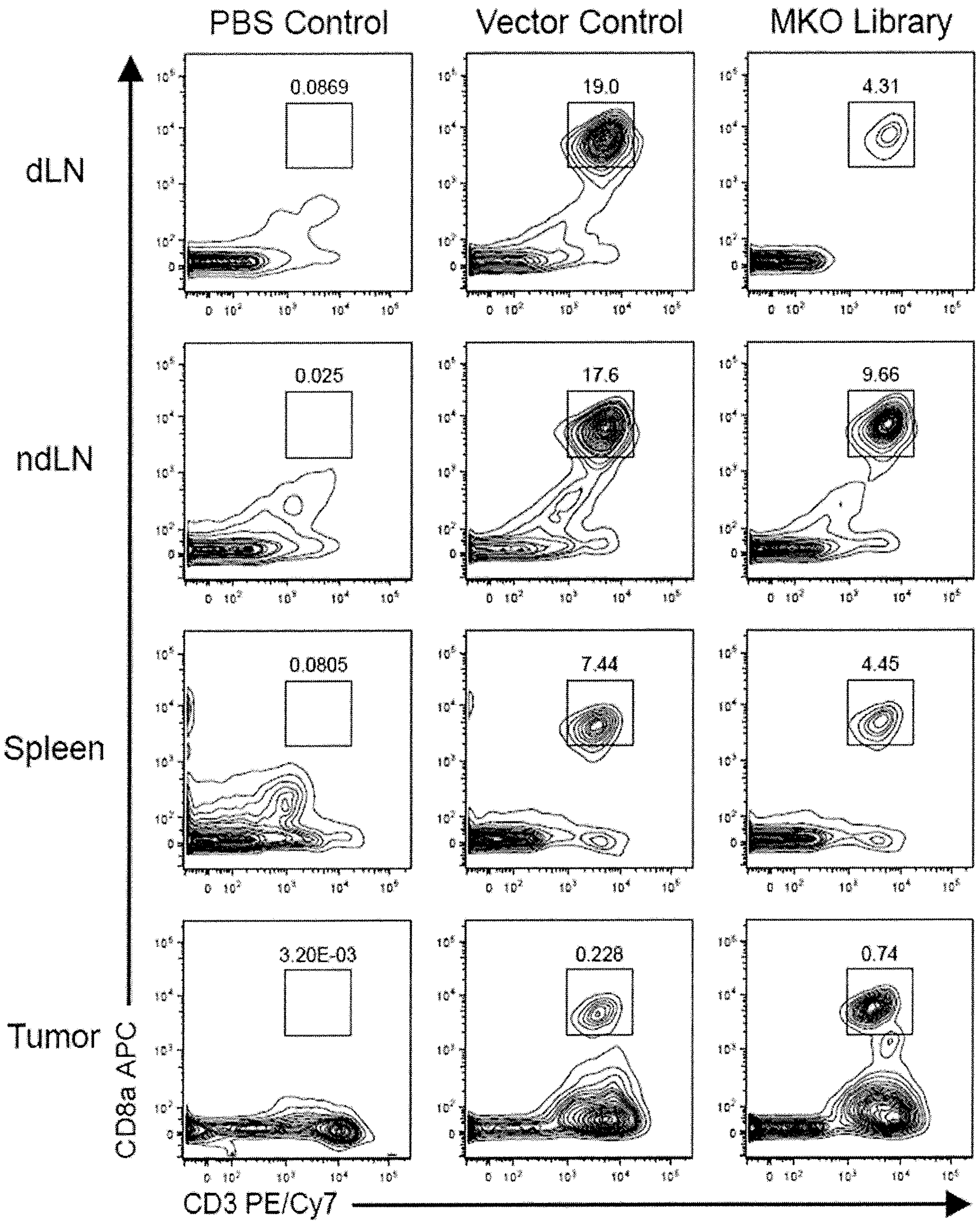
Figure 21D:
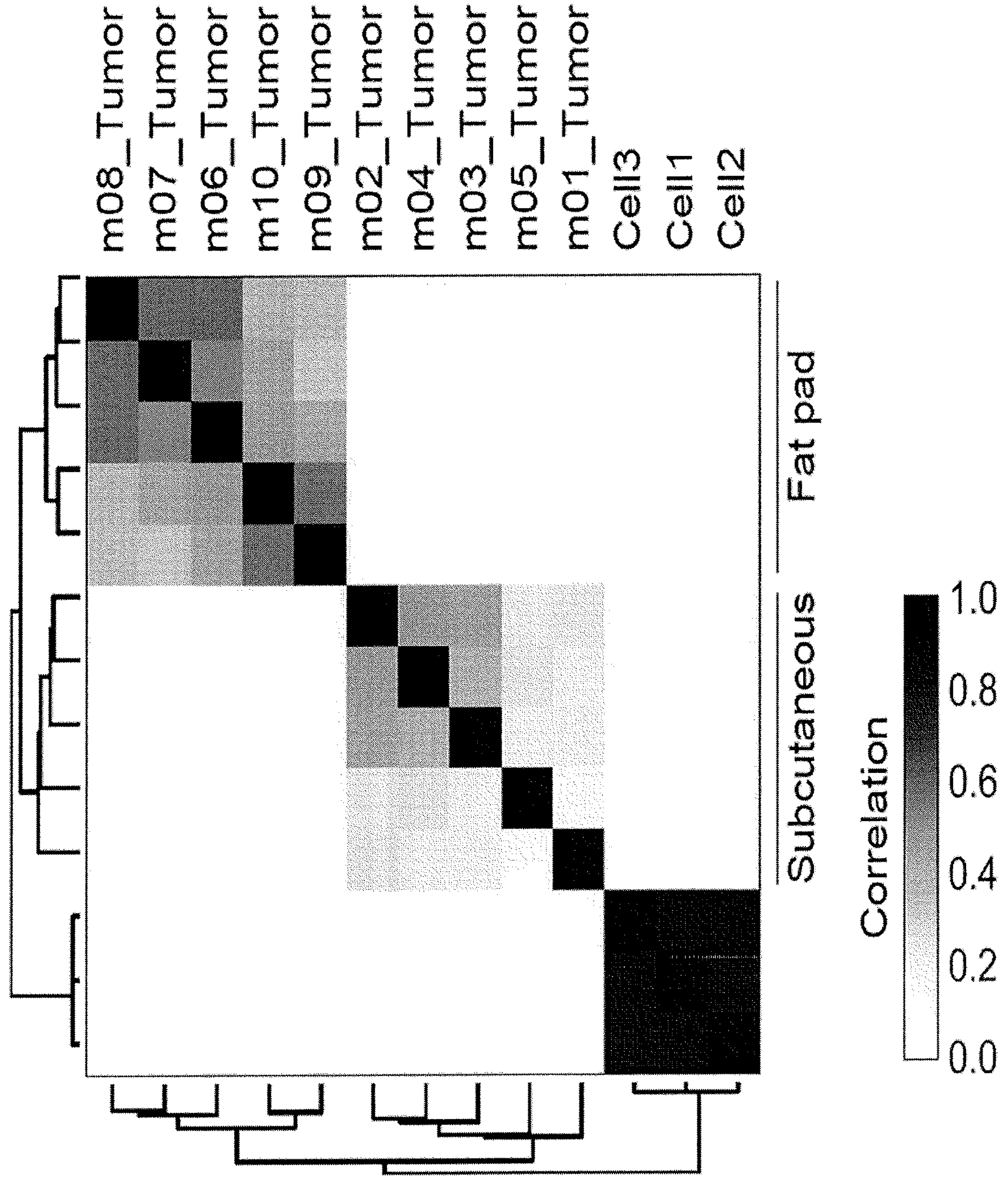

A T cell infiltration screen was performed in a mouse model of cancer. E0771 is a commonly used triple-negative breast cancer cell line that originated from C57BL/6 mice. Of note, although parental E0771 cells grew robustly as transplant tumors in a syngeneic C57BL/6 host (100% transplanted cells grew tumors on mice), all E0771-mCherry-cOVA clones tested were rejected by the same host (0% grew tumors), potentially caused by $CD4^+$/$CD8^+$ T cell mediated immune rejection of the antigenic cOVA. Thus, $5\times10^6$ clone 3 cells were transplanted into immunodeficient $Rag1^{-/-}$ mice, and rapid tumor formation was observed in 10 days (FIG. 3D, FIGS. 21A-21B). Naïve $CD8^+$ T cells were isolated from OT-I; Cas9 mice, mutagenized with the MKO sgRNA library, adoptively transferred $1\times10^7$ into $Rag1^{-/-}$ mice with tumors expressing cOVA antigen, and analyzed for trafficking to different organs and survival in vivo by flow cytometry and sgRNA library sequencing (FIG. 3A, FIG. 10A). Tumor size was measured throughout the experiment and it was discovered that T cell injections (either vector or MKO transduced) mitigated tumor growth, in sharp contrast with PBS (Endpoint tumor size vector vs PBS, unpaired two-sided t-test, p=0.02; MKO vs PBS, p<0.0001) (FIG. 3D). The MKO transduced population had a stronger therapeutic effect compared to vector controls (Endpoint tumor size MKO vs vector, unpaired two-sided t-test, p=0.03) (FIG. 3D). This anti-tumor effect also holds in a subcutaneous transplant model, although to a lesser extent (FIG. 21A). Seven days after adoptive transfer (17 days after cancer cell transplantation), the mice were sacrificed and the tumors, draining lymph nodes (dLNs) near the tumors, non-draining lymph nodes (ndLNs) and the spleens were isolated for analyses of $T_{eff}$ cell trafficking and survival in vivo. The tumors were also analyzed for tumor-infiltrating lymphocytes (TILs). Histological and pathological analysis revealed the existence of lymphocytes in the tumors from mice injected with vector and MKO $CD8^+$ $T_{eff}$ cells, but not in tumors of PBS treated mice (FIG. 21B). Flow cytometric analysis (n=3 mice) of single-cell suspensions of organs and tumors detected a large number of $CD8^+$ $T_{eff}$ cells in $Rag1^{-/-}$ mice receiving T cell injections but not those receiving PBS (FIGS. 3B-3C, FIGS. 10B-10E), indicating that the $CD8^+$ $T_{eff}$ cells present in these samples were adoptively transferred. Representative lymphoid organs (dLNs, ndLNs and spleens), nonlymphoid organs (lungs) and tumors from a parallel cohort of mice were subjected to high-throughput sgRNA library sequencing (FIG. 4A), which revealed the sgRNA representations of MKO mutagenized OT-I; Cas9 $CD8^+$ $T_{eff}$ cells before injection as well as in all the in vivo samples (FIG. 4B, FIG. 4G, FIG. 11A, FIG. 21D).

Figure 4B:
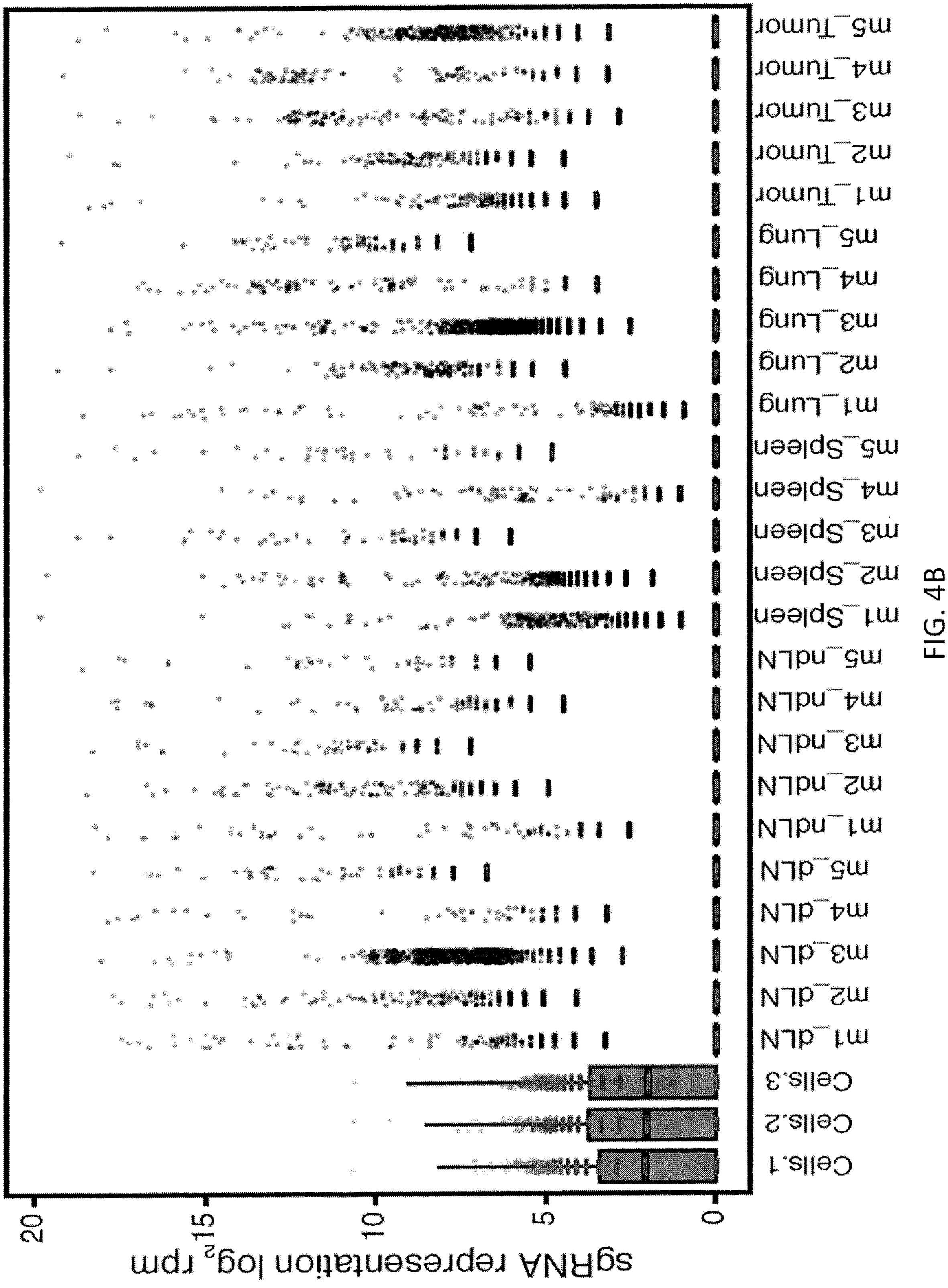
Figure 4C:
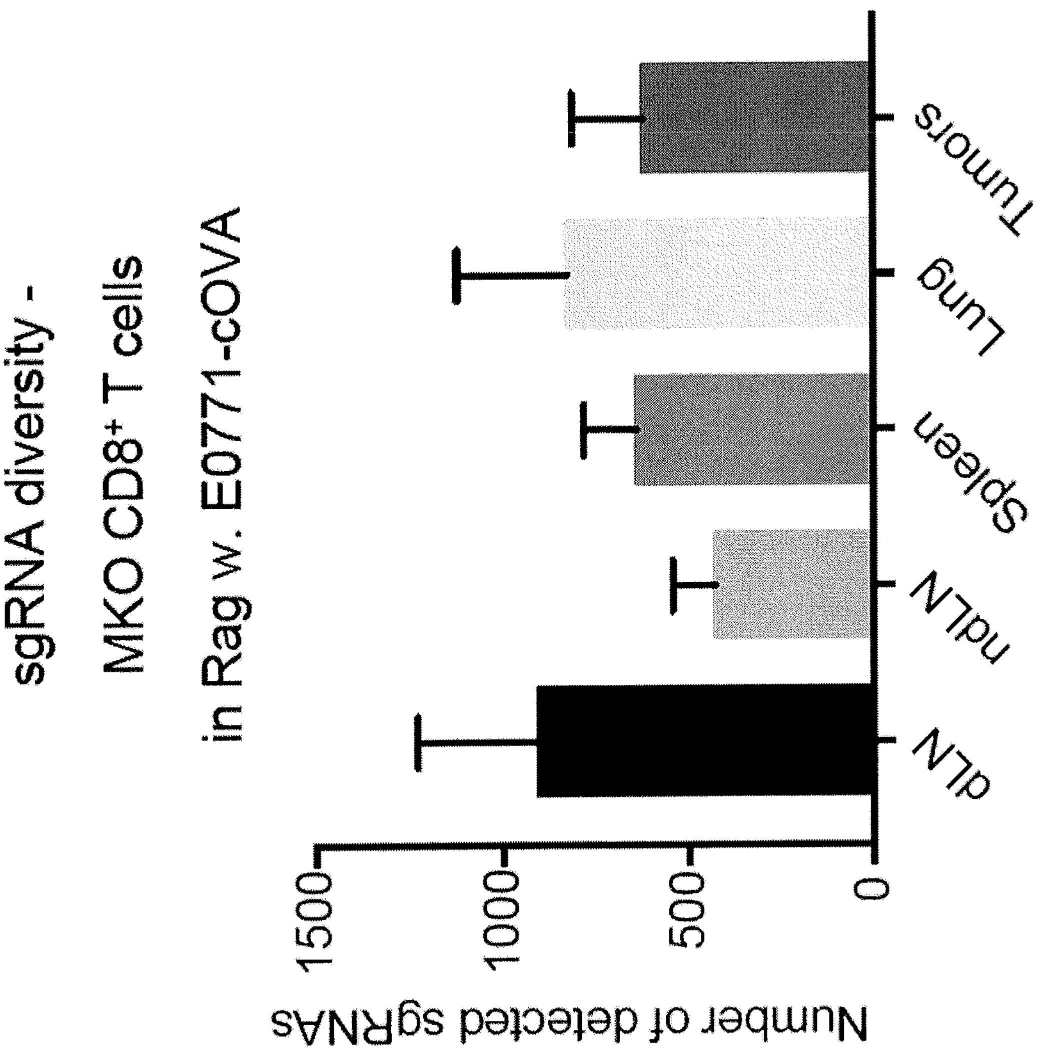
Figure 4D:
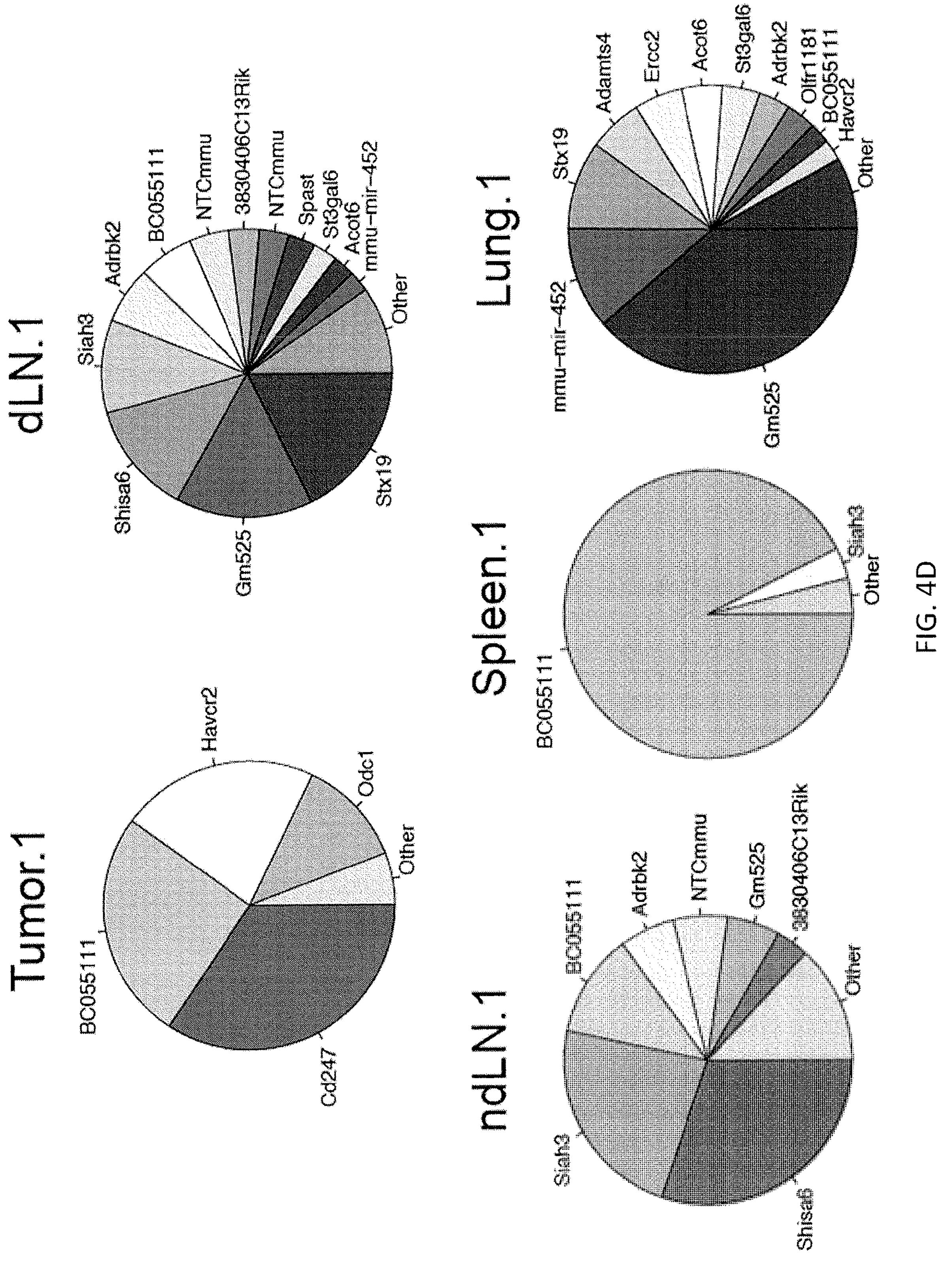
Figure 4E:
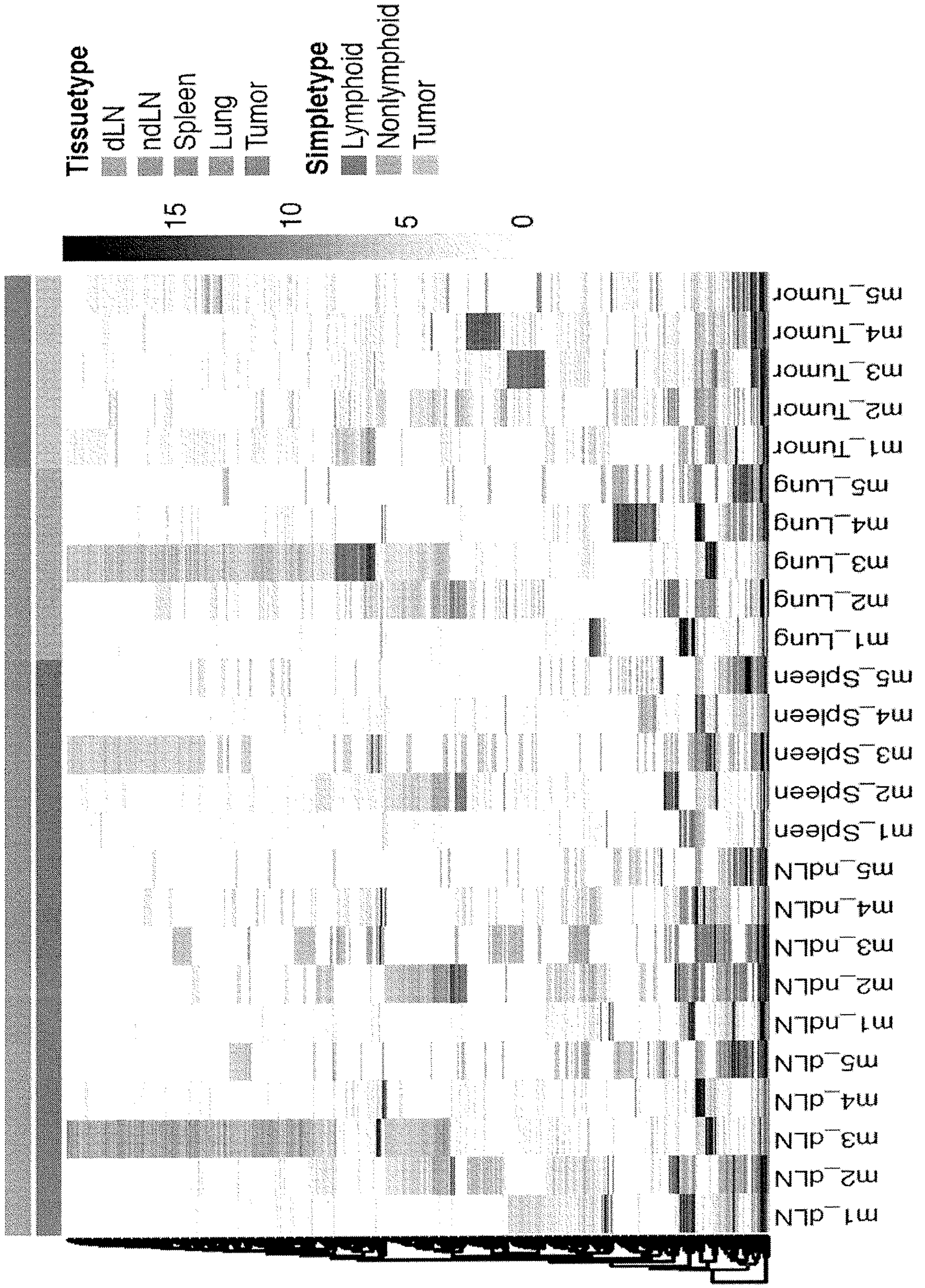
Figure 4F:
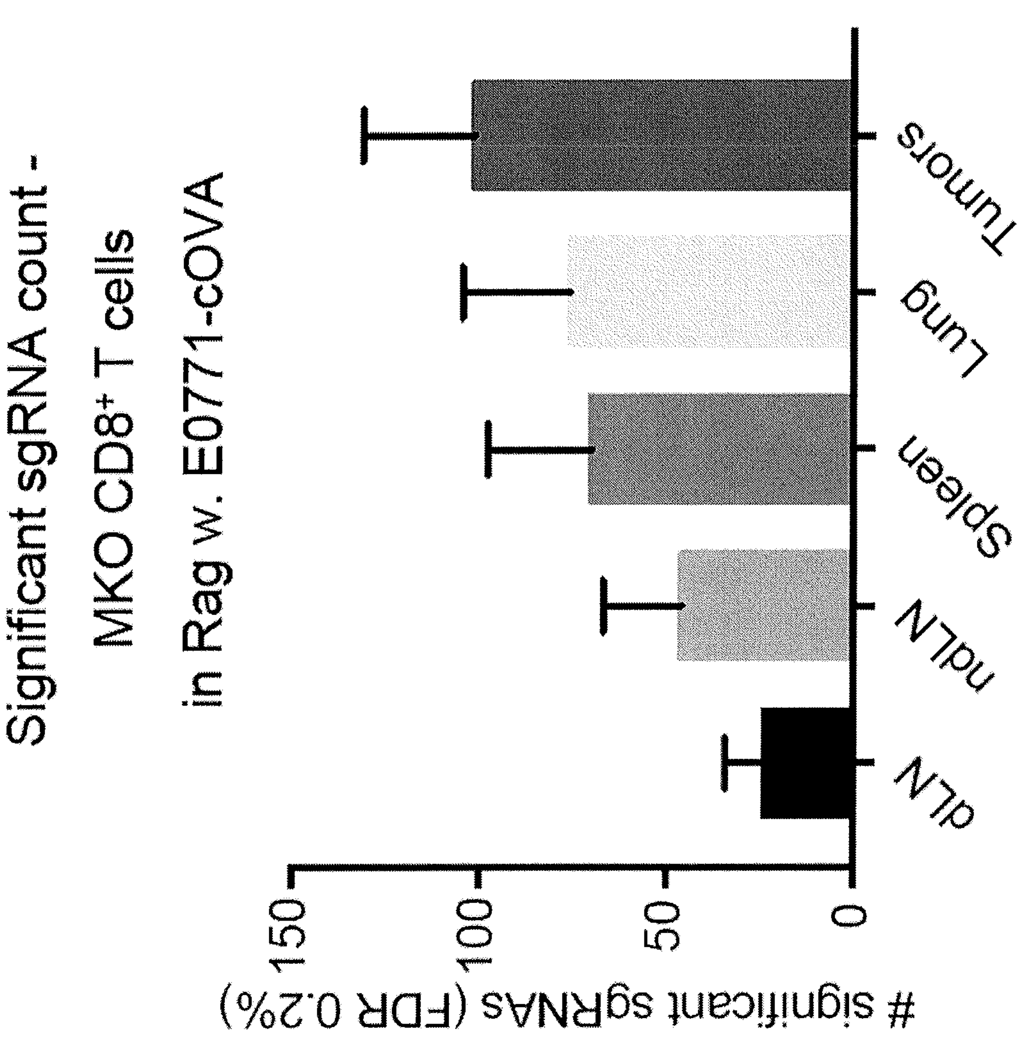
Figure 4G:
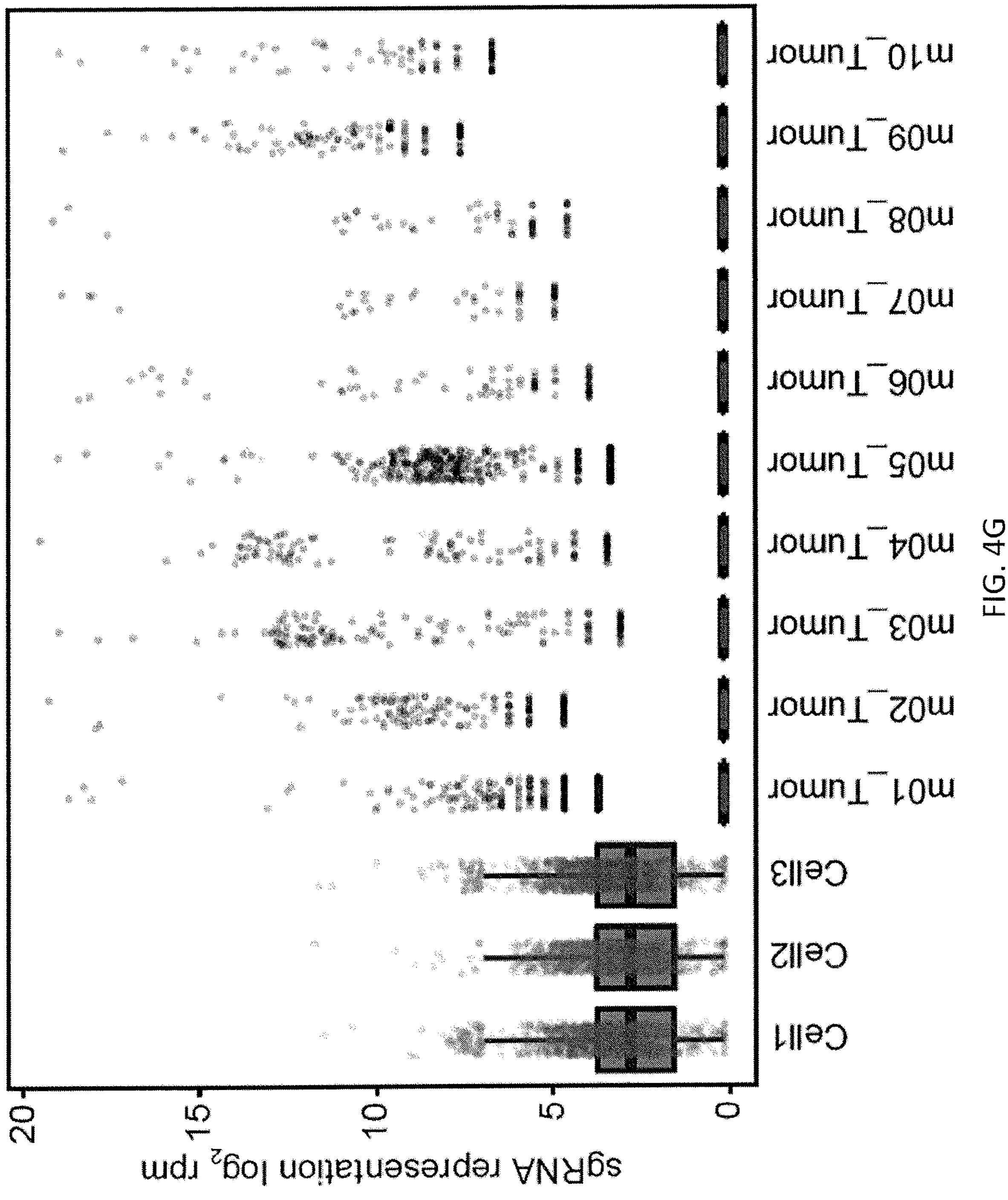
Figure 11A:
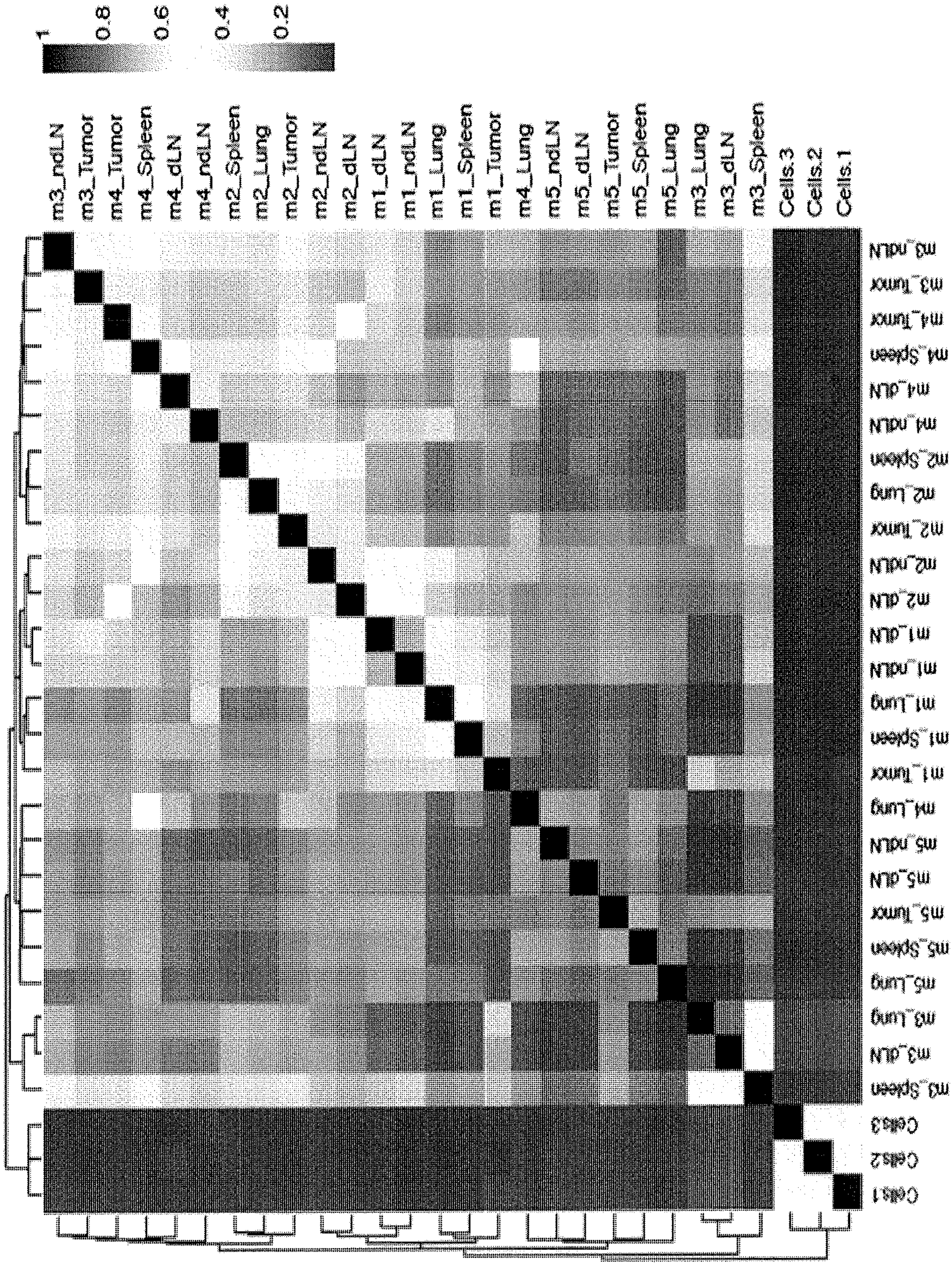
FIGS. 11A-11D are a series of plots illustrating overall sgRNA quantification for the analysis of MKO mutagenized OT-I; Cas9 $CD8^+$ $T_{eff}$ cells in $Rag1^{-/-}$ mice with transplanted tumors expressing cOVA antigen.
Figure 11C:
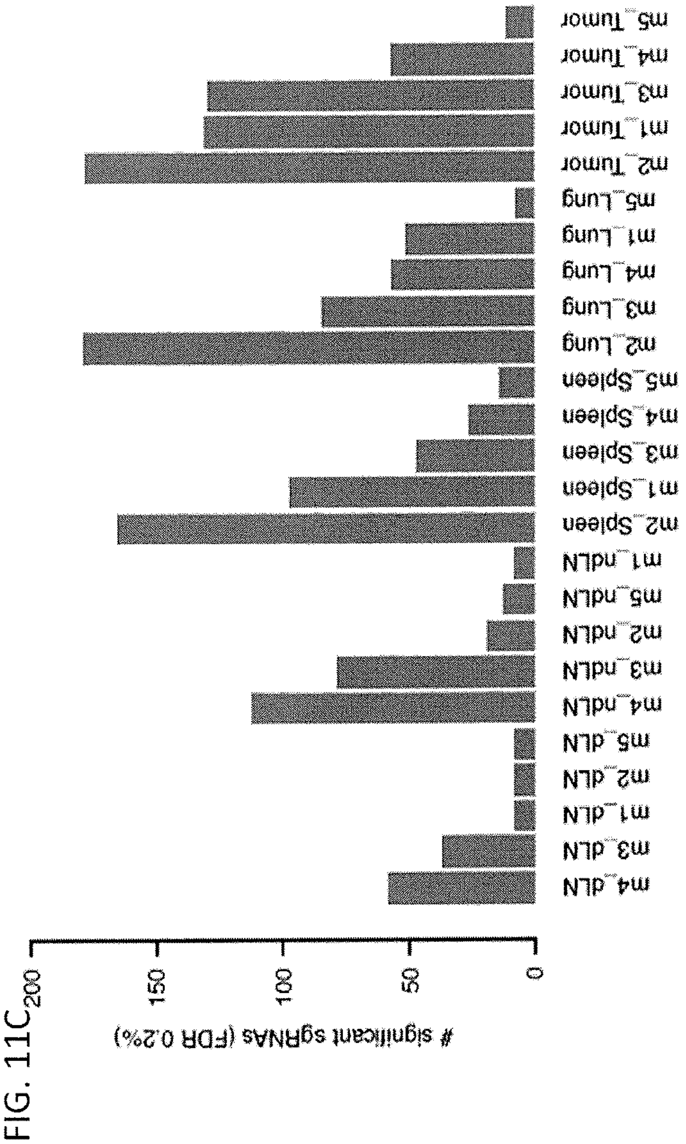
Figure 11D:
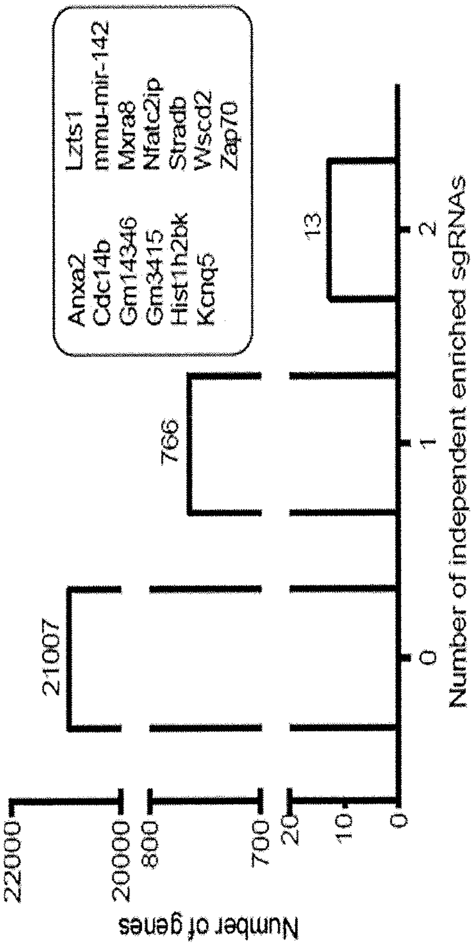
Figure 11B:
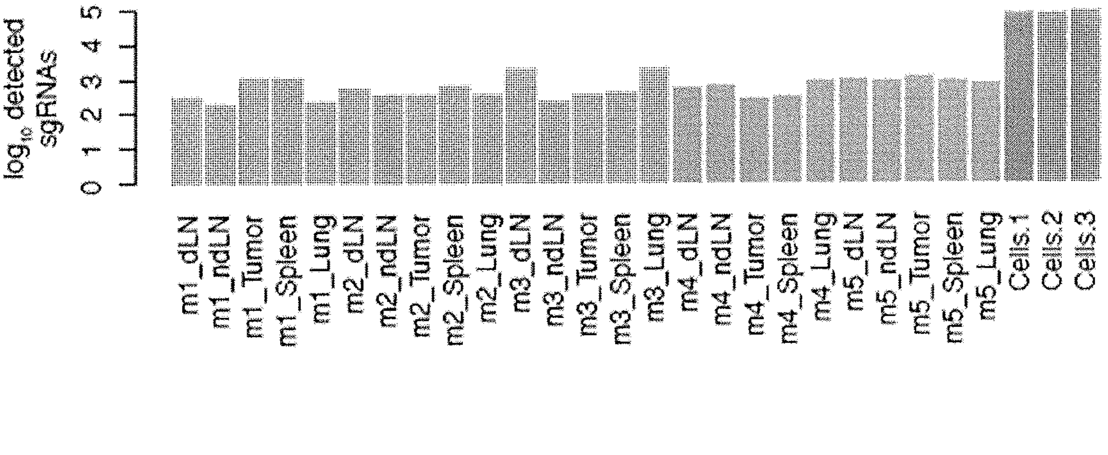
Figure 12A:
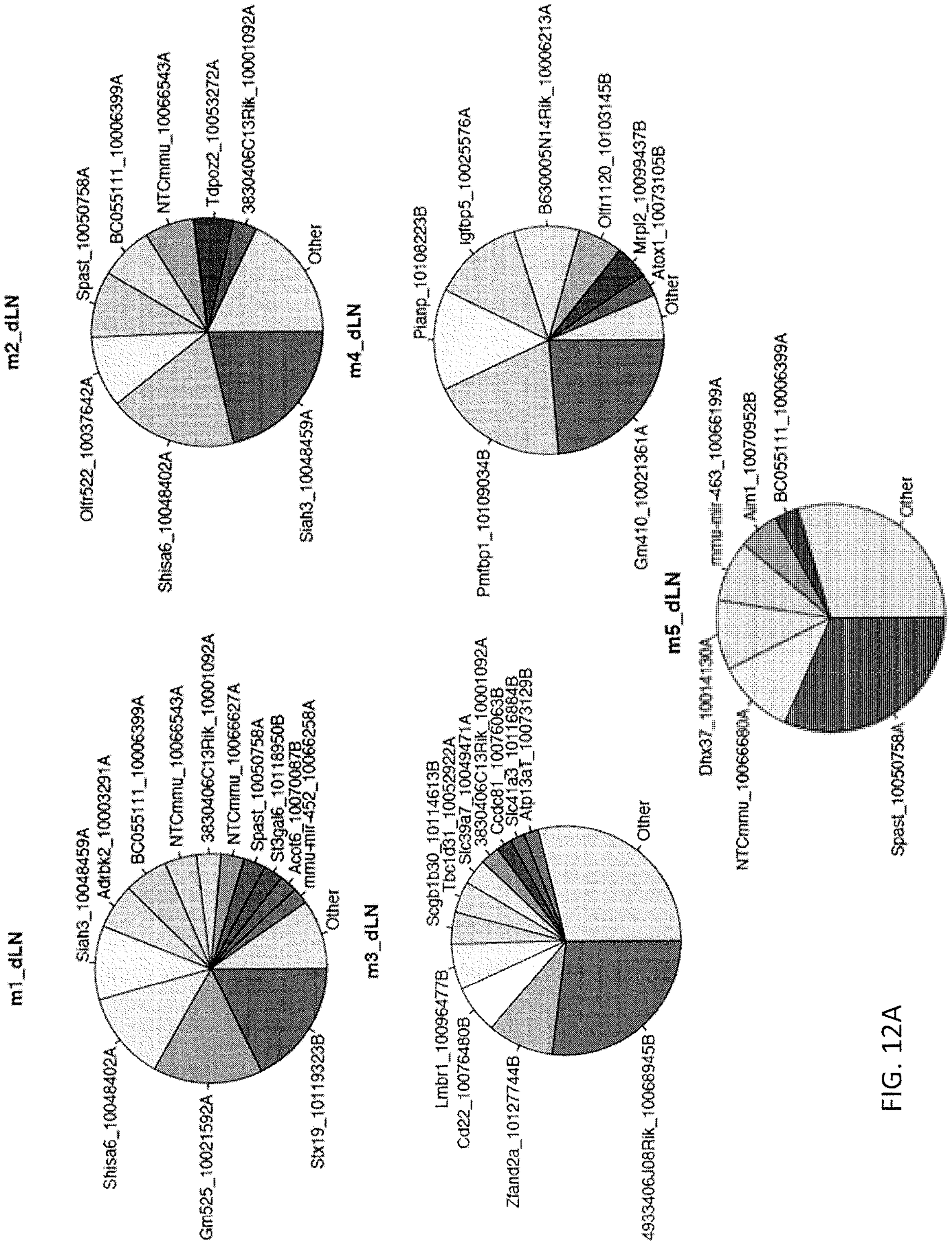
FIGS. 12A-12E are a series of pie charts depicting the analysis of MKO mutagenized OT-I; Cas9 $CD8^+$ $T_{eff}$ cells in $Rag1^{-/-}$ mice with transplanted tumors expressing cOVA antigen. All pie charts of sgRNA compositions in organ samples are depicted. SgRNAs that comprised≥2% of total reads for each sample are shown, with the remaining reads classified as "Other.
Figure 12B:
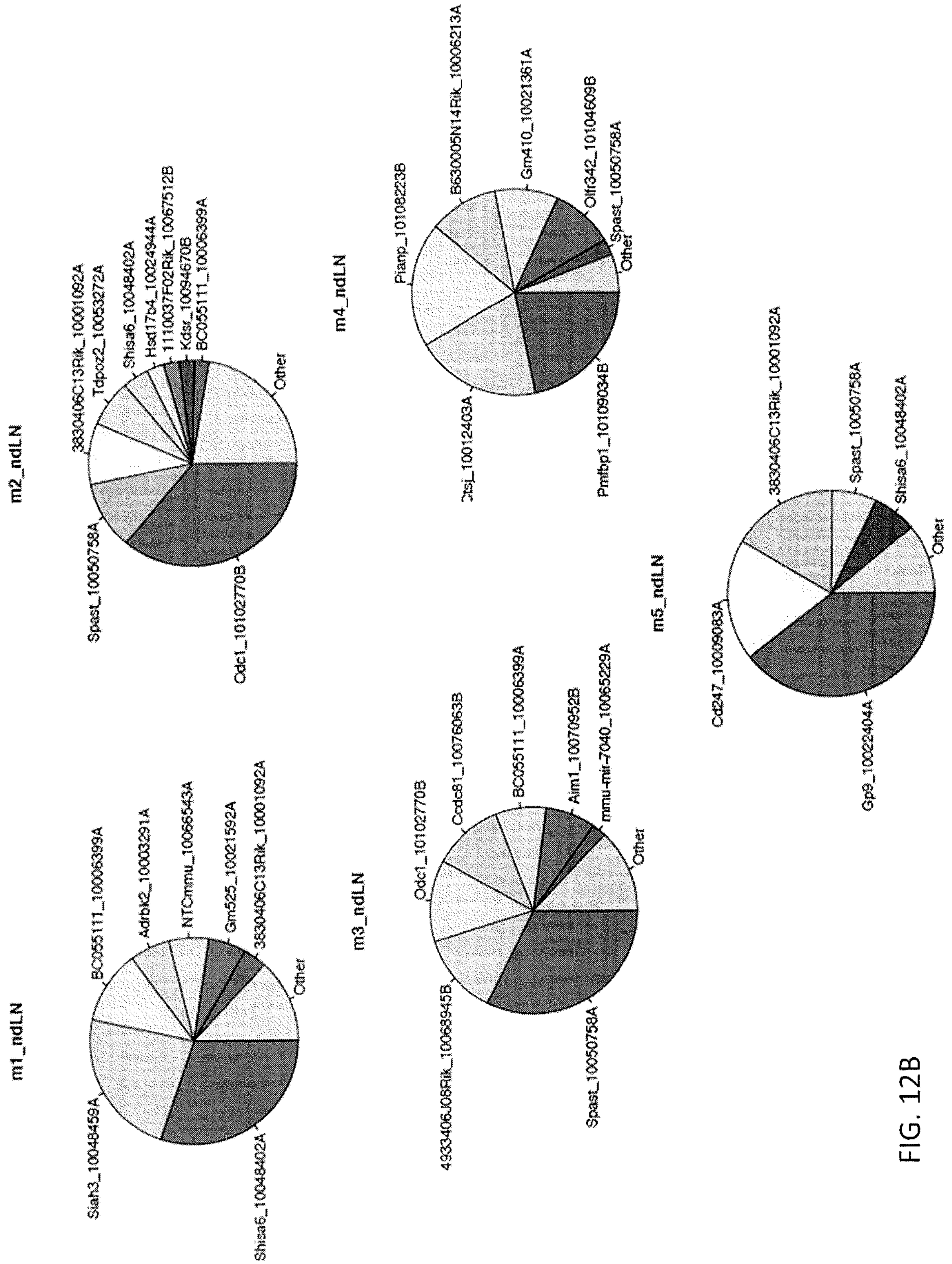
Figure 12C:
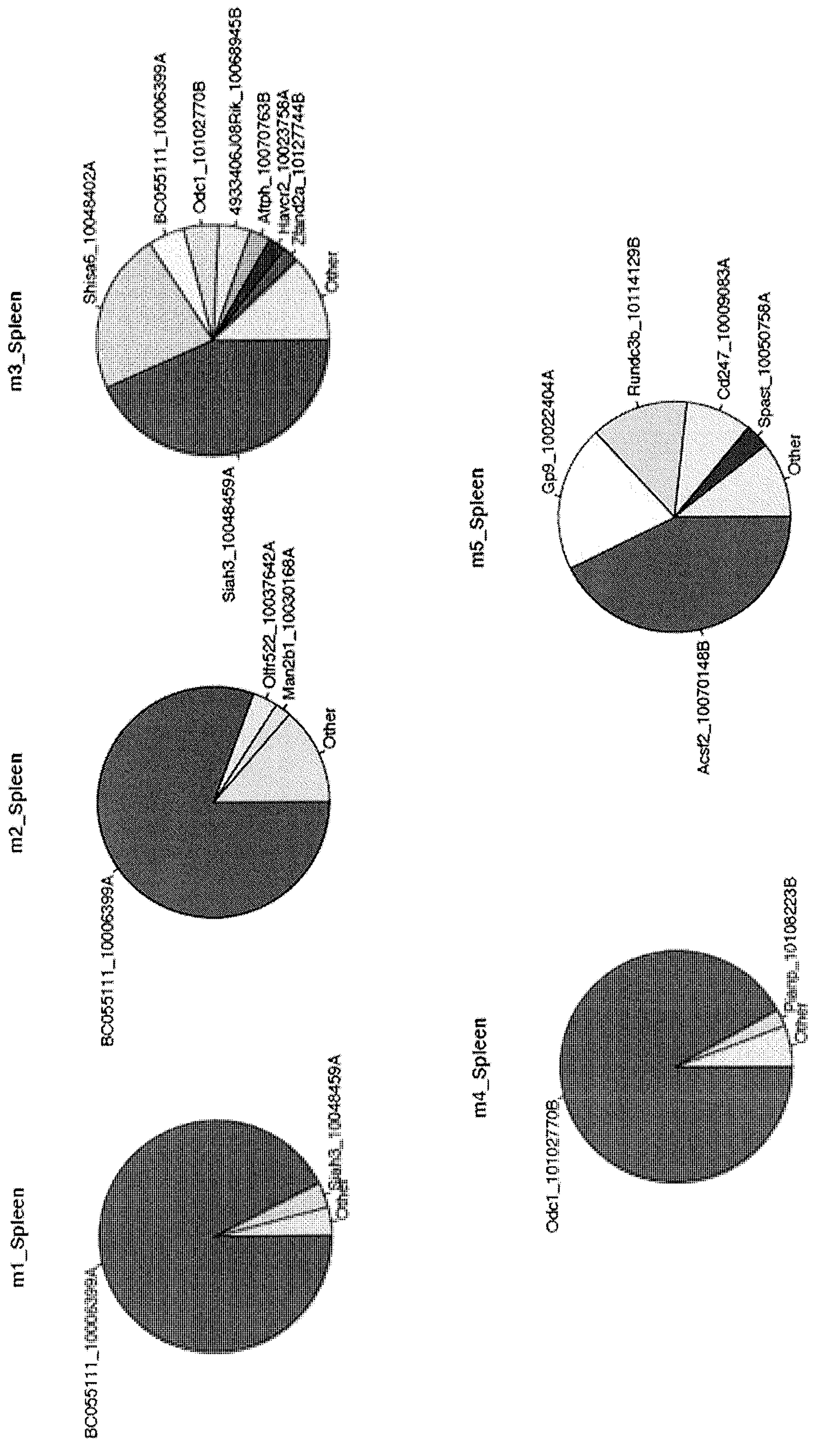
Figure 12D:
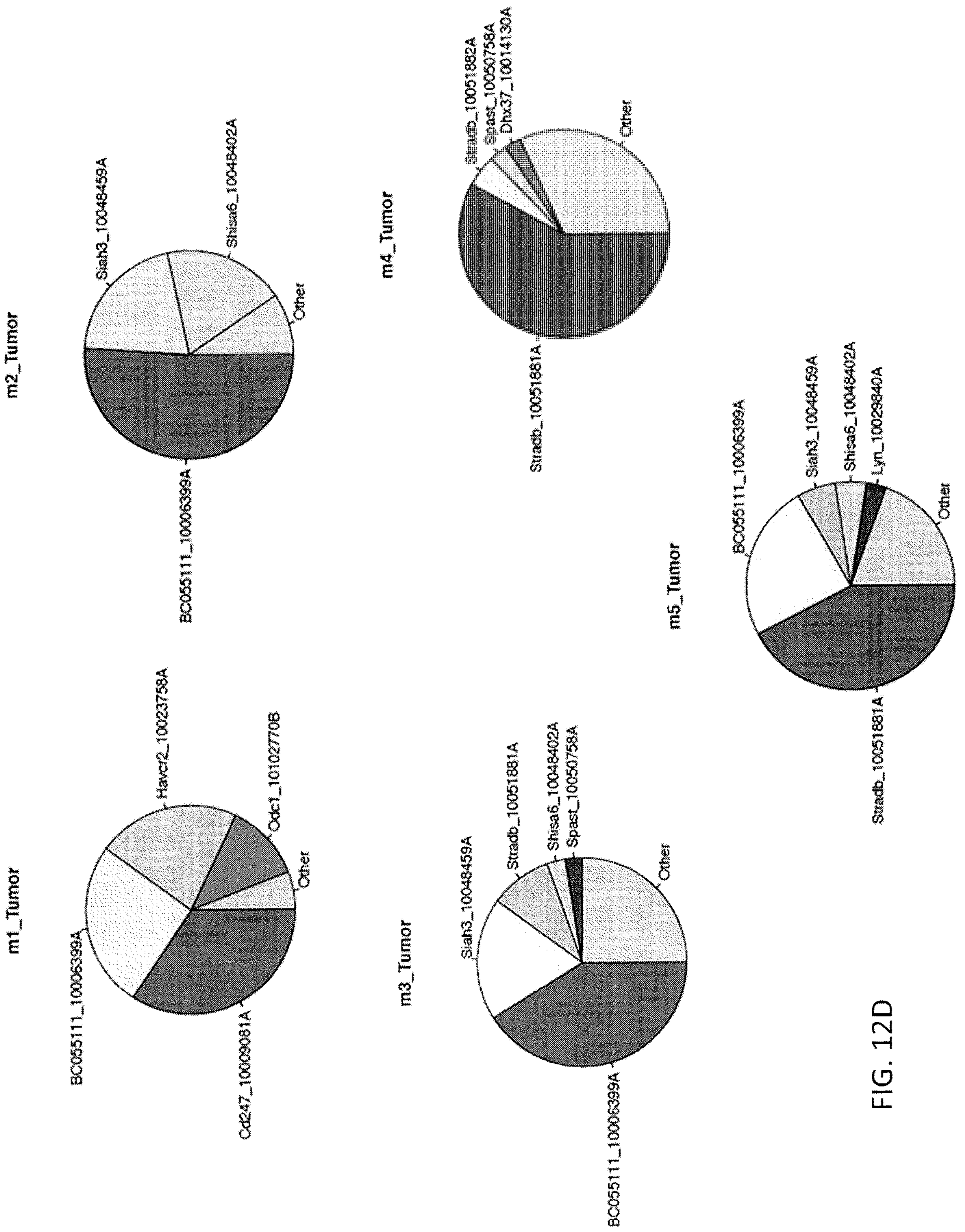
Figure 12E:
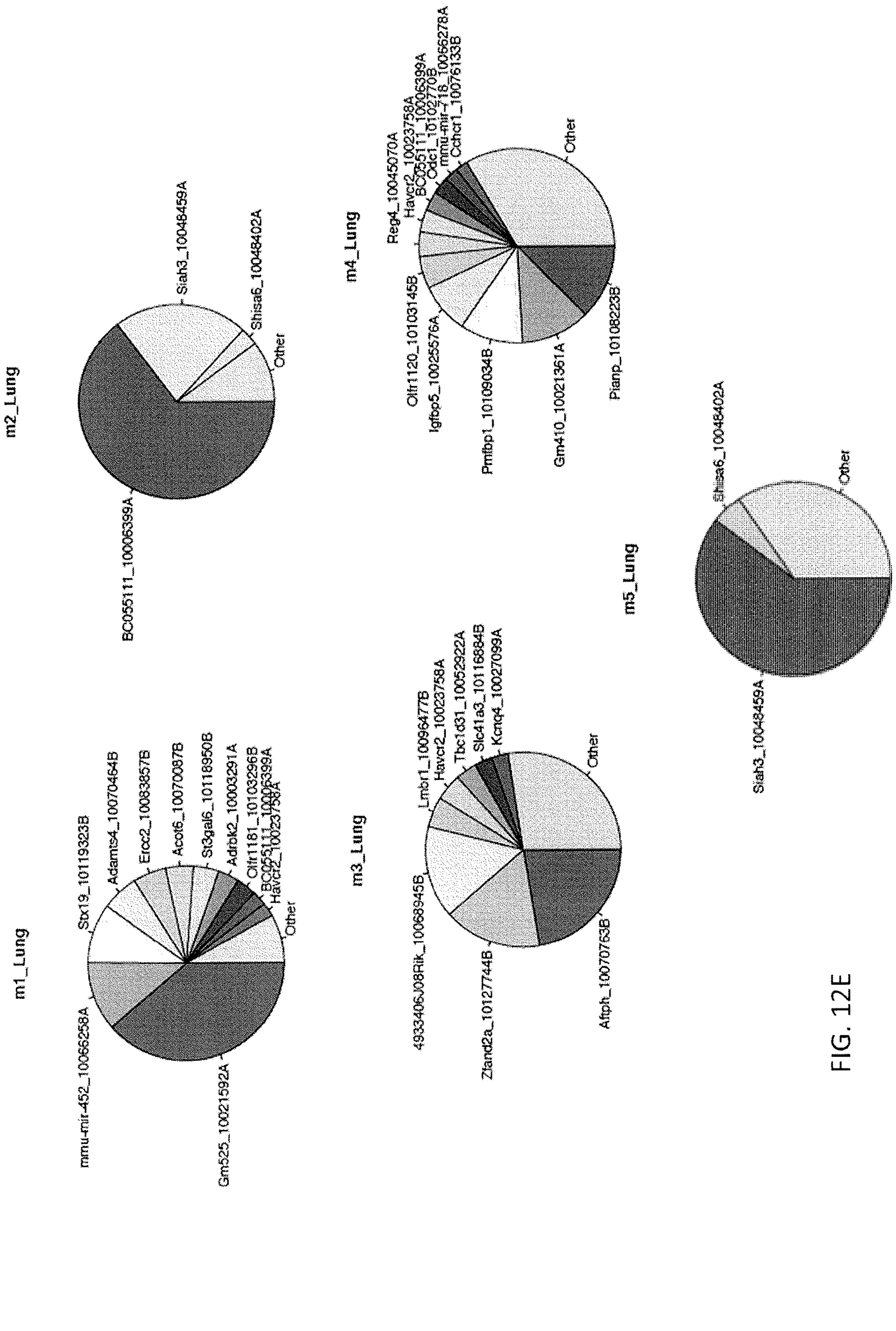

Similar to the first screen, the sgRNA library representation was characterized by a high level of diversity in the pre-injected $CD8^+$ T cell population (FIGS. 4B & 11B). Among the organ samples, the dLN group had the highest number of detected sgRNAs (FIG. 4C). On the contrary, the ndLN group had lowest number of detected sgRNAs, while tumors had the second lowest number of detected sgRNAs (FIG. 4C). Monoclonal, oligoclonal and polyclonal compositions of mutant $CD8^+$ $T_{eff}$ cells were observed in lymphoid, non-lymphoid organs and tumors (FIGS. 4D & 12A-12E). Using the same criteria (FDR<0.2%), significantly enriched sgRNAs were identified in each organ or tumor (FIG. 11C). These sgRNAs had a heterogeneous pattern of abundance across organs and tumors (FIG. 4E). Although the tumor group had a relatively low number of detected sgRNAs, it had the highest number of significantly enriched sgRNAs (FIGS. 4F & 11C). In contrast, although the dLN group had a relatively high number of detected sgRNAs, it had the lowest number of significantly enriched sgRNAs (FIGS. 4F & 11C) (Tumor significant sgRNA (101±30, n=5) vs. dLN (24±10, n=5) (Mann-Whitney test, two-sided, p=0.048) (FIG. 4F). This might be explained by the fact that the tumors expressed cOVA antigen recognized by the OT-I; Cas9 $CD8^+$ $T_{eff}$ cells, which flowed into tumors from adjacent dLNs.

Figure 5B:
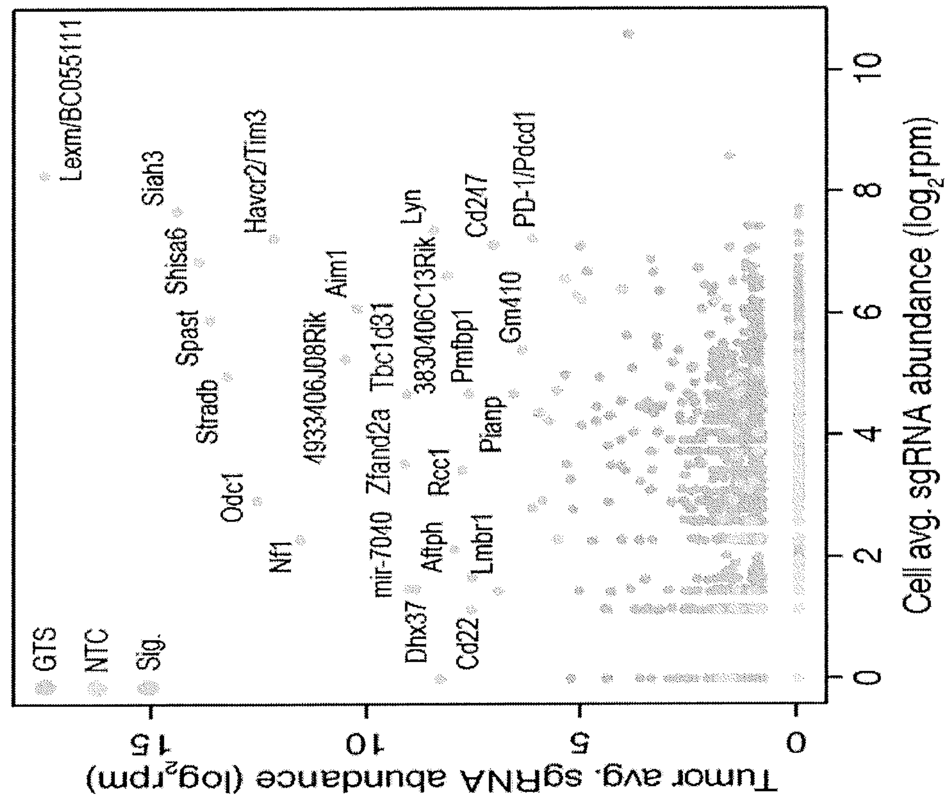
Figure 5A:
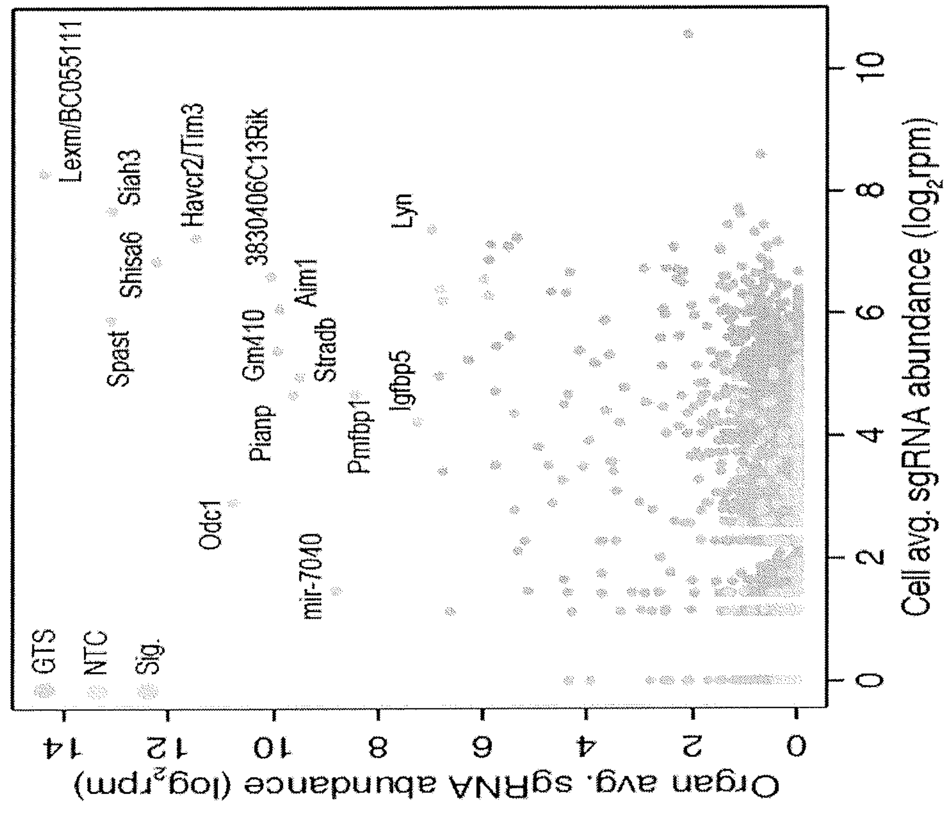

Example 7: Significantly Enriched sgRNAs and Genes in Lymphoid, Nonlymphoid Organs and cOVA-Expressing Tumors Ranking sgRNAs by their overall average abundance in organs (FIG. 5A) or tumors (FIG. 5B) again revealed dominant signatures of immune genes (such as Tim3/Havcr2, Lexm/BC055111, Lyn, Cd247 and PD-1/Pdcd1), tumor suppressor genes (such as Aim1 and Nf1), as well as genes with undocumented function in $CD8^+$ T cells or generally uncharacterized genes (such as Shisa6, Siah3, Odc1, Dhx37, and 3830406C13Rik) (FIGS. 5A-5B). Ranking sgRNAs by their prevalence across multiple samples, or by the number of independent enriched sgRNAs, revealed similar signatures (FIGS. 5C & 11D). All significant genes are collectively enriched in functional categories with immune functions (FIG. 5D). These data together suggest the loss-of-function of these genes make $CD8^+$ $T_{eff}$ cells consistently better survivors in organs and tumors in vivo.

Figure 5E:
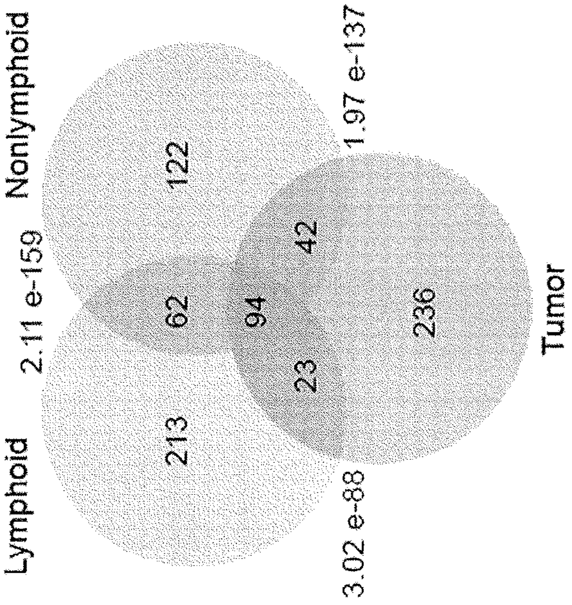
Figure 5F:
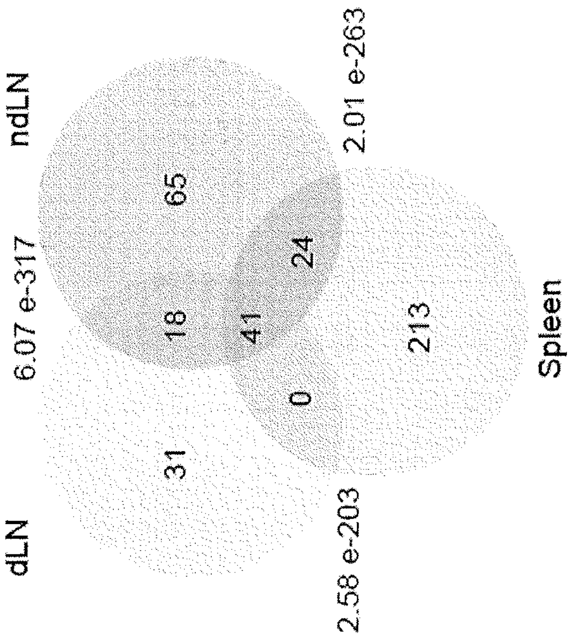
Figure 5G:
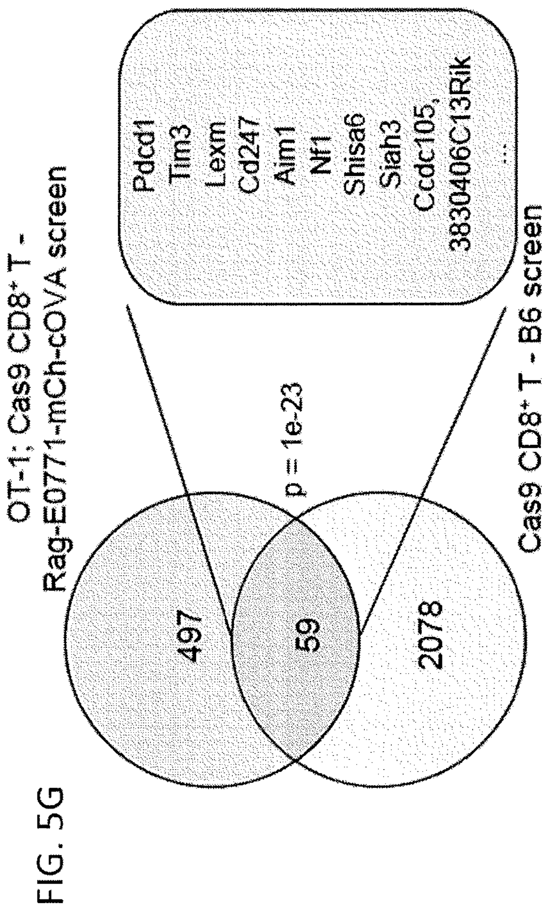

By comparing the set of enriched sgRNAs between different sample types, it was discovered that the significantly enriched sgRNAs in each of the three groups (lymphoid organ, non-lymphoid organ and tumor) significantly overlapped with one other (pairwise hypergeometric test, lymphoid vs. non-lymphoid $p=2.11\times10^{-159}$, lymphoid vs. tumor $p=3.02\times10^{-88}$, and non-lymphoid vs. tumor $p=1.97\times10^{-137}$) (FIG. 5E). There were enriched sgRNAs unique to each sample type (FIG. 5E). Among lymphoid organs, the three groups (dLN, ndLN and spleen) also significantly overlapped (pairwise hypergeometric test, dLN vs. ndLN $p=6.07\times10^{-317}$, dLN vs. spleen $p=2.58\times10^{-203}$, and ndLN vs. spleen $p=2.01\times10^{-263}$) (FIG. 5F). By comparing the hits from this screen (OT-I; Cas9 $CD8^+$ $T_{eff}$ cells in $Rag1^{-/-}$ host bearing tumors with cOVA antigen) to the first screen (Cas9 $CD8^+$ $T_{eff}$ cells in WT host), a highly significant overlap of genes was seen (hypergeometric test, $p=1\times10^{-23}$) (FIG. 5G). The shared genes included multiple immune genes (such as Tim3/Havcr2, Lexm/BC055111, Zap70, Cd247 and PD-1/Pdcd1), a few tumor suppressor genes (Aim1 and Nf1), as well as many genes with undocumented function in $CD8^+$ T cells or genes with little information (such as Shisa6, Siah3, Ccdc105, Ccdc81 and 3830406C13Rik) (FIG. 5G). These data suggest that there exist a common set of genes that modulate the trafficking and survival of $CD8^+$ $T_{eff}$ cells in organs and tumors, with or without antigen.

Figure 4I:
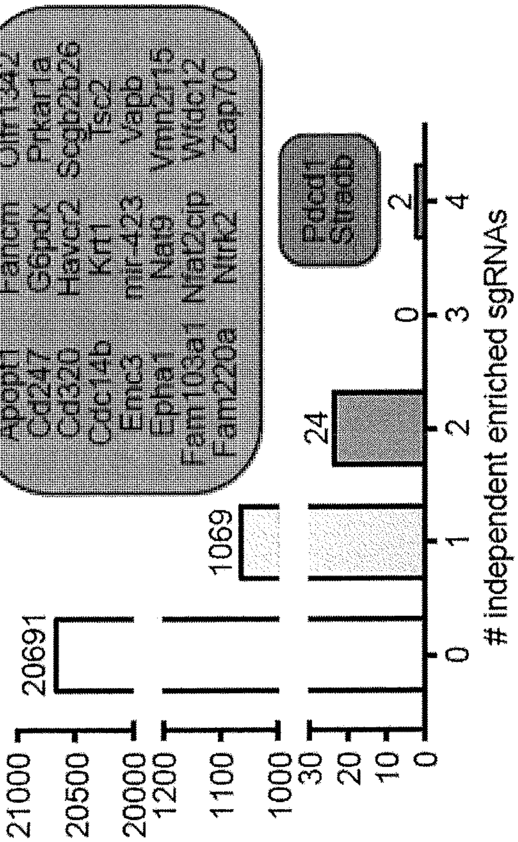
Figure 4J:
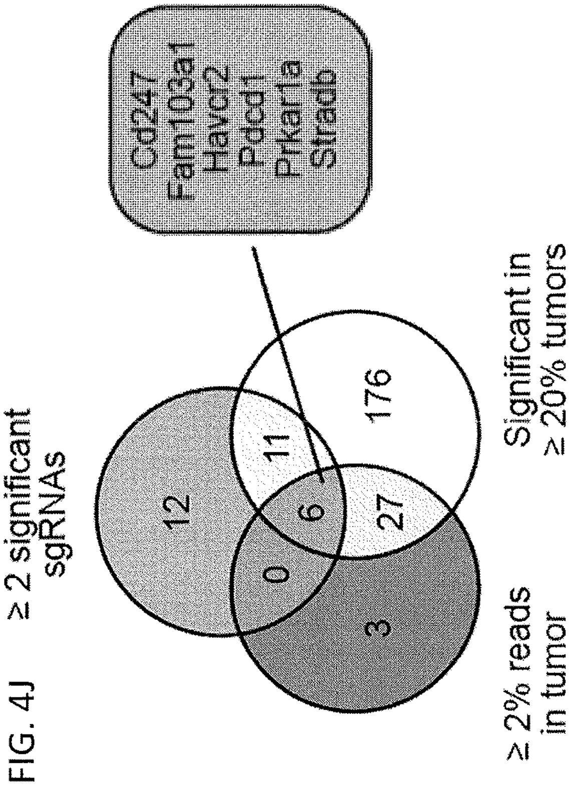
Figure 4H:
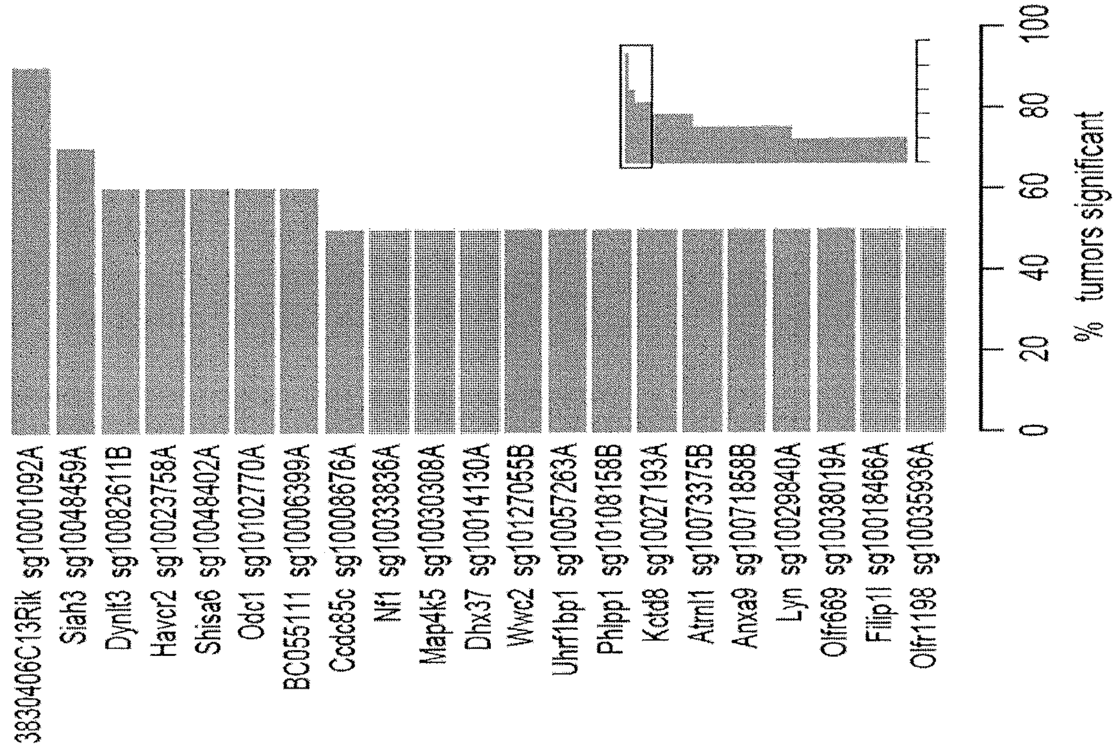
Figure 21F:
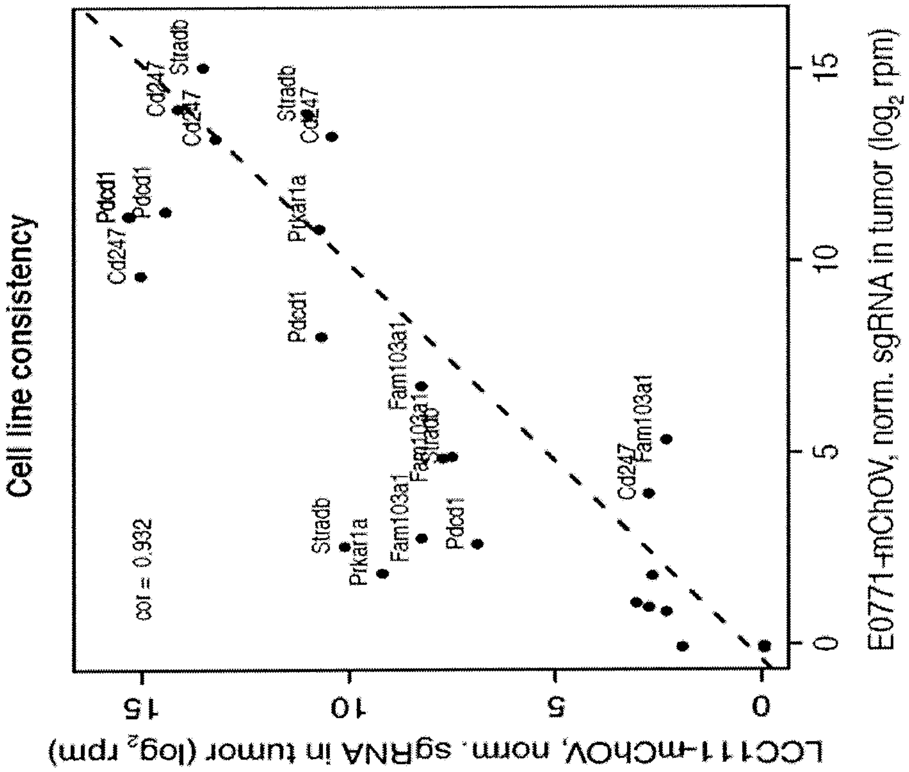
Figure 21E:
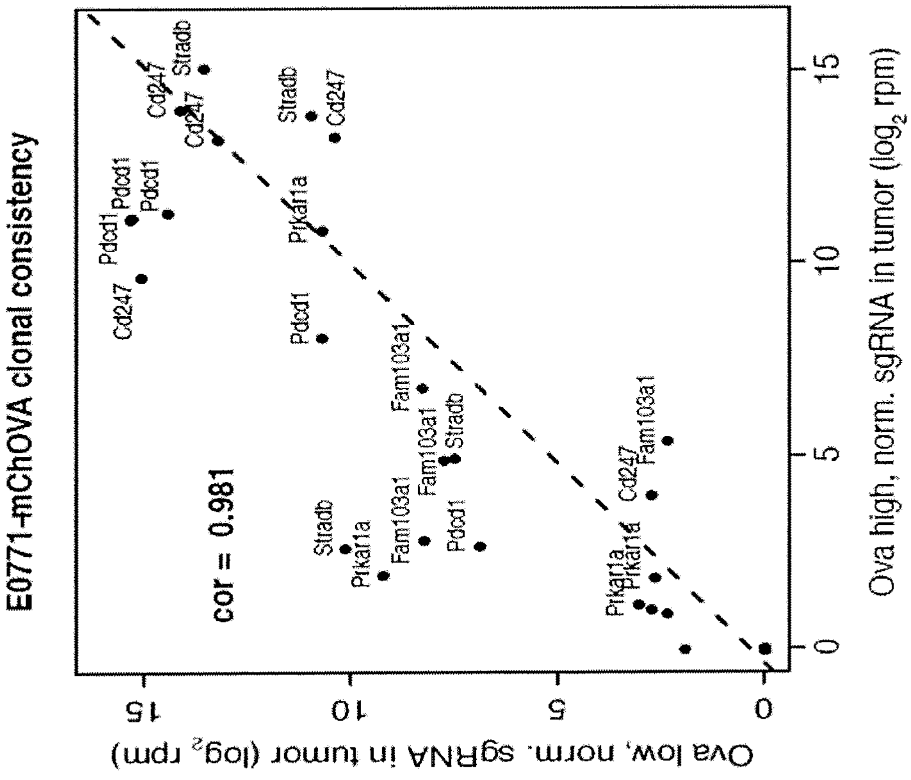

Using the criteria of FDR<0.5%, significantly enriched sgRNAs were identified in each tumor (FIG. 4H). Ranking sgRNAs by their prevalence across tumors again revealed dominant signatures of immune genes (such as Tim3/Havcr2, BC055111, and Lyn), growth genes (e.g. Nf1), as well as genes with undocumented function in $CD8^+$ T cells or generally uncharacterized genes (such as Shisa6, Siah3, Odc1, Dhx37, and 3830406C13Rik) (FIG. 4H). Ranking sgRNAs by the number of independent enriched sgRNAs revealed 26 genes with multiple enriched sgRNAs (FIG. 4I). Notably, two genes (Pdcd1 and Stradb) had 4 enriched sgRNAs, representing independent evidence for their phenotypes (FIG. 4I). After considering a third criteria of sgRNA abundance (≥2% of total reads in a single tumor) representing substantial TIL clones, a total of 6 genes are significantly enriched across all three criteria (Cd247, Fam103a1, Hacvr2, Pdcd1, Prkar1a, and Stradb) (FIG. 4J). To test the clonal effect of cOVA antigen expression level, we took the top hits from the screen and performed a minipool screen with two clones expressing different levels of cOVA (cl.3 and cl.5), and found that the sgRNA representation is highly consistent between the two (Pearson correlation=0.981) (FIG. 21E). To test if the results hold across cancer cell types, we performed a minipool screen with two cell lines, E0771-mCh-cOVA (breast cancer) and LCC-mCh-cOVA (lung cancer), and found that the sgRNA representation is highly correlated with each other (Pearson correlation=0.932) (FIG. 21F). These data together suggest that the CRISPR perturbation of these genes make $CD8^+$ $T_{eff}$ cells consistently better in terms of tumor infiltration and survival in the tumor microenvironment.

Example 8: Further Testing of a Selected Set of Significantly Enriched Genes

Figure 6A:
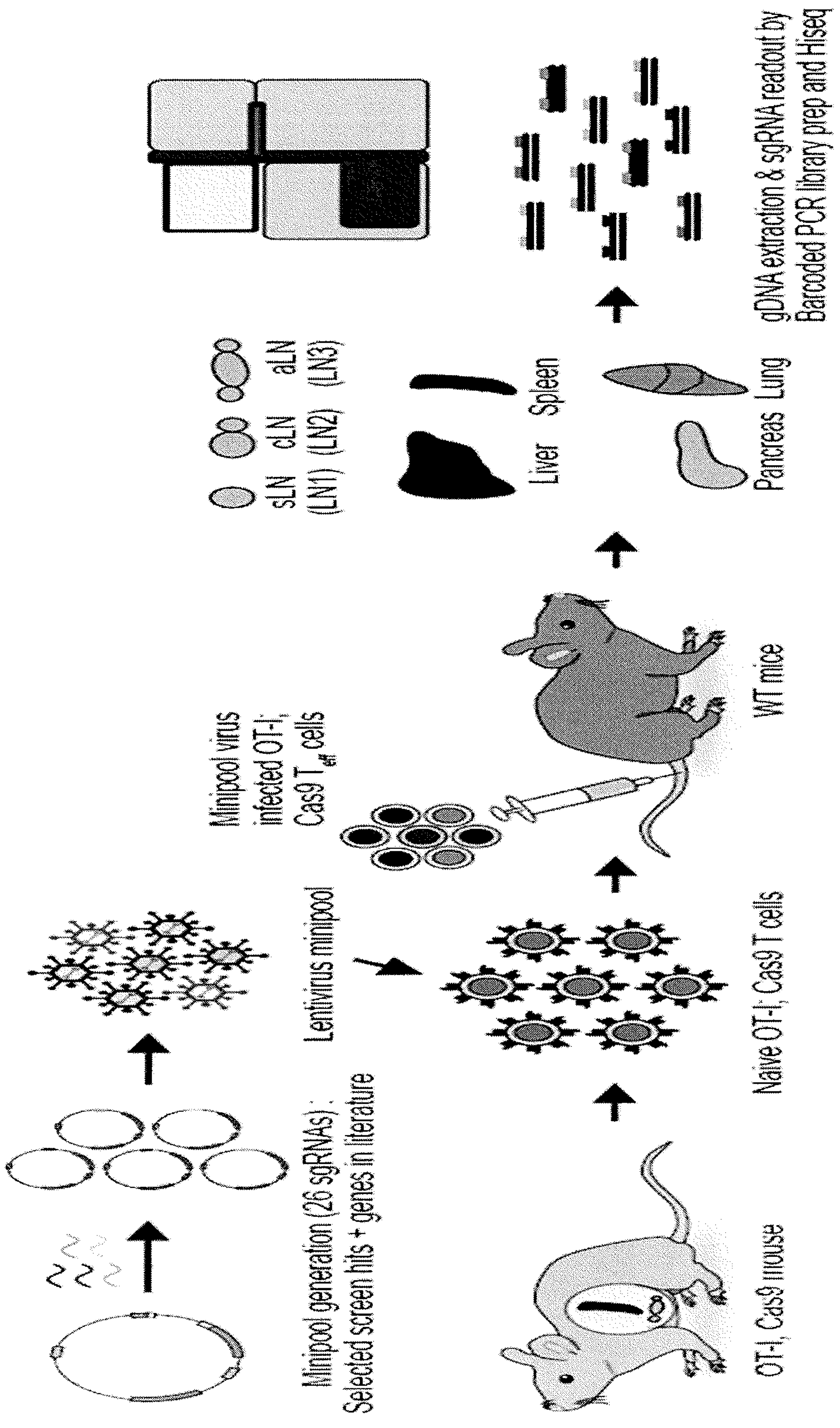
Figure 6B:
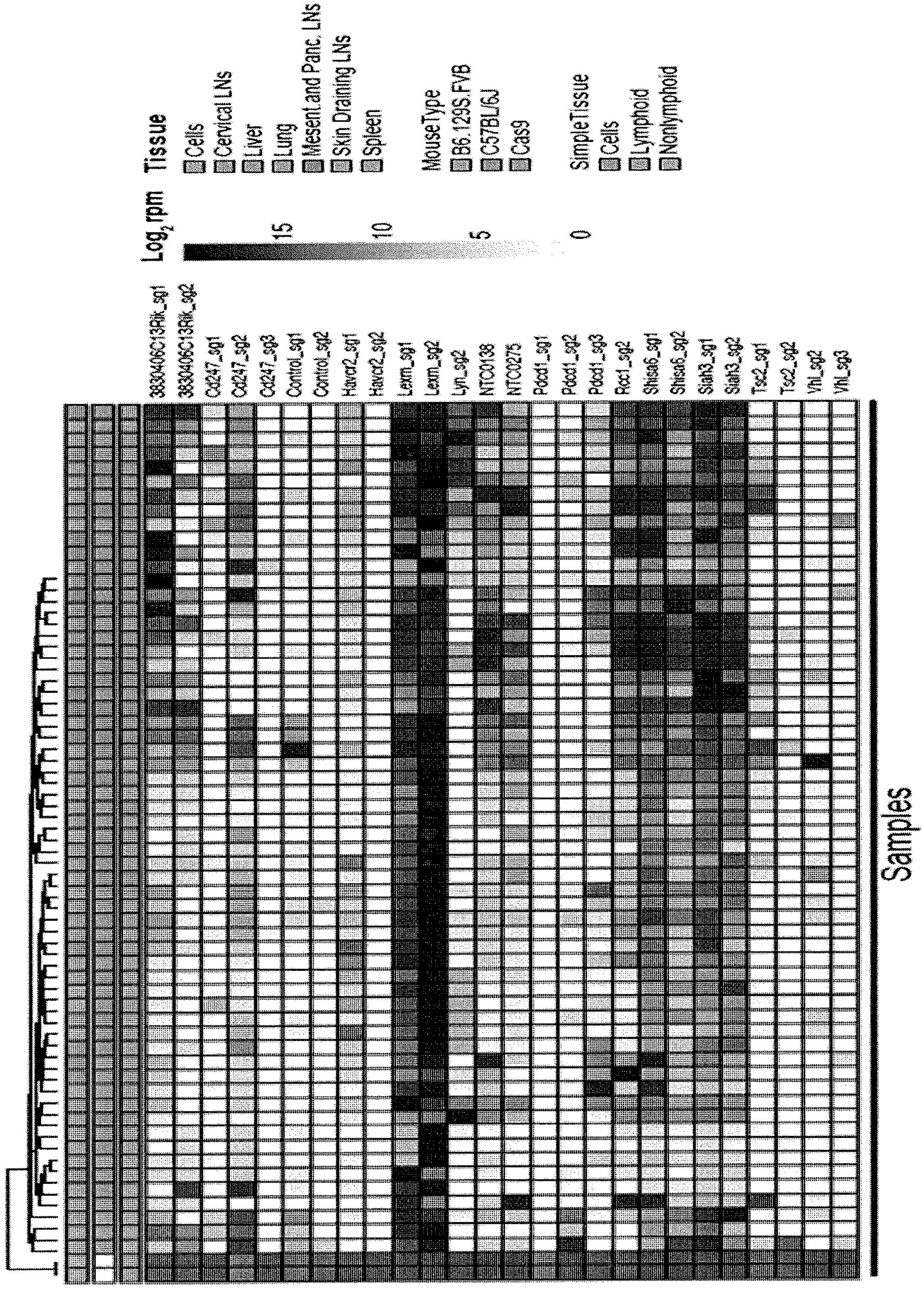

To further test the T cell trafficking and survival signature for the genes enriched in the two genome-scale screens described herein, a selected set of genes highly enriched in either or both screens were focused on, and a small pool of sgRNAs targeting these genes were generated (minipools) (FIG. 6A). Lentivirus was generated from these minipools and OT-I; Cas9 $CD8^+$ $T_{eff}$ cells were mutagenized, and then intravenously injected into various strains of WT mice (FIG. 6A). Seven days after adoptive transfer, representative lymphoid (sLN, cLN and aLN) and non-lymphoid organs (liver, lung and pancreas) were isolated, and the sgRNA representation sequenced in each sample (FIG. 6A). The representation of relative sgRNA abundance was measured in all samples (FIG. 6B). All sgRNAs were found at approximately even abundance in the transduced, pre-injected cell population (FIG. 6B), whereas the internal organs showed a more dynamic picture of sgRNA abundance, with certain sgRNAs being absent, low abundance, medium abundance, or high abundance (FIGS. 6B-6C). Compared to control sgRNAs, 17/22 (77%) of the gene-targeting sgRNAs were significantly enriched in organs, targeting genes such as Lexm, Shisa6, Siah3, Tim3/Havcr2, PD-1/Pdcd1, Cd247, Tsc2 and Rccl (FIGS. 6B-6C & 13). A total of 17 sgRNAs were enriched in lymphoid organs and 14 were enriched in non-lymphoid organs, all of which were included in those in lymphoid organs (hypergeometric test, p=0.0021) (FIG. 6D). These data suggested that the hits from both screens have strong sgRNA enrichment across multiple organs, with little effect in culture.

Figure 22A:
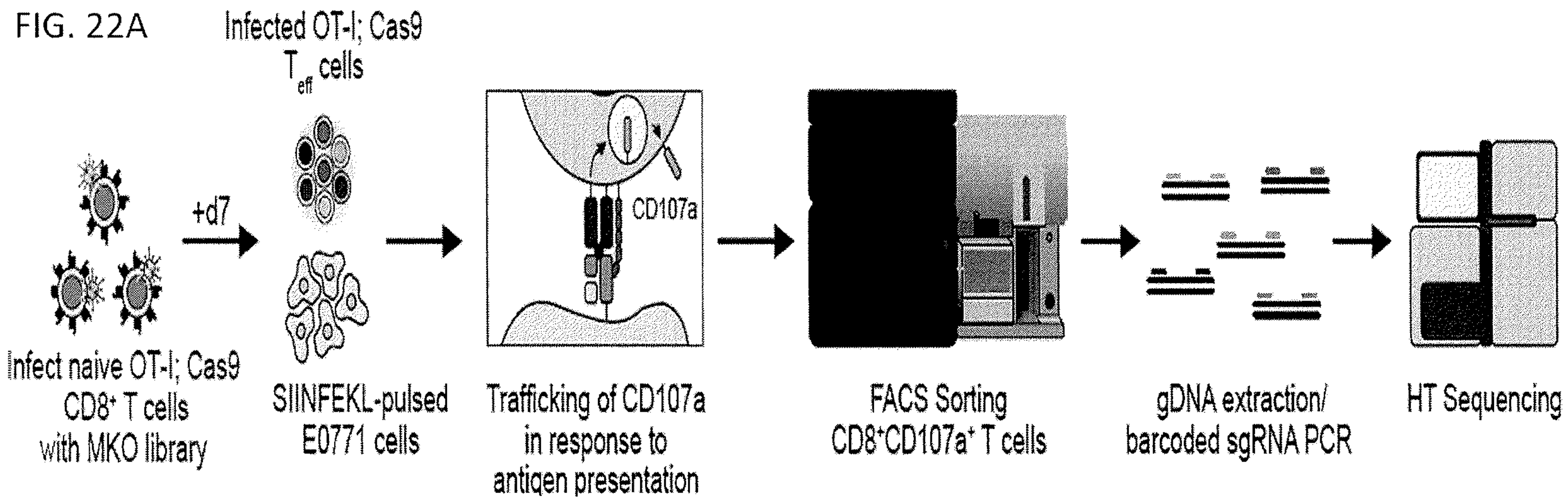
FIGS. 22A-22H are a series of plots and images illustrating high-throughput identification of genes modulating effector CD8+ T cell degranulation upon encountering tumor antigen.
Figure 22B:
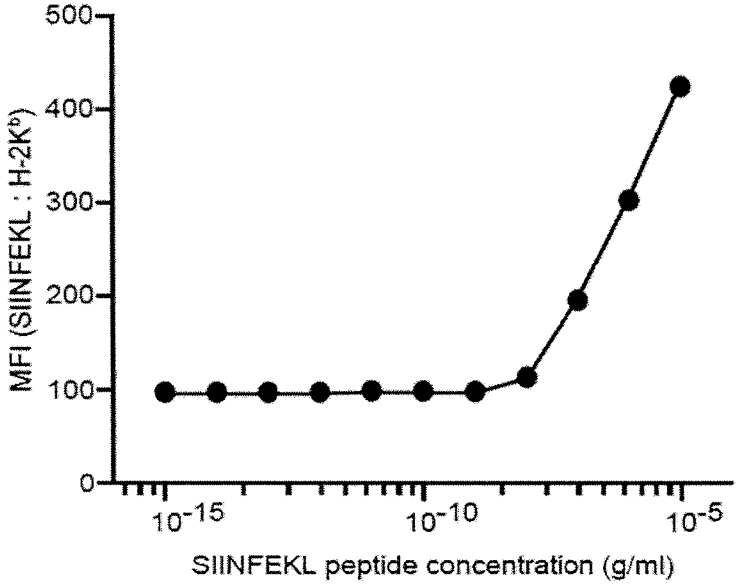
Figure 22C:
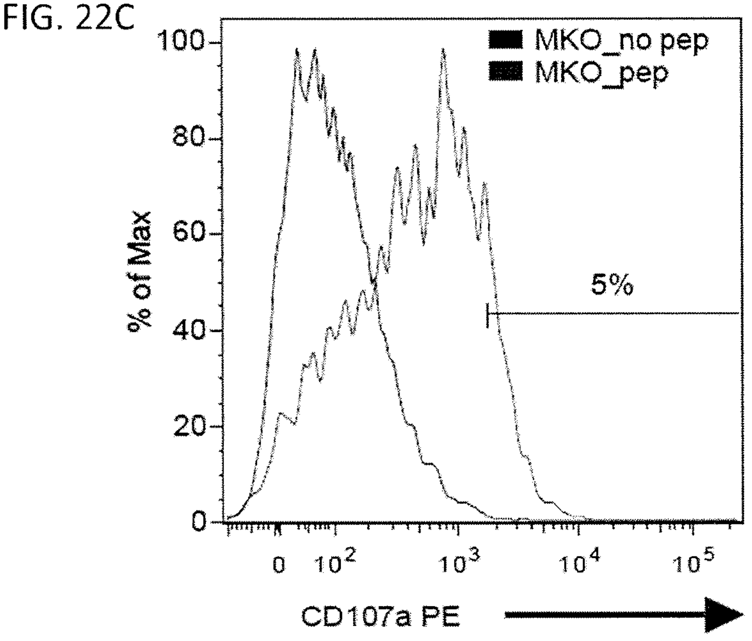
Figure 22D:
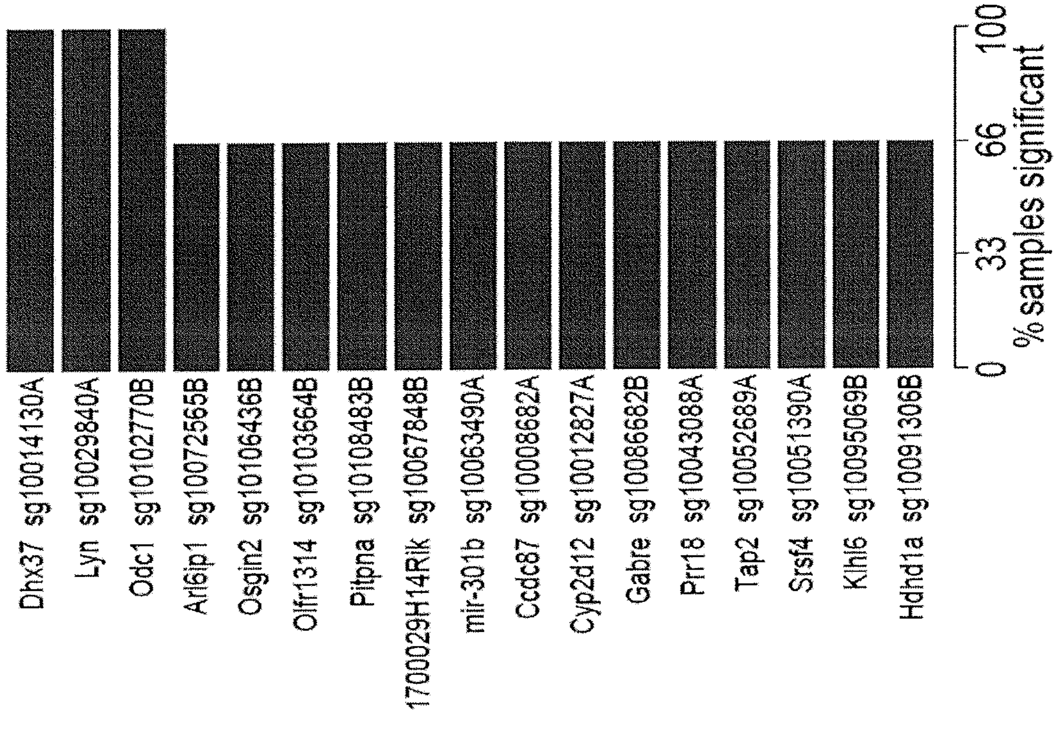
Figure 22E:
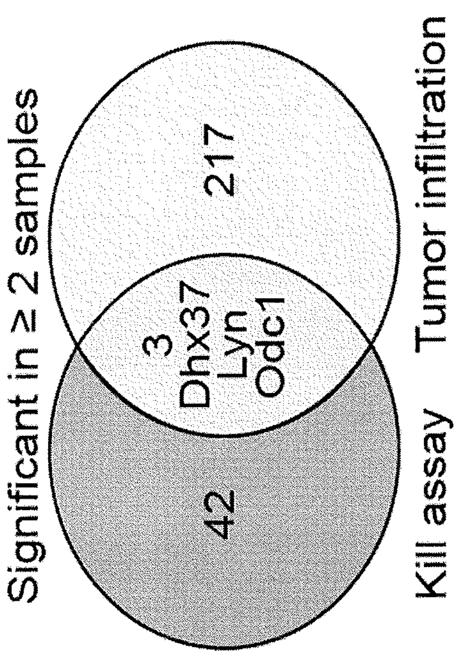

Example 9: High-Throughput Identification of Genes Modulating Effector $CD8^+$ T Cell Degranulation Upon Encountering Tumor Antigen Having observed an anti-tumor effect in vivo, the next aim was to identify genes that could modulate the ability of $CD8^+$ $T_{eff}$ cells to target and kill cancer cells bearing tumor-specific antigen. To do this, a degranulation screen was developed using a co-culture system in which OT-I; Cas9 $CD8^+$ $T_{eff}$ cells would degranulate in response to E0771 cancer cells presenting SIINFEKL peptide (FIG. 22A). E0771 cells were pulsed with varying concentrations of SIINFEKL peptide, and found to present SIINFEKL peptide on surface MHC-I in a dose-dependent manner (FIG. 22B). To perform a high-throughput CRISPR degranulation screen, naive OT-I; Cas9 $CD8^+$ T cells were isolated and transduced with MKO library. The cells were incubated in cRPMI supplemented with IL-2, IL-12, anti-CD28 and anti-CD3 for stimulation for 6 days, rested for 12 hours prior to the experiment on untreated plates, and then the MKO transduced $CD8^+$ $T_{eff}$ cells were co-cultured with SIINFEKL-pulsed E0771 cells at 1:1 (T cell:cancer cell) ratio (Methods). T cells were incubated in media containing anti-CD107a antibody to label the transient deposition of surface CD107a, a marker of T cell granules that is temporarily presented on the cell surface when T cells encounter cognate antigen on MHC. A total of $1\times10^7$ T cells were analyzed per replicate with three biological replicates, and the top 5% $CD107a^+$ cells were sorted (FIG. 22C), then subjected to genomic DNA extraction, CRISPR library readout, and screen data analysis (FIG. 22A). Using the FDR<0.5% significance cutoff, significantly enriched sgRNAs were identified in sorted $CD8^+CD107a^+$ T cells after exposure to SIINFEKL-pulsed E0771 tumor cells in co-culture (FIG. 22D). Remarkably, three genes were significantly enriched in all three samples (Dhx37, Lyn, and Odc1), and they were also found to be significant in the tumor infiltration screen (FIG. 22E). These data together pinpointed Dhx37, Lyn, and Odc1 as promising targets for potentially augmenting anti-tumor activity in vivo by $CD8^+$ T cells.

Figure 22F:
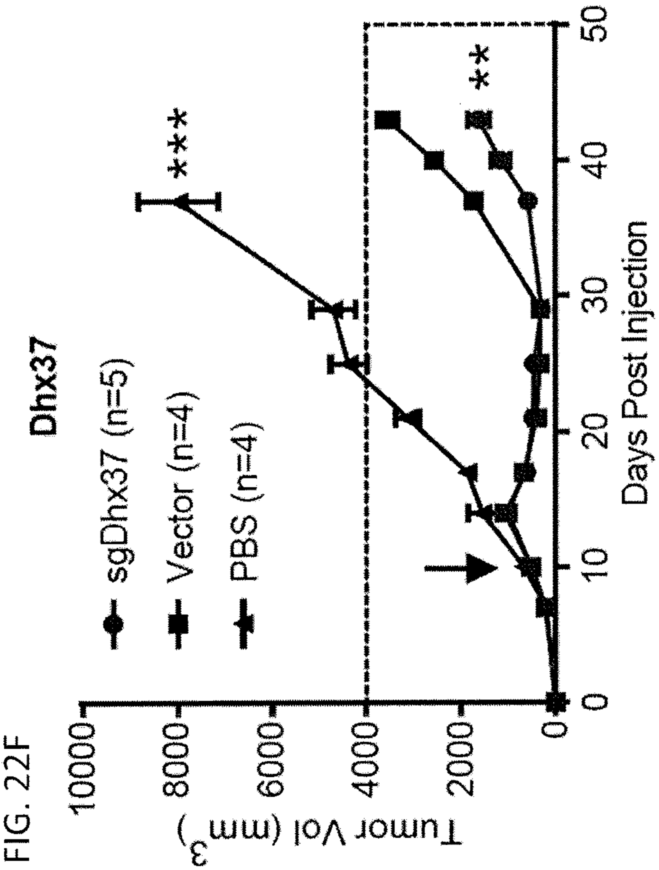

Example 10: Enhanced Anti-Tumor Function and Single-Cell Transcriptomic Signatures of OT-I; Cas9 $CD8^+$ $T_{eff}$ Cells with Dhx37 Perturbation The phenotype of Dhx37 in a model of immunotherapy was examined. Two sgRNAs targeting Dhx37 were cloned into the T cell CRISPR vector, virus preparation and T cell infection were performed as described herein. $5\times10^6$ sgDhx37 or vector lentivirus transduced OT-I; Cas9 $CD8^+$ T cells were adoptively transferred into mice bearing breast tumors, 10 days post mammary fat pad transplantation of $5\times10^6$ clone 3 $mCh^+cOVA^+E0771$ cells. Again, a 1:1 (T cell:cancer cell) ratio was adopted at the time of their respective injections (of note, the cancer cells in a day-10 tumor might largely outnumber $5\times10^6$ T cells). Despite initially growing for 3-days post adoptive transfer, the tumors regressed in the ensuing 2.5 weeks (FIG. 22F). Both vector and sgDhx37 infected OT-I; Cas9 $CD8^+$ $T_{eff}$ cells demonstrated strong anti-tumor effects beginning 7 days after adoptive transfer (Vector or sgDhx37 vs PBS, two-sided t-test, adjusted $p<0.001$ from d17 onwards (Benjamini, Krieger and Yekutieli method)) (FIG. 22F). As a result, sgDhx37 infected OT-I; Cas9 $CD8^+$ $T_{eff}$ cells (n=5 mice) significantly suppressed relapse when compared to mice treated with vector-infected OT-I; Cas9 $CD8^+$ $T_{eff}$ T cells (n=4 mice) (two-sided t-test, adjusted $p<0.01$ from d37 onwards) (FIG. 22F). These data suggest that targeting Dhx37 with CRISPR/Cas9 and sgRNAs enhanced the anti-tumor effects of OT-I; Cas9 $CD8^+$ $T_{eff}$ cells against E0771 tumors expressing cognate antigen cOVA.

Figure 22G:
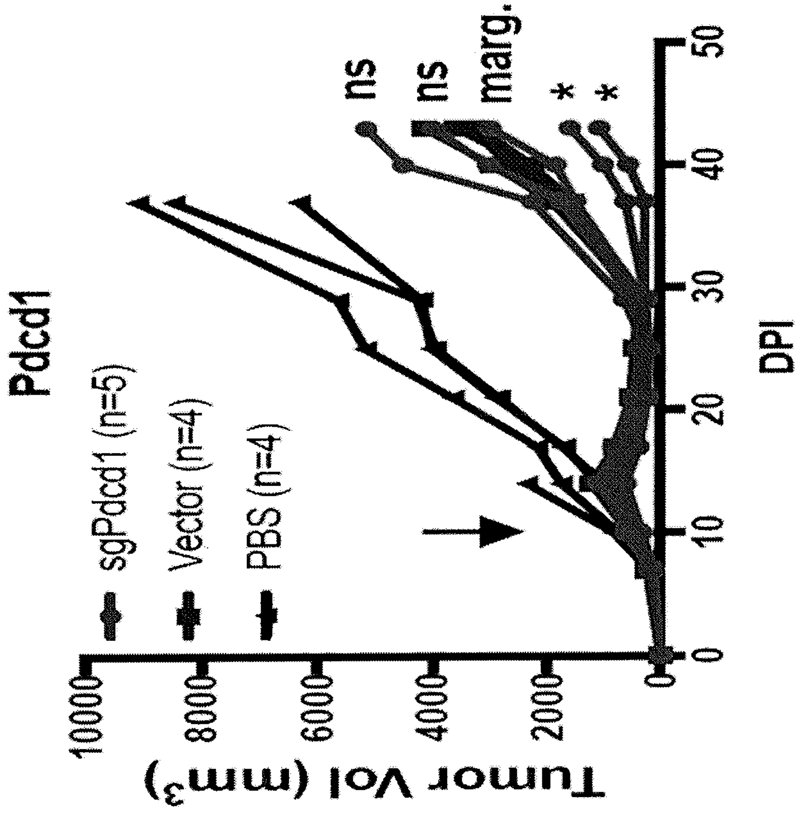
Figure 22H:
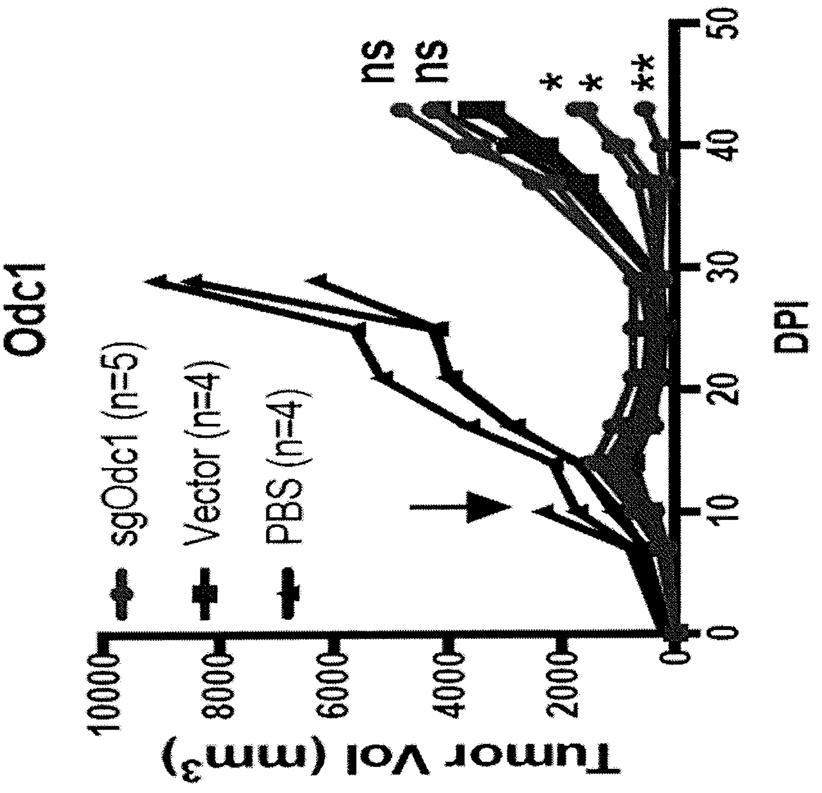

To further test other screen hits for their potential to serve as potential immunotherapy targets, additional studies were performed to investigate possible anti-tumor effects. Two additional genes were tested, Pdcd1 and Odc1. Pdcd1 encodes PD-1, a well-established immunotherapy target, although with varying response rates across different patients and different cancer types. Odc1 encodes an ornithine decarboxylase as an rate-limiting enzyme of the polyamine biosynthesis pathway which catalyzes ornithine to putrescine. With the same assay, it was observed that 2/5 (40%) of mice with sgPdcd1 OT-I; Cas9 $CD8^+$ $T_{eff}$ cells adoptive transfer had tumors significantly smaller than those in the vector control group, although 3/5 do not (FIG. 22G), with variable response rate reminiscent of PD-1 blockade in patients. Similarly, we observed that 3/5 (60%) of mice with sgOdc1 OT-I; Cas9 $CD8^+$ $T_{eff}$ cells adoptive transfer have tumors significantly smaller than those in the vector control group (FIG. 22H). SgRNA perturbation against these two genes showed partial efficacy, although to a lesser extent as compared to Dhx37 (5/5, 100%).

Figure 23A:
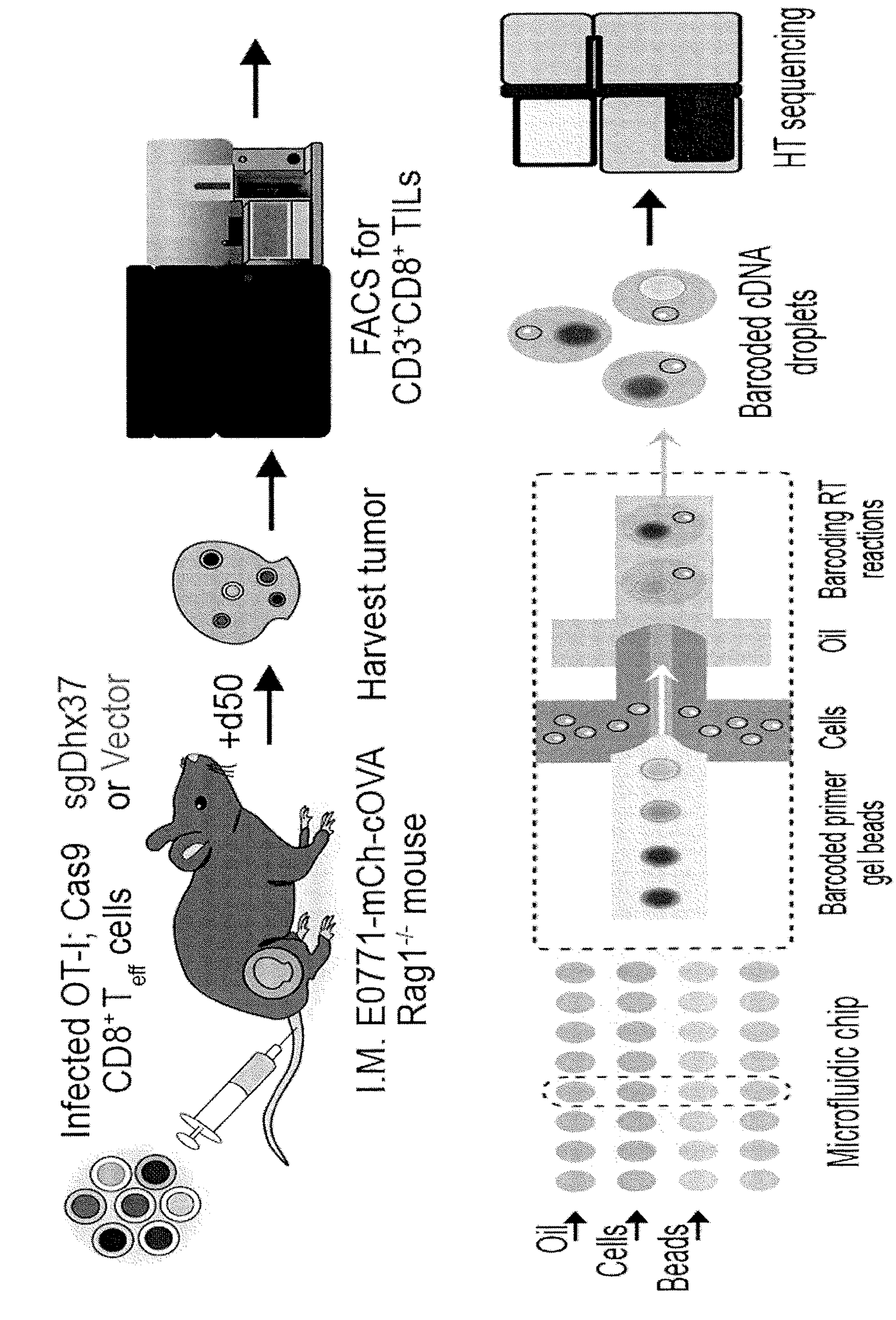
FIGS. 23A-23G are a series of plots and images illustrating single-cell transcriptomics of sgDhx37 OT-I; Cas9 $CD8^+$ TILs in E0771-mCh-cOVA tumors.

Dhx37 is a DEAH box RNA helicase reported to regulate escape behavior via glycine receptor expression in zebrafish, but has not been previously associated with T cell function in mammalian species. The putative ATP-Dependent RNA Helicase domain and conservation implies that it might affect gene expression and cellular function. To investigate the effect of gene expression alteration upon Dhx37 perturbation, transcriptome analysis of sgDhx37 OT-I; Cas9 $CD8^+$ T cells in the form of TILs was performed. Because TILs are in the heterogeneous tumor microenvironment, which might influence the state of TILs leading to highly variable gene expression, single cell RNA-seq (scRNAseq) was performed to investigate the transcriptomes of sgDhx37 TILs. Tumor-bearing mice were euthanized, single-cell suspensions generated from tumors by physical dissociation and enzymatic digestion, and then TILs collected by staining and sorting the live $CD3^+$ $CD8^+$ cells with FACS. Because TILs only consisted of a tiny fraction of cells in these tumors, the vast majority of single cell suspensions were sorted from whole tumors, and $3\times10^3$ to $2\times10^4$ live $CD3^+$ $CD8^+$ TILs per tumor were collected (FIG. 23A). These freshly collected TILs were subjected to an emulsion-based microfluidic device to barcode the $CD8^+$ TILs from sgDhx37 and vector groups, and scRNAseq library preparation was performed. The library was sequenced with Illumina Hiseq platform for unique molecular identifiers (UMIs), cellular barcodes, and the transcriptome in each cell was quantified.

Figure 23B:
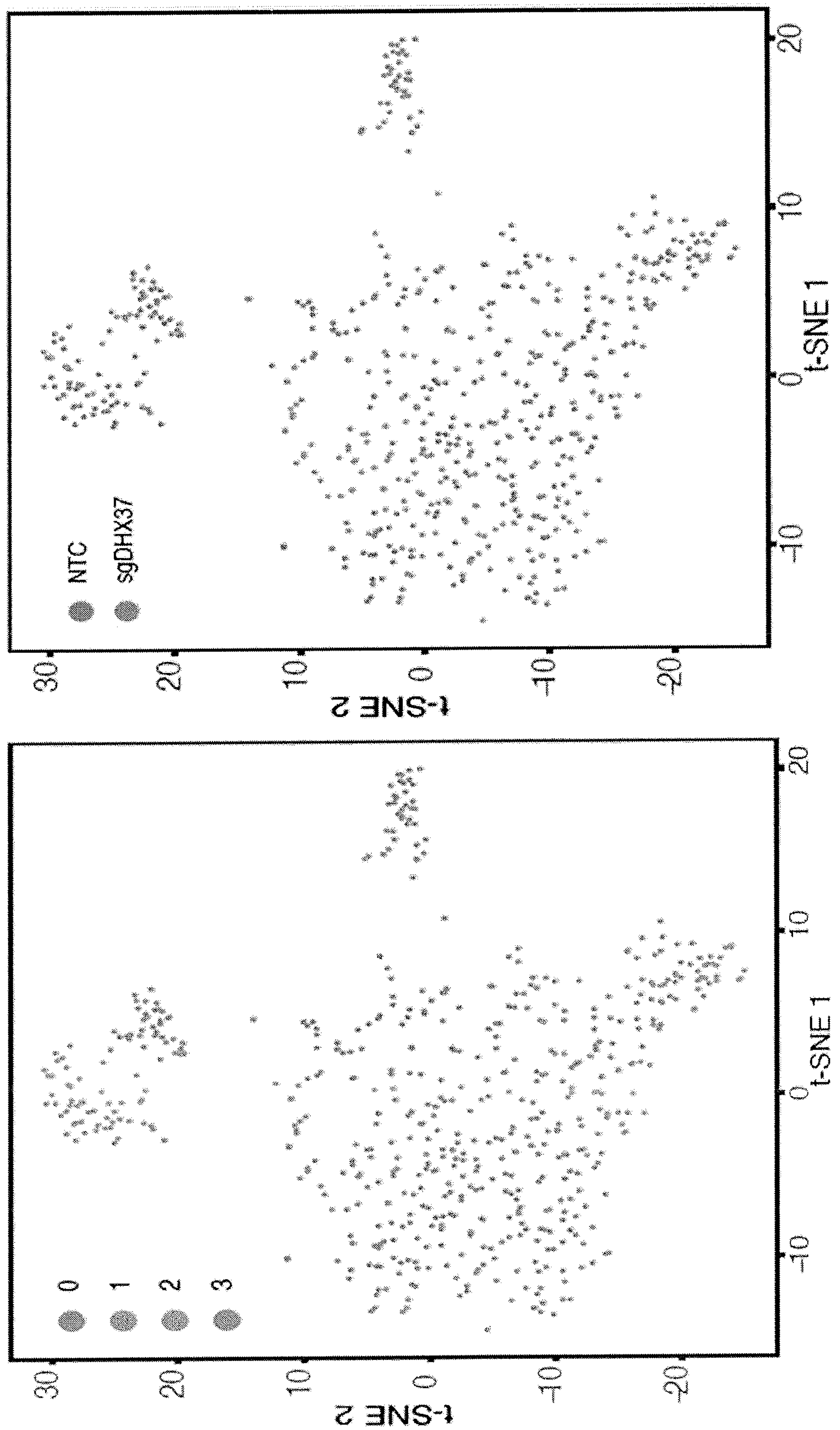
Figure 23C:
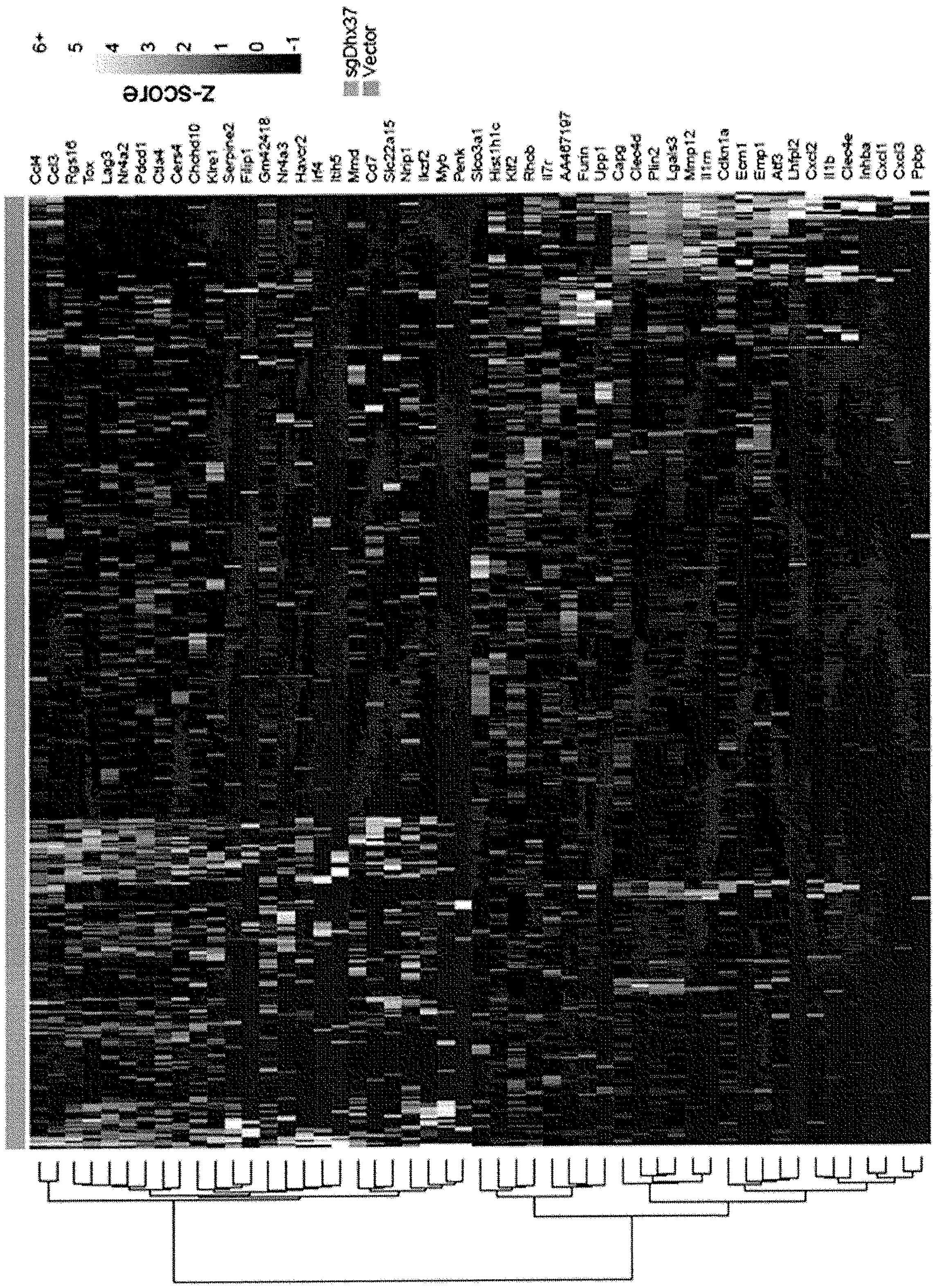
Figures 23D, 23E, 23F:
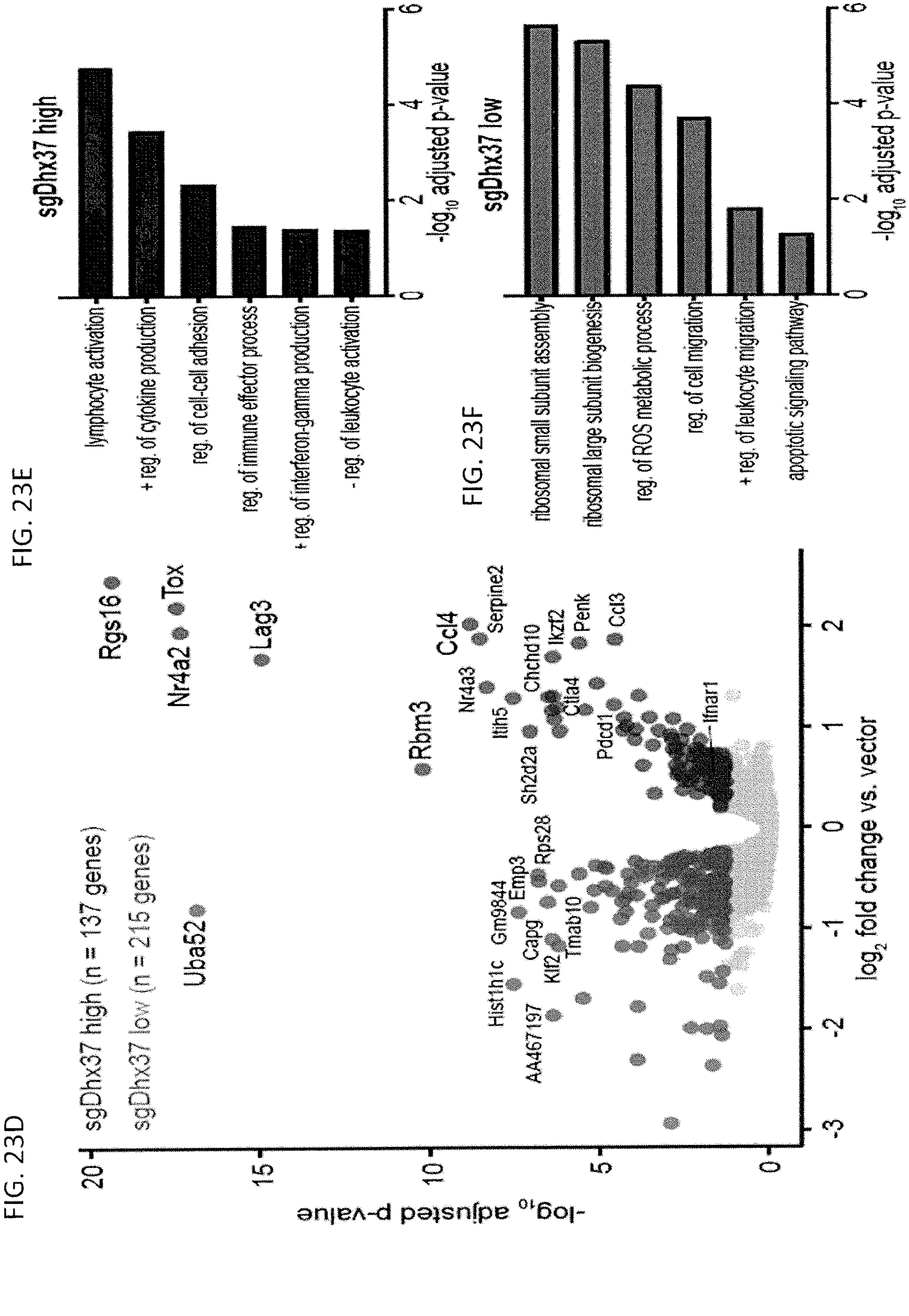
Figure 23G:
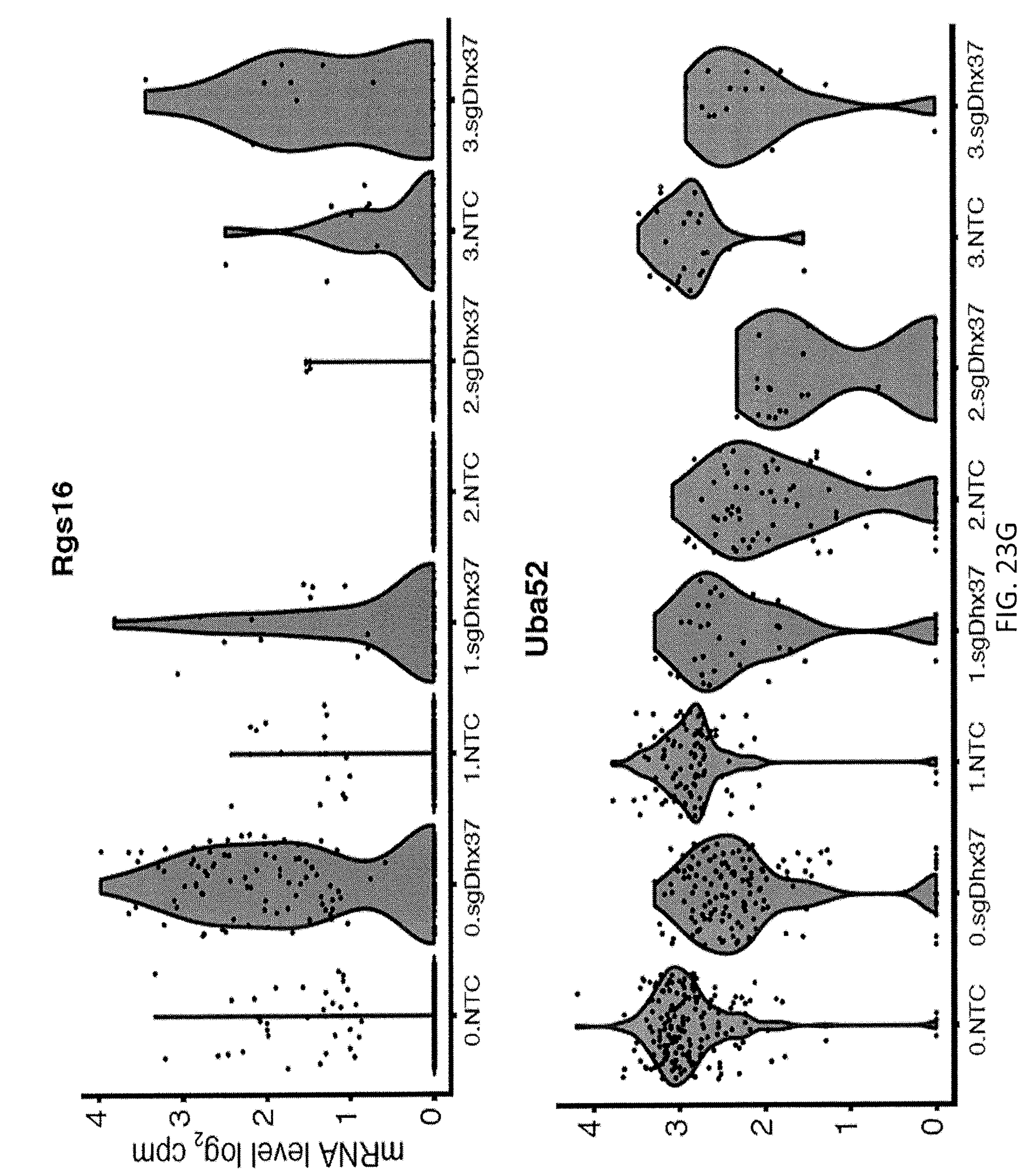

After processing, stringent filtering, and normalizing the raw scRNA-seq data, the final dataset was comprised of 552 cells (sgDhx37, n=191 cells; vector, n=361 cells), measuring a total of 8,244 expressed genes in TILs. t-SNE dimensional reduction was first performed to visualize the overall transcriptomic landscape of these cells (FIG. 23B). With this analysis 4 major clusters (k0 to k3) were uncovered as major subpopulations of these T cells based on their transcriptome (FIG. 23B). Differential expression analysis was subsequently performed between sgDhx37 and vector treated TILs, identifying sets of significantly upregulated and downregulated genes. 215 genes were significantly downregulated in sgDhx37 TILs, while 137 genes were significantly upregulated (Benjamini-Hochberg adjusted $p<0.05$) (FIGS. 23C-23D), with the mostly highly upregulated genes as Rgs16, Tox and Nr4a2 (FIG. 23D). Rgs16 was found as an IL-2-dependent activation gene in human T lymphocytes, and is enriched in activated/effector T cells. Nr4a2 is a nuclear receptor essential for thymic regulatory T cell ($T_{reg}$) development and homeostasis, and associated with T cell activation, although its specific function in $CD8^+$ T cell or TILs is not well characterized. Tox encodes a HMG box protein involved in both $CD8^+$ and $CD4^+$ T cell development, to some degree without the requirement of MHC-TCR interactions. Other significantly upregulated genes included known immune-related genes such as Eomes, Nr4a3, Lag3, Ccl4, Ifnar1, and Ikzf2, as well as genes with less knowledge in $CD8^+$ T cells or TILs (FIG. 23D). Collectively as a gene set, gene ontology analysis revealed multiple immune-related pathways that were significantly upregulated in sgDhx37 TILs (adjusted $p<0.05$), including lymphocyte activation, positive regulation of cytokine production, regulation of cell-cell adhesion, regulation of immune effector process, and positive regulation of interferon-gamma production (FIG. 23E). Somewhat intriguingly, sgDhx37 upregulated genes also include genes involved in negative regulation of leukocyte activation such as Ctla4 and Pdcd1, albeit to a lesser extent, which mirrors the positive correlation of T cell cytotoxic scores with these markers in TILs from human melanoma patients. Lag3, Ctla4 and Pdcd1 are T cell activation-induced markers, with their blockade improving antitumor activity, but their presence does not inhibit adoptive cell transfer therapy. Lag3 is expressed at a high level together with Rgs16, Nr4a2 and Tox, while Ctla4 and Pdcd1 are expressed at a lower level together with the other immune activating transcripts. On the other hand, downregulated genes in sgDhx37 TILs are enriched in ribosomal small subunit assembly and ribosomal large subunit biogenesis (FIG. 23F), consistent with the hypothesized role of human DHX37 protein in rRNA modification and processing in the nucleus and cytosol (UniProtKB—Q8IY37). The top upregulated gene (Rgs16) and downregulated gene (Uba52) are consistently upregulated or downregulated in each of the 4 clusters (FIG. 23G). Taken together, the scRNAseq data revealed significant changes in the transcriptomes of sgDhx37 TILs in the heterogeneous tumor microenvironment at the single-cell level.

Example 11: Investigation of DHX37 in Human

Figure 24A:
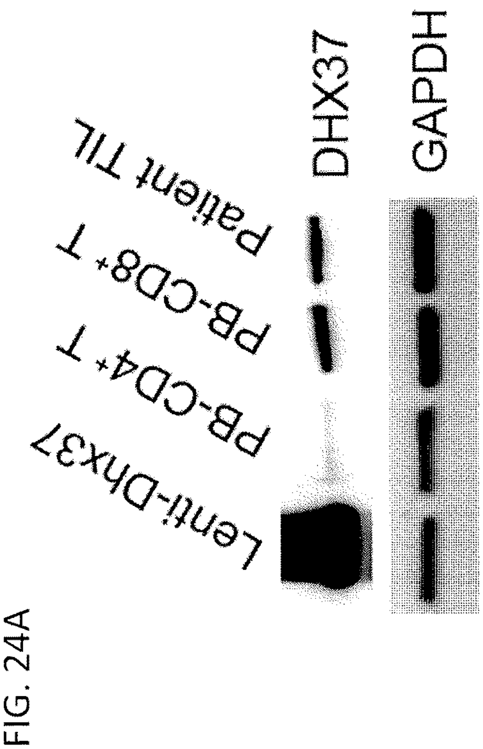
FIGS. 24A-24E are a series of plots and images illustrating analysis of DHX37 in human cells.
Figure 24B:
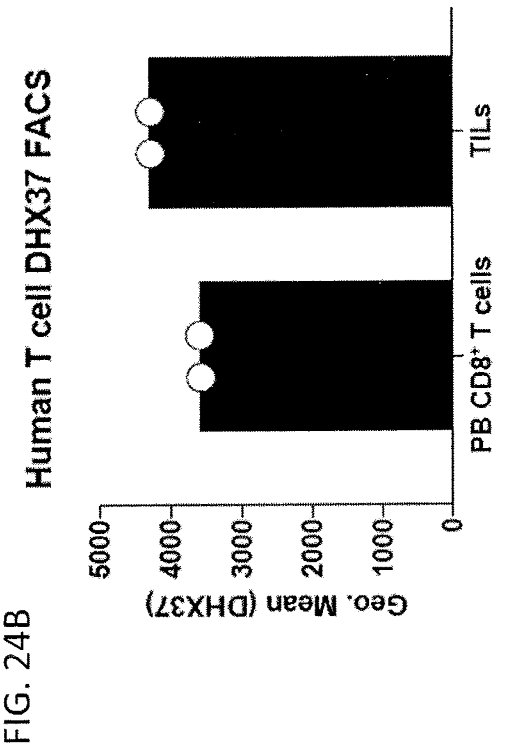
Figure 24C:
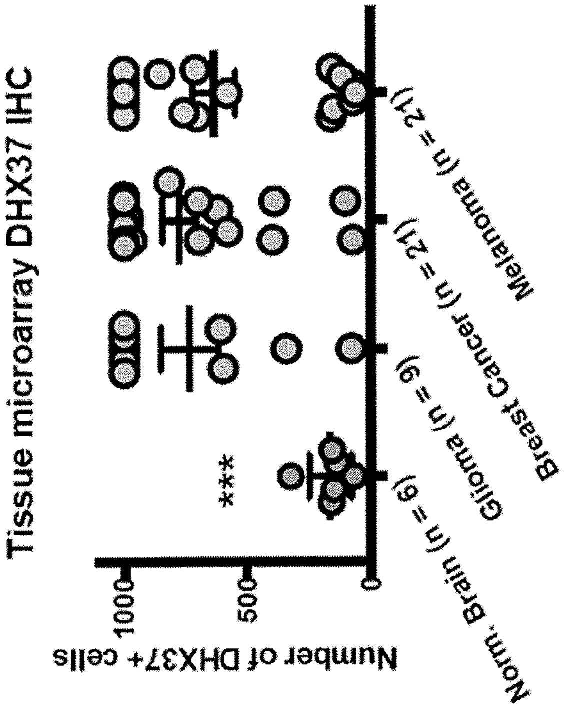
Figure 24D:
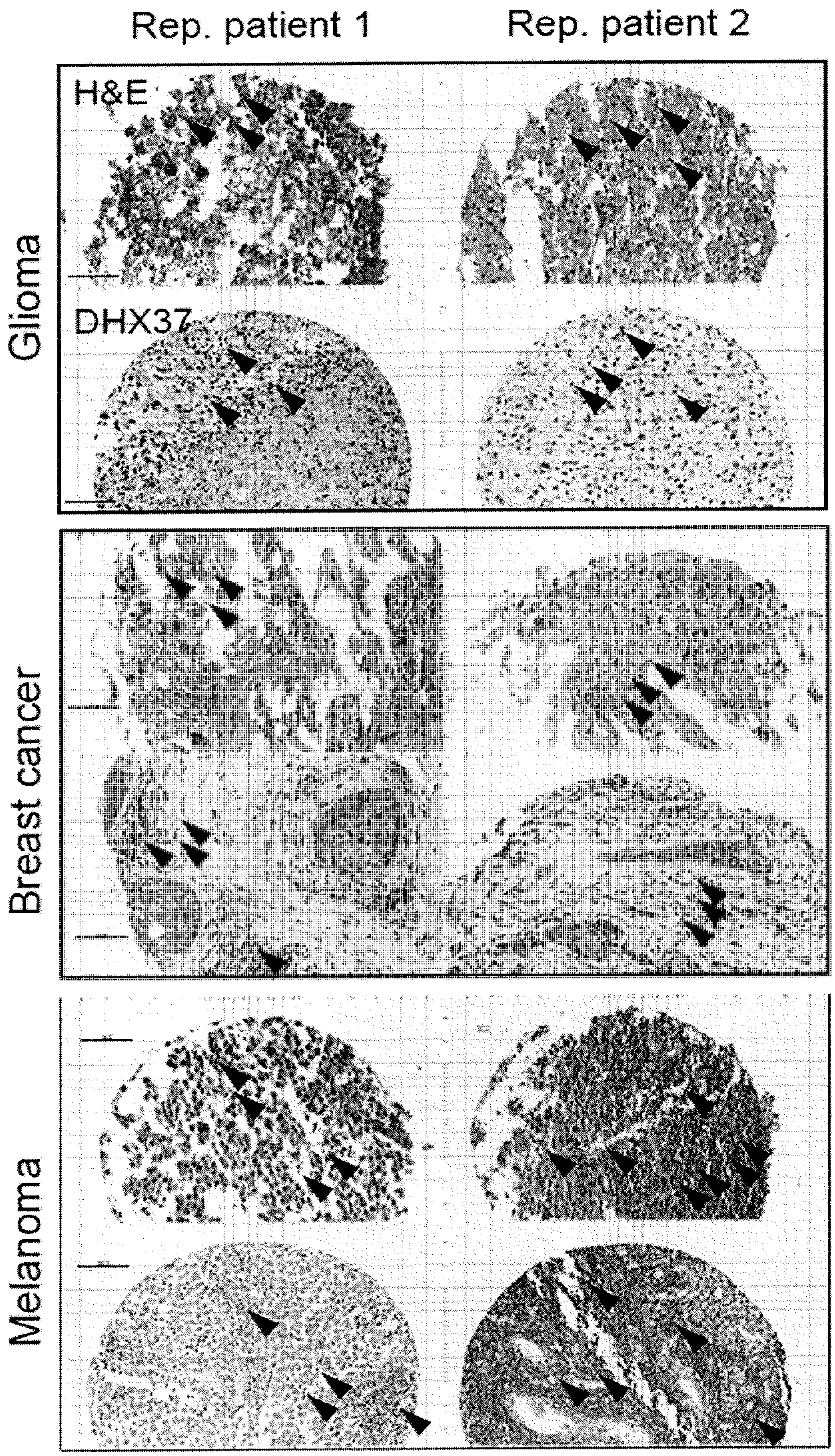
Figure 24E:
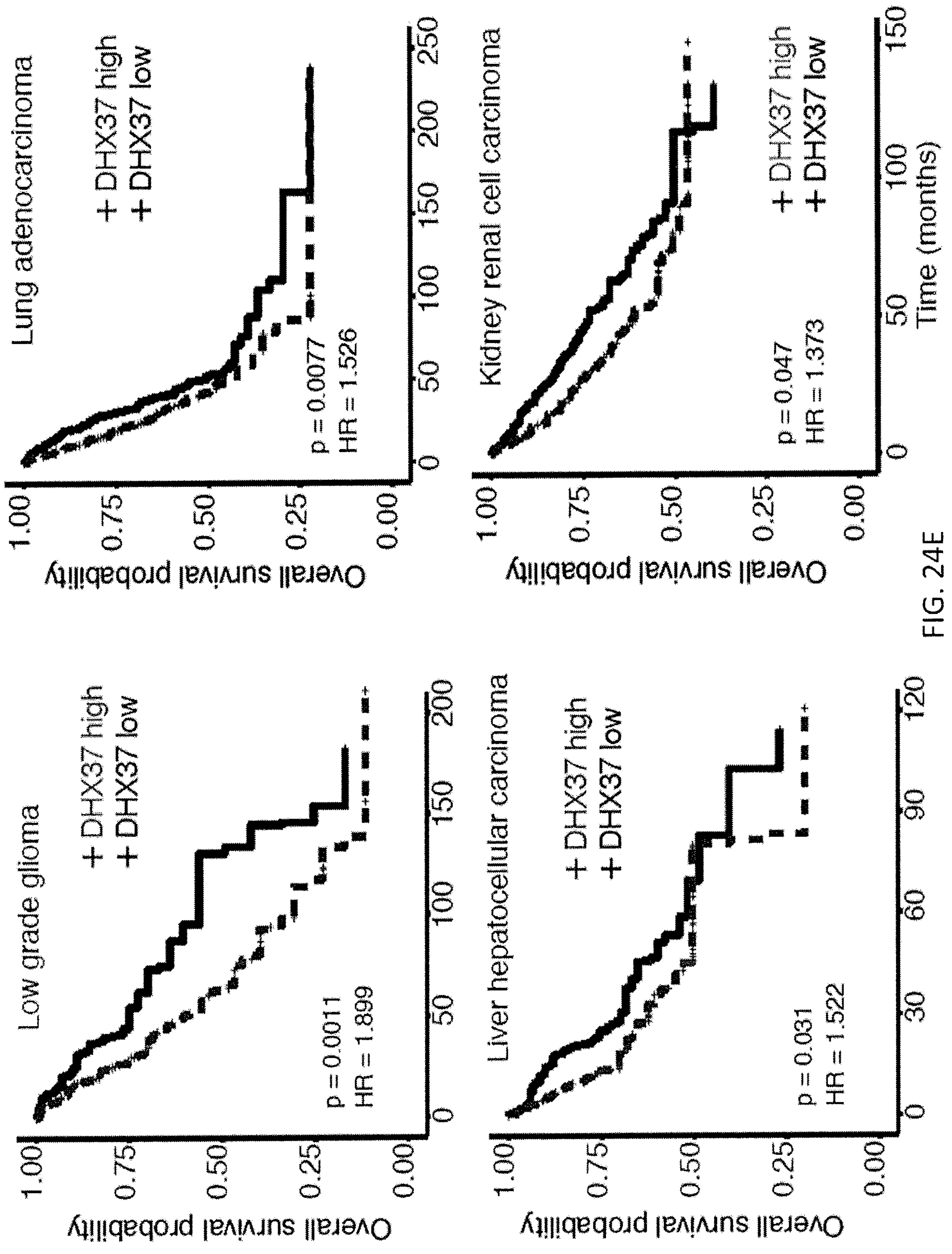

Human DHX37 is expressed in most organs, with highest expression in lymphoid tissues such as the bone marrow, lymph nodes, spleen and appendix. To examine the relevant roles of DHX37 in human T cells, its endogenous expression at the protein level was assayed. A lentiviral overexpression vector was generated as a positive control. The presence of DHX37 protein was detected in human peripheral blood (PB) $CD8^+$ and $CD4^+$ T cells, as well as TILs from a lung cancer patient (FIG. 24A). This finding was further corroborated using intracellular staining and FACS analysis (FIG. 24B). To analyze DHX37 expression at a spatial level, available tissue microarrays (TMAs) were retrieved for several cancer types including glioma, breast cancer and melanoma. H&E staining as well as immunohistochemistry (IHC) staining was performed for DHX37. A significantly higher level of $DHX37^+$ cells in glioma was observed as compared to normal brain tissues (unpaired t-test, two-sided, $p<0.001$) (FIG. 24C). Breast cancer and melanoma tumor samples also had high numbers of $DHX37^+$ cells at a comparable level to glioma, while matched normal tissues were not available for breast cancer and melanoma for these TMAs (FIG. 24C). Various populations of TILs were observed in all three cancer types (FIG. 24D). DHX37 is primarily localized in the nucleus, with strong staining at nuclear membranes (FIG. 24D). Importantly, with available patient survival data from TCGA, that high-DHX37 level was found to be linked to poor survival across multiple cancer types including glioma, liver hepatocellular carcinoma, lung adenocarcinoma and kidney renal cell carcinoma (FIG. 24E). These data together point to DHX37's expression in human T cells, patient TILs and prognostic relevance.

Figure 25A:
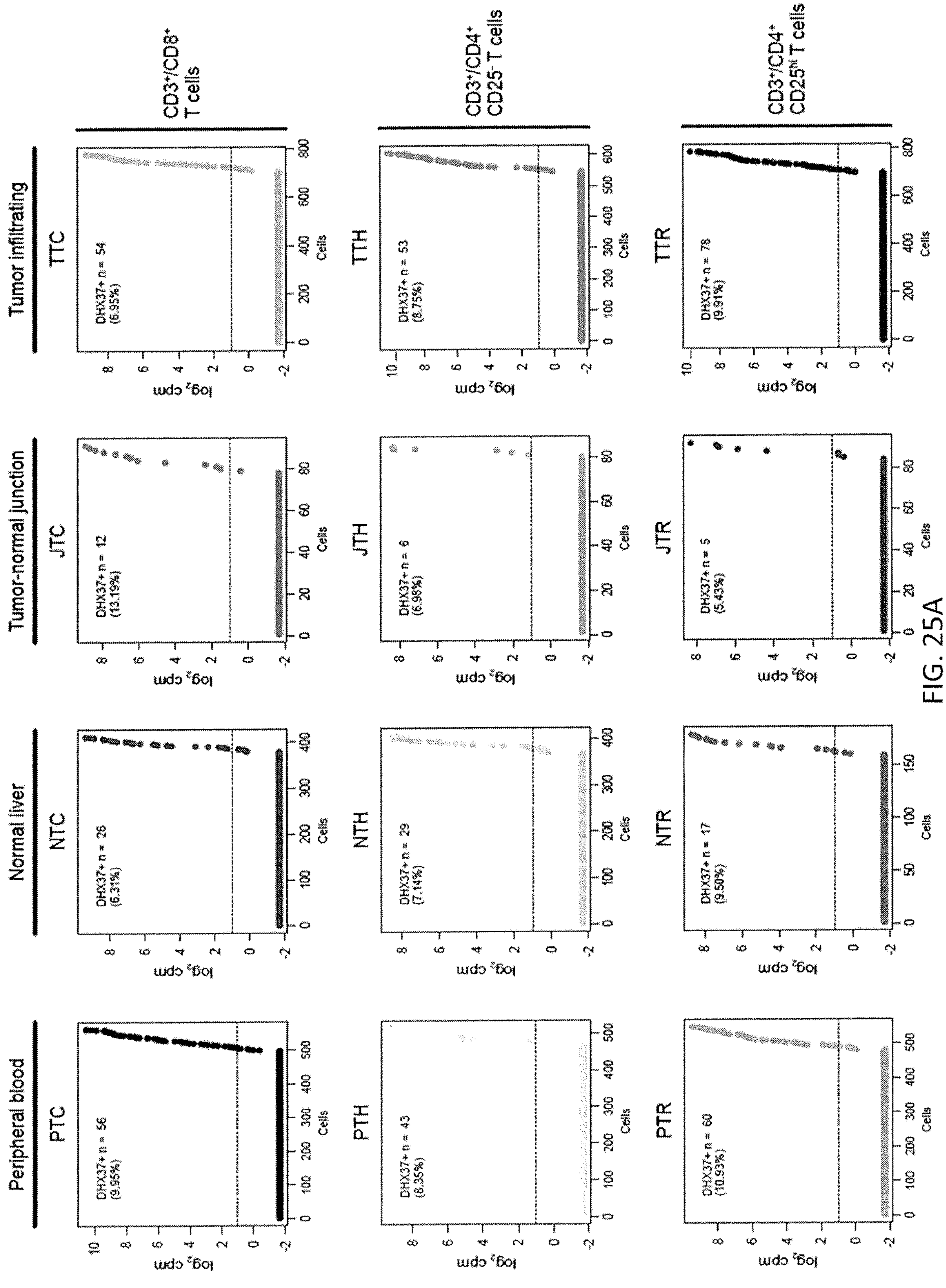
FIGS. 25A-25E are a series of plots illustrating gene expression signature of DHX37 in populations of single human T cells.
Figure 25B:
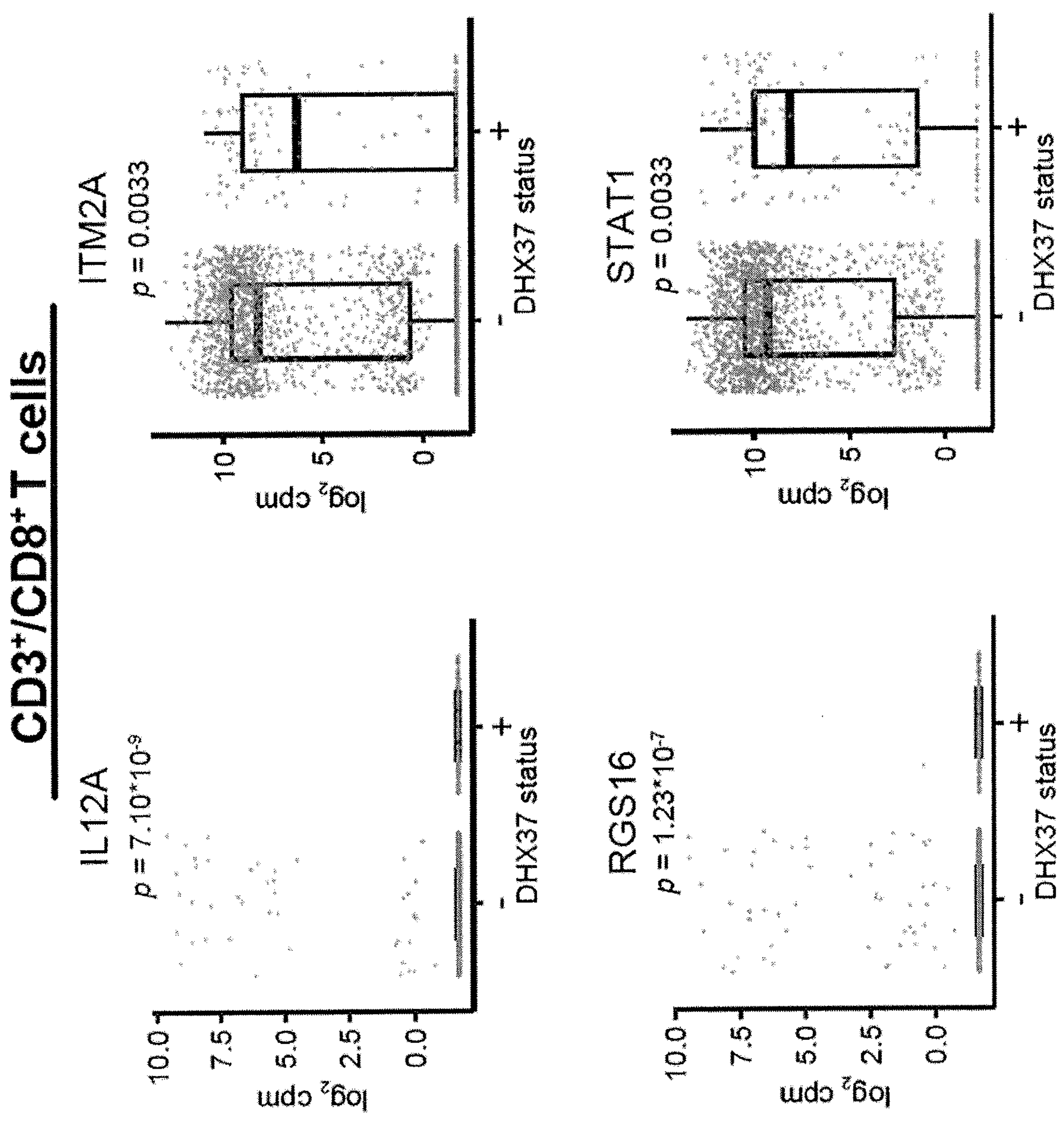
Figure 25C:
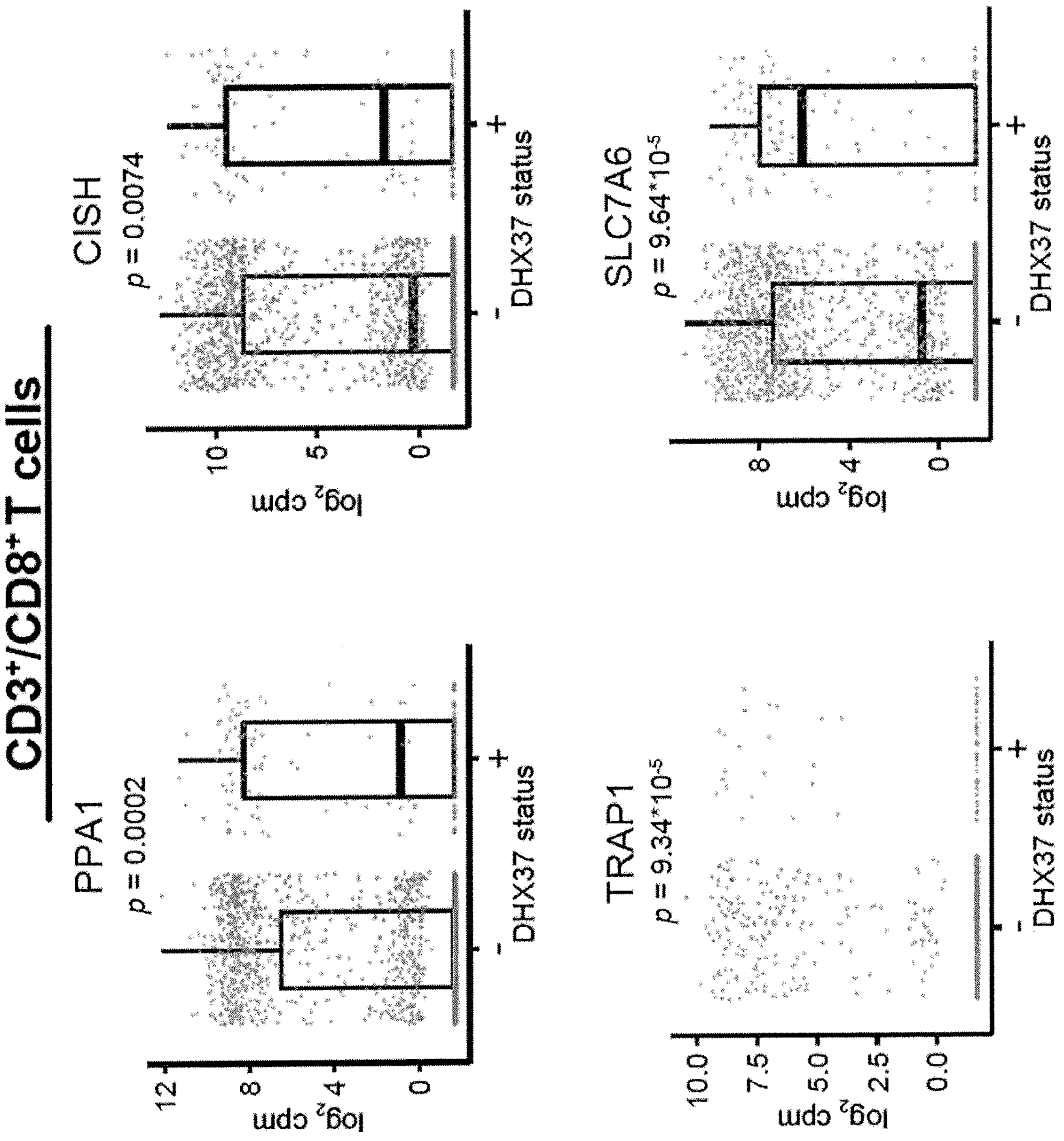
Figure 25D:
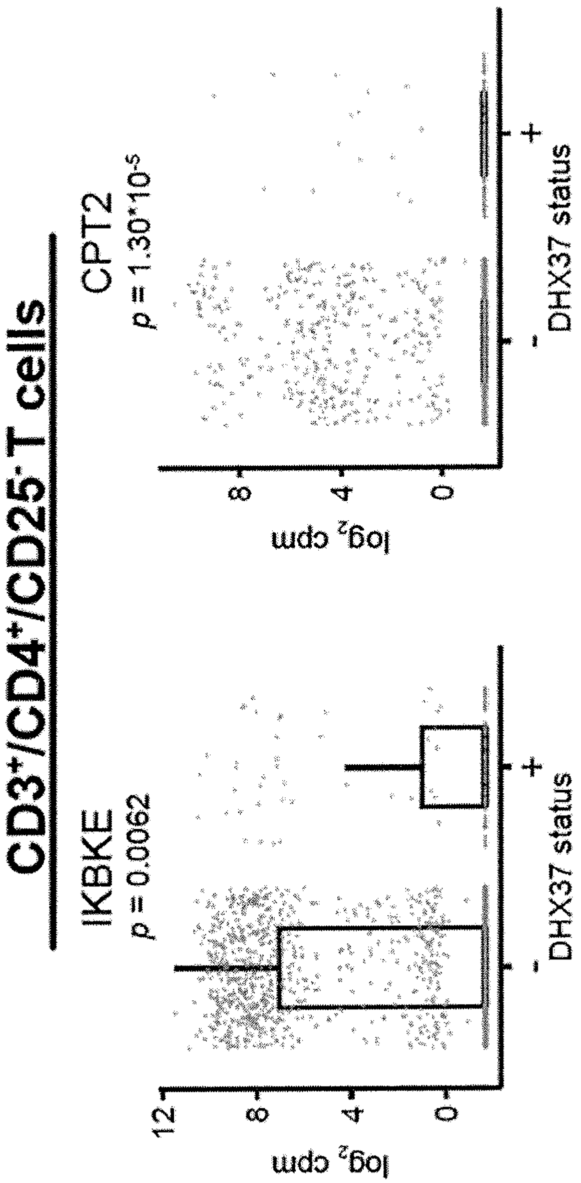
Figure 25E:
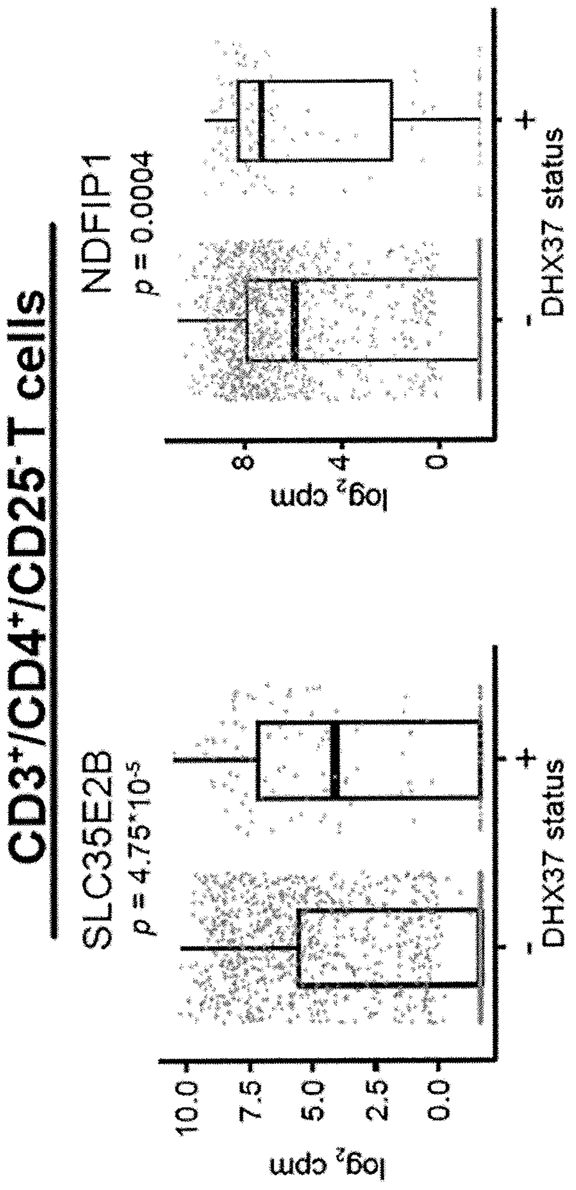

To further explore the signature of DHX37 in human T cells, a recent single-cell transcriptomics dataset of human TILs was analyzed. DHX37 expression was detected in a fraction of peripheral blood T cells, tissue-resident T cells and tumor-infiltrating T cells (FIG. 25A). DHX37 was expressed in $CD3^+/CD8^+$ (cytotoxic T cell), $CD3^+/CD4^+/CD25^-$ (T helper cell), and $CD3^+/CD4^+/CD25^+$ (Treg) populations (FIG. 25A). In the subpopulation of cells that express relatively higher level of DHX37 ($DHX37^+$ T cells), a variety of genes were differentially expressed compared to those expressing lower or undetectable levels ($DHX37^-$ T cells). Interestingly, $DHX37^+$ cytotoxic T cells downregulate multiple immune genes with documented roles in cytotoxicity, T cell activation, cytokine-mediated cell signaling, regulatory function and anti-cancer immunity, including IL12A, ITM2A, RGS16, and STAT1 (Fig. S9b), again consistent with our mouse TIL scRNA-seq. Genes that were more highly expressed in $DHX37^+$ cells included PPA1, CISH, TRAP1, and SLC7A6 (FIG. 25C). In $CD3^+/CD4^+/CD25^-$ helper T cells, the expression of genes such as IKBKE and CPT2 was significantly lower in $DHX37^+$ cells, while SLC35E2B and NDFIP1 are significantly lower (FIG. 25D-25E). Collectively, the analysis of human T cell scRNAseq data revealed signatures of gene expression changes in $DHX37^+$ vs. $DHX37^-$ T cells. Many of these differentially expressed genes have known roles in T cells, suggesting that natural cell population-wide variation in DHX37 expression may influence the function of human T cells.

Figure 26A:
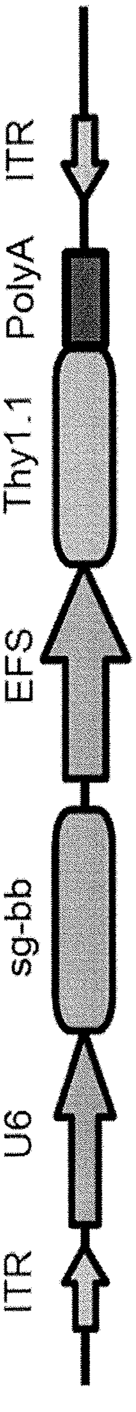
FIGS. 26A-26F are a series of plots and images illustrating development of a new AAV-CRISPR system and integrated interrogation of acute Dhx37 loss in $CD8^+$ $T_{eff}$ cells.
Figure 26B:
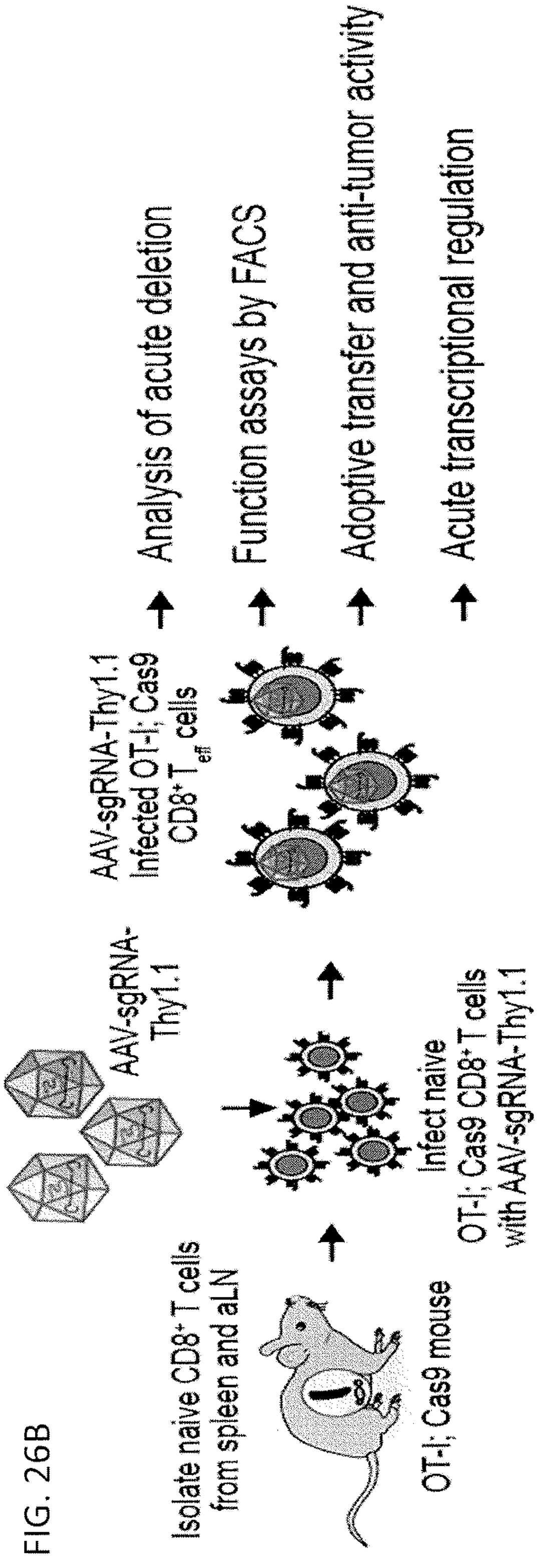
Figure 26C:
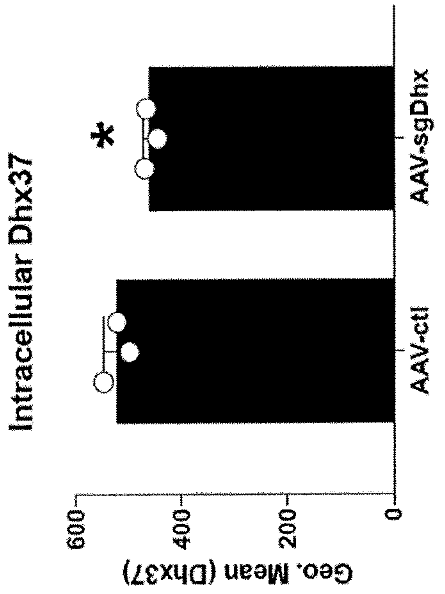
Figure 26D:
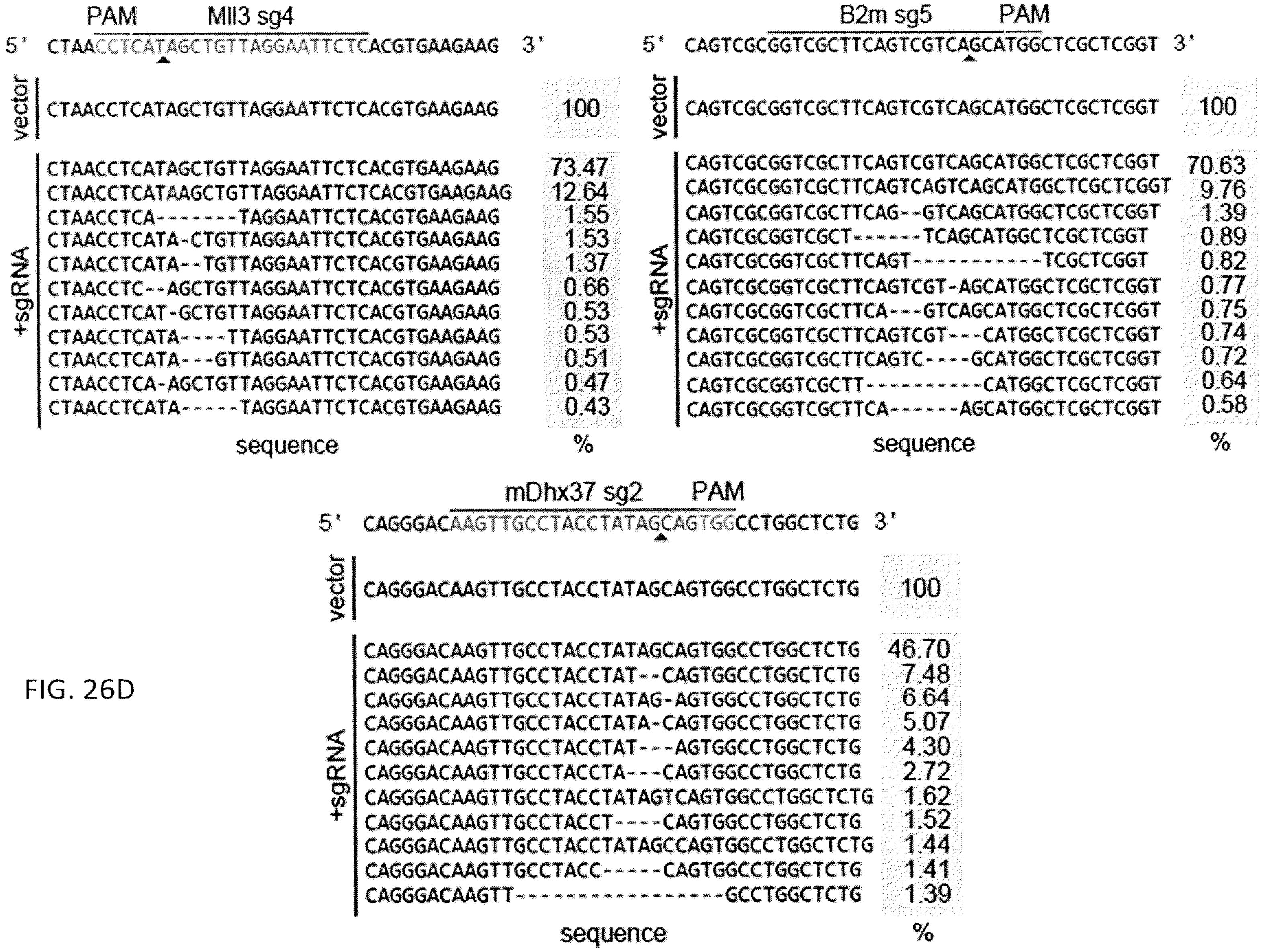
Figure 26F:
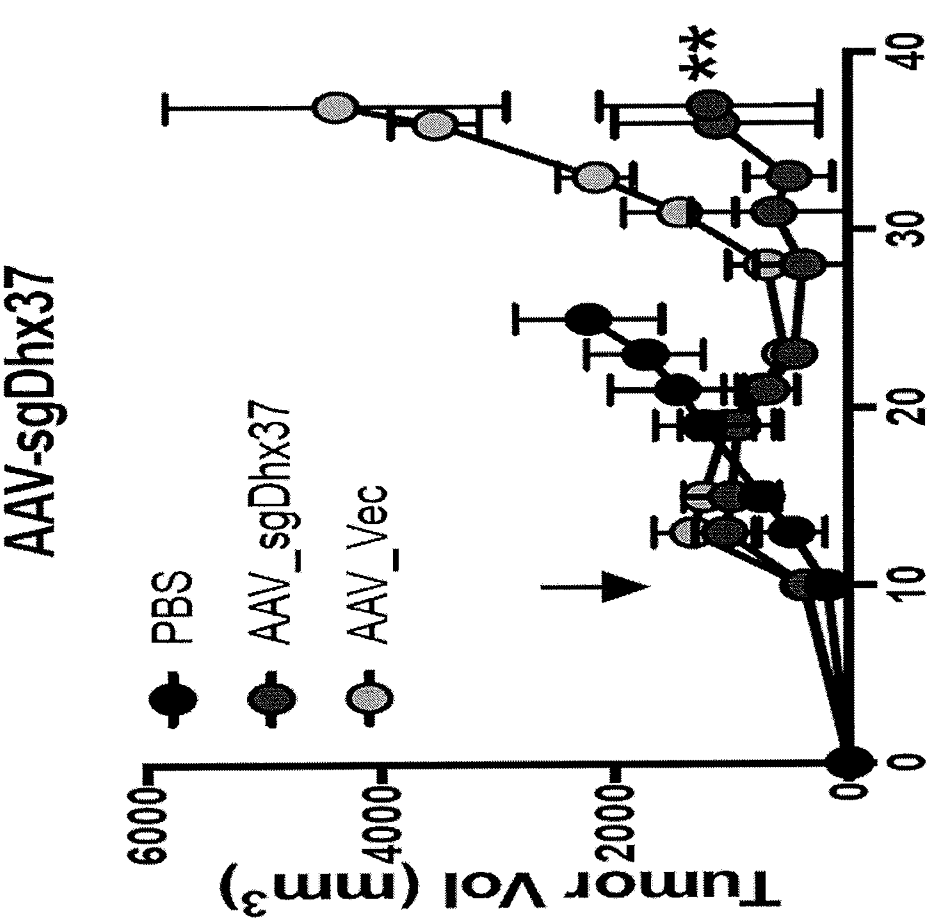
Figure 26E:
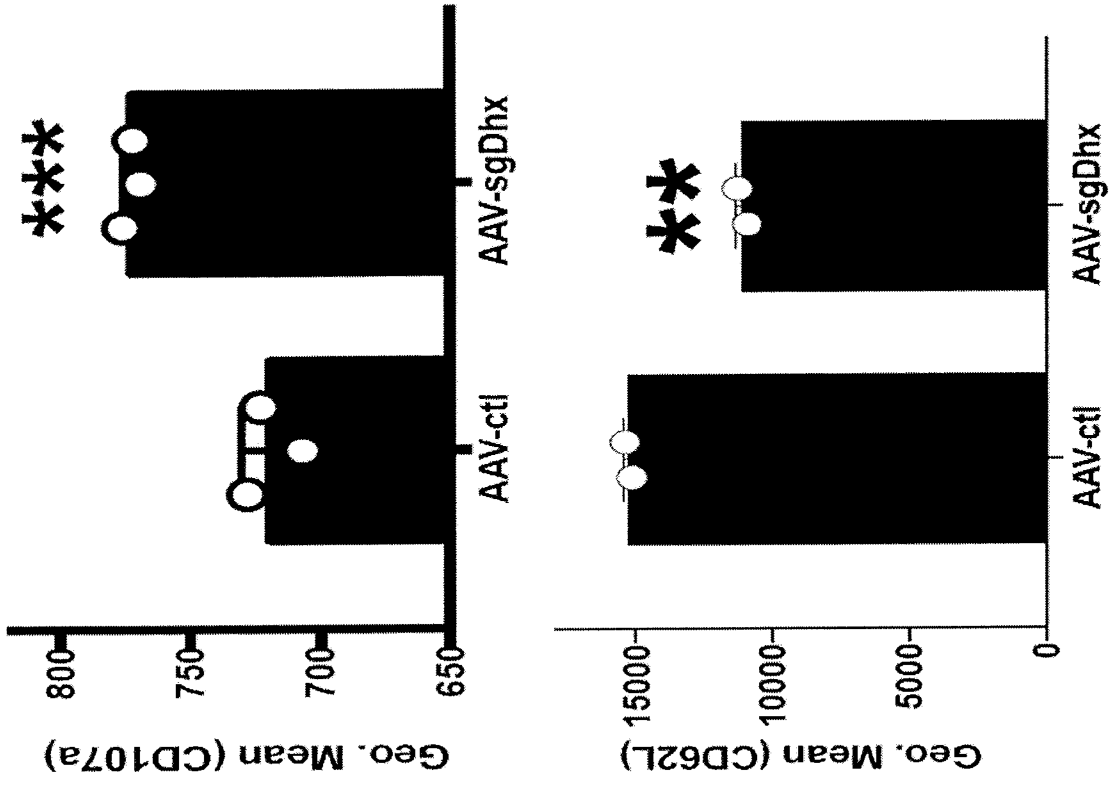

Example 12: Investigation of Acute Dhx37 Loss in $CD8^+$ $T_{eff}$ Cells with AAV-CRISPR Mediated T Cell Gene Editing The function of Dhx37 was further investigated directly in cultured $CD8^+$ T cells. Because mouse primary $CD8^+$ T cells are challenging for long-term culture as the majority of cells undergo apoptosis after day 7 in culture, adeno-associated virus (AAV) was adopted as a vehicle for gene editing in primary $CD8^+$ T cells. A new AAV CRISPR vector capable of targeting primary T cells was generated (FIG. 26A). OT-I; Cas9 $CD8^+$ $T_{eff}$ cells were isolated and infected with AAV-sgRNA-Thy1.1 vectors, then molecular and functional analyses were performed upon acute Dhx37 loss, in addition to gene regulation and anti-tumor activities (FIG. 26B). It was demonstrated that AAV-sgDhx37 as well as AAV-sgMll3 and AAV-sgB2m potently mutagenized the targeted loci 5 days after in vitro culture (FIG. 26D). This observation is corroborated with reduction of intracellular Dhx37 protein level (FIG. 26C). The partial knockdown is likely due to Dhx37 protein stability at this time point, as well as that not all indels lead to effective loss-of-protein. As compared to vector control, AAV-sgDhx37 treated OT-I; Cas9 $CD8^+$ $T_{eff}$ cells had significantly increased levels of surface CD107a when co-cultured with cognate SIINFEKL-pulsed E0771 cancer cells (t test, two sided, p=0.001, FIG. 26E), which further validated the kill assay screen. AAV-sgDhx37 treated OT-I; Cas9 $CD8^+$ $T_{eff}$ cells also showed decreased levels of CD62L (FIG. 26E). Adoptive transfer of AAV-sgDhx37 treated OT-I; Cas9 $CD8^+$ $T_{eff}$ cells significantly enhanced the anti-tumor activity in vivo as compared to AAV-vector (FIG. 26F). These experiments established AAV-CRISPR as an independent system for potent and acute T cell gene editing, further elucidated the cellular phenotypes of acute loss of Dhx37, and validated the anti-tumor effect of Dhx37 blockade in T cells.

Figure 27D:
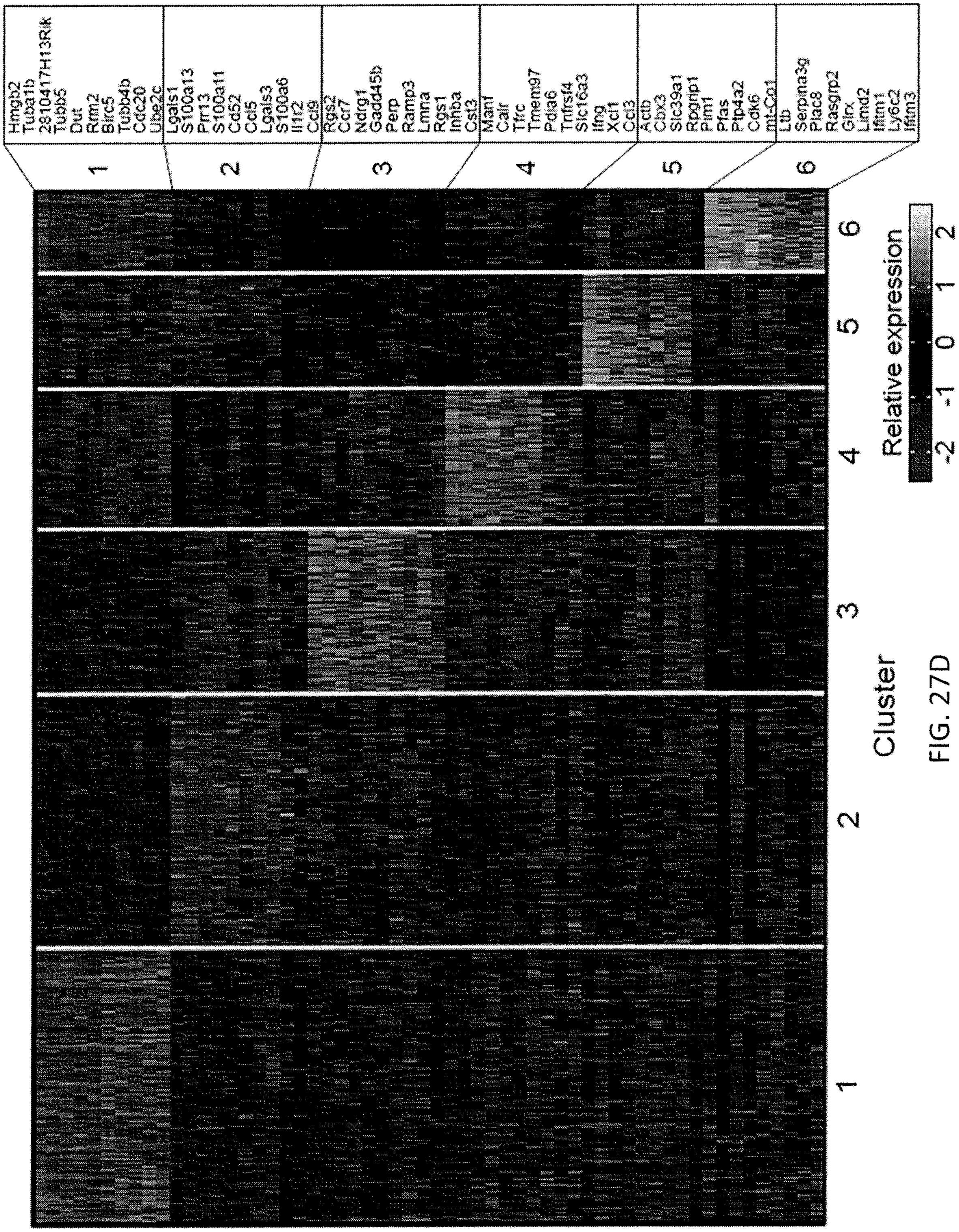
Figure 27E:
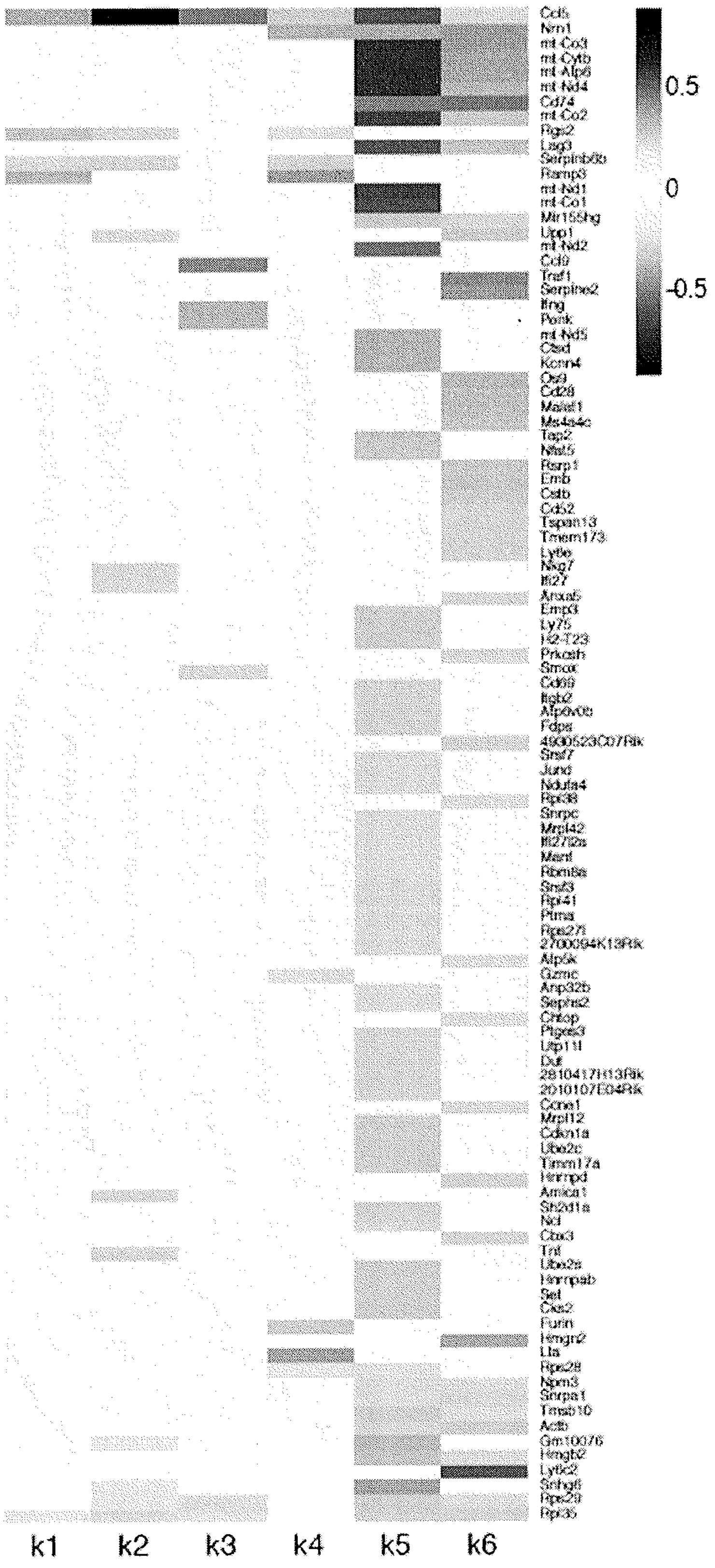
Figure 27F:
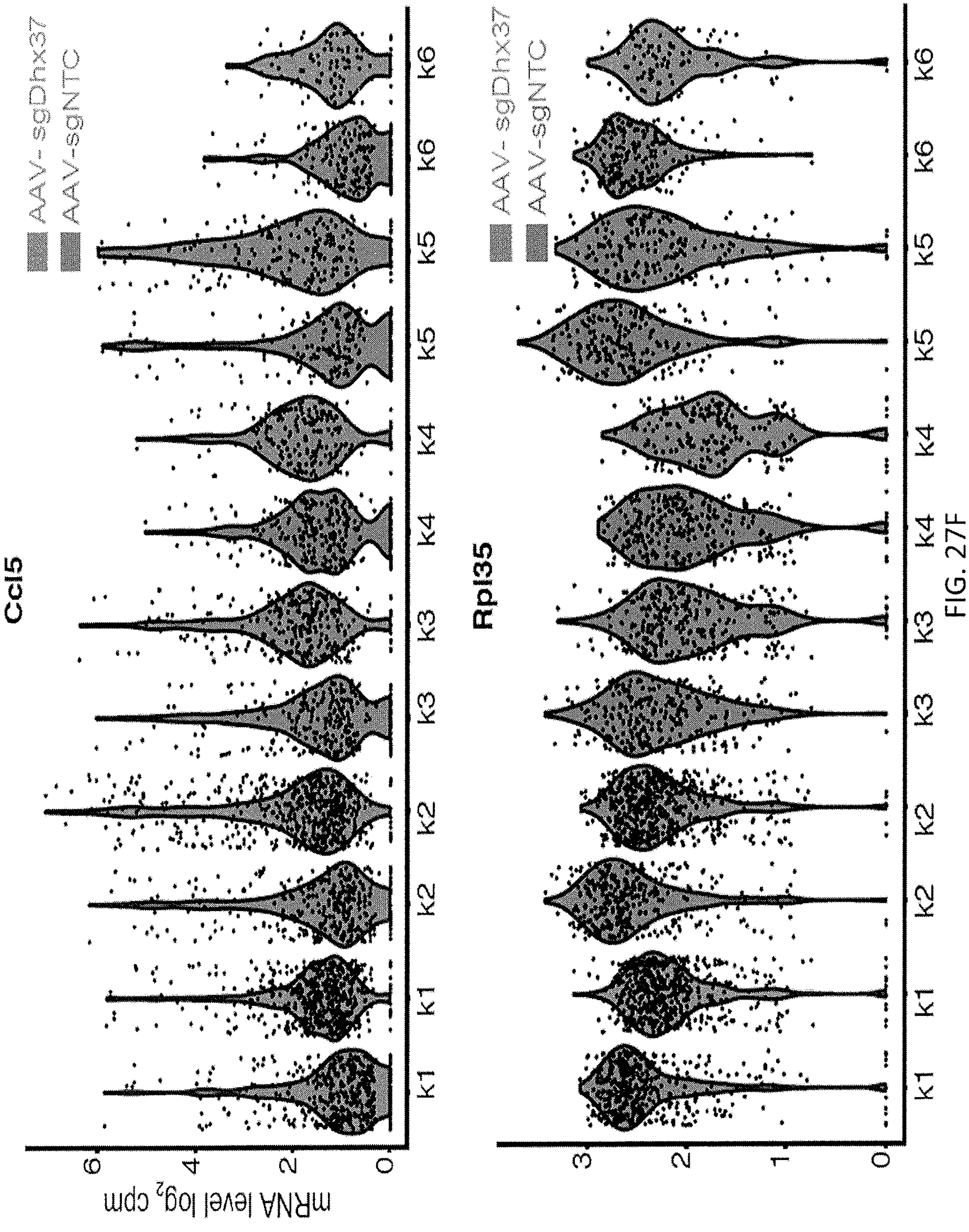
Figure 28A:
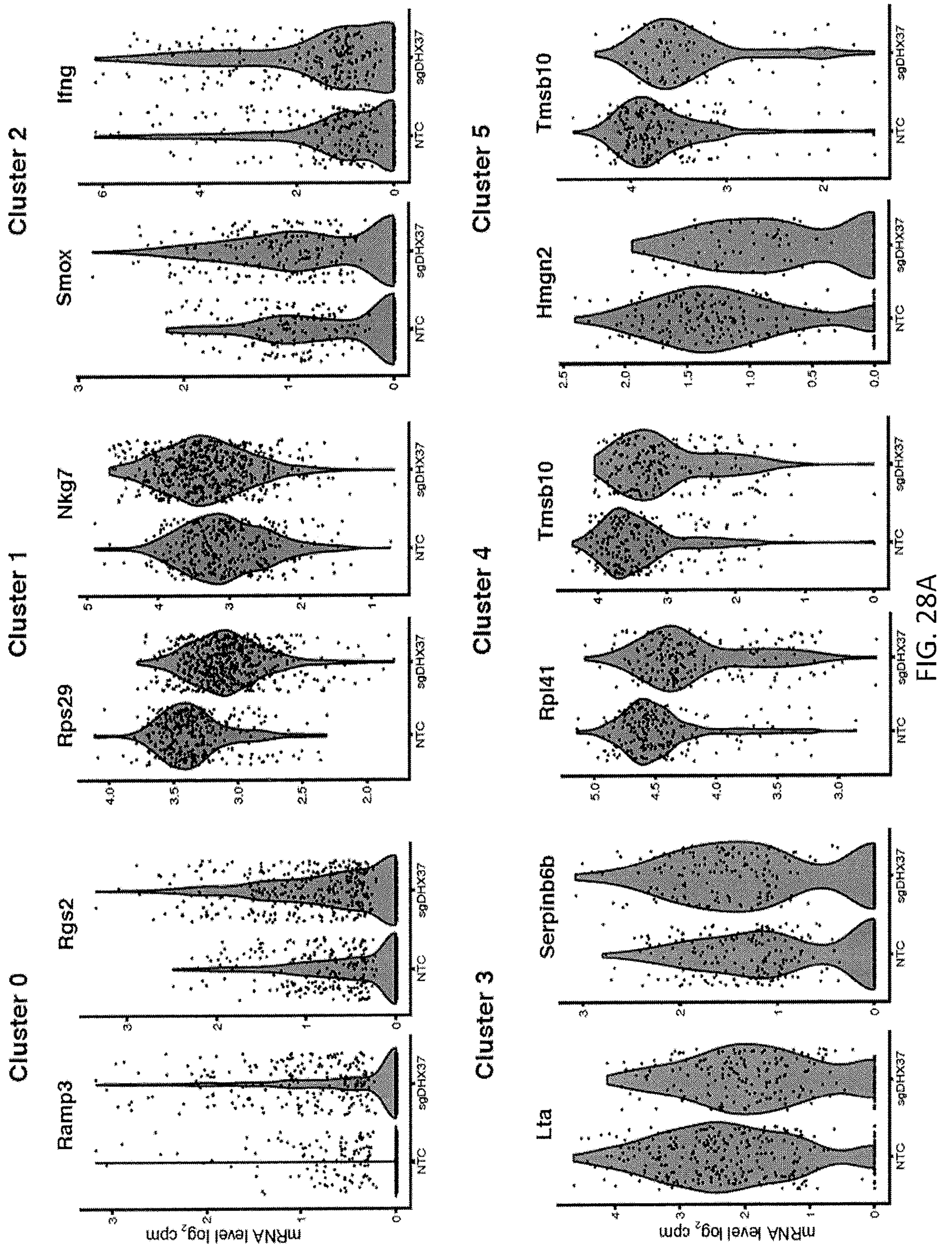
FIGS. 28A-28C shows additional analysis of gene regulation upon Dhx37 loss in mouse and human $CD8^+$ cells.
Figures 28B, 28C:
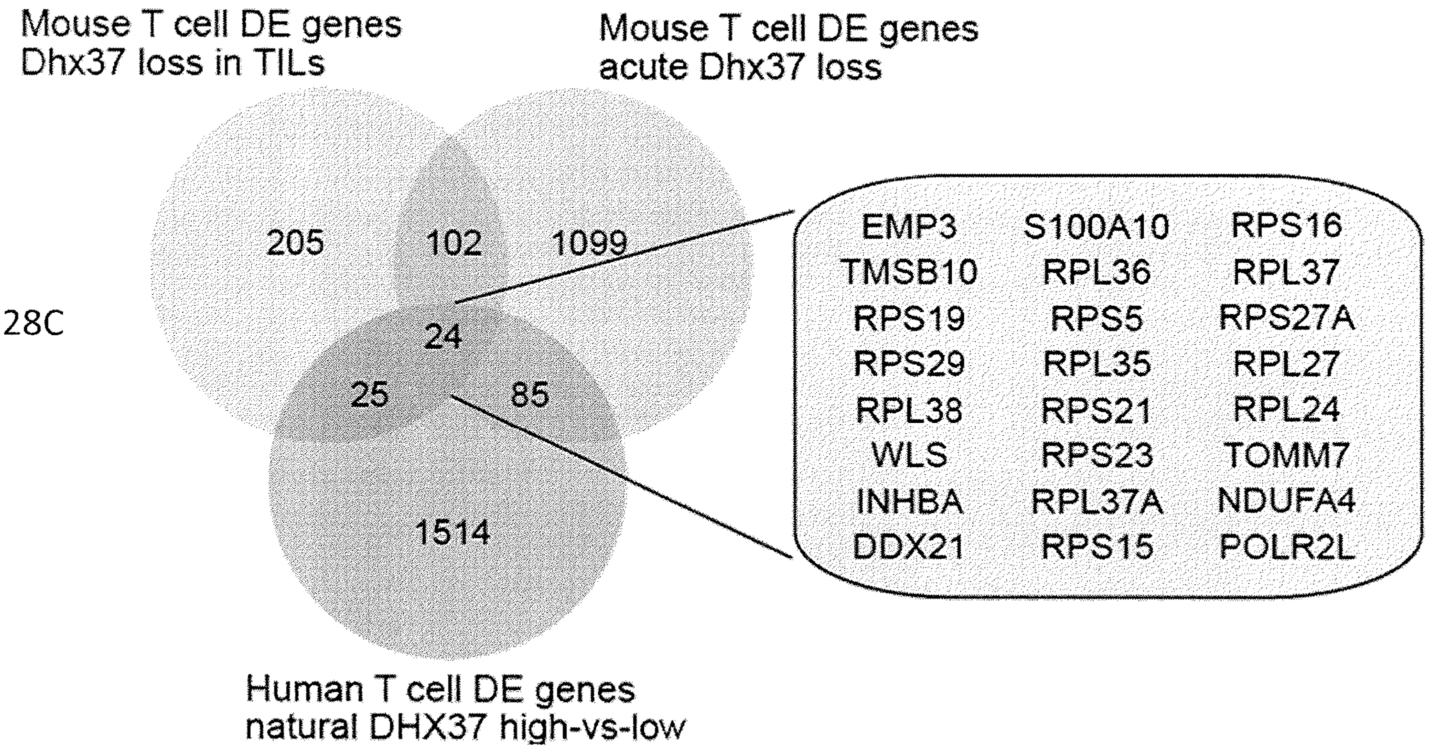

AAV-sgDhx37 generated a mixture of mutants at Dhx37 locus and mouse primary T cells do not grow as single cell clones. Thus, to better understand the transcriptional changes upon acute Dhx37 loss in a heterogeneous T cell population at a more refined resolution, single cell transcriptome profiling was again performed, with a much larger set of cells (establishing knockouts in in vitro culture eliminates the barrier of low availability of $CD8^+$ T cells as TILs). A total of 1,883 AAV-sgDhx37 treated OT-I; Cas9 $CD8^+$ $T_{eff}$ cells were profiled 6 days post infection, in parallel with 1,735 AAV-sgNTC treated ones (FIG. 27A). Dimension reduction analysis showed 6 major clusters for these cells (FIG. 27B). Each cluster was represented by a distinct gene signature (FIG. 27D), revealing a substantial level of transcriptomic heterogeneity even with T cells of clonal TCR (in both AAV-sgNTC and AAV-sgDhx37). Intriguingly, AAV-sgDhx37 $CD8^+$ T cells are enriched in cluster 2 but depleted in clusters 4 and 6 (hypergeometric test, $p<0.001$) (FIG. 27C). Differential expression analysis was performed in all 6 clusters with sufficient cell numbers to provide statistical power in each one, and a panel of genes deregulated upon acute Dhx37 loss was unveiled (FIG. 27E). There are a small number of genes consistently deregulated across all clusters, with a larger number of cluster-specific differentially regulated genes (FIG. 27E). For example, Ccl5 is significantly upregulated upon acute Dhx37 loss in all 6 clusters, and Rpl35 is significantly downregulated in 5/6 clusters (FIG. 27F). Multiple genes were found to be differentially regulated only in specific clusters (e.g. Rgs2, Lag3, Ifng, Ramp3, Rps29, Nkg7, Smox, Lta, Serpinb6b, Rpl41, Tmsb10, Hmgn2, Npm3 and Ly6c2) (FIG. 27E, FIG. 28A), reflecting sub-population specific dynamic gene regulation across a heterogeneous cell population. The upregulated genes upon acute Dhx37 loss are also highly enriched in the gene set categories involving immune function (FIG. 28B), while the downregulated gene sets are ribosomal components. Although under different experimental settings, the differentially regulated genes upon Dhx37 loss by three different kinds of mechanisms, lenti-CRISPR mediated perturbation in mouse TILs, AAV-CRISPR mediated acute loss in culture, and naturally low-expression population in human T cells, converged on a total of 24 genes (FIG. 28C).

Example 13: Demonstration of Gene Editing in Human T Cells

Figure 29:
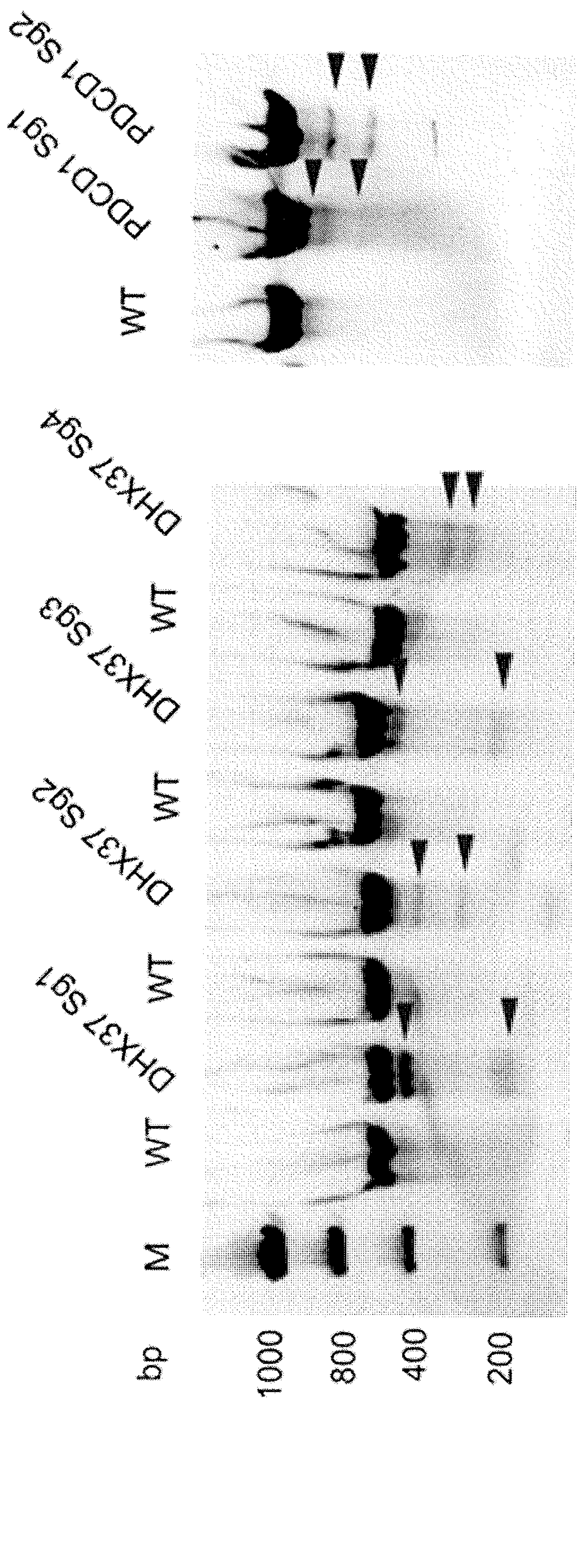
FIG. 29 is an image illustrating gene editing in human T cells with the vectors of the present invention. Surveyor assay of human DHX37 gene (3 independent sgRNAs) and PDCD1 gene (2 independent sgRNAs). The arrows point to cleavage product bands as a result of on-target gene editing in human T cells.

Gene editing was performed in human T cells using the compositions and methods of the present invention (FIG. 29). Results from a Surveyor assay of human DHX37 gene (3 independent sgRNAs) and PDCD1 gene (2 independent sgRNAs) are shown in FIG. 29. The arrows pointed to cleavage product bands as a result of on-target gene editing in human T cells.

Example 14

Herein, genome editing was coupled to high-throughput screening approaches and directly applied to systematically study the trafficking and survival of $CD8^+$ T cells in vivo, both in physiological and pathological (cancer) settings. Although the data presented herein focused on $CD8^+$ T cells, this approach can readily be applied to study $CD4^+$ T helper cells and regulatory T cells ($T_{reg}$). The present cancer immunotherapy model was developed based on orthotopic transplantation of breast cancer cells followed by adoptive transfer of CRISPR-targeted $CD8^+$ $T_{eff}$ cells, while a variety of cancer models such as genetically engineered mouse models and genome-editing based cancer models are all possible alternatives. Direct high-throughput genetic manipulation of T cells in vivo without adoptive transfer should render direct mutagenesis of the T cell population feasible.

$CD8^+$ T cells play fundamental roles in the adaptive immune response mounted against intracellular pathogens and tumors, with a central role in the cancer-immune response. Herein, high-throughput in vivo CRISPR screens were performed in $CD8^+$ $T_{eff}$ cells in wildtype animals and in a setting of immunotherapy, which generated genome-scale maps of genetic factors modulating the trafficking and survival of in $CD8^+$ cytotoxic T cells in the presence and absence of known antigens, and identified enriched genes belonging to various functional categories including multiple that were not documented in literature. This study demonstrates a new approach for high-throughput genetic interrogation of T cells in vivo, which can be broadly applied for diverse studies in immunology and immunotherapy.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

SEQUENCE LISTING

The patent contains a lengthy sequence listing. A copy of the sequence listing is available in electronic form from the USPTO web site (https://seqdata.uspto.gov/?pageRequest=docDetail&DocID=US11926839B2). An electronic copy of the sequence listing will also be available from the USPTO upon request and payment of the fee set forth in 37 CFR 1.19(b)(3).

---

What is claimed is:

1. A vector comprising a 5' long terminal repeat (LTR) sequence, a U6 promoter sequence, a BsmB1 restriction site, an EFS sequence, an sgRNA expression cassette, a Thy1.1 cassette, a 3' LTR sequence and an ampicillin a resistance gene sequence (AmpR) wherein the vector comprises a nucleic acid sequence selected from the group consisting of SEQ ID NO: 129,213, SEQ ID NO: 129,214, and SEQ ID NO: 129,215.

2. A vector comprising a 5' long terminal repeat (LTR) sequence, a U6 promoter sequence, a BsmB1 restriction site, an EFS sequence, an sgRNA expression cassette, a Thy1.1 cassette, a 3' LTR sequence and an ampicillin resistance gene sequence (AmpR), wherein the sgRNA expression cassette expresses an sgRNA comprising a nucleotide sequence selected from the group consisting of SEQ ID NOs: 1-129,209.

3. The vector of claim 2, wherein the sgRNA expression cassette expresses an sgRNA consisting of a nucleotide sequence selected from the group consisting of SEQ ID NOs: 1-129,209.

* * * * *